United States Patent
White et al.

(10) Patent No.: US 11,464,928 B2
(45) Date of Patent: Oct. 11, 2022

(54) FLOW THERAPY

(71) Applicant: Fisher & Paykel Healthcare Limited, Auckland (NZ)

(72) Inventors: Craig Karl White, Auckland (NZ); Alicia Jerram Hunter Evans, Auckland (NZ); Samantha Dale Oldfield, Auckland (NZ); Callum James Thomas Spence, Auckland (NZ); Salman Mansoor Javed, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 494 days.

(21) Appl. No.: 14/916,516

(22) PCT Filed: Sep. 4, 2014

(86) PCT No.: PCT/IB2014/064245
§ 371 (c)(1),
(2) Date: Mar. 3, 2016

(87) PCT Pub. No.: WO2015/033288
PCT Pub. Date: Mar. 12, 2015

(65) Prior Publication Data
US 2016/0193438 A1 Jul. 7, 2016

Related U.S. Application Data

(60) Provisional application No. 62/036,769, filed on Aug. 13, 2014, provisional application No. 62/011,221, (Continued)

(51) Int. Cl.
*A61M 16/00* (2006.01)
*A61M 16/16* (2006.01)
(Continued)

(52) U.S. Cl.
CPC .... *A61M 16/0069* (2014.02); *A61M 16/0003* (2014.02); *A61M 16/0051* (2013.01);
(Continued)

(58) Field of Classification Search
CPC ........... A61M 16/0069; A61M 16/0666–0677; A61M 16/006; A61M 2205/3334
See application file for complete search history.

(56) References Cited

U.S. PATENT DOCUMENTS

| 3,410,264 A | 11/1968 | Frederik |
| 4,155,356 A | 5/1979 | Venegas |

(Continued)

FOREIGN PATENT DOCUMENTS

| CN | 101448539 | 12/2012 |
| EP | 0127923 A2 | 12/1984 |

(Continued)

OTHER PUBLICATIONS

Extended European Search Report, European Application No. EP 14 84 1727, dated Mar. 7, 2017, 7 pages.

(Continued)

*Primary Examiner* — Samchuan C Yao
*Assistant Examiner* — Cana A Gallegos
(74) *Attorney, Agent, or Firm* — Knobbe, Martens, Olson & Bear, LLP

(57) ABSTRACT

A method of estimating a parameter indicative of respiratory flow of a patient being administered flow therapy, comprising: optionally administering a gas at a flow rate to the patient using a flow therapy apparatus with a patient interface, determining a terminal pressure in, at or proximate the outlet of the patient interface or in, at or proximate the nares of the patient, determining nasal RTF, determining a nasal flow parameter being or indicative of nasal flow based on the
(Continued)

pressure and a nasal RTF, and optionally outputting the nasal flow parameter or parameter derived therefrom.

26 Claims, 64 Drawing Sheets

Related U.S. Application Data filed on Jun. 12, 2014, provisional application No. 62/010,905, filed on Jun. 11, 2014, provisional application No. 61/994,374, filed on May 16, 2014, provisional application No. 61/944,800, filed on Feb. 26, 2014, provisional application No. 61/918,620, filed on Dec. 19, 2013, provisional application No. 61/910,812, filed on Dec. 2, 2013, provisional application No. 61/906,328, filed on Nov. 19, 2013, provisional application No. 61/886,921, filed on Oct. 4, 2013, provisional application No. 61/873,710, filed on Sep. 4, 2013.

(51) Int. Cl.
   *A61M 16/10* (2006.01)
   *A61M 16/06* (2006.01)

(52) U.S. Cl.
   CPC ...... *A61M 16/026* (2017.08); *A61M 16/0666* (2013.01); *A61M 16/1005* (2014.02); *A61M 16/16* (2013.01); *A61M 16/0006* (2014.02); *A61M 16/1095* (2014.02); *A61M 16/161* (2014.02); *A61M 2016/0027* (2013.01); *A61M 2016/0036* (2013.01); *A61M 2205/3334* (2013.01); *A61M 2205/3368* (2013.01); *A61M 2205/3569* (2013.01); *A61M 2205/502* (2013.01); *A61M 2205/505* (2013.01); *A61M 2230/005* (2013.01); *A61M 2230/202* (2013.01); *A61M 2230/42* (2013.01); *A61M 2230/432* (2013.01); *A61M 2230/435* (2013.01)

(56) References Cited

U.S. PATENT DOCUMENTS

| | | | |
|---|---|---|---|
| 4,719,910 A | 1/1988 | Jensen | |
| 4,821,709 A | 4/1989 | Jensen | |
| 5,165,398 A | 11/1992 | Bird | |
| 6,029,664 A | 2/2000 | Zdrojkowski et al. | |
| 6,029,665 A | 2/2000 | Berthon-Jones | |
| 6,085,747 A | 7/2000 | Axe et al. | |
| 6,193,677 B1 | 2/2001 | Cady | |
| 6,390,092 B1* | 5/2002 | Leenhoven | A61M 16/0096 128/204.23 |
| 6,446,629 B1* | 9/2002 | Takaki | A61M 16/0096 128/204.18 |
| 6,557,554 B1* | 5/2003 | Sugiura | A61M 16/0096 128/204.18 |
| 6,934,579 B2 | 8/2005 | Mantzaridis et al. | |
| 7,861,716 B2* | 1/2011 | Borrello | A61M 16/0096 128/204.18 |
| 8,631,799 B2 | 1/2014 | Davenport et al. | |
| 2004/0069304 A1 | 4/2004 | Jam | |
| 2005/0121033 A1 | 6/2005 | Starr et al. | |
| 2005/0178383 A1* | 8/2005 | Mackie | A61M 16/209 128/203.16 |
| 2005/0257788 A1 | 11/2005 | Aylsworth et al. | |
| 2006/0005842 A1 | 1/2006 | Rashad et al. | |
| 2006/0042638 A1 | 3/2006 | Niklewski et al. | |
| 2006/0162727 A1 | 7/2006 | Biondi et al. | |
| 2006/0174885 A1 | 8/2006 | Aylsworth et al. | |
| 2006/0174889 A1 | 8/2006 | Noble | |
| 2007/0113847 A1 | 5/2007 | Acker et al. | |
| 2007/0175473 A1 | 8/2007 | Lewis et al. | |
| 2007/0215154 A1* | 9/2007 | Borrello | A61M 16/0096 128/204.21 |
| 2008/0142019 A1 | 6/2008 | Lewis et al. | |
| 2009/0007913 A1 | 1/2009 | Lee | |
| 2009/0126731 A1 | 5/2009 | Dunsmore et al. | |
| 2009/0145428 A1 | 6/2009 | Sward et al. | |
| 2009/0156952 A1 | 6/2009 | Hunter et al. | |
| 2009/0253995 A1 | 10/2009 | Lewis et al. | |
| 2010/0078024 A1 | 4/2010 | Andreiux et al. | |
| 2010/0252037 A1 | 10/2010 | Wondka et al. | |
| 2010/0319691 A1 | 12/2010 | Lurie et al. | |
| 2011/0114098 A1 | 5/2011 | Mcauley et al. | |
| 2011/0125052 A1* | 5/2011 | Davenport | A61M 16/0051 600/561 |
| 2011/0214676 A1 | 9/2011 | Allum | |
| 2012/0017904 A1 | 1/2012 | Ratto et al. | |
| 2012/0060840 A1 | 3/2012 | Refsland et al. | |
| 2012/0103337 A1 | 5/2012 | Avni | |
| 2012/0266882 A1 | 10/2012 | Dellaca et al. | |
| 2013/0012828 A1 | 1/2013 | Aylsworth | |
| 2013/0133655 A1 | 5/2013 | Kimm et al. | |
| 2014/0190481 A1 | 7/2014 | Jam | |
| 2014/0283834 A1* | 9/2014 | Ahmad | A61M 16/0069 128/204.23 |
| 2014/0350429 A1* | 11/2014 | Truschel | A61M 16/0066 600/533 |
| 2015/0059751 A1* | 3/2015 | Cortez, Jr. | A61M 16/20 128/204.21 |
| 2015/0119743 A1 | 4/2015 | Maksym | |
| 2015/0128942 A1 | 5/2015 | Tatkov et al. | |
| 2015/0182713 A1 | 7/2015 | Phuah et al. | |
| 2015/0258291 A1 | 9/2015 | Richards-Kortum et al. | |
| 2015/0335851 A1* | 11/2015 | Cullen | A61M 16/0066 128/204.25 |
| 2015/0359982 A1* | 12/2015 | Garde | A61M 16/024 128/202.22 |
| 2016/0193438 A1 | 7/2016 | White et al. | |
| 2016/0228661 A1 | 8/2016 | Larsson | |
| 2016/0339191 A1 | 11/2016 | Kaczka | |
| 2016/0367779 A1* | 12/2016 | Landis | A61M 16/1075 |
| 2017/0087316 A1 | 3/2017 | White et al. | |
| 2017/0303821 A1 | 10/2017 | Hete | |
| 2018/0104426 A1 | 4/2018 | Oldfield et al. | |
| 2018/0126110 A1 | 5/2018 | Payton et al. | |
| 2021/0052844 A1 | 2/2021 | Oldfield et al. | |

FOREIGN PATENT DOCUMENTS

| | | |
|---|---|---|
| EP | 3259001 | 10/2018 |
| GB | 2357037 | 6/2001 |
| GB | 2357037 | 7/2002 |
| GB | 2442875 A | 4/2008 |
| JP | 2001-500039 | 10/2004 |
| JP | 2007-530079 | 11/2007 |
| JP | 2015-506802 | 3/2015 |
| WO | WO 98/10818 A1 | 3/1998 |
| WO | WO 03/066145 A1 | 8/2003 |
| WO | WO 2005/006941 | 1/2005 |
| WO | WO 2005/011556 | 2/2005 |
| WO | WO 2006/088007 A1 | 8/2006 |
| WO | WO 2008/030261 | 3/2008 |
| WO | WO 2008/039703 A2 | 4/2008 |
| WO | WO 2009/094532 | 7/2009 |
| WO | WO 2010/076704 | 7/2010 |
| WO | WO 2011/007346 | 1/2011 |
| WO | WO 2013/042007 | 3/2013 |
| WO | WO 2013/042007 A1 | 3/2013 |
| WO | WO 2013/137753 | 9/2013 |
| WO | WO 2013/137757 | 9/2013 |
| WO | WO 2013/148754 | 10/2013 |
| WO | WO 2013/148901 A1 | 10/2013 |
| WO | WO 2013/172722 A1 | 11/2013 |
| WO | WO 2013/179181 A1 | 12/2013 |
| WO | WO 2014/007659 | 1/2014 |
| WO | WO 2014/111828 | 7/2014 |
| WO | WO 2014/140278 | 9/2014 |
| WO | WO 2014/196875 | 12/2014 |

(56) References Cited

FOREIGN PATENT DOCUMENTS

| WO | WO 2015/033288 | 3/2015 |
| WO | WO 2015/174864 | 11/2015 |
| WO | WO 2016/063172 | 4/2016 |
| WO | WO 2016/079703 A1 | 5/2016 |
| WO | WO 2016/157106 | 10/2016 |
| WO | WO 2017/187390 | 11/2017 |

OTHER PUBLICATIONS

EPO Examination Report; dated Jun. 7, 2018; 7 pages.
International Search Report; PCT/IB2014/064245; dated Feb. 2, 2015; 7 pages.
Written Opinion; PCT/IB2014/064245; dated Feb. 2, 2015; 11 pages.
Australian Examination Report, dated Dec. 10, 2018, 4 pages.
De Luca et al., Noninvasive high frequency oscillatory ventilation; Intensive Care Med (2010); Published Sep. 21, 2010; 7 pages.
De Luca et al., Effect of Amplitude and Inspiratory Time in a Bench Model; Pediatric Pulmonology (2012); Copyright 2012 Wiley Periodicals, Inc.; 7 pages.
DiBlasi_et_al_Effective_gas_exchange_paralyzedJuvenile_rabbits_ Apr. 7, 2010; Pediatric Research; 26 pages.
DeBlasi_et_al_Noninvasive_Respiratory_Support_Junenile_Rabbits_ vol. 67, No. 6, 2010, Pediatric Research; 6 pages.
Caring for Premature Baby (Accessed on Nov. 23, 2019) (Priority Date—Oct. 27, 2014) (Year: 2014).
European Examination Report dated Jun. 12, 2019 for European Application No. EP 16 771 502.8-1122.
European Examination Report dated Jun. 7, 2018 for European Application No. EP 14 841 727.2-1122.
Examination report for Chinese Application No. 201680027864.X dated Nov. 18, 2019, 8 pages.
Examination Report for Japanese Patent Application 2017-551616 dated Mar. 3, 2020.
International Searching Authority, International Search Report in re Int'l Appl. No. PCT/IB/206/051820, dated Jun. 30, 2016.
International Searching Authority, Written Opinion of the International Searching Authority in re Int'l Appl. No. PCT/IB2016/051820, dated Jun. 30, 2016.
Examination Report for Australian Application No. 2019275640 dated Jun. 18, 2020; 5 pages.
Summons to attend oral proceedings for European Application No. 14841727.2 dated Dec. 12, 2019 in 2 pages.
Summary of objections for European Application No. 14841727.2 dated Dec. 12, 2019 in 6 pages.
Examination Report for EP Application No. 16771502.8 dated Nov. 9, 2020; 5 pages.
Brighenti, C. et al., 'Effects of the Ventilator Patient Circuit on the Respiratory Parameter estimates: A Simulation Study', IFMBE Proceedings MEDICON, Modelling and Simulation of Physiological Systems, Jun. 12-15, 2001, Part II, pp. 915-918.
Georgia State University, Ohm's Law-Poiseuille's Law, Hyperphysics, http://hyperphysics.phy-astr-gsu-edu/hbase/electric/watcir2.html, Dec. 6, 2007.
Lim, M. W et al., 'Relationship of inspiratory and expiratory times to upper airway resistance during pulsatile needle cricothyrotomy ventilation with generic delivery circuit', British Journal of Anaesthesia, 2010, V104(1), pp. 98-107.
Meraz, E. et al., 'Modeling Human Respiratory Impedance in Hispanic Asthmatic Children', Proceedings of the 29th Annual International Conference of the IEEE EMBS, Aug. 23-26, 2007, pp. 4251-4254.
Nguyen, T-U. et al., 'A Study of IOS Data Using the aRIC+Ip Model of Respiratory Impedance', 31st Annual International Conference of the IEEE EMBS, Sep. 2-6, 2009, pp. 2875-2878.
Australian Examination Report for Application No. 2016241573 dated Apr. 14, 2020, 5 pages.
International Search Report and Written Opinion for PCT/NZ2015/050062, dated Aug. 7, 2015, in 18 pages.
Great Britain Examination Report for Application No. 1715384.2 dated Mar. 26, 2020, Part 1, 2 pages.
Great Britain Examination Report for Application No. 1715384.2 dated Mar. 26, 2020, Part 2, 2 pages.
Great Britain Examination Report for Application No. 1715384.2 dated Dec. 14, 2020, 2 pages.
Examination Report for JP Application No. 2017-5516616 dated Jan. 3, 2021; 2 pages.
Examination Report for CN Application No. 201680027864 dated Jan. 7, 2021; 9 pages.
International Search Report and Written Opinion for PCT/IB/2017/052457, dated Aug. 15, 2017 in 31 pages.

* cited by examiner

Temperature during natural breathing

Temperature during 20L/min flow

Temperature during 30L/min flow

Temperature during 35L/min flow

Temperature during 40L/min flow

Temperature during 50L/min flow

Graph of Av temp over 0-60L/min flow

Peak inspiratory demand
30L/min

Peak inspiratory demand
30L/min

*Wye-connection for combination of flows*

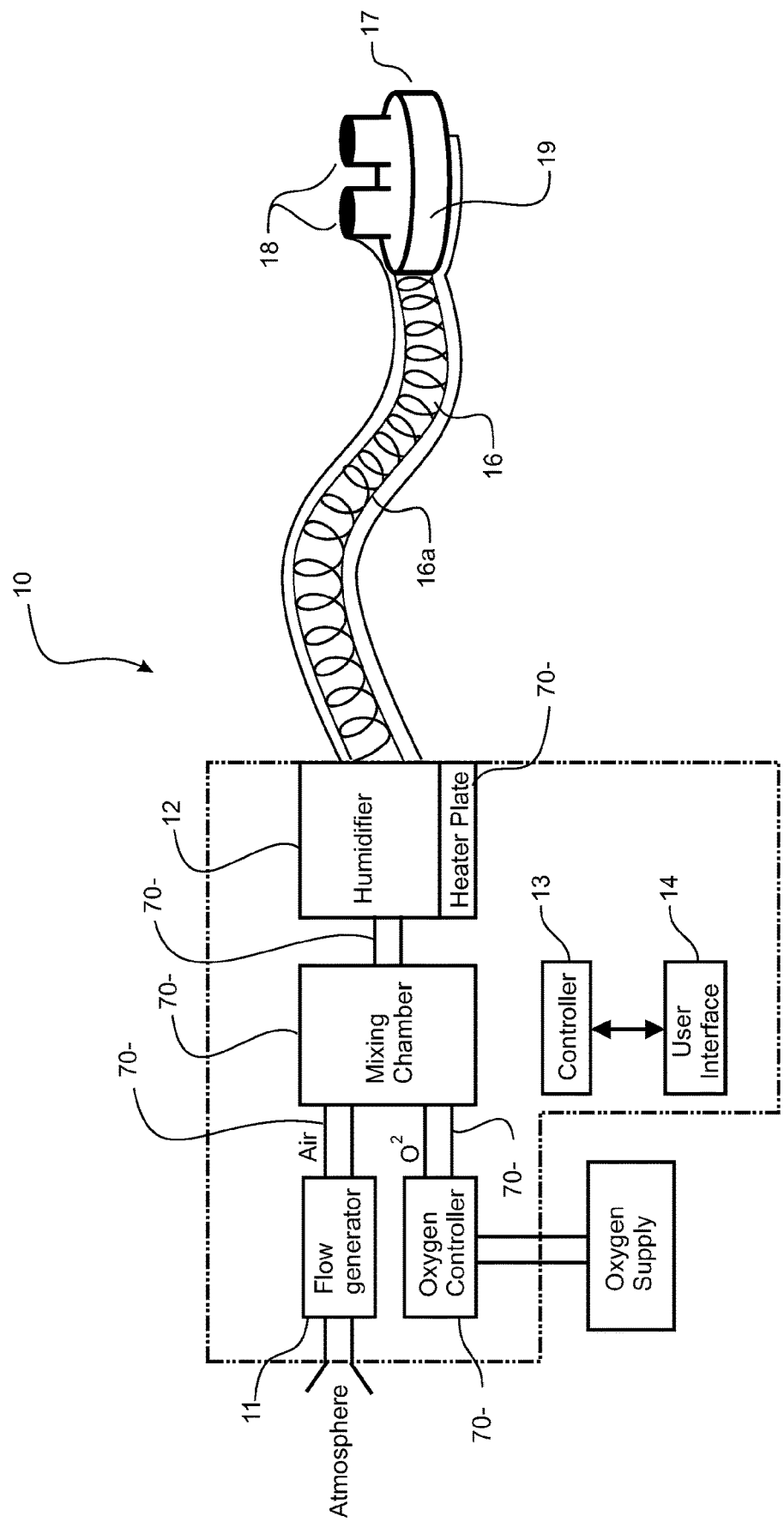

(All trends on)

(Only patient monitoring trend displayed)

(All trends on)     (Only patient monitoring trend displayed)

(Short term pressure displayed)     (long term maximum pressure displayed)

FLOW THERAPY

FIELD OF THE INVENTION

The present invention relates to method and apparatus for providing flow therapy.

SUMMARY OF INVENTION

It is an object of the invention to provide method and apparatus for providing flow therapy.

In some embodiments, methods and apparatus enable prioritisation of therapy types in a manner that balances the trade-offs between comfort, risks of therapy, efficacy of therapy and mutually exclusive therapies.

In some embodiments, methods and apparatus enable the determination/estimation of the respiratory flow rate including inspiratory and/or expiratory flow rate.

In some embodiments, methods and apparatus enable determination of whether inspiratory demand is being met.

In some embodiments, methods and apparatus enable improved gaze exchange through improved CO2 washout and/or increase $O_2$ in a patient's airways using an apparatus for administering flow therapy using oscillation of pressure and/or flow provided to the patient.

In some embodiments, methods and apparatus enable determination of the airway pressure of a patient using a flow therapy apparatus. Desirably, this can be determined by non-invasively determining total delivered patient pressure in a flow therapy apparatus that delivers gas flow to a patient with a non-sealing patient interface.

This information can be utilised in other embodiments.

In some embodiments, methods and apparatus provide an improved flow therapy which can be controlled in a manner to deliver gasflow according to one or more selected prioritised therapy mechanisms.

In some embodiments, methods and apparatus provide for display of various parameters determined by the embodiments described.

One, some or all of the embodiments can be used alone and/or in various combinations to provide flow therapy.
Meeting and/or Determining Inspiratory Demand In another aspect the present invention comprises a patient interface, a circuit, a device, wherein said device has a display to provide feedback to a user regarding an inspiratory demand of a patient, where said inspiratory demand is calculated by said device.

In another aspect the present invention comprises a system to deliver flow comprising: a patient interface, a circuit, a device, wherein said device automatically adjusts a flow rate to meet or exceed an inspiratory demand of a patient, where said inspiratory demand is calculated by said device.

In another aspect the present invention comprises a flow therapy breathing apparatus comprising: a flow generator for generating gasflow for delivery to a patient, a patient interface coupled to or for coupling to the flow generator, either directly or indirectly via e.g. a breathing conduit, for conveying generated gasflow to a patient, a temperature sensor or other device for measuring or otherwise determining the temperature of gasflow, a controller for receiving output indication of the gasflow temperature from the temperature sensor or other device, wherein based on the relationship between the gasflow temperature and a) delivered temperature or related value, and/or b) ambient temperature or related value, the controller is configured to take an action, being do one or more of: determine and/or indicate whether during use the patient is entraining ambient air, determine and/or indicate the inspiratory demand of the patient, determine and/or indicate whether generated gasflow is meeting (including not meeting or exceeding) inspiratory demand of the patient, control the flow generator to: provide sufficient generated gasflow to meet inspiratory demand, or generate less gasflow so as to avoid exceeding inspiratory demand, or generate more gas flow to exceed inspiratory demand (the amount of excess flow could be defined by the user Eg: as an absolute flow rate value, or a percentage greater than inspiratory demand) indicate to a user that there is insufficient, sufficient (or more than sufficient) generated gasflow to meet in inspiratory demand, and/or indicate manual required control of the flow generator to provide generated gasflow (either more or less) to meet inspiratory demand or a flow rate related to inspiratory demand.

Preferably the patient interface is a cannula with nasal prongs.

Preferably the temperature sensor or other device measures or otherwise determines the temperature of gasflow to and from the patient interface.

Preferably the temperature sensor or other device is disposed externally on a nasal prong to measure or otherwise determine the temperature of gasflow external to the patient interface.

Preferably the relationship is whether the gasflow temperature is: a) different to (e.g. less than, greater than or within a range of) the delivered temperature or related value, or b) approaching or within a range of the ambient temperature or related value, and wherein if the gasflow temperature is different to (e.g. less than or greater than or within a range of) the delivered temperature or related value, or approaching or within a range of the ambient temperature or related value, the controller is configured to do one or more of: indicate that there is entrainment of air, indicate the inspiratory demand of the patient, indicate the entrained flow of the patient indicate that inspiratory demand is not being met, indicate a parameter that takes into account the difference between the patient's inspiratory demand and a flow target set by the user, control the flow generator to increase/change the flow rate of gasflow for delivery to the patient, indicate to a user to increase the flow rate of gasflow for delivery to the patient, display current or peak inspiratory demand.

Preferably if the gas flow temperature is not different to the delivered temperature or related value or not approach or within a range of the ambient temperature or related value, the controller is configured to do one or more of: indicate that there is not entrainment of air, indicate to a user that inspiratory demand is met, maintain or decrease the flow rate, indicate to a user that inspiratory demand is exceeded, control the flow generator to decrease or maintain the flow rate of gasflow for delivery to the patient, indicate to a user to decrease or maintain the flow rate of gasflow for delivery to the patient, display current or peak inspiratory demand.

Preferably the gasflow temperature is an instantaneous temperature or an average temperature over time.

In another aspect the present invention comprises a method of operating a flow breathing apparatus comprising: generating gasflow for delivery to a patient, measuring the temperature of gasflow into a patient, and based on the relationship between the gasflow temperature and a) target temperature or related value, and/or) ambient temperature or related value, one or more of: determining and/or indicating whether during use the patient is entraining ambient air, determining and/or indicating the inspiratory demand of the patient, determining and/or indicating whether generated gasflow is meeting (including not meeting or exceeding) inspiratory demand of the patient, generating more gasflow to provide sufficient generated gasflow to meet inspiratory demand, or generating less gasflow to reduce gasflow so as to avoid exceeding inspiratory demand, or increasing to meet a target defined with respect to inspiratory demand, indicating to a user that there is insufficient (or more than sufficient) generated gasflow to meet inspiratory demand, and/or indicating manual required control of the flow breathing apparatus to generate more (or less) gasflow to meet inspiratory demand.

Preferably the relationship is whether the gasflow temperature is: a) different to (e.g. less than, greater than or within a range of) the target temperature or related value, or b) approaching or within a range of the ambient temperature or related value, and wherein if the gasflow temperature is different to (e.g. less than, greater than or within a range of) the target temperature or related value, or approaching or within a range of the ambient temperature or related value, the method comprises one or more of: indicating that there is entrainment of air, indicating the inspiratory demand of the patient, indicating that inspiratory demand is not being met, increasing the flow rate of gasflow for delivery to the patient, indicating to a user to increase the flow rate of gasflow for delivery to the patient.

Preferably if the gasflow temperature is not different to (e.g. less than, greater than or within a range of) the target temperature or related value, or is not approaching or within a range of the ambient temperature or related value, the method comprises one or more of: indicating that there is not entrainment of air, indicating to a user that inspiratory demand is met, maintaining the flow rate, indicating to a user that inspiratory demand is exceeded, controlling the flow generator to decrease or maintain the flow rate of gasflow for delivery to the patient, indicating to a user to decrease or maintain the flow rate of gasflow for delivery to the patient, displaying current or peak inspiratory demand.

In another aspect the present invention comprises a patient interface (for example a cannula) for use with a flow therapy breathing apparatus comprising a temperature sensor or other device for measuring or otherwise determining the temperature of gasflow passing to a patient that uses the interface in conjunction with a flow therapy breathing apparatus, wherein the temperature sensor or other device is adapted to communicate with a controller that determines based on the temperature of gasflow whether a patient is taking entrained ambient air indicating that gasflow provided by flow therapy breathing apparatus is not meeting inspiratory demand.

In another aspect the present invention comprises a flow therapy breathing apparatus comprising: a flow generator for generating gasflow for delivery to a patient, a patient interface coupled to or for coupling to the flow generator, either directly or indirectly via e.g. a breathing conduit, for conveying generated gasflow to a patient, a pressure sensor and/or pressure line for measuring the airway pressure of a patient, a controller for receiving output indicative of the airway pressure from the pressure sensor and/or pressure line, wherein based on the airway pressure, the controller is configured to take an action, being do one or more of: determine and/or indicate whether during use the patient is entraining ambient air, determine and/or indicate the inspiratory demand of the patient, determine and/or indicate whether generated gasflow is meeting (including not meeting or exceeding) inspiratory demand of the patient, control the flow generator to: provide sufficient generated gasflow to meet inspiratory demand, or generate less gasflow so as to avoid exceeding inspiratory demand, indicate to a user that there is insufficient (or more than sufficient) generated gasflow to meet inspiratory demand, and/or indicate manual required control of the flow generator to provide generated gasflow (either more or less) to meet inspiratory demand.

Preferably the patient interface is a cannula with nasal prongs and the pressure sensor and/or pressure line is disposed externally on a nasal prong to measure the airway pressure.

Preferably if the airway pressure is below zero or a threshold, the controller is configured to do one or more of: indicate that there is entrainment of air, indicate the inspiratory demand of the patient, indicate that inspiratory demand is not being met, control the flow generator to increase the flow rate of gasflow for delivery to the patient, indicate to a user to increase the flow rate of gasflow for delivery to the patient, display current or peak inspiratory demand.

Preferably if the airway pressure is equal to or above zero or a threshold, the controller is configured to do one or more of: indicate that there is not entrainment of air, indicate to a user that inspiratory demand is met, maintain the flow rate, indicate to a user that inspiratory demand is exceeded, control the flow generator to decrease or maintain the flow rate of gasflow for delivery to the patient, indicate to a user to decrease or maintain the flow rate of gasflow for delivery to the patient, display current or peak inspiratory demand.

Preferably the airway pressure is an instantaneous pressure or an average pressure over time.

In another aspect the present invention comprises a method of operating a flow breathing apparatus comprising: generating gasflow for delivery to a patient, measuring the airway pressure a patient, and based on the airway pressure one or more of: determining and/or indicating whether during use the patient is entraining ambient air, determining and/or indicating the inspiratory demand of the patient, determining and/or indicating whether generated gasflow is meeting (including not meeting or exceeding) inspiratory demand of the patient, generating more gasflow to provide sufficient generated gasflow to meet inspiratory demand, or generating less gasflow to reduce gasflow so as to avoid exceeding inspiratory demand indicating to a user that there is insufficient (or more than sufficient) generated gasflow to meet inspiratory demand, and/or indicating manual required control of the flow breathing apparatus to generate more (or less) gasflow to meet inspiratory demand.

Preferably the method comprises one or more of: indicating that there is entrainment of air, indicating the inspiratory demand of the patient, indicating that inspiratory demand is not being met, increasing the flow rate of gasflow for delivery to the patient, indicating to a user to increase the flow rate of gasflow for delivery to the patient.

In another aspect the present invention comprises a patient interface (for example a cannula) for use with a flow therapy breathing apparatus comprising a pressure sensor and/or pressure line for measuring the airway pressure of a patient that uses the interface in conjunction with a flow therapy breathing apparatus, wherein the pressure sensor and/or pressure line is adapted to communicate with a controller that determines based on the airway pressure whether a patient is taking entrained ambient air indicating that gasflow provided by flow therapy breathing apparatus is not meeting inspiratory demand.

In another aspect the present invention comprises a flow therapy breathing apparatus comprising: a flow generator for generating gasflow for delivery to a patient, a patient interface coupled to or for coupling to the flow generator, either directly or indirectly via e.g. a breathing conduit, for conveying generated gasflow to a patient, a pressure sensor to measure system back pressure (for example disposed in the patient interface), a controller for receiving output indicative of the system back pressure from the pressure sensor, wherein based on the system pressure, the controller is configured to take an action, being do one or more of: determine and/or indicate whether during use the patient is entraining ambient air, determine and/or indicate the inspiratory demand of the patient, determine and/or indicate whether generated gasflow is meeting (including not meeting or exceeding) inspiratory demand of the patient, control the flow generator to: provide sufficient generated gasflow to meet inspiratory demand, or generate less gasflow so as to avoid exceeding inspiratory demand, indicate to a user that there is insufficient (or more than sufficient) generated gasflow to meet inspiratory demand, and/or indicate manual required control of the flow generator to provide generated gasflow (either more or less) to meet inspiratory demand.

Preferably the patient interface is a cannula with a manifold and the pressure sensor is disposed in the manifold to measure the system back pressure.

Preferably if the system back pressure is below a characteristic pressure, the controller is configured to do one or more of: indicate that there is entrainment of air, indicate the inspiratory demand of the patient, indicate that inspiratory demand is not being met, control the flow generator to increase the flow rate of gasflow for delivery to the patient, indicate to a user to increase the flow rate of gasflow for delivery to the patient, display current or peak inspiratory demand.

Preferably if the system back pressure is above a characteristic pressure, the controller is configured to do one or more of indicate that there is not entrainment of air, indicate to a user that inspiratory demand is met or exceeded, maintain the flow rate, indicate to a user that inspiratory demand is exceeded, control the flow generator to decrease or maintain the flow rate of gasflow for delivery to the patient, indicate to a user to decrease or maintain the flow rate of gasflow for delivery to the patient, display current or peak inspiratory demand.

Preferably the system back pressure is an instantaneous pressure or an average pressure over time.

In another aspect the present invention comprises a method of operating a flow breathing apparatus comprising: generating gasflow for delivery to a patient, measuring the system back pressure, and based on the system back pressure one or more of: determining and/or indicating whether during use the patient is entraining ambient air, determining and/or indicating the inspiratory demand of the patient, determining and/or indicating whether generated gasflow is meeting (including not meeting or exceeding) inspiratory demand of the patient, generating more gasflow to provide sufficient generated gasflow to meet inspiratory demand, or generating less gasflow to reduce gasflow so as to avoid exceeding inspiratory demand, indicating to a user that there is insufficient (or more than sufficient) generated gasflow to meet inspiratory demand, and/or indicating manual required control of the flow breathing apparatus to generate more (or less) gasflow to meet inspiratory demand.

Preferably if the system back pressure is below a characteristic pressure, the method comprises one or more of: indicating that there is entrainment of air, indicating the inspiratory demand of the patient, indicating that inspiratory demand is not being met, increasing the flow rate of gasflow for delivery to the patient, indicating to a user to increase the flow rate of gasflow for delivery to the patient.

In another aspect the present invention comprises a patient interface (for example a cannula) for use with a flow therapy breathing apparatus comprising a pressure sensor for measuring the system back pressure when a patient uses the interface in conjunction with a flow therapy breathing apparatus, wherein the pressure sensor is adapted to communicate with a controller that determines based on the system back pressure whether a patient is taking entrained ambient air indicating that gasflow provided by flow therapy breathing apparatus is not meeting inspiratory demand.

Determining Respiratory Flow

In another aspect the present invention comprises a method of estimating respiratory flow rate of a patient being administered flow therapy, comprising: optionally administering a gas flow rate to the patient using a flow therapy apparatus with a patient interface, measuring a pressure parameter indicative of or being the pressure at a location in the apparatus, determining a patient pressure in the apparatus based on the pressure parameter and a characteristic pressure for the gas flow rate, from the patient pressure, determining a nasal flow rate using a relationship, the nasal flow rate indicating the difference or combination of the gas flow rate and the respiratory flow rate, and optionally determining respiratory flow rate, and optionally displaying a numerical and/or graphical representation of a periodic or continuous real-time and/or historical nasal flow rate and/or respiratory flow rate.

Preferably the respiratory flow rate is the inspiratory flow rate (demand)

Preferably the pressure parameter is indicative of or is the minimum pressure in the patient interface and the inspiratory flow rate is the peak inspiratory flow rate and/or the characteristic pressure is the characteristic pressure of the patient interface.

Preferably the respiratory flow rate is the expiratory flow rate.

Preferably the pressure parameter is indicative of or is the maximum pressure in the patient interface and the expiratory flow rate is the peak expiratory flow rate and/or the characteristic pressure is the characteristic pressure of the patient interface.

Preferably the pressure parameter is indicative of the minimum pressure in the patient interface for a particular breath cycle, or alternatively is indicative of a representative minimum pressure over a plurality of breath cycles.

Preferably the relationship is a look up table, graph or mathematical function that relates patient pressure to the nasal flow rate from peak respiratory flow rate.

Preferably the patient pressure is the difference between or the combination of the pressure at the patient interface and the patient interface characteristic pressure for the flow rate being administered, and optionally can be calculated using $$P_{pmin} = M_{pmin} - C_p$$

where $P_{pmin}$=(minimum) patient pressure
$C_p$=characteristic pressure
$M_{pmin}$=minimum manifold pressure.

In another aspect the present invention comprises a method of estimating peak respiratory flow rate of a patient being administered flow therapy, comprising: optionally administering a gas flow rate to the patient, measuring a pressure parameter indicative of or being the actual pressure in a patient interface, determining a patient pressure in the patient interface based on the pressure parameter and a patient interface characteristic pressure for the gas flow rate, from the patient pressure, determining a peak nasal flow rate using a relationship, the peak nasal flow rate indicating the difference between or combination of the gas flow rate and the peak respiratory flow rate, and optionally: determining respiratory flow rate, and displaying a numerical and/or graphical representation of a periodic or continuous real-time and/or historical nasal flow rate and/or respiratory flow rate.

In another aspect the present invention comprises an apparatus configured for estimating respiratory flow rate of a patient being administered flow therapy, comprising: optionally a flow generator for administering a gas flow rate to the patient through a patient interface, a sensor or connection for a sensor for measuring a pressure parameter indicative of or being the pressure at a location in the apparatus, a controller for: determining a patient pressure in the apparatus based on the pressure parameter, and a characteristic pressure for the gas flow rate, and from the patient pressure, determining a nasal flow rate using a relationship, the nasal flow rate indicating the difference between or combination of the gas flow rate and the respiratory flow rate.

Preferably the pressure parameter is indicative of or is the maximum or minimum pressure in the patient interface and the respiratory flow rate is the peak respiratory flow rate and/or the characteristic pressure is the characteristic pressure of the patient interface.

Preferably the pressure parameter is indicative of the maximum or minimum pressure of in the patient interface for a particular breath cycle, or alternatively is indicative of a representative maximum or minimum pressure over a plurality of breath cycles.

Preferably the apparatus comprises an output for displaying a peak respiratory flow rate determined by the controller.

Preferably the relationship is a look up table, graph or mathematical function that relates patient pressure to the nasal flow rate offset from peak respiratory flow rate.

Preferably the patient pressure is the difference between or combination of the pressure at the patient interface and the patient interface characteristic pressure for the flow rate being administered, and optionally can be calculated using:

$$P_{pmin} = M_{pmin} - C_p$$

where
$P_{pmin}$; (minimum) patient pressure
$C_p$=characteristic pressure
$M_{pmin}$=minimum manifold pressure In another aspect the present invention comprises an apparatus configured for estimating peak respiratory flow rate of a patient being administered flow therapy, comprising: optionally a flow generator for administering a gas flow rate to the patient through a patient interface, a sensor or a connection for a sensor for measuring a pressure parameter indicative of or being the pressure in a patient interface, a controller for: determining a patient pressure in the patient interface based on the pressure parameter, and a patient interface characteristic pressure for the gas flow rate, and from the patient pressure, determining a peak nasal flow rate using a relationship, the peak nasal flow rate indicating the difference between or combination of the gas flow rate and the peak respiratory flow rate.

In another aspect the present invention comprises a method of estimating respiratory flow rate of a patient being administered flow therapy, comprising: optionally administering a gas flow rate to the patient using flow therapy apparatus with a patient interface, measuring a pressure parameter indicative of or being the pressure at a location in the apparatus, determining a patient pressure in the apparatus based on the pressure parameter and a characteristic pressure for the gas flow rate.

Preferably the patient pressure is indicative of respiratory flow rate, and optionally determining a parameter from patient pressure that is or is indicative of respiratory flow rate.

Preferably the pressure at a location in the apparatus is a pressure in the patient interface and the characteristic pressure is the characteristic pressure of the patient interface.

Preferably the pressure parameter is indicative of the maximum or minimum pressure in the patient interface and the respiratory flow rate is the peak respiratory flow rate.

Preferably the pressure parameter is indicative of the maximum or minimum pressure at the location in the apparatus and the respiratory flow rate is the peak respiratory flow rate.

In another aspect the present invention comprises an apparatus configured for estimating respiratory flow rate of a patient being administered flow therapy, comprising: optionally a flow generator for administering a gas flow rate to the patient through a patient interface, a sensor or connection for a sensor for measuring a pressure parameter indicative of or being the pressure at a location in the apparatus, a controller for: determining a patient pressure in the apparatus based on the pressure parameter, and a characteristic pressure for the gas flow rate.

Preferably the patient pressure is indicative of respiratory flow rate, and the controller optionally determines a parameter from patient pressure that is or is indicative of respiratory flow rate.

Preferably the pressure at a location in the apparatus is a pressure in the patient interface and the characteristic pressure is the characteristic pressure of the patient interface.

Preferably the pressure parameter is indicative of the maximum or minimum pressure in the patient interface and the respiratory flow rate is the peak respiratory flow rate.

Preferably the pressure parameter is indicative of the maximum or minimum pressure at the location in the apparatus and the respiratory flow rate is the peak respiratory flow rate.

In another aspect the present invention comprises a method of estimating respiratory flow rate of a patient being administered flow therapy, comprising: optionally administering a gas flow rate to the patient using a flow therapy apparatus with a patient interface, measuring a pressure parameter indicative of or being the pressure in a patient interface, determining a patient pressure in the patient interface based on the pressure parameter and a patient interface characteristic pressure for the gas flow rate, from the patient pressure, determining a nasal flow rate using a relationship, the nasal flow rate indicating the difference between or combination of the gas flow rate and the respiratory flow rate.

In another aspect the present invention comprises an apparatus configured for estimating respiratory flow rate of a patient being administered flow therapy, comprising: optionally a flow generator for administering a gas flow rate to the patient through a patient interface, a sensor or connection for a sensor for measuring a pressure parameter indicative of or being the pressure in a patient interface, a controller for: determining a patient pressure in the patient interface based on the pressure parameter, and a patient interface characteristic pressure for the gas flow rate, and from the patient pressure, determining a nasal flow rate using a relationship, the nasal flow rate indicating the difference between or combination of the gas flow rate and the inspiratory respiratory flow rate.

In another aspect the present invention comprises method of estimating a parameter indicative of respiratory flow of a patient being administered flow therapy, comprising: optionally administering a gas at a flow rate to the patient using a flow therapy apparatus with a patient interface, determining a terminal pressure in, at or proximate the outlet of the patient interface or in, at or proximate the nares of the patient, determining nasal RTF, determining a nasal flow parameter being or indicative of nasal flow based on the pressure and a nasal RTF, and optionally outputting the nasal flow parameter or parameter derived therefrom.

Preferably the respiratory flow rate is the inspiratory flow rate (demand)

Preferably the respiratory flow rate is the expiratory flow rate.

Preferably the terminal pressure is determined using a pressure determined at a location in the apparatus and a characteristic pressure of the apparatus for the location.

Preferably the inspiratory flow rate is peak inspiratory flow rate and the terminal pressure is a minimum pressure during a breath cycle.

Preferably the expiratory flow rate is peak expiratory flow rate and the terminal pressure is a maximum pressure during a breath cycle.

Preferably further comprising measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{nasal} = \sqrt{\frac{|P_{(t)} - P_{char}|}{R_{nasal}}} \qquad (10')$$

Where $Q_{nasal}$ is the nasal flow at time t
$P_{(t)}$ is the system pressure at time t
$P_{char}$ is the characteristic pressure at the delivered gas flow rate
$R_{nasal}$ is the nasal resistance to flow.
Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ (or more generally $Q_{nasal}$) is the flow at the location
$P_{trans}$ is the pressure at the location during breath transition
where the second equation is used for laminar flow and the first for turbulent flow.

In another aspect the present invention comprises a method of estimating a parameter indicative of respiratory flow of a patient being administered flow therapy, comprising: optionally administering a gas at a flow rate to the patient using a flow therapy apparatus with a patient interface, determining a pressure at a location in the apparatus, and determining a nasal flow parameter being or indicative of nasal flow based on the pressure, characteristic pressure of the apparatus for the location and a nasal RTF, and optionally outputting the leakage parameter or parameter derived therefrom.

In another aspect the present invention comprises an apparatus configured for estimating respiratory flow of a patient being administered flow therapy, comprising: optionally a flow generator for administering a gas flow rate to the patient through a patient interface, a sensor or connection for a sensor for measuring a pressure parameter indicative of or being the terminal pressure, in, at or proximate the outlet of the patient interface or in, at or proximate the nares of the patient, or from which terminal pressure can be determined, a controller for: determining a terminal pressure based on the pressure parameter, determining a nasal RTF, determining a nasal flow parameter being or indicative of nasal flow based on the terminal pressure and a nasal RTF, and optionally outputting the nasal flow parameter or parameter derived therefrom.

Preferably the terminal pressure is determined using a pressure parameter determined at a location in the apparatus and a characteristic pressure of the apparatus for the location.

Preferably the respiratory flow rate is peak inspiratory flow rate and the terminal pressure is a minimum pressure during a breath cycle.

Preferably further comprising a sensor for measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{nasal} = \sqrt{\frac{|P_{(t)} - P_{char}|}{R_{nasal}}}$$

Where $Q_{nasal}$ is the nasal flow at time t
$P_{(t)}$ is the system pressure at time t
$P_{char}$ is the characteristic pressure at the delivered gas flow rate
$R_{nasal}$ is the nasal resistance to flow.
Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ (more generally $Q_{nasal}$) is the flow at the location
$P_{trans}$ is the pressure at the location during breath transition where the second equation is used for laminar flow and the first for turbulent flow.

In another aspect the present invention comprises an apparatus configured for estimating respiratory flow rate of a patient being administered flow therapy, comprising: optionally a flow generator for administering a gas flow rate to the patient through a patient interface, a sensor or connection for a sensor for measuring a pressure at a location in the apparatus, a controller for: determining a nasal RTF, determining a nasal flow parameter being or indicative of nasal flow based on the pressure, characteristic pressure of the apparatus for the location and a nasal RTF, and optionally outputting the nasal flow parameter or parameter derived therefrom.

Determining Expiratory Flow

In another aspect the present invention comprises a method of estimating expiratory flow rate of a patient being administered flow therapy, comprising administering a gas flow rate to the patient using a flow therapy apparatus with a patient interface, measuring a pressure parameter indicative of or being the pressure at a location in the apparatus, determining a patient pressure in the apparatus based on the pressure parameter and a characteristic pressure for the gas flow rate, from the patient pressure, determining a nasal flow rate using a relationship, the nasal flow rate indicating the combination of the gas flow rate and the expiratory flow rate.

Preferably the pressure parameter is indicative of or is the maximum pressure in the patient interface and the expiratory flow rate is the peak expiratory flow rate and/or the characteristic pressure is the characteristic pressure of the patient interface.

Preferably the pressure parameter is indicative of the maximum pressure in the patient interface for a particular breath cycle, or alternatively is indicative of a representative maximum pressure over a plurality of breath cycles.

Preferably the method comprises determining and optionally displaying the expiratory flow rate or peak expiratory flow rate.

Preferably, based on the expiratory flow rate, peak expiratory flow rate or some indicator thereof, one or more of:
- automatically or manually adjusting the gas flow rate based on the expiratory flow rate or peak expiratory flow rate,
- automatically or manually adjusting the gas flow rate to a level relative to the expiratory flow rate or peak expiratory flow rate,
- using expiratory flow rate or peak expiratory flow rate for diagnostics, comprising for example determining high metabolic requirement, or determining an indicator for work of breathing,
- providing alarms, for example: detecting and alarming when the expiratory flow rate exceeds a certain pre-defined limit, or when the expiratory flow rate increases faster than a pre-defined rate,
- providing an alarm, and/or automatically increasing the delivered flow rate and/or oxygen,
- providing a treatment recommendation to the user, or providing a recommendation that the patient be escalated to a higher level of respiratory support, Preferably the relationship is a look up table, graph or mathematical function that relates patient pressure to the nasal flow rate from peak expiratory flow rate.

Preferably the patient pressure is the difference of the pressure at the patient interface and the patient interface characteristic pressure for the flow rate being administered, and optionally can be calculated using $$P_{pmax} = M_{pmax} - C_p$$

where
$P_{pmax}$=(max) patient pressure
$C_p$=characteristic pressure
$M_{pmax}$=maximum manifold pressure.

In another aspect the present invention comprises a method of estimating peak expiratory flow rate of a patient being administered flow therapy, comprising administering a gas flow rate to the patient, measuring a pressure parameter indicative of or being the actual pressure in a patient interface, determining a patient pressure in the patient interface based on the pressure parameter and a patient interface characteristic pressure for the gas flow rate, from the patient pressure, determining a nasal flow rate using a relationship, the nasal flow rate indicating the combination of the gas flow rate and the peak expiratory flow rate.

In another aspect the present invention comprises a flow therapy apparatus configured for estimating expiratory flow rate of a patient being administered flow therapy, comprising: a flow generator for administering a gas flow rate to the patient through a patient interface, a sensor for measuring a pressure parameter indicative of or being the pressure at a location in the apparatus, a controller for: determining a patient pressure in the apparatus based on the pressure parameter, and a characteristic pressure for the gas flow rate, and from the patient pressure, determining a nasal flow rate using a relationship, the nasal flow rate indicating the combination of the gas flow rate and the expiratory flow rate.

Preferably the pressure parameter is indicative of or is the maximum pressure in the patient interface and the expiratory flow rate is the peak expiratory flow rate and/or the characteristic pressure is the characteristic pressure of the patient interface.

Preferably the pressure parameter is indicative of the maximum pressure of in the patient interface for a particular breath cycle, or alternatively is indicative of a representative maximum pressure over a plurality of breath cycles.

Preferably comprising an output for displaying a peak expiratory flow rate determined by the controller.

Preferably the relationship is a look up table, graph or mathematical function that relates patient pressure to the flow rate offset from peak expiratory flow.

Preferably the patient pressure is the difference between the pressure at the patient interface and the patient interface characteristic pressure for the flow rate being administered, and optionally can be calculated using $$P_{pmax} = M_{pmax} - C_p$$

where
$P_{pmax}$=(max) patient pressure
$C_p$=characteristic pressure
$M_{pmax}$=max manifold pressure In another aspect the present invention comprises a flow therapy apparatus configured for estimating peak expiratory flow rate of a patient being administered flow therapy, comprising: a flow generator for administering a gas flow rate to the patient through a patient interface, a sensor for measuring a pressure parameter indicative of or being the pressure in a patient interface, a controller for: determining a patient pressure in the patient interface based on the pressure parameter, and a patient interface characteristic pressure for the gas flow rate, and from the patient pressure, determining a peak nasal flow rate using a relationship, the peak nasal flow rate indicating the combination of the gas flow rate and the peak expiratory flow rate.

In another aspect the present invention comprises a method of estimating expiratory flow rate of a patient being administered flow therapy, comprising administering a gas flow rate to the patient using flow therapy apparatus with a patient interface, measuring a pressure parameter indicative of or being the pressure at a location in the apparatus, determining a patient pressure in the apparatus based on the pressure parameter and a characteristic pressure for the gas flow rate.

Preferably the patient pressure is indicative of expiratory flow rate, and optionally determining a parameter from patient pressure that is or is indicative of expiratory flow rate.

Preferably the pressure at a location in the apparatus is a pressure in the patient interface and the characteristic pressure is the characteristic pressure of the patient interface.

Preferably the pressure parameter is indicative of the maximum pressure in the patient interface and the expiratory flow rate is the peak expiratory flow rate.

Preferably the pressure parameter is indicative of the maximum pressure at the location in the apparatus and the expiratory flow rate is the peak expiratory flow rate.

In another aspect the present invention comprises a flow therapy apparatus configured for estimating expiratory flow rate of a patient being administered flow therapy, comprising: a flow generator for administering a gas flow rate to the patient through a patient interface, a sensor for measuring a pressure parameter indicative of or being the pressure at a location in the apparatus, a controller for: determining a patient pressure in the apparatus based on the pressure parameter, and a characteristic pressure for the gas flow rate.

Preferably the patient pressure is indicative of expiratory flow rate, and the controller optionally determines a parameter from patient pressure that is or is indicative of expiratory flow rate.

Preferably the pressure at a location in the apparatus is a pressure in the patient interface and the characteristic pressure is the characteristic pressure of the patient interface.

Preferably the pressure parameter is indicative of the maximum pressure in the patient interface and the expiratory flow rate is the peak expiratory flow rate.

Preferably the pressure parameter is indicative of the maximum pressure at the location in the apparatus and the expiratory flow rate is the peak expiratory flow rate.

In another aspect the present invention comprises method of estimating expiratory flow rate of a patient being administered flow therapy, comprising administering a gas flow rate to the patient using a flow therapy apparatus with a patient interface, measuring a pressure parameter indicative of or being the pressure in a patient interface, determining a patient pressure in the patient interface based on the pressure parameter and a patient interface characteristic pressure for the gas flow rate, from the patient pressure, determining a nasal flow rate using a relationship, the nasal flow rate indicating the combination of the gas flow rate and the expiratory flow rate.

In another aspect the present invention comprises flow therapy apparatus configured for estimating expiratory flow rate of a patient being administered flow therapy, comprising: a flow generator for administering a gas flow rate to the patient through a patient interface, a sensor for measuring a pressure parameter indicative of or being the pressure in a patient interface, a controller for determining a patient pressure in the patient interface based on the pressure parameter, and a patient interface characteristic pressure for the gas flow rate, and from the patient pressure, determining a nasal flow rate using a relationship, the nasal flow rate indicating the combination of the gas flow rate and the expiratory flow rate.

In another aspect the present invention comprises a method of estimating a parameter indicative of expiratory flow rate of a patient being administered flow therapy, comprising administering a gas at a flow rate to the patient using a flow therapy apparatus with a patient interface, determining a terminal pressure in, at or proximate the outlet of the patient interface or in, at or proximate the nares of the patient, determining nasal RTF, determining a nasal flow parameter being or indicative of nasal flow based on the pressure and a nasal RTF, and optionally outputting the nasal flow parameter or parameter derived therefrom and/or altering the flow therapy based on the nasal flow or parameter derived therefrom.

Preferably the terminal pressure is determined using a pressure determined at a location in the apparatus and a characteristic pressure of the apparatus for the location.

Preferably the expiratory flow rate is peak expiratory flow rate and the terminal pressure is a maximum pressure during a breath cycle.

Preferably further comprising measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{offset} = \sqrt{\frac{|P_{(t)} - P_{char}|}{R_{nasal}}}$$

Wherein $Q_{offset}$ (or more generally $Q_{nasal}$) is the nasal flow
P(t) is the pressure at the location at time t
$P_{char}$ is the characteristic pressure due to resistance to flow of the apparatus for the location
$R_{nasal}$ is the resistance to flow due to nasal resistance
Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ (or more generally $Q_{nasal}$) is the flow at the location
$P_{trans}$ is the pressure at the location during breath transition
where the second equation is used for laminar flow and the first for turbulent flow.

In another aspect the present invention comprises a method of estimating a parameter indicative of expiratory flow (rate) of a patient being administered flow therapy, comprising: administering a gas at a flow rate to the patient using a flow therapy apparatus with a patient interface, determining a pressure at a location in the apparatus, and determining a nasal flow parameter being or indicative of nasal flow based on the pressure, characteristic pressure of the apparatus for the location and a nasal RTF, and optionally outputting the leakage parameter or parameter derived therefrom and/or altering the flow therapy based on the leakage flow or parameter derived therefrom.

In another aspect the present invention comprises a flow therapy apparatus configured for estimating expiratory flow (rate) of a patient being administered flow therapy, comprising: a flow generator for administering a gas flow rate to the patient through a patient interface, a sensor for measuring a pressure parameter indicative of or being the terminal pressure, in, at or proximate the outlet of the patient interface or in, at or proximate the nares of the patient, or form which terminal pressure can be determined, a controller for: determining a terminal pressure based on the pressure parameter, determining a nasal RTF, determining a nasal flow parameter being or indicative of nasal flow based on the terminal pressure and a nasal RTF, and optionally outputting the nasal flow parameter or parameter derived therefrom and/or altering the flow therapy based on the nasal flow or parameter derived therefrom.

Preferably the terminal pressure is determined using a pressure parameter determined at a location in the apparatus and a characteristic pressure of the apparatus for the location.

Preferably the expiratory flow rate is peak expiratory flow rate and the terminal pressure is a maximum pressure during a breath cycle.

Preferably further comprising a sensor for measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{offset} = \sqrt{\frac{|P_{(t)} - P_{char}|}{R_{nasal}}}$$

Wherein $Q_{offset}$ (or more generally $Q_{nasal}$) is the nasal flow
P(t) is the pressure at the location at time t
$P_{char}$ is the characteristic pressure due to resistance to flow of the apparatus for the location
$R_{nasal}$ is the resistance to flow due to nasal resistance
Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ (or more generally $Q_{nasal}$) is the flow a the location
$P_{trans}$ is the pressure at the location during breath transition
where the second equation is used for laminar flow and the first for turbulent flow.

In another aspect the present invention comprises a flow therapy apparatus configured for estimating expiratory flow rate of a patient being administered flow therapy, comprising: a flow generator for administering a gas flow rate to the patient through a patient interface, a sensor for measuring a pressure at a location in the apparatus, a controller for: determining a nasal RTF, determining a nasal flow parameter being or indicative of nasal flow based on the pressure, characteristic pressure of the apparatus for the location and a nasal RTF, and optionally outputting the nasal flow parameter or parameter derived therefrom and/or altering the flow therapy based on the nasal flow or parameter derived therefrom.

Determining Inspiratory Flow

In another aspect the present invention comprises a method of estimating inspiratory demand of a patient being administered flow therapy, comprising administering a gas flow rate to the patient using a flow therapy apparatus with a patient interface, measuring a pressure parameter indicative of or being the pressure at a location in the apparatus, determining a patient pressure in the apparatus based on the pressure parameter and a characteristic pressure for the gas flow rate, from the patient pressure, determining an inspiratory demand flow rate offset using a relationship, the inspiratory demand flow rate offset indicating the difference between the gas flow rate and the inspiratory demand.

Preferably the pressure parameter is indicative of or is the minimum pressure in the patient interface and the inspiratory demand is the peak inspiratory demand and/or the characteristic pressure is the characteristic pressure of the patient interface.

Preferably the pressure parameter is indicative of the minimum pressure in the patient interface for a particular breath cycle, or alternatively is indicative of a representative minimum pressure over a plurality of breath cycles.

Preferably comprising determining and optionally displaying the inspiratory demand or peak inspiratory demand.

Preferably comprising, based on the inspiratory flow, peak inspiratory flow or some indicator thereof, one or more of:
automatically or manually adjusting the gas flow rate to meet the inspiratory demand or peak inspiratory demand,
automatically or manually adjusting the gas flow rate to a level relative to the inspiratory demand or peak inspiratory demand,
using inspiratory demand or peak inspiratory demand for diagnostics, comprising for example determining high metabolic requirement, or determining an indicator for work of breathing, providing alarms, for example: detecting and alarming when the inspiratory demand exceeds
a certain pre-defined limit, or when the inspiratory demand increases faster than a pre-defined rate, providing an alarm, and/or automatically increasing the delivered flow rate and/or oxygen, providing a treatment recommendation to the user, or providing a recommendation that the patient be escalated to a higher level of respiratory support, determining the patient's weaning process, where a decreasing inspiratory demand could indicate a decreasing metabolic requirement and optionally automatically reducing the delivered flow rate and/or oxygen and/or or providing a recommendation to the user.

Preferably the relationship is a look up table, graph or mathematical function that relates patient pressure to the flow rate offset from peak inspiratory demand.

Preferably the patient pressure is the difference between the pressure at the patient interface and the patient interface characteristic pressure for the flow rate being administered, and optionally can be calculated using $$P_{pmin} = M_{pmin} - C_p$$

where
$P_{pmin}$ (minimum) patient pressure
$C_p$=characteristic pressure
$M_{pmin}$=minimum manifold pressure.

In another aspect the present invention comprises method of estimating peak inspiratory demand of a patient being administered flow therapy, comprising administering a gas flow rate to the patient, measuring a pressure parameter indicative of or being the actual pressure in a patient interface, determining a patient pressure in the patient interface based on the pressure parameter and a patient interface characteristic pressure for the gas flow rate, from the patient pressure, determining a peak inspiratory demand flow rate offset using a relationship, the peak inspiratory demand flow rate offset indicating the difference between the gas flow rate and the peak inspiratory demand.

In another aspect the present invention comprises a flow therapy apparatus configured for estimating inspiratory demand of a patient being administered flow therapy, comprising: a flow generator for administering a gas flow rate to the patient through a patient interface, a sensor for measuring a pressure parameter indicative of or being the pressure at a location in the apparatus, a controller for: determining a patient pressure in the apparatus based on the pressure parameter, and a characteristic pressure for the gas flow rate, and from the patient pressure, determining an inspiratory demand flow rate offset using a relationship, the inspiratory demand flow rate offset indicating the difference between the gas flow rate and the inspiratory demand.

Preferably the pressure parameter is indicative of or is the minimum pressure in the patient interface and the inspiratory demand is the peak inspiratory demand and/or the characteristic pressure is the characteristic pressure of the patient interface.

Preferably the pressure parameter is indicative of the minimum pressure of in the patient interface for a particular breath cycle, or alternatively is indicative of a representative minimum pressure over a plurality of breath cycles.

Preferably comprising an output for displaying a peak inspiratory demand determined by the controller.

Preferably the relationship is a look up table, graph or mathematical function that relates patient pressure to the flow rate offset from peak inspiratory demand.

Preferably the patient pressure is the difference between the pressure at the patient interface and the patient interface characteristic pressure for the flow rate being administered, and optionally can be calculated using $$P_{pmin} = M_{pmin} - C_p$$

where
$P_{pmin}$ (minimum) patient pressure
$C_p$=characteristic pressure
$M_{pmin}$=minimum manifold pressure In another aspect the present invention comprises a flow therapy apparatus configured for estimating peak inspiratory demand of a patient being administered flow therapy, comprising: a flow generator for administering a gas flow rate to the patient through a patient interface, a sensor for measuring a pressure parameter indicative of or being the pressure in a patient interface, a controller for: determining a patient pressure in the patient interface based on the pressure parameter, and a patient interface characteristic pressure for the gas flow rate, and from the patient pressure, determining a peak inspiratory demand flow rate offset using a relationship, the peak inspiratory demand flow rate offset indicating the difference between the gas flow rate and the peak inspiratory demand.

In another aspect the present invention comprises a method of estimating inspiratory demand of a patient being administered flow therapy, comprising:
  administering a gas flow rate to the patient using flow therapy apparatus with a patient interface,
  measuring a pressure parameter indicative of or being the pressure at a location in the apparatus,
  determining a patient pressure in the apparatus based on the pressure parameter and a characteristic pressure for the gas flow rate.

Preferably the patient pressure is indicative of inspiratory demand, and optionally determining a parameter from patient pressure that is or is indicative of inspiratory demand.

Preferably the pressure at a location in the apparatus is a pressure in the patient interface and the characteristic pressure is the characteristic pressure of the patient interface.

Preferably the pressure parameter is indicative of the minimum pressure in the patient interface and the inspiratory demand is the peak inspiratory demand.

Preferably the pressure parameter is indicative of the minimum pressure at the location in the apparatus and the inspiratory demand is the peak inspiratory demand.

In another aspect the present invention comprises a flow therapy apparatus configured for estimating inspiratory demand of a patient being administered flow therapy, comprising:
  a flow generator for administering a gas flow rate to the patient through a patient interface,
  a sensor for measuring a pressure parameter indicative of or being the pressure at a location in the apparatus,
  a controller for:
    determining a patient pressure in the apparatus based on the pressure parameter, and a characteristic pressure for the gas flow rate.

Preferably the patient pressure is indicative of inspiratory demand, and the controller optionally determines a parameter from patient pressure that is or is indicative of inspiratory demand.

Preferably the pressure at a location in the apparatus is a pressure in the patient interface and the characteristic pressure is the characteristic pressure of the patient interface.

Preferably the pressure parameter is indicative of the minimum pressure in the patient interface and the inspiratory demand is the peak inspiratory demand.

Preferably the pressure parameter is indicative of the minimum pressure at the location in the apparatus and the inspiratory demand is the peak inspiratory demand.

In another aspect the present invention comprises a method of estimating inspiratory demand of a patient being administered flow therapy, comprising administering a gas flow rate to the patient using a flow therapy apparatus with a patient interface, measuring a pressure parameter indicative of or being the pressure in a patient interface, determining a patient pressure in the patient interface based on the pressure parameter and a patient interface characteristic pressure for the gas flow rate, from the patient pressure, determining an inspiratory demand flow rate offset using a relationship, the inspiratory demand flow rate offset indicating the difference between the gas flow rate and the inspiratory demand.

In another aspect the present invention comprises a flow therapy apparatus configured for estimating inspiratory demand of a patient being administered flow therapy, comprising: a flow generator for administering a gas flow rate to the patient through a patient interface, a sensor for measuring a pressure parameter indicative of or being the pressure in a patient interface, a controller for: determining a patient pressure in the patient interface based on the pressure parameter, and a patient interface characteristic pressure for the gas flow rate, and from the patient pressure, determining a inspiratory demand flow rate offset using a relationship, the inspiratory demand flow rate offset indicating the difference between the gas flow rate and the inspiratory demand.

In another aspect the present invention comprises a method of estimating a parameter indicative of inspiratory demand of a patient being administered flow therapy, comprising: administering a gas at a flow rate to the patient using a flow therapy apparatus with a patient interface, determining a terminal pressure in, at or proximate the outlet of the patient interface or in, at or proximate the nares of the patient, determining nasal RTF, determining a nasal flow parameter being or indicative of nasal flow based on the pressure and a nasal RTF, and optionally outputting the nasal flow parameter or parameter derived therefrom and/or altering the flow therapy based on the nasal flow or parameter derived therefrom.

Preferably the terminal pressure is determined using a pressure determined at a location in the apparatus and a characteristic pressure of the apparatus for the location.

Preferably the inspiratory demand is peak inspiratory demand and the terminal pressure is a minimum pressure during a breath cycle.

Preferably comprising measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{offset} = \sqrt{\frac{|P_{(t)} - P_{char}|}{R_{nasal}}}$$

Wherein $Q_{offset}$ is the nasal flow
$P(t)$ is the pressure at the location at time t
$P_{char}$ is the characteristic pressure due to resistance to flow of the apparatus for the location
$R_{nasal}$ is the resistance to flow due to nasal resistance
Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ is the flow at the location
$P_{trans}$ is the pressure at the location during breath transition
where the second equation is used for laminar flow and the first for turbulent flow.

In another aspect the present invention comprises a method of estimating a parameter indicative of inspiratory demand of a patient being administered flow therapy, comprising: administering a gas at a flow rate to the patient using a flow therapy apparatus with a patient interface, determining a pressure at a location in the apparatus, and determining a nasal flow parameter being or indicative of nasal flow based on the pressure, characteristic pressure of the apparatus for the location and a nasal RTF, and optionally outputting the leakage parameter or parameter derived therefrom and/or altering the flow therapy based on the leakage flow or parameter derived therefrom.

In another aspect the present invention comprises a flow therapy apparatus configured for estimating inspiratory demand of a patient being administered flow therapy, comprising: a flow generator for administering a gas flow rate to the patient through a patient interface, a sensor for measuring a pressure parameter indicative of or being the terminal pressure, in, at or proximate the outlet of the patient interface or in, at or proximate the nares of the patient, or from which terminal pressure can be determined, a controller for: determining a terminal pressure based on the pressure parameter, determining a nasal RTF, determining a nasal flow parameter being or indicative of nasal flow based on the terminal pressure and a nasal RTF, and optionally outputting the nasal flow parameter or parameter derived therefrom and/or altering the flow therapy based on the nasal flow or parameter derived therefrom.

Preferably the terminal pressure is determined using a pressure parameter determined at a location in the apparatus and a characteristic pressure of the apparatus for the location.

Preferably the inspiratory demand is peak inspiratory demand and the terminal pressure is a minimum pressure during a breath cycle.

Preferably further comprising a sensor for measuring a gas flow rate in the apparatus and wherein the nasal RTF is determined based on a parameter being or indicative of pressure during a breath transition at the or another location in the apparatus, a characteristic pressure of the apparatus for the location and the gas flow rate.

Preferably the parameter indicative of pressure at the location during a breath transition is the pressure or alternatively is the mean pressure at the location over a time period.

Preferably the characteristic pressure is determined from a look up table, algorithm, equation, calculation or other relationship or calibration step that relates characteristic pressure to flow rate for the apparatus at the location.

Preferably the nasal flow is determined from $$Q_{offset} = \sqrt{\frac{|P_{(t)} - P_{char}|}{R_{nasal}}}$$

Wherein $Q_{offset}$ is the nasal flow

P(t) is the pressure at the location at time t $P_{char}$ is the characteristic pressure due to resistance to flow of the apparatus for the location $R_{nasal}$ is the resistance to flow due to nasal resistance Preferably $R_{nasal}$ is determined from $$R_{nasal} = \frac{P_{trans} - P_{char}}{Q_{offset}^2}$$

or $$R_{nasal} = \frac{P_{trans} - P_{char}}{Q_{offset}}$$

Where $Q_{offset}$ is the flow a the location $P_{trans}$ is the pressure at the location during breath transition where the second equation is used for laminar flow and the first for turbulent flow.

In another aspect the present invention comprises a flow therapy apparatus configured for estimating inspiratory demand of a patient being administered flow therapy, comprising: a flow generator for administering a gas flow rate to the patient through a patient interface, a sensor for measuring a pressure at a location in the apparatus, a controller for: determining a nasal RTF, determining a nasal flow parameter being or indicative of nasal flow based on the pressure, characteristic pressure of the apparatus for the location and a nasal RTF, and optionally outputting the nasal flow parameter or parameter derived therefrom and/or altering the flow therapy based on the nasal flow or parameter derived therefrom.

Oscillating Pressure and/or Flow

In another aspect the present invention comprises in the realization that anatomical dead space may be minimized by causing the delivered flow to oscillate between two or more flow rates. In addition, an aspect of at least one of the embodiments disclosed herein includes the realization that the minimization of dead space when using such oscillatory therapy is greatest when the frequency of the oscillation is one that resonates with one or more volumes of space within the airway of the patient.

Thus, in accordance with at least one of the embodiments disclosed herein, a respiratory therapy system is disclosed comprising a flow generator, a flow oscillation arrangement, a controller, a patient interface, and a conduit, wherein the controller is configured to actuate a flow generator to generate a flow of gas at a given flow rate and/or pressure, and impart an oscillation to the flow rate and/or pressure of the flow of gas generated by the flow generator using the flow oscillation arrangement, wherein the oscillation is at a given amplitude and frequency, and the frequency of the oscillation imparted corresponds to one or more resonance frequencies of one or more volumes of airspace within the body of a patient.

In some configurations, the frequency of the oscillation imparted may be determined by user input. In some configurations, the frequency of the oscillation imparted may be determined by a controller by using an automatic frequency sweep testing routine. The patient interface may be a non-sealing nasal cannula. In some configurations, the flow oscillation arrangement is configured to vary the speed of the motor of the flow generator. In some configurations, the flow oscillation arrangement may comprise a linear actuator.

In another aspect the present invention comprises a respiratory therapy system comprising: a flow generator, a flow oscillation arrangement, a controller, a patient interface, and a conduit, wherein the controller is configured to: activate a flow generator to generate a flow of gas at a given flow rate and/or pressure, and impart an oscillation to the flow rate and/or pressure of the flow of gas generated by the flow generator using the flow oscillation arrangement, wherein the oscillation is at a given amplitude and frequency, and the frequency of the oscillation imparted corresponds to one or more resonance frequencies of one or more volumes of airspace within the body of a patient.

Preferably the frequency of the oscillation imparted is determined using user input.

Preferably the frequency of the oscillation imparted is determined by the controller using an automatic frequency sweep testing routine.

Preferably the patient interface is a non-sealing nasal cannula.

Preferably the flow oscillation arrangement is configured to vary the speed of the motor.

Preferably the flow oscillation arrangement comprises a linear actuator.

In another aspect the present invention comprises a method of promoting gas exchange in a patient's airway comprising: providing a gas flow at a base flow rate and modulating the gas flow flow rate and/or gas flow pressure at least one modulation frequency to provide a varying gas flow oscillating about the base flow rate.

Preferably the modulation frequency at least one resonant frequency of the patient's airway (optionally comprising the airspace within the airway) and the varying gas flow oscillates about the base flow rate at the modulation frequency.

Preferably the base flow rate of the varying gas flow provides a bulk flow of gas to the patient.

Preferably the base flow rate of the varying gas flow provides flow therapy to the patient.

Preferably the base flow rate is sufficient to ensure the varying gas flow flow rate is always positive.

Preferably the gas flow is provided by a flow therapy apparatus with a blower operated by a controller.

Preferably the controller operates the fan of the blower at a base speed to provide the base flow rate and varies the fan speed to modulate the gas flow at the modulating frequency to provide the varying gas flow.

Preferably a gas flow modulating device, wherein the controller operates the fan of the blower at a base speed to provide the base flow rate and operates the modulating device to modulate the gas flow at a modulating frequency provide the varying gas flow.

Preferably promotion of gas exchange promotes: $CO_2$ washout of, and/or increased $O_2$ in the patient's airway.

In another aspect the present invention comprises an apparatus for promoting gas exchange in a patient's airway comprising: a flow generator for providing a gas flow, a controller for: operating the flow generator to generate a gas flow at a base flow rate, and operating the flow generator and/or a gas flow modulating device to modulate the gas flow flow rate and/or gas flow pressure at least one frequency to provide a varying gas flow oscillating about the base flow rate.

Preferably the controller is configured to vary the speed of the flow generator to provide the varying gas flow oscillating about the base flow rate.

Preferably the apparatus further comprises the gas flow modulating device.

Preferably the gas flow modulating device is coupled to the controller and comprises one or more of: an oscillatable diaphragm device, inline linear actuator, flow chopper, aerodynamic or mechanical flutter valve, compressed gas source, in or coupled to the gas flow.

Preferably the modulation frequency is a resonant frequency of the patient's airway (optionally comprising the airspace within the airway) and the varying gas flow oscillates about the base flow rate at the modulation frequency.

Preferably the base flow rate of the varying gas flow provides a bulk flow of gas to the patient.

Preferably the base flow rate of the varying gas flow provides flow therapy to the patient.

Preferably the base flow rate is sufficient to ensure the varying gas flow flow rate is always positive.

In another aspect the present invention comprises a flow therapy apparatus comprising: a flow generator, a flow oscillation arrangement, a controller, a patient interface, and a conduit, wherein the controller is configured to: activate a flow generator to generate a flow of gas at a given flow rate and/or pressure, and impart an oscillation to the flow rate and/or pressure of the flow of gas generated by the flow generator using the flow oscillation arrangement, wherein the oscillation is at a amplitude and frequency, and the frequency of the oscillation imparted corresponds to one or more resonance frequencies of one or more volumes of airspace within the body of a patient.

Preferably the frequency of the oscillation imparted is determined using user input.

Preferably the frequency of the oscillation imparted is determined by the controller using an automatic frequency sweep testing routine optionally wherein the automatic frequency sweep testing routine determines the frequency that achieves the best $CO_2$ washout and/or increase in $O_2$.

Preferably the patient interface is a non-sealing nasal cannula.

Preferably the flow oscillation arrangement is configured to vary the speed of the motor.

Preferably the flow oscillation arrangement comprises a linear actuator.

Preferably
amplitude could be set by user or could be controlled by device within user set limits,
frequency can be contained by user-defined limits,
could also have an amplitude sweep routine,
could also have a base flow rate sweep routine (within user-defined limits),
sweep routines could be performed at the start of operation, at regular periods throughout the patient's treatment, when initiated by the user or when a change in patient condition is detected, and/or
oscillation frequency could be made up of a variety of frequencies eg: white noise.

Determining Pressure

In another aspect the present invention comprises a method of non-invasively estimating total pressure delivered to patient airway using a (non-sealing) flow therapy apparatus comprising determining static pressure and dynamic pressure at a location in the flow therapy apparatus using at least one pressure sensor for sensing one or both of static and dynamic pressure and/or calculating one or both of static and dynamic pressure.

In another aspect the present invention comprises a method of non-invasively estimating total delivered patient pressure in a patient airway using a flow therapy apparatus that delivers gas at a flow rate to the patient comprising: determining a static pressure at a location in the apparatus, optionally using a pressure sensor, determining a dynamic pressure at the location in the apparatus based on the velocity of gas delivered to the patient, calculating an estimate of total delivered patient pressure from the determined static pressure and dynamic pressure.

Preferably the method further comprises displaying or otherwise communicating the total delivered patient pressure and/or controlling manually or automatically operation of the apparatus and/or performing diagnostics using the total delivered patient pressure.

Preferably the location is in a patient interface of the apparatus and the pressure sensor is disposed in or proximate the patient interface.

Preferably the velocity of gas is determined from the delivered gas flow rate and a patient interface outlet size.

Preferably the method further comprises determining the patient interface to ascertain the outlet size.

Preferably determining the patient interface comprises one or more of: detecting an RFID tag associated with the patient interfaces that identifies the patient interface, receiving user input identifying the patient interface, delivering a sweep of flow rates to the patient interface, determining the pressure or other parameter at each flow, and using a look up table, graph, algorithm, equations, reference or the like to determine the patient interface from the flow rates and/or pressure or other parameter.

Preferably the dynamic pressure is determined using:

$$P_{dyn} = \tfrac{1}{2} f Q\, v^2$$

Where
$P_{dyn}$ is the dynamic pressure
$\varrho$ is the density of gas
v is the velocity of gas.
f is an empirically derived constant or function (which is optional)

Preferably the patient interface is a cannula and the outlet is one or both prongs.

Preferably the method comprises displaying total delivered patient pressure or some indication thereof.

In another aspect the present invention comprises a flow therapy apparatus configured for non-invasively estimating total delivered patient pressure in a patient airway, comprising: a flow generator for administering a gas flow rate to the patient through a patient interface, a sensor for measuring a static pressure and/or a dynamic pressure at a location in the apparatus, and/or a controller for calculating one or both of static and dynamic pressure.

In another aspect the present invention comprises a flow therapy apparatus configured for non-invasively estimating total delivered pressure in a patient airway, comprising: a flow generator for administering a gas flow rate to the patient through a patient interface, a sensor for measuring a static pressure at a location in the apparatus, a controller for: determining a dynamic pressure at a location in the apparatus based on the velocity of gas delivered to the patient, calculating an estimate of total delivered patient pressure from the determined static pressure and dynamic pressure.

Preferably the method further comprises an output for displaying or otherwise communicating the total delivered patient pressure and/or wherein the controller is configured for controlling manually or automatically operation of the apparatus and/or performing diagnostics using the total delivered patient pressure.

Preferably the location is in a patient interface of the apparatus and the pressure sensor is disposed in or proximate the patient interface.

Preferably the velocity of gas is determined from the delivered gas flow rate and a patient interface outlet size.

Preferably the controller further determines the patient interface to ascertain the outlet size.

Preferably determining the patient interface comprises one or more of: detecting an RFID tag associated with the patient interfaces that identifies the patient interface, receiving user input identifying the patient interface, delivering a sweep of flow rates to the patient interface, determining the pressure or other parameter at each flow, and using a look up table, graph, algorithm, equations, reference or the like to determine the patient interface from the flow rates and/or pressure or other parameter.

Preferably the dynamic pressure is determined using:

$$P_{dyn} = \frac{1}{2}\varrho\, v^2$$

Where
 $P_{dyn}$ is the dynamic pressure
 $\varrho$ is the density of gas
 v is the velocity of gas.

Preferably the patient interface is a cannula and the outlet is one or both prongs.

Preferably the method further comprises displaying total delivered patient pressure or some indication thereof.

In another aspect the present invention comprises a method of non-invasively estimating total delivered patient pressure in a patient airway using a (non-sealing) flow therapy apparatus comprising determining and using one or more of: static pressure, dynamic pressure, system pressure, (system) characteristic pressure, gas flow velocity, system pressure at no flow, and/or gas density at a location in the flow therapy apparatus and/or patient interface outlet size and using at least one pressure sensor when/if sensing one or both of static and dynamic pressure and/or calculating one or both of static and dynamic pressure.

Mechanism Prioritisation

In another aspect the present invention comprises a method of controlling a flow therapy breathing apparatus to deliver a flow of breathable gas (gasflow) to a patient in accordance with a therapy mode defined by one or more prioritised therapy mechanisms selected by a user from a list of therapy mechanisms (therapy mechanism list), the method comprising:

receiving input control data via a user interface of the apparatus that is indicative of one or more prioritised therapy mechanisms that have been selected from the therapy mechanism list;

processing the input control data to select a therapy mode from a list of therapy modes (therapy mode list) that matches the one or more prioritized therapy mechanisms selected, each therapy mode defining a set of gas properties for the gas flow; and operating the apparatus to deliver the gasflow with gas properties defined by the selected therapy mode.

In an embodiment, the list of therapy mechanisms and therapy modes are defined by electronic data stored in or accessible by the apparatus.

In an embodiment, the therapy mechanism list comprising at least two of the following therapy mechanisms: pressure support, carbon dioxide flushing, oxygenation, mucous clearance, and humidification.

In one embodiment, the input control data defines the selected prioritised therapy mechanisms in non-ranked order, such that they are equally prioritised relative to each other. In another embodiment, the input control data defines the selected prioritised therapy mechanisms in ranked order, such that at least one prioritised therapy mechanism has a higher priority than another prioritised therapy mechanism.

In an embodiment, the therapy mode list may comprise single-priority therapy modes corresponding to input control data that defines a single priority therapy mechanism being selected, and multiple-priority therapy modes corresponding to input control data that defines a combination of two or more prioritised therapy mechanisms being selected, whether ranked or non-ranked relative to each other.

In one embodiment, the method further comprises presenting the user via the user interface with every therapy mechanism for selection or deselection as a priority. In this embodiment, the therapy mechanisms may be presented to the user sequentially one at a time or in groups, or all at once. In this embodiment, the user is required to make an active binary decision via the user interface on whether to prioritise each therapy mechanism in the list, such that the input control data generated represents data indicative of which therapy mechanisms have been selected, and which have been deselected.

In another embodiment, the method further comprises presenting the user, via the user interface, with all the therapy mechanisms, either sequentially one at a time or in groups, or all at once, such that the user can select the desired therapy mechanisms to prioritise to generate the representative input control data. In this embodiment, it is assumed that non-selected therapy mechanisms have been actively deselected.

In an embodiment, the apparatus may be operable to control a flow source to generate the gasflow.

In an embodiment, the apparatus comprises the flow source. In one form, the flow source is a flow generator that receives a supply of gases and pressurizes the supply of gases to generate the gasflow.

In an embodiment, the apparatus may further comprise a humidifier that is configured to heat and humidify the gasflow. In one arrangement, the humidifier may be located before the flow generator. In another arrangement, the humidifier may be located after the flow generator. The humidifier may be in the path of the gasflow or alternatively may be configured to inject humidity into the gasflow path by nebulisation or similar, e.g. by jetting of water or mist into the gasflow path.

In another arrangement, the humidifier may be in the form of one or more Humidification Moisture Exchangers (HMEs) that are provided at one or multiple locations in the gasflow path. The HMEs may comprise foam or any other suitable material.

In a further embodiment, the apparatus may further comprise a breathing circuit configured to deliver the gasflow to the patient. In one configuration, the breathing circuit comprises a flexible breathing conduit that transports the gasflow output from the humidifier; and a patient interface that is coupled to an end of the breathing conduit and which is configured to deliver the gasflow to the patient's airway. The breathing conduit may comprise an integrated heater wire.

In an embodiment, the apparatus is configured to provide nasal high flow therapy, and the patient interface is a nasal interface, such as a nasal mask or nasal cannula.

Preferably the apparatus further comprises an oxygen controller that is operable to control the oxygen flow rate into the mixing chamber to thereby alter the oxygen concentration of the gasflow delivered to the patient.

In an embodiment, the supply of gases may be atmospheric air, or atmospheric air blended with a supplementary gas such as oxygen. In one form, the apparatus may further comprise a mixing chamber, before the flow generator, that receives a supply of atmospheric air or air from a central gases supply and a supply of oxygen from an oxygen supply and mixes the gases before they are input to the flow generator. In another form, the mixing chamber may be provided after (downstream of) the flow generator, such that the mixing chamber receives a supply of oxygen for blending with the pressurised air gasflow output from the flow generator. The air and oxygen may be blended so that the gasflow has a particular oxygen concentration or fraction.

In an embodiment, each therapy mode in the therapy mode list defines a set of apparatus operating parameter settings for controlling the apparatus to deliver the gasflow with particular gas properties defined for the therapy mode.

In an embodiment, each therapy mode defines one or more of the following gas properties for the gasflow delivered to the patient: flow rate, pressure, oxygen concentration, humidity and temperature. The flow rate may be constant or may be a bi-level or multi-level flow rate that varies over a patient's breathing cycle, such as having different or varying flow rates for inspiration and expiration.

In an embodiment, each gas property of the gas flow is controlled by a respective apparatus operating parameter setting having an associated control signal or signals. In an embodiment:

the flow rate may be controlled by a flow generator control signal that controls the flow generator to generate the desired or demanded gasflow flow rate (for example, the flow generator control signal may control the speed of the flow generator to alter the flow rate), the oxygen concentration may be controlled by a oxygen concentration control signal that controls the oxygen supply to generate the desired or demanded gasflow oxygen concentration (for example, the oxygen concentration control signal may control the oxygen supply flow rate being received by a mixing chamber located before or after the flow generator), and the temperature and humidity level may be controlled by temperature control signals that control the humidifier and/or any breathing circuit heater wire to generate the desired or demanded gasflow temperature and humidity (for example, the temperature control signal may control the power delivered to a heater plate of the humidifier and/or power delivered to any heater wire integrated with the breathing conduit).

In another aspect the present invention comprises a method of controlling a flow therapy breathing apparatus to deliver a flow of breathable gas (gasflow) to a patient with gas properties in accordance with one or more prioritised therapy mechanisms selected by a user from a list of therapy mechanisms (therapy mechanism list), the method comprising:

receiving input control data via a user interface of the apparatus that is indicative of whether each therapy mechanism in the therapy mechanism list has been selected as a prioritised therapy mechanism or deselected;

processing the input control data to generate a set of apparatus operating parameter settings based on stored operating parameter data for each therapy mechanism, each therapy mechanism being associated with a gas property of the gasflow; and operating the apparatus in accordance with the generated apparatus operating parameter settings to deliver the gasflow with gas properties in accordance with the input control data.

In one embodiment, the input control data defines the selected prioritised therapy mechanisms in non-ranked order, such that they are equally prioritised relative to each other. In another embodiment, the input control data defines the selected prioritised therapy mechanisms in ranked order, such that at least one prioritised therapy mechanism has a higher priority than another prioritised therapy mechanism.

In an embodiment, the gas property of the gasflow associated with each therapy mechanism is controlled by a respective operating parameter setting of the apparatus.

In an embodiment, the stored operating parameter data for each therapy mechanism defines a first operating parameter setting for achieving the associated gas property when the therapy mechanism is selected as a priority and a second operating parameter setting when the therapy mechanism is not selected.

In an embodiment, the method further comprises identifying when the generated operating parameter settings based on the input control data conflict, and resolving the conflict to generate the final operating parameter settings. For example, some therapy mechanisms may be associated with the same gas property of the gasflow, and a conflict of operating parameter settings may arise if both such therapy mechanisms are selected as a priority. In one embodiment, for input control data that results in generated operating parameter settings conflicting, the conflict is resolved in favour of the higher ranked therapy mechanism, or alternatively where the therapy mechanisms are equally ranked, a default rule setting is used to resolve the conflict.

In another aspect the present invention comprises in a method of controlling a flow therapy breathing apparatus to deliver a flow of breathable gas (gasflow) to a patient with gas properties in accordance with one or more prioritised therapy mechanisms selected by a user from a list of therapy mechanisms (therapy mechanism list), the method comprising:

receiving input control data via a user interface of the apparatus that is indicative of the one or more prioritised therapy mechanisms that have been selected from the therapy mechanism list, each therapy mechanism being associated with a gas property of the gasflow;

processing the input control data to retrieve operating parameter settings for each selected prioritized therapy mechanism from stored operating parameter data;

modifying one or more apparatus operating parameter settings relative to their respective default settings in accordance with the retrieved operating parameter settings; and operating the apparatus in accordance with the modified operating parameter settings and any unmodified default operating parameter settings to deliver the gasflow with gas properties in accordance with the selected prioritized therapy mechanisms.

In one embodiment, the input control data defines the selected prioritised therapy mechanisms in non-ranked order, such that they are equally prioritised relative to each other. In another embodiment, the input control data defines the selected prioritised therapy mechanisms in ranked order, such that at least one prioritised therapy mechanism has a higher priority than another prioritised therapy mechanism.

In an embodiment, the gas property of the gasflow associated with each therapy mechanism is controlled by a respective operating parameter setting of the apparatus.

In an embodiment, the stored operating parameter data comprises an operating parameter setting for each therapy mechanism that controls the gas property of the gasflow associated with the therapy mechanism.

In an embodiment, processing the input control data to retrieve operating parameter settings for each selected prioritized therapy mechanism from stored operating parameter data further comprises identifying whether any of the retrieved operating parameter settings conflict, and resolving the conflict to generate a final operating parameter setting. For example, some therapy mechanisms may be associated with the same gas property of the gasflow, and a conflict of operating parameter settings may arise if both such therapy mechanisms are selected as a priority. In one embodiment, for input control data which results in generated operating parameter settings conflicting, the conflict is resolved in favour of the higher ranked therapy mechanism, or alternatively where the therapy mechanisms are equally ranked, a default rule setting is used to resolve the conflict.

The second and third aspects of the invention may have any one or more of the features mentioned in respect of the first aspect of the invention.

In another aspect the present invention comprises a flow therapy breathing apparatus for generating a flow of breathable gas (gasflow) for a patient with gas properties in accordance with one or more prioritised therapy mechanisms selected by a user from a list of therapy mechanisms (therapy mechanism list), comprising:
 a user interface that is configured to receive control input data from a user; and
 a control system that is configured to control apparatus in accordance with any one of the methods of the first three aspects of the invention above.

Preferably the apparatus is operable to control a flow source to generate the gasflow.

Preferably the apparatus comprises the flow source and the flow source is a flow generator that receives a supply of gases and pressurizes the supply of gases to generate the gasflow.

In an embodiment, the apparatus may further comprise a flow generator that receives a supply of gases and pressurizes the supply of gases to generate the gasflow.

In an embodiment, the apparatus may further comprise a humidifier that is configured to heat and humidify the gasflow. In one arrangement, the humidifier may be located before the flow generator. In another arrangement, the humidifier may be located after the flow generator. The humidifier may be in the path of the gasflow or alternatively may be configured to inject humidity into the gasflow path by nebulisation or similar, e.g. by jetting of water or mist into the gasflow path.

In another arrangement, the humidifier may be in the form of one or more Humidification Moisture Exchangers (HMEs) that are provided at one or multiple locations in the gasflow path. The HMEs may comprise foam or any other suitable material.

In an embodiment, the apparatus further comprises a breathing circuit configured to deliver the gasflow to the patient.

In an embodiment, the breathing circuit comprises a flexible breathing conduit that transports the gasflow output from the humidifier; and a patient interface that is coupled to an end of the breathing conduit and which is configured to deliver the gasflow to the patient's airway. The breathing conduit may comprise an integrated heater wire.

In an embodiment, the apparatus is configured to provide nasal high flow therapy, and the patient interface is a nasal interface, such as a nasal mask or nasal cannula.

In an embodiment, the user interface may be in the form of a graphical user interface (GUI) on a touch screen display, or additionally or alternatively may be provided in the form of one or more control buttons, knobs, dials, switches, or a combination thereof.

Preferably the apparatus further comprises an oxygen controller that is operable to control the oxygen flow rate into the mixing chamber to thereby alter the oxygen concentration of the gasflow delivered to the patient.

In an embodiment, the supply of gases may be atmospheric air, or atmospheric air blended with a supplementary gas such as oxygen. For example, the flow generator may receive a supply of atmospheric air or air from a central gases supply and a supply of oxygen from an oxygen supply. The air and oxygen may be blended so that the gasflow has a particular oxygen concentration or fraction. In one such embodiment, the apparatus may further comprise a mixing chamber (located before or after the flow generator) that receives a supply of atmospheric air (either from a supply or the surrounding environment) and a supply of oxygen from an oxygen supply, and which mixes or blends the air and oxygen. In one embodiment, the flow rate of the oxygen supplied to the mixing chamber may be controlled by an oxygen controller.

The another aspect of the invention may have any one or more of the features mentioned in respect of the first-third aspects of the invention.

In another aspect the present invention comprises a non-transitory computer-readable medium having stored thereon computer executable instructions that, when executed on a processing device, cause the processing device to perform a method according to any one the first-third aspects of the invention.

The another aspect of the invention may have any one or more of the features mentioned in respect of the first three aspects.

Displaying Parameters

In another aspect the present invention comprises a method of flow therapy, the method comprising: delivering high flow; and determining a peak inspiratory demand.

Preferably, the method further comprises: displaying the peak inspiratory demand.

Preferably, the method further comprises: determining an entrained flow.

Preferably, the determining the entrained flow comprises: comparing the peak inspiratory demand and the delivered flow rate.

Preferably, the determining the entrained flow comprises: determining a difference between the delivered flow rate and the peak inspiratory demand.

Preferably, the method comprises: displaying the entrained flow.

Preferably, the method comprises: adjusting the delivered flow rate to meet and/or exceed the peak inspiratory demand.

Preferably, the method further comprises: adjusting the delivered flow rate such that the entrained flow is approximately zero or a negative value.

Preferably, the method further comprises: displaying an excess flow or a flow support when the entrained flow is approximately zero or a negative value.

Preferably, the method further comprises: displaying a flow deficit when the entrained flow is a positive value.

Preferably, the method further comprises: displaying any combination of mean pressure, maximum pressure, minimum pressure, inspiratory pressure, expiratory pressure, pressure amplitude, pressure-time product, change or trend in any one of these values over a time, or a ratio or other combination of these parameters.

Preferably, the method further comprises: displaying more than one of the following values, or various combinations of the following values, simultaneously: mean pressure, maximum pressure, minimum pressure, inspiratory pressure, expiratory pressure, pressure amplitude, pressure-time product, change or trend in any one of these values over a time, or a ratio or other combination of these parameters and/or a graph of any one of these values over a time.

Preferably, the method further comprises: displaying respiratory rate and/or a graph of respiratory rate over time.

Preferably, the method further comprises: displaying time on therapy and/or a graph of time on therapy over time.

Preferably, a flow therapy apparatus is configured to perform the method of flow therapy.

In another aspect the present invention comprises a method of flow therapy, the method comprising: delivering high flow; and determining a peak inspiratory demand.

Preferably the method further comprising: displaying the peak inspiratory demand.

Preferably the method determining an entrained flow.

Preferably the determining the entrained flow comprises: comparing the peak inspiratory demand and the flow rate.

Preferably the determining the entrained flow comprises: determining a difference between the flow rate and the peak inspiratory demand.

Preferably the method further comprising: displaying the entrained flow.

Preferably the method further comprising: adjusting flow rate to meet and/or exceed the peak inspiratory demand.

Preferably the method further comprising: adjusting the flow rate such that the entrained flow is approximately zero or a negative value.

Preferably the method further comprising: displaying an excess flow or a flow support when the entrained flow is approximately zero or a negative value.

Preferably the method further comprising: displaying an excess flow or a flow support when the entrained flow is approximately zero or a negative value.

Preferably the method further comprising: displaying any combination of the following: mean pressure, maximum pressure, minimum pressure, inspiratory pressure, expiratory pressure, pressure amplitude, pressure-time product, change or trend in one of these values over a time, or a ratio or other combination of these parameters.

Preferably the method further comprising: displaying more than one of the following values, or various combinations of the following values, simultaneously: mean pressure, maximum pressure, minimum pressure, inspiratory pressure, expiratory pressure, pressure amplitude, pressure-time product, change or trend in one of these values over a time, or a ratio or other combination of these parameters.

Preferably the method further comprising: displaying respiratory rate and/or a graph of respiratory rate over time.

Preferably the method further comprising: displaying time on therapy and/or a graph of time on therapy over time.

Definitions

The term "gasflow" and "airflow" as used in this specification and claims should be interpreted broadly to refer to any flow or stream of breathable gas, including e.g. air and/or oxygen. Use of the term "air" throughout the specification should not be considered limiting and is exemplary only. It more generally could encompass any type of gas (e.g. oxygen or oxygen/air mixture) as will be understood by those skilled in the art.

The phrase "flow therapy apparatus" as used in this specification and claims is intended to mean, unless the context suggests otherwise, any apparatus, system or device, that is capable of providing or controlling the delivery of a flow or stream of gases to a user for therapeutic purposes, including any respiratory assistance apparatus that may provide respiratory assistance to patients or users who require a supply of gases for respiratory therapies such as, but not limited to, humidification and/or flow therapy, Positive Airway Pressure (PAP) therapies, including but not limited to CPAP therapy, Bi-PAP therapy, and OPAP therapy, and which are typically used for the treatment of diseases such as Obstructive Sleep Apnea (OSA), snoring, or Chronic Obstructive Pulmonary Disease (COPD), and including ventilators.

The phrase "operating parameter settings" as used in this specification and claims is intended to mean, unless the context suggests otherwise, any control setting or scheme or function that controls one of more operating parameters or conditions of the apparatus via control signals including, but not limited to, settings relating to the flow generator, humidifier, gases supply or the like, or any other setting that can control the gas property or properties of the gasflow generated by the apparatus, such as its flow rate, oxygen concentration, temperature, humidity level, and pressure and variation of these properties over the breathing cycle or over longer periods of time.

The phrase "gas property" as used in this specification and claims is intended to mean, unless the context suggests otherwise, any gas property of the gasflow, including, but not limited to, flow rate, oxygen concentration, temperature, humidity level, and pressure received by and/or delivered to the patient.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features. Where, in the foregoing description reference has been made to integers or components having known equivalents thereof, those integers are herein incorporated as if individually set forth.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

The term "high flow therapy" is used in the art and in place throughout this specification to refer to apparatus, methods and treatments using or implementing flow therapy. The term "high" is relative and should not be considered limiting to the actual flow rate of the therapy being delivered. Any embodiments or description referring to "high flow therapy" should be considered to apply to any arrangement of a flow therapy method and apparatus irrespective on.

The term "respiratory flow rate" refers to the (breath) flow rate of the patient during inspiration (inspiratory flow rate) or expiration (expiratory flow rate—that is, the flow rate to and/or from the lungs). The term "inspiratory flow rate" can be interchangeably used with "inspiratory demand" being the flow rate required ("demanded" by the patient) to be provided to the patient to meet inspiration flow rate. "Inspiratory flow rate (demand)" is a general term that can refer to:
- instantaneous inspiratory flow rate (demand), which is the inspiratory flow rate at any particular time during the inspiration portion of the breath flow, and
- peak inspiratory flow rate (demand), which is the peak inspiratory flow rate at the peak inspiration portion of the breath flow.

"Expiratory flow rate" is a general term that can refer to:
- instantaneous expiratory flow rate, which is the expiratory flow rate at any particular time during the expiration portion of the breath flow, and
- peak expiratory flow rate, which is the peak expiratory flow rate at the peak expiration portion of the breath flow.

Certain features, aspects and advantages of some configurations of the present disclosure have been described with reference to use by a patient or user. However, certain features, aspects and advantages of the use of the humidification system as described may be advantageously practiced by other people on behalf of the patient, including medical professionals, medical device dealers, or medical device providers. Certain features, aspects and advantages of the methods and apparatus of the present disclosure may be equally applied to usage by other people.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

BRIEF DESCRIPTION OF DRAWINGS

FIG. 44a shows graphs of patient flow rate versus pressure curves for determining the relationship in FIG. 5a.

FIG. 70A is a schematic diagram of a flow therapy breathing apparatus in accordance with a first embodiment of the invention in which the mixing chamber for air and oxygen is located after the flow generator;

DETAILED DESCRIPTION OF PREFERRED EMBODIMENTS

Figure 1:
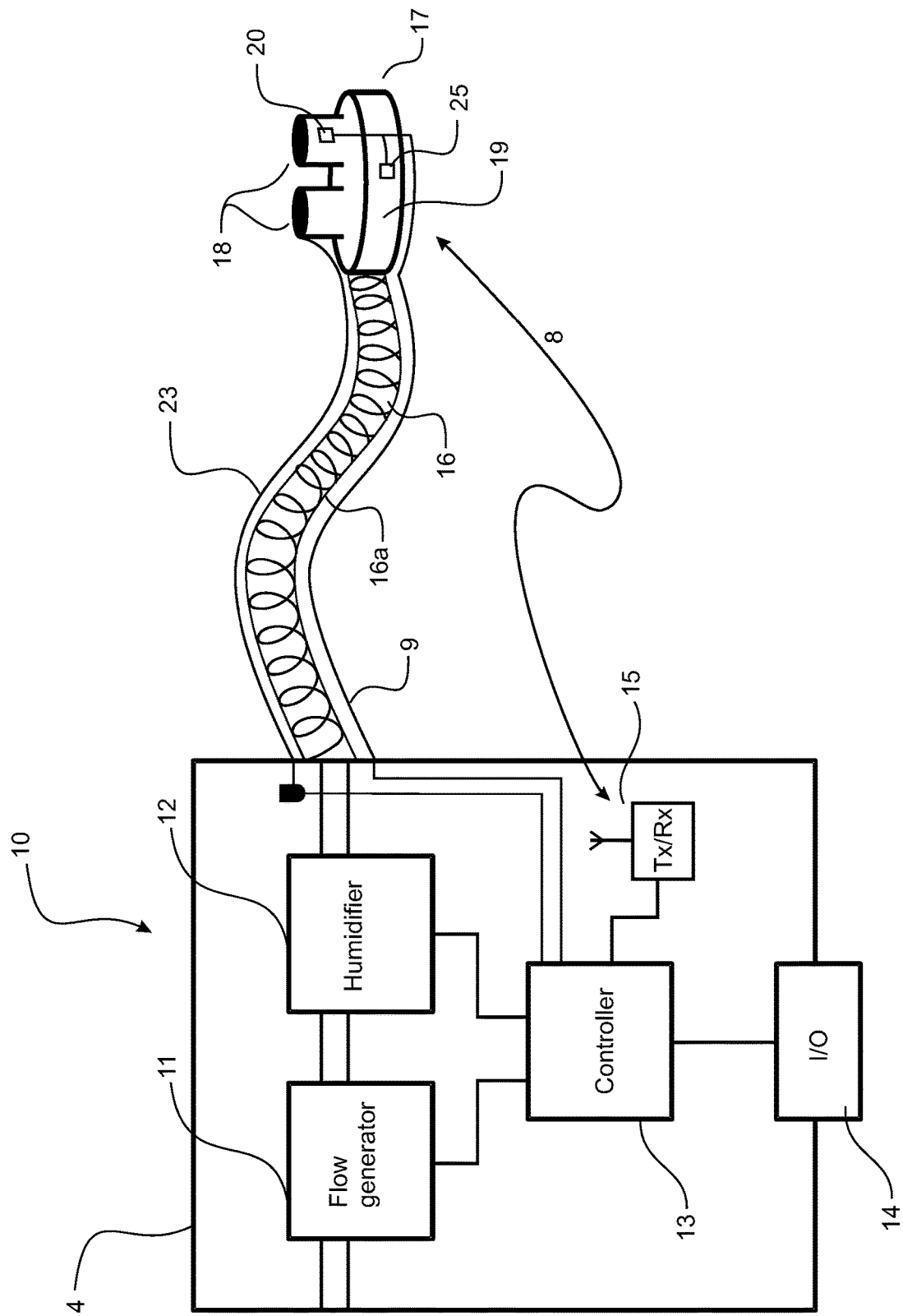
FIG. 1 is a (e.g. high) flow therapy apparatus adapted to provide or assist to provide high flow therapy that meets inspiratory demand of a patient.

Throughout the specification equation and table numbers are used. The equation and table numbering restarts in each top heading, so any reference to an equation or table will refer to the number in that section, or otherwise as will be apparent by context.

1. Determining Inspiratory Flow Rate (Demand)

Some embodiments herein relate to a flow therapy apparatus (such as a high flow therapy apparatus) and/or its method of use and/or methods for providing information and control of the apparatus in relation to the inspiratory demand of a patient using the apparatus. Embodiments will now be described relating to methods and apparatus for determining inspiratory flow rate (demand) and/or determining whether inspiratory demand is being met, exceeded or not met. These embodiments can be used to provide information to users and/or enable users and/or the apparatus to be configured with a flow rate that meets inspiratory demand, or a flow rate that is based on knowledge of inspiratory demand.

1.1 Overview of Determining Inspiratory Flow Rate (Demand)

Although flows of gas delivered via a patient interface exist in the prior art, an aspect of at least one of the embodiments disclosed herein includes the realisation that there are problems with the implementation and use of these high flow systems in the prior art. Nasal high flow systems in the prior art may not meet the inspiratory demand of a patient. Inspiratory demand as herein described may refer to the amount of gas a patient may require during inspiration. Prior art systems may not measure or calculate this inspiratory demand, or may not determine inspiratory demand for individual patients. Thus the flow rate delivered to patients may not reflect their specific respiratory condition or individual demand, which may provide inadequate respiratory support and/or may compromise the effectiveness of the therapy. Flows delivered to a patient that are below their inspiratory demand may cause entrainment of room air during inspiration as the patient may require more gas to meet their inspiratory demand. Entrainment of room air may dilute the humidity, temperature, oxygen concentration, or other gases mixed into the delivered gas to the patient compromising the treatment and preventing effective control of the therapy. Flows delivered to a patient that are above inspiratory demand may cause undesired physiological outcomes, discomfort to the patient and may be associated with excess noise generation. In other cases it may be desirable for the delivered gasflow to exceed, or be less than a patient's inspiratory demand by an amount Currently clinicians may be unsure as to the specific inspiratory demand of their patients, thus to prescribe a flow rate may be difficult and may not reflect the flow rate that best meets their patients' needs.

The present invention relates to embodiments of a flow therapy apparatus (typically called a high flow therapy apparatus) and its method of use. The apparatus and its method of use enable operation to provide gasflow (the more general term for "airflow") that meets inspiratory demand, or at least provides assistance (e.g. through provision of information) to achieve this. Meeting inspiratory demand means to supply a flow of gas through a patient interface at a rate that approximates, equals or exceeds the flowrate of gas desired by a patient's normal or augmented inspiratory breath pattern such that little or no ambient air is required or entrained to supplement the supplied flowrate. In the case of providing a constant flow, providing gasflow that meets inspiratory demand will mean providing a gasflow that meets peak inspiratory demand, although this is not essential in other cases.

In general terms, apparatus and methods are disclosed that may calculate or measure the inspiratory demand of a patient or measure some parameter indicative of whether inspiratory demand is being met. Determining the inspiratory demand of a patient or some parameter indicative of whether it is being met may enable a flow to be delivered to the patient which may equal or exceed the determined inspiratory demand. The inspiratory demand may be met by delivering a constant flow rate corresponding to the determined peak demand of a patient that may be similar to, equal or exceed the peak inspiratory demand of the patient over a time period, number of breaths or the like. The inspiratory demand may also be continuously monitored and thus a variable flow that may match or exceed the instantaneous demand of the patient during the inspiratory phase may be supplied by the device. Other ways of delivering inspiratory demand may also be possible. Delivering inspiratory demand may prevent entrainment of room air during inspiration which may prevent dilution of the humidity or gases delivered to the patient and may increase the efficacy of the therapy. Clinicians may also have more confidence that accurate levels of inhaled oxygen concentration may be delivered to the patient as less dilution of flow may occur.

Apparatus and methods can display the determined inspiratory demand or parameter indicative of whether inspiratory demand is being met to the user. This may allow the user to manually adjust the therapy or the device may automatically adjust the therapy to meet the particular demand of a patient. The apparatus and methods may provide feedback to the user regarding the flow being delivered to the patient and may indicate if inspiratory demand is being met which may allow the user to alter the flow to better meet inspiratory demand. The flow may be increased until it is sufficient to meet inspiratory demand, or it may be decreased so that excess flow may not be delivered to the patient, which may increase patient comfort. In other embodiments the apparatus and methods may automatically adjust the delivered flow rate in a way that may satisfy the inspiratory demand of the patient. The display may include information to the user regarding whether the apparatus is meeting the inspiratory demand of the patient. An automated apparatus may have upper and lower limits set by the user for the flow or these limits may be determined by the device.

Humidifiers are used to provide humidified respiratory gases to a patient. Gases are delivered to a patient via a patient interface. Patient interfaces as herein described refer to, but are not limited to, a face mask, an oral mask, a nasal mask, a nasal cannula, a combination of oral and nasal mask, or the like. Gases delivered to patients at 100% relative humidity and 37° C. mimic the transformation of air that occurs as it passes through the nose to the lungs. This promotes efficient gas exchange and ventilation in the lungs, aids defense mechanisms in the airways and increases patient comfort during treatment. Nasal high flow is a therapy that typically delivers a high flow of humidified gas to a patient through a patient interface. It is a therapy that may deliver the inspiratory demand of a patient. Inspiratory demand as herein described refers to the amount of air that may satisfy a patient's need during inspiration. Meeting inspiratory demand is not limited to being achieved with a nasal cannula, but may be achieved using patient interfaces such as a face mask, oral mask, nasal mask, nasal cannula, combination of oral and nasal mask, or the like, as described above. If inspiratory demand is met the patient may not entrain room air during inspiration. This is beneficial as entrainment of air may dilution of the inspired gas which may compromise the therapy. Inspiratory demand may vary between patients or with patient condition and therefore may require constant or regular monitoring.

In embodiments, the inspiratory demand may be met by delivering a constant flow rate corresponding to the determined peak demand of a patient that may be similar to, equal or exceed the peak inspiratory demand of the patient over a time period, number of breaths or the like. The inspiratory demand may also or alternatively be continuously monitored and thus a variable flow that may match or exceed the instantaneous inspiratory demand of the patient during the inspiratory phase may be supplied by the device. Over a period of time or a number of breathing cycles this peak inspiratory flow rate may change and may be delivered as the average of the peak flow rates over the previous cycles or time period. By matching or exceeding the peak flow demand of the patient, it may be possible to reduce the entrainment of room air that may occur during inspiration at delivered flow rates (see FIG. 1). In this way the delivered therapy may not be diluted, and the correct humidity, gas concentration, or both, may be delivered to the patient. Accurate oxygen delivery is important because it may be necessary to deliver high concentrations of oxygen to a patient if entrainment of room air is occurring. This may cause the user to unnecessarily escalate the therapy to ensure the oxygen requirements are met. By continuously monitoring a patient's inspiratory demand may be met by delivering a flow that may reflect the instantaneous inspiratory flow rate of the patient. In this way the flow being delivered may meet the inspiratory demand of a patient across a breathing cycle, may improve patient comfort and may reduce the delivered flow rate when it may not be required.

In embodiments, the apparatus may calculate and display information regarding the inspiratory flow rate to the user. This information may include but is not limited to, an estimation of the patient's (peak or instantaneous) inspiratory demand, whether the demand is being met by the current delivered flow, the parameters that describe the current flow, any combination of these, or the like. This may be displayed but is not limited to a visual or light indicator to indicate if inspiratory demand has been met. A visual indicator may refer to but is not limited to a display that may use colour such as, red to indicate inspiratory demand is not being met, and green to indicate that inspiratory demand is being met. Any symbols, colours or combination of colours and symbols may be used, a single colour may be used, or more than two colours may be used. The display may also be used to indicate the proportion of the patient's inspiratory demand is being met. The display may allow a user to alter the delivered flow rate. Alterations may increase the delivered flow rate so it may match or exceed inspiratory demand, or they may decrease the delivered flow rate to reduce noise or patient discomfort.

In one embodiment the user may set a constant flow rate to be delivered to a patient. This flow rate may sufficiently meet the peak inspiratory demand of a patient or may be a flow rate that is a proportion of the estimated inspiratory demand. An example of a flow rate that may be a proportion of the estimated inspiratory demand of a patient may be but is not limited to 0-200% of the peak inspiratory demand of a patient. A user may also set a delivered flow that may have a different inspiratory and expiratory flow rate, where either or both flow rates may vary over the breathing cycle. The inspiratory flow rate may be used to provide feedback to the user regarding the current flow being delivered and may provide an indication of whether this is a sufficient flow using a display, coloured indicators, or the like. This may allow the user to manually alter the settings of the device, or they may be able to manually monitor the inspiratory demand of the patient. In some embodiments the device may automatically adjust the delivered flow rate, in a way that may meet the inspiratory demand of the patient. In another embodiment, if the device detects the inspiratory demand of the patient is not met, it may provide a recommendation for the delivered flow rates to the user, who may then accept or reject the recommendation. If the recommendation is accepted, the recommended flow rates are implemented. If it is rejected the user may then choose to maintain or manually alter the delivered flow rates. This feedback mechanism may be combined with automatic adjustment, or any other combinations not limited to the above, may be formed.

A general description of a flow therapy apparatus (typically a high flow therapy apparatus) will be provided, and particular embodiments of the apparatus and its use will then be described.

1.2 Flow Therapy Apparatus Adapted for Determining Inspiratory Flow Rate (Demand)

A flow therapy apparatus 10 is shown in FIG. 1. It comprises a housing 4 that contains a flow generator 11, humidifier 12, controller 13 and user I/O interface 14 (comprising, for example, a display and input devices such as buttons or the like). The controller 13 is programmed to control the components of the apparatus, including: operating the flow generator 11 to create a flow of gas (gasflow) for delivery to a patient, operating the humidifier 12 to humidify and/or heat the generated gasflow, receive user input from the user interface 14 for reconfiguration and/or user-defined operation of the apparatus 10, output information (for example on the display) to the user. The user could be a patient, healthcare professional or anyone else interested in using the apparatus.

A patient breathing conduit 16 is coupled to a gasflow output in the housing 4 of the high flow therapy apparatus 10, and is coupled to a patient interface 17, such as a nasal cannula with a manifold 19 and nasal prongs 18. The humidified gasflow that is generated by the high flow therapy apparatus is delivered to the patient via the patient conduit 16 through the cannula 17. The patient conduit 16a can have a heater wire to heat gasflow passing through to the patient, under control of the controller 13. The patient conduit 16 and/or patient interface can be considered part of the high flow therapy apparatus 10, or alternatively peripheral to it. Use of the term "(high) flow therapy apparatus" can be utilised for either alternative.

General operation of a flow therapy breathing apparatus 10 will be known to those skilled in the art, and need not be described in detail here. However, in general terms the controller 13: controls the flow generator 11 to generate a gasflow of the desired flow rate (generated gasflow), controls the humidifier 12 to humidify the gasflow and/or heat it. The gasflow is directed out through the patient conduit 16 and cannula 17 to the patient. The controller 13 can also control heating elements 16a in the humidifier and/or patient conduit to heat the gas to a desired temperature (also termed "target temperature" or "set point") that achieves the required level of therapy and/or comfort for the patient. The controller 13 can be programmed with or determine a suitable target temperature.

Operation sensors, such as flow, temperature, humidity and/or pressure sensors can be placed in various locations in the flow therapy apparatus and/or the breathing conduit and/or cannula. Output from the sensors can be received by the controller 13, to assist it to operate the flow therapy apparatus in a manner that provides optimal therapy, including meeting inspiratory demand.

Embodiments described below will describe apparatus and methods for utilising sensor information and the controller to operate the flow therapy apparatus to indicate compliance with and/or achieve inspiratory demand. Each of the embodiments provides one or more inspiratory flow functions, being functions such as:

- determining a parameter indicative of ambient air entrainment and/or insufficient generated gasflow to meet inspiratory demand,
- determining if ambient entrainment and/or insufficient generated gasflow to meet inspiratory demand is occurring,
- providing an indication (e.g. on a display) of the entrainment parameter, and/or whether entrainment and/or insufficient generated gasflow to meet inspiratory demand is occurring,
- providing an indication (e.g. on a display) of the entrained flow rate, and/or the inspiratory demand flow rate,
- controlling the flow generator to meet inspiratory demand,
- providing an indication (e.g. on a display) of inspiratory demand compliance to a user in order to manually control (e.g. through the user interface) the flow generator to meet inspiratory demand,
- providing a recommendation to the user of a flow rate that meets or exceeds the measured peak inspiratory flow.

1.3 Estimating Peak Inspiratory Flow Rate (Demand) Using Tidal Volume

Figure 2:
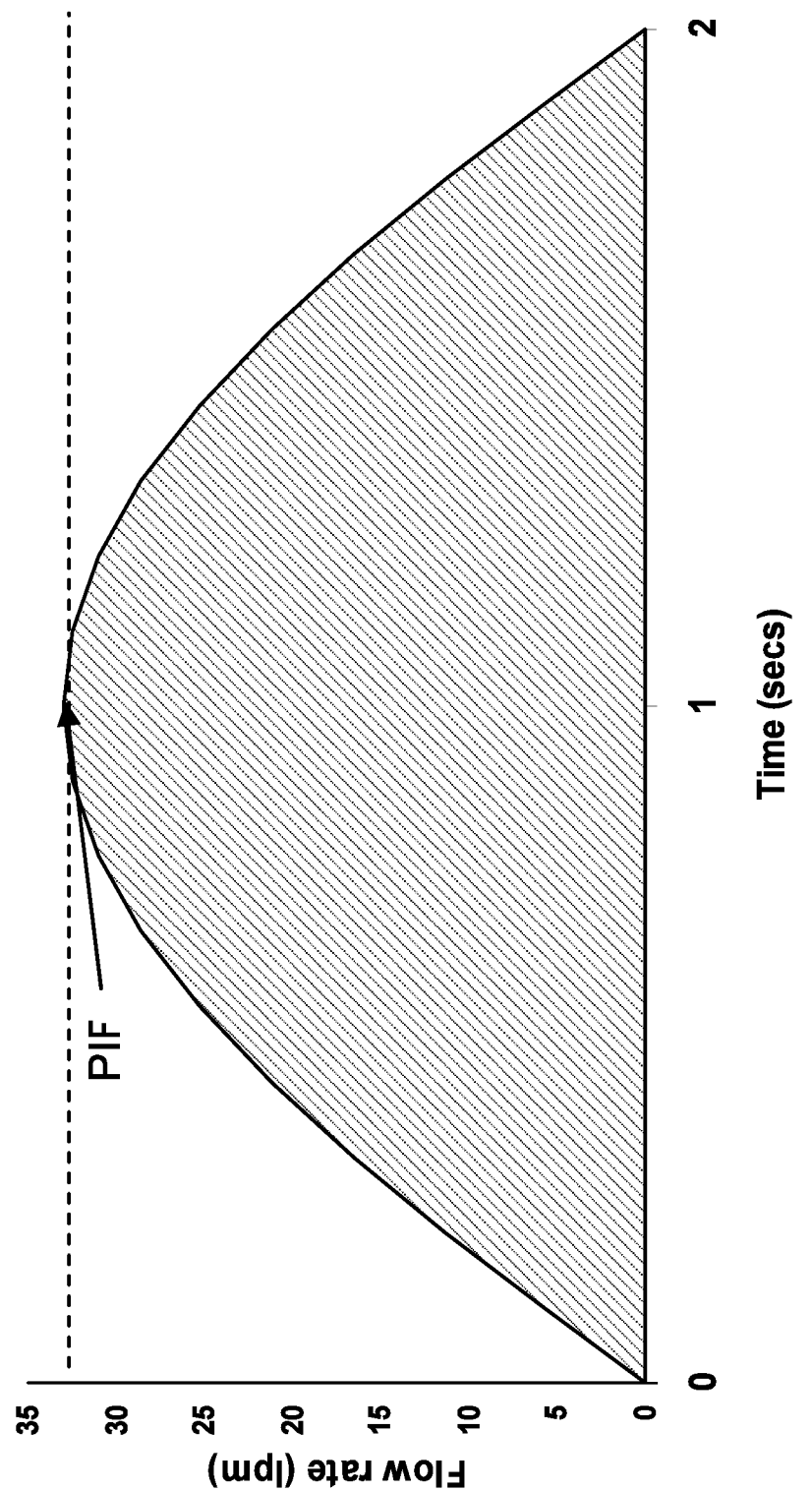
FIG. 2 is an example of an inspiratory sine wave approximation.

The patient's peak inspiratory flow may be estimated using the patient's tidal volume and integration of an inspiratory flow wavefrom. The patient's tidal volume may be estimated with regards to patient weight or the patient's ideal weight. An ideal weight may be estimated using Broca's index or Devine Formula, where the ideal weight of a patient may be calculated by subtracting 100 from the patient's height in centimetres. This may be a useful body weight value for a patient that is obese or overweight, as they may have the same lung size as lighter people of the same height. The patient's inspiratory flow waveform b may be modelled by a function, for example, the inspiratory cycle may be represented by the first half of a sine wave (see FIG. 2), where the amplitude of the curve will estimate the patient's peak inspiratory flow demand. Patients that suffer from lung conditions or respiratory problems such as but not limited to chronic obstructive pulmonary disease (COPD) or acute respiratory distress syndrome (ARDS), may have tidal volumes that may be less than those of a healthy individual. This may be reflected in the calculation of tidal volume by the use of different multipliers. To estimate tidal volume, the formula used is:

$$\text{Tidal Volume (mL)} = \text{Patient Weight (kg)} \times \text{Disease Factor} \left(\frac{mL}{kg}\right),$$

where the disease factor represents the multiplier for different patient conditions. An example of different disease factors may be but is not limited to, COPD at 10 mL/kg, ARDS at 6-8 mL/kg, or other lung conditions at 12 mL/kg. A user may be supplied with a range of multiplier values and may be able to select the value that best reflects the patient, or they may be supplied with a list of patient conditions, where they may select the condition which best reflects the patient and where each condition corresponds to an appropriate multiplier, or they may use a default multiplier value. The tidal volume may then be used to estimate the peak inspiratory flow for the patient. An example is given below where the inspiratory flow rate is estimated using an inspiratory flow waveform modelled by a sine wave:

$$\text{Tidal Volume} = \int_0^{T_i} PIF \cdot \sin\left(\frac{\pi t}{T_i}\right) dt$$

$$= \left(-PIF \cdot \frac{T_i}{\pi} \cos\left(\frac{\pi t}{T_i}\right) dt\right)_0^{T_i}$$

$$= 2 \cdot PIF \frac{T_i}{\pi}$$

$$PIF = \frac{\text{Tidal Volume} \cdot \pi}{2 T_i}$$

where Ti is the inspiratory time in minutes, PIF is the patient's peak inspiratory flow in L/min and Tidal Volume is in L.

For example, a 70 kg patient with COPD may have a tidal volume of 700 mL, and an inspiratory time of 2 seconds which may return a peak inspiratory flow of 33 L/min By continuously monitoring a patient, it may be possible to responsively change the delivered flow rate based on changes in the patient's breathing pattern (inspiratory time). The device may average the inspiratory time of the patient for any amount of breaths between, but not limited to the following examples: 3-720 breaths, or any amount of time between 5 seconds-1 hour, or the like. Any changes in the breathing pattern may periodically alter the flow rate.

Figure 3:
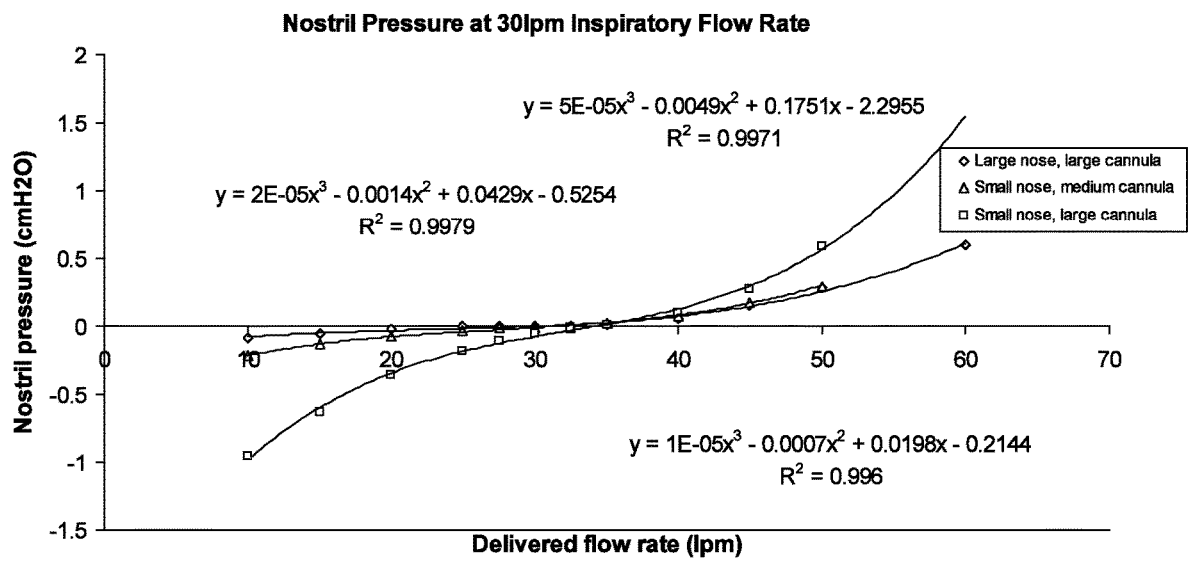
FIG. 3 shows nose pressure for delivered flow rates.

1.4 Determining (Peak) Inspiratory Flow Rate (Demand) is Met Using Nasal Pressure Another embodiment estimates the inspiratory flow using nostril pressure measured over different flow rates. The airway pressure could be measured, or estimated/determined in a number of ways. For example in FIG. 3 the airway pressure was monitored via a pressure line positioned on the outside of a cannula prong, which is then placed inside the nasal cavity The airway pressures may follow an S-shaped curve with an increasing flow rate (FIG. 3 which (shows nostril pressures collected at the point of peak inspiration over a range of flow rates in an in vitro model)). The minimum gradient may occur as the delivered flow rate meets the peak inspiratory flow rate. Thus by calculating the minimum gradient it may be possible to determine the peak inspiratory flow rate. At the start of the therapy it may be necessary to undergo a calibration step. In this calibration step, the nostril pressure may be measured over a range of delivered flow rates to determine the flow rate at which the minimum gradient occurs and thus the patient's peak inspiratory flow rate. Calibration may be done periodically, such as but not limited to every 30-180 minutes, to reassess the patient's peak inspiratory demand. A clinician may then manually set, or a device may automatically set a flow rate which is equal to or greater than that which occurred at the minimum gradient to ensure the peak inspiratory demand may be met. The following ways to determine the minimum gradient are not an exhaustive list of ways, and therefore this calculation is not limited to the following. Firstly a third degree polynomial may be fitted to the pressure curve. By taking the second derivative of this polynomial it may be possible to solve for the point of inflection which may give the flow rate at which inspiratory demand is met. Using the small nose, medium cannula patient as an example, the peak inspiratory flow rate was calculated to be 23 L/min A second approach may calculate the linear gradient between each consecutive measured pressure data point, and may determine the flow rate at which a minimum gradient may occur. Using the small nose, medium cannula patient as an example, the peak inspiratory flow rate was calculated to be within a range of 30-32.5 L/min. The peak inspiratory flow rate for the in-vitro model used in FIG. 3 is 30 L/min. The two approaches may be compared, averaged or weighted to provide a more accurate representation of the peak inspiratory flow rate. Weightings may be determined from the $R^2$ values, an $R^2$ value of >0.95 may indicate good curve fitting.

In some embodiments airway pressure monitoring may be used to determine the flow rate at which the pressure equals zero at any point during the respiratory cycle. This may be determined using the S-curve of FIG. 3. To find the inspiratory demand at a particular point in the breath cycle (eg: peak) the airway pressures taken across the flow rate range are measured at the same point in the breath cycle A delivered flow greater than inspiratory demand may create a backpressure in the airway of the patient. If the inspiratory airway pressure is zero it may be estimated that inspiratory demand may have been met and hence this can be used to provide an estimation of the inspiratory demand flow rate. For example, using FIG. 3 the point where nostril pressure may equal zero may be solved from the fitted polynomial at a flow rate of 26.5 L/min which in this test is during peak inspiration.

Figure 4:
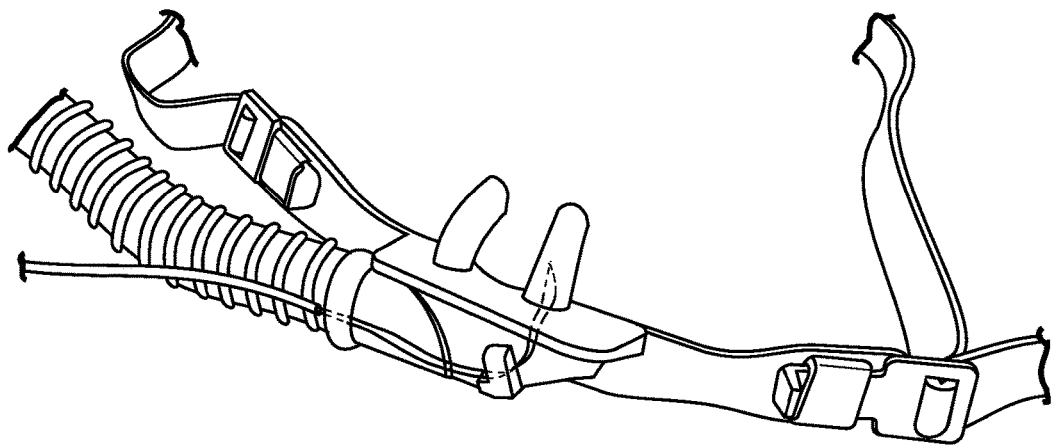
FIG. 4 is a nasal cannula with a temperature sensor.
Figure 5:
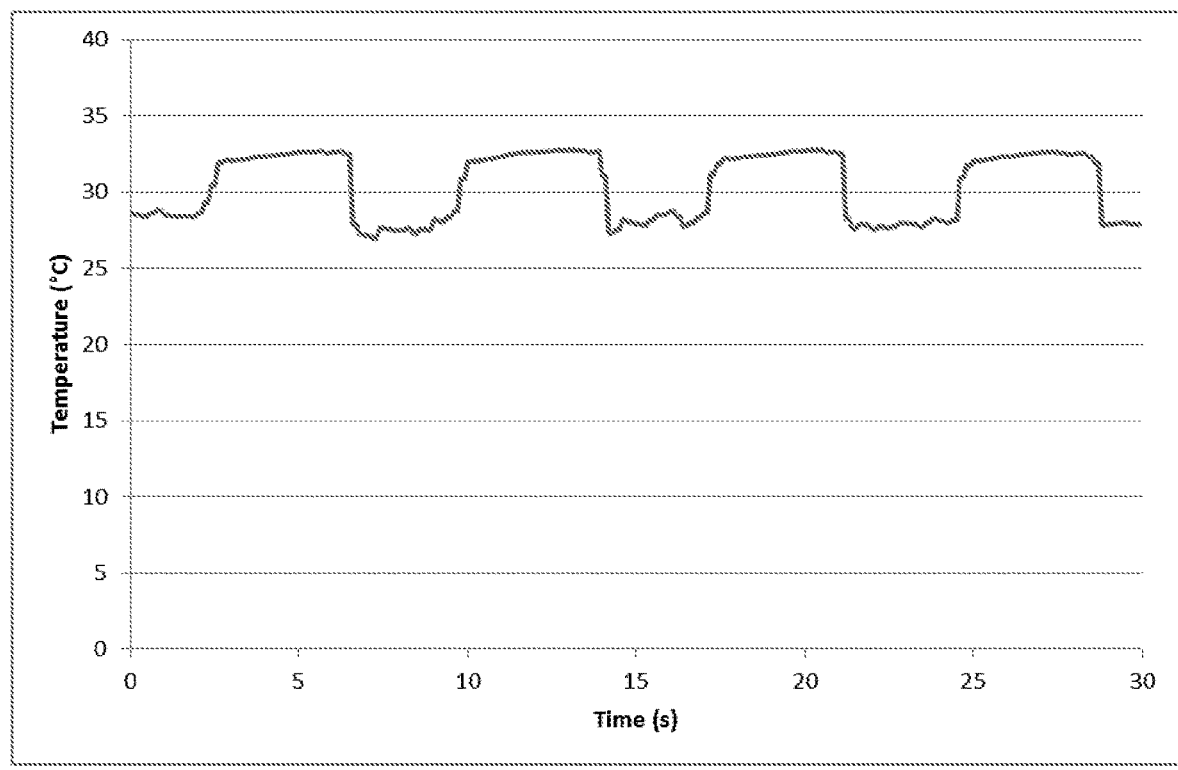
FIGS. 5-10 are graphical depictions of temperature at an interface over time.
Figure 6:
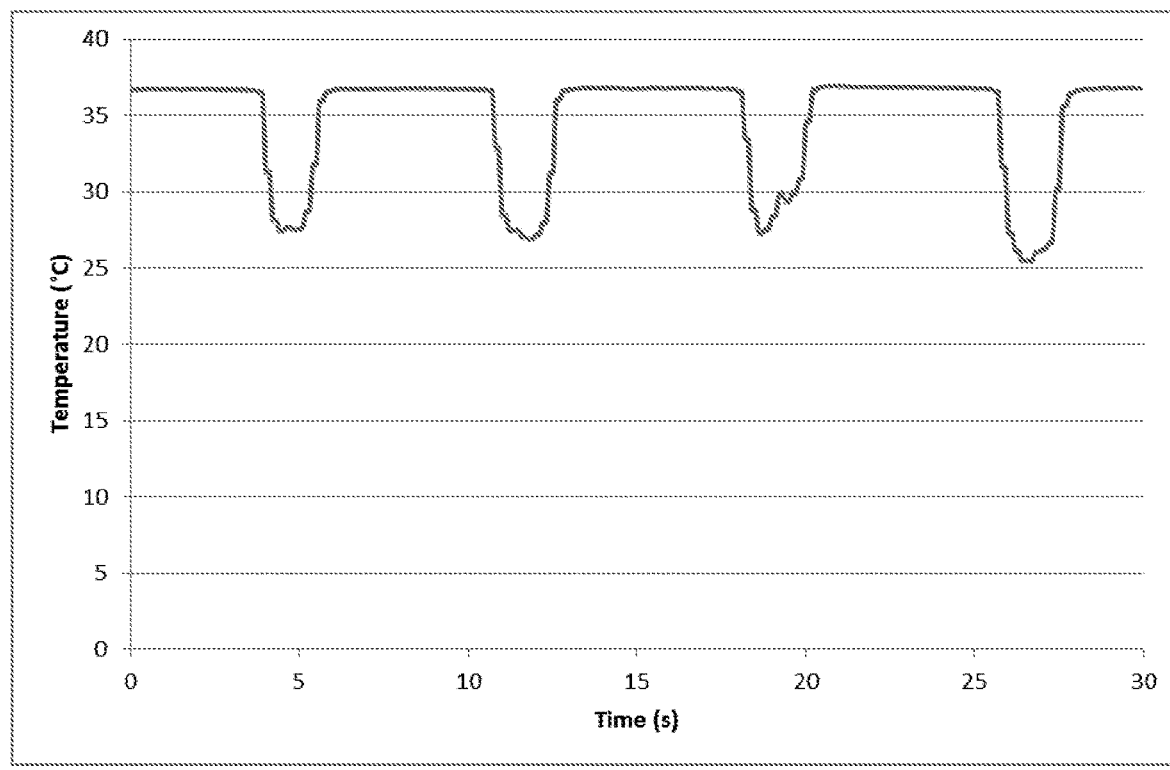
Figure 7:
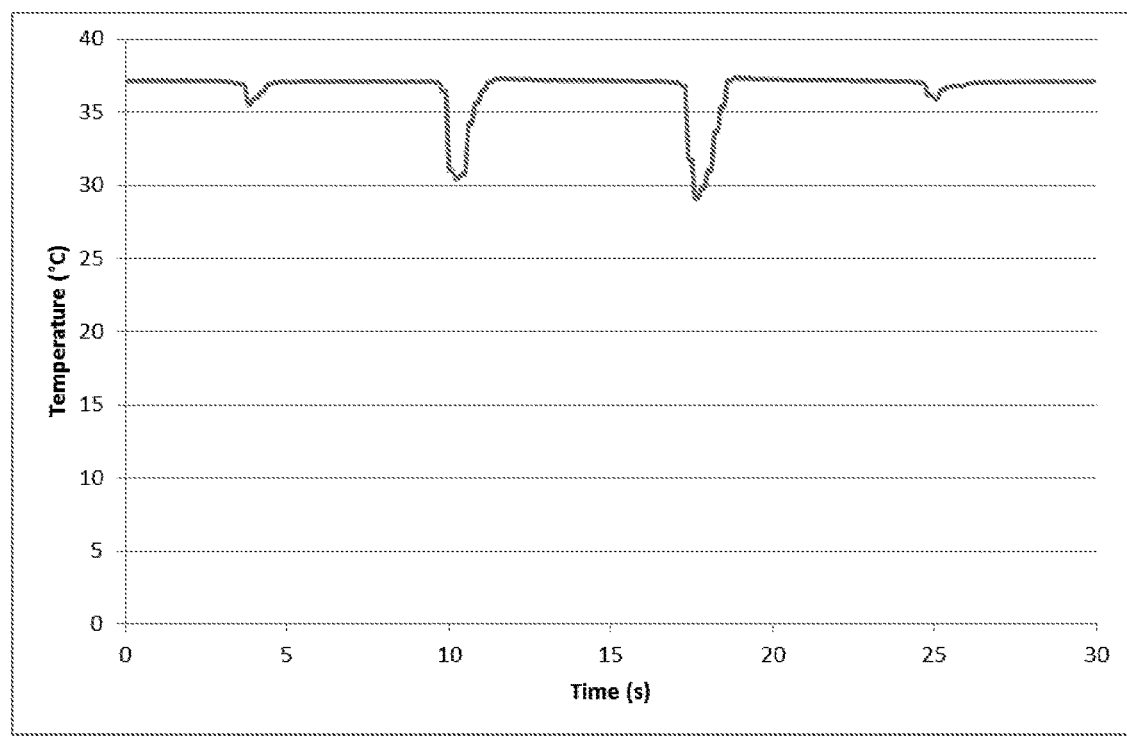
Figure 8:
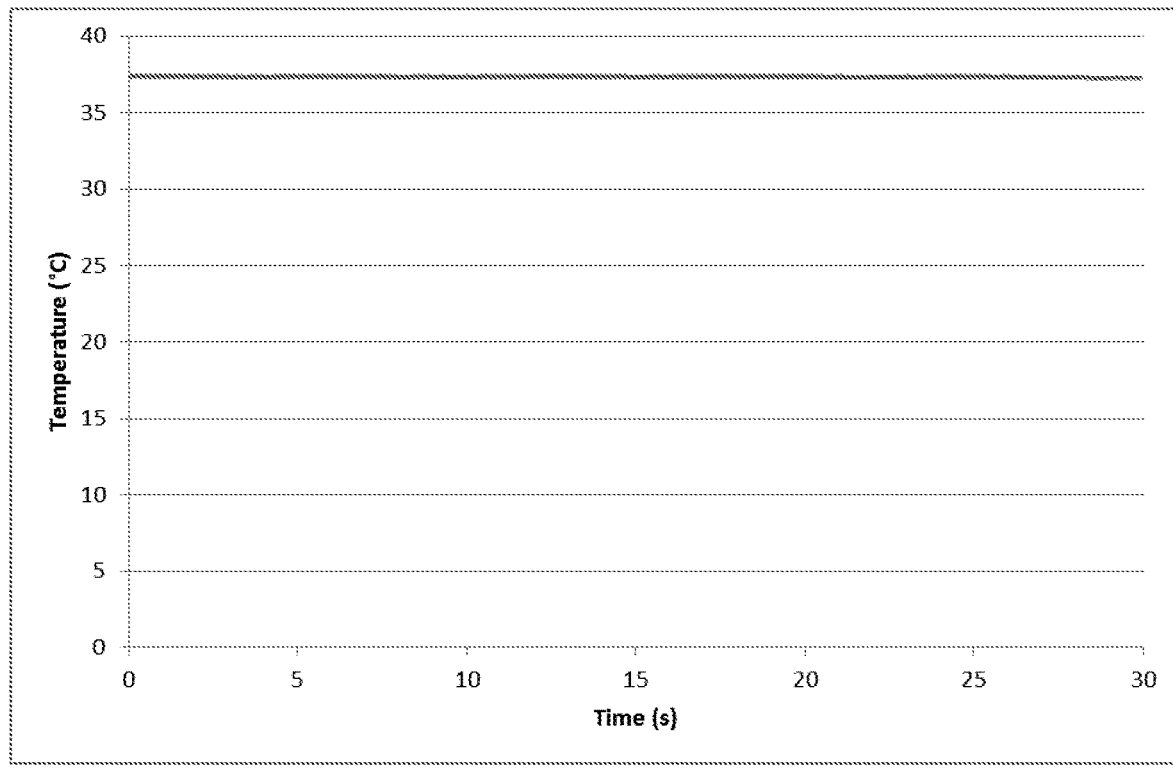
Figure 9:
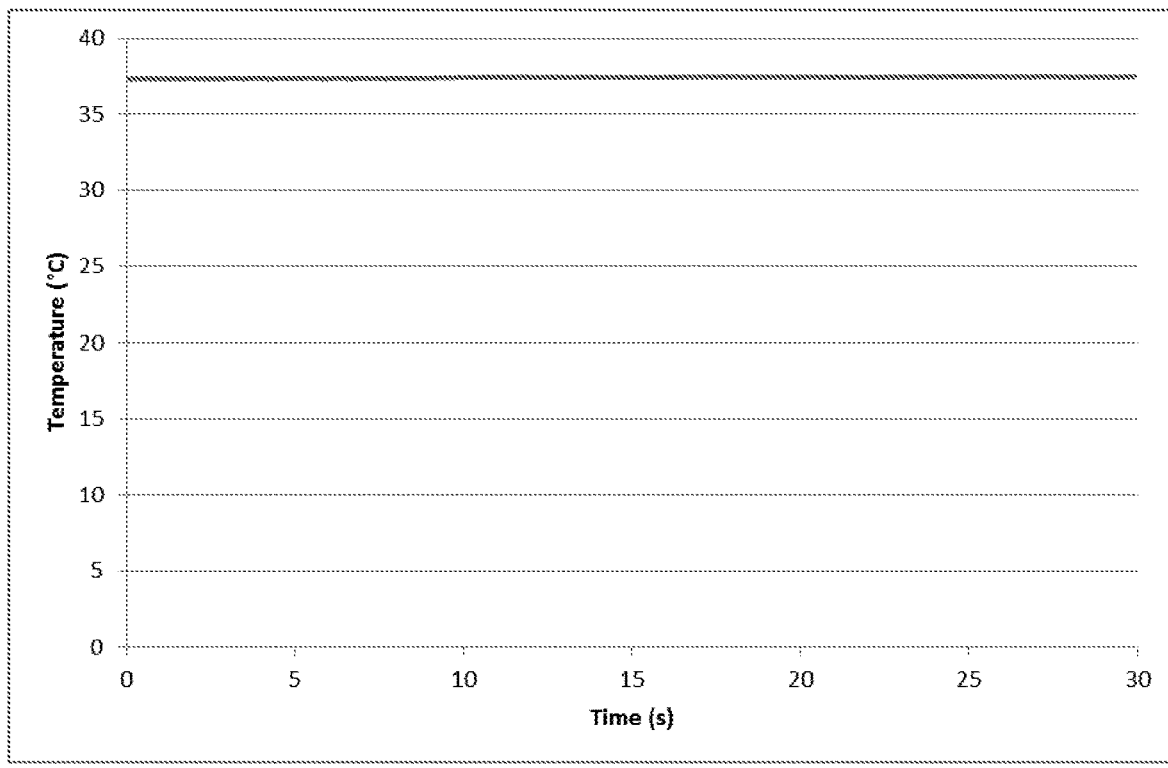
Figure 10:
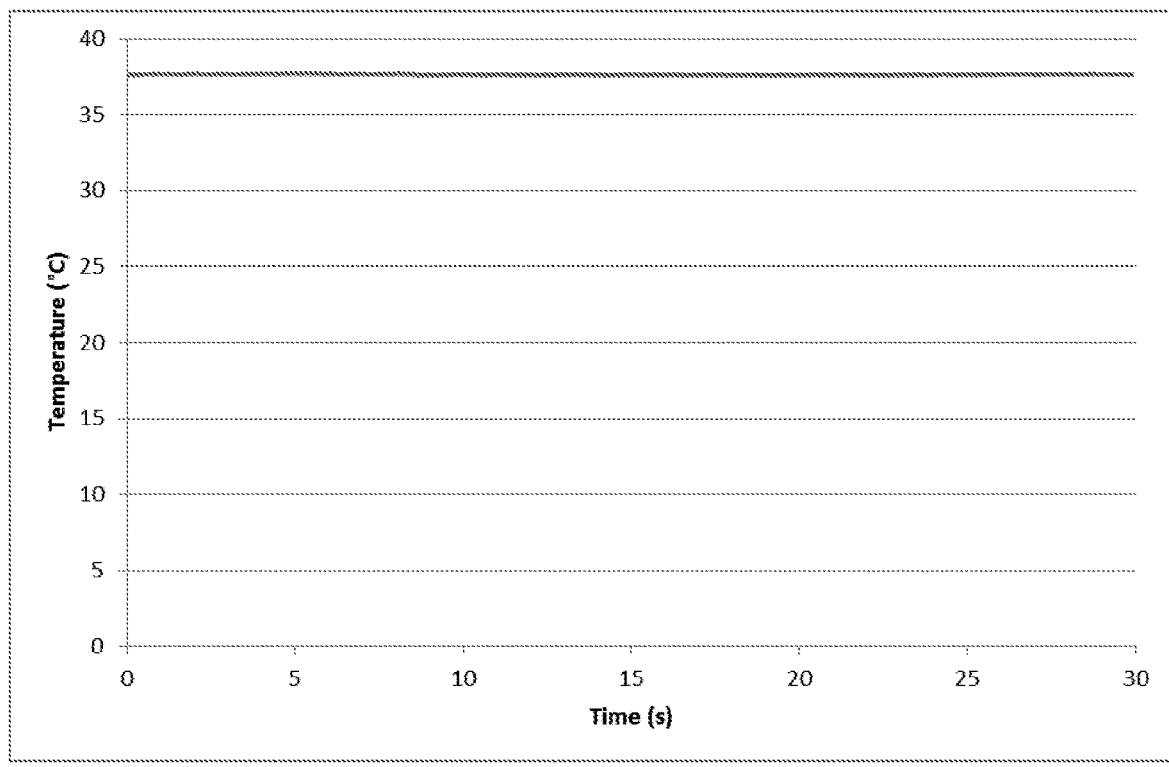
Figure 11:
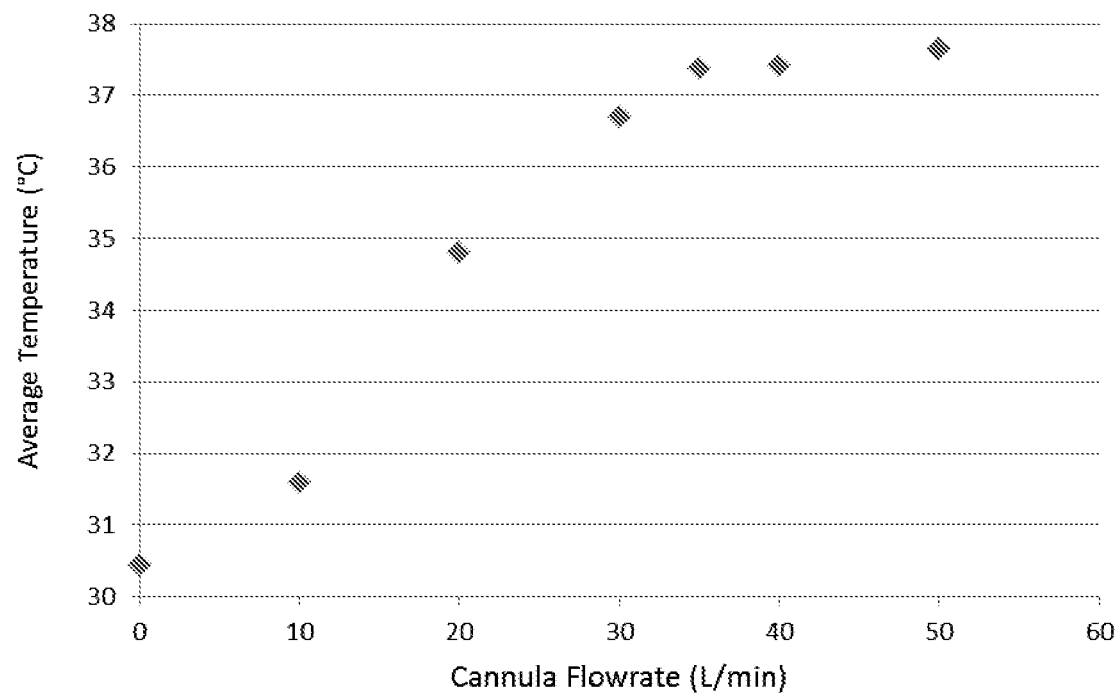
FIG. 11 is the average temperature generated at different flow rates.

1.5 Determining if Peak Inspiratory Flow Rate (Demand) is Met Using Temperature Monitoring 1.5.1 General Description In some embodiments temperature monitoring may be used to determine if any room air may have been entrained during inspiration. The flow delivered by the device or exhaled from the airways may be at a temperature that is different to room air. Room air as described herein, may be but is not limited to being between 20° C.-24° C. Therefore a fast response temperature sensor, such as, but not limited to a thermocouple, thermistor, or the like, may be positioned on the interface (FIG. 4), to detect if room air is passing over the interface or if it may be warmer air from the airways or interface. If inspiratory demand is not met, flow may be entrained over the interface and the temperature may approach room temperature thus may deviate from the temperature delivered by the device or exhaled from the airways. Thus, FIGS. 5-10 show in-vivo tests that were performed on a 28 year old male. The delivered gas temperature is approximately 37° C., thus, troughs represent where cooler room air may have been entrained. As the flow rate is increased, the figures show fewer troughs, until the point where the peak inspiratory flow demand may be met, which in this example may be greater than 35 L/min Here the figures show no troughs, which may indicate that no room air has been entrained. An alternative embodiment may log the average temperature, which may result in the average temperature approaching the temperature of the delivered flow if inspiratory demand is being met, or exceeded (FIG. 11). To determine if the peak inspiratory demand has been met the average temperature may be within a specific range of the delivered flow temperature at the interface. An example uses in-vivo tests on a 28 year old male to show that in this case the range may be within ±0.5° C. of the set point and may plateau at the set point between 30-35 L/min, which may indicate the peak inspiratory demand falls within this range. These approaches are not limited to the above examples and may be used to determine and meet the peak inspiratory demand of a patient.

Using these approaches, the temperature may be continuously monitored so that the flow rate may be adjusted with the patient's inspiratory demand. Monitoring may involve but is not limited to measuring the temperature at the interface for any amount of breaths between 3-720 breaths, or any time period between 5 seconds-1 hour. These ranges serve as examples of possible ranges that could be used to determine monitoring intervals and are in no way limiting to the scope of the patent. Monitoring may allow the flow rate to be periodically changed based on any changes in the temperature of the patient. An example may be if greater than a threshold value, for example, 50% of the measured inspiratory breaths showed a temperature less than the delivered temperature, the flow rate may be increased by 5 L/min. The threshold may be a percentage between 1-100% or may be an absolute number of breaths for example 1-720 breaths. When a threshold is crossed the increase in flow rate may be between 1-20 L/min.

1.5.2 Detailed Description of One Embodiment Using Temperature Monitoring to Determine Inspiratory Demand and/or Compliance with Inspiratory Demand In some embodiments, temperature monitoring is utilised to carry out one or more of the inspiratory flow functions above. An apparatus and method are provided that implement temperature monitoring for this purpose.

Figure 19:
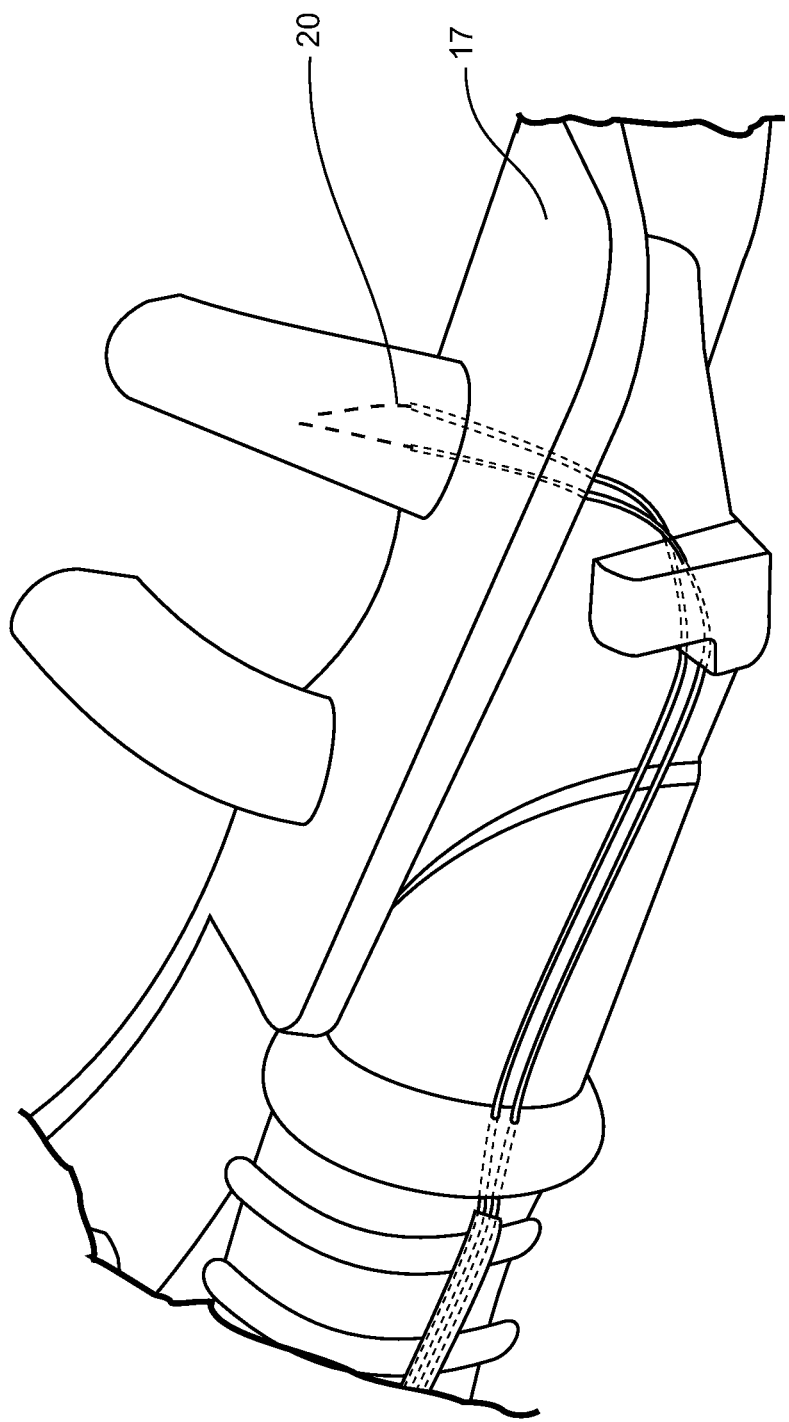
FIG. 19 is a cannula with a temperature sensor for use with a high flow therapy apparatus according to one embodiment.

Referring to FIGS. 1 and 19, the patient interface 17 of the flow therapy breathing apparatus 10 is a cannula or similar that comprises a temperature sensor 20 for measuring the temperature (or parameter indicative of temperature) of gasflow external to the patient interface that enters/leaves the nares of the patient during use of the apparatus. The temperature sensor 20 can be any suitable sensor, and need not necessarily be a sensor that actually measures temperature. The term "temperature sensor" refers to any sensor that determines a parameter indicates temperature or from which temperature could be determined. Alternatively, the temperature could be determined in some other manner, such as inferred from other parameters, so a temperature sensor is not the only possibility for obtaining temperature. In the present embodiment, preferably a thermocouple or similar fast response temperature sensor is disposed on an external part of the patient interface 17 to measure gasflow entering/exiting the nares. The temperature sensor preferably is placed on a nasal prong 18 of the cannula 17, although this is not essential. That said, it is preferable to have the temperature sensor as close to the area between the prong and the nare as possible so as to measure the temperature of the gasflow actually entering/exiting the nare. The temperature sensor 17 is connected via a wire or other suitable conductor 9 to an input of the controller 13 for transmitting output from the temperature sensor 20 to the controller. Alternatively, the temperature sensor 17 could have or be connected to a transmitter for wireless transmission 8 of output from the temperature sensor to the controller, via a transceiver 15 coupled to the controller.

The temperature of the gasflow entering the nare (as determined from the temperature sensor 20) can be used to determine if any room (ambient) air has been entrained during inspiration. As described above if, during use of the apparatus, a patient is inhaling entrained ambient air, it means that the gasflow generated by the flow generator 11 is not at a sufficient flow rate to meet the inspiratory demand (also termed "inspiratory flow"). This results in sub-optimal therapy for the patient. Usually, the ambient air temperature is lower than the target or delivered temperature. If the temperature measured at the sensor 20/nare remains at or near the target temperature of generated gasflow for delivery to the patient, then this indicates that (usually cooler) ambient air has not been entrained into the inspiratory flow and inspiratory demand is being met by the delivered flow rate of the apparatus. If, however, the temperature measured by the temperature sensor deviates from the target temperature and approaches the ambient temperature, then this is an indication that ambient air has been entrained into the inspiratory gasflow—the ambient air causing a reduction in temperature (with respect to target temperature) at the nares. This means that the flow generator is not delivering sufficient gasflow to meet the inspiratory demand and the shortfall is being made up from the entrained ambient air. This may provide sub-optimal therapy, and may be desirable to take some action to increase the flow rate of gas generated and delivered by the apparatus to meet respiratory demand or at least to indicate this to the user. The controller 13 can therefore be programmed based on a relationship between the measured temperature and the ambient temperature and/or target temperature to utilise the temperature sensor output to carry out one or more of the respiratory flow functions mentioned above.

The relationship between temperature, ambient air entrainment, target temperature and inspiratory demand will now be described in more detail with reference to FIGS. 21 to 27. The flow generated by the flow generator 11 and delivered/conveyed to the patient by the flow therapy breathing apparatus 10 or exhaled from the airways of the patient during expiration typically is at a temperature that is different to room (ambient) air. Room (ambient) air described herein, for example can be (but is not limited) to between 20° C.-24° C. The fast response temperature sensor 20, such as, but not limited to a thermocouple, thermistor, or the like, positioned on the interface, takes temperature readings that enables the controller 13 to detect if cooler room air is passing over the interface or if warmer air from the patient airways or interface is passing over.

If inspiratory demand is not met, ambient gasflow is entrained over the interface as the patient draws on ambient air to make up the shortfall in gasflow. As the ambient temperature is lower than the temperature of gasflow delivered to the patient, the temperature at the temperature sensor approaches room temperature and thus deviates from the (target) temperature delivered by the device or exhaled from the airways. If inspiratory demand is being met, the gasflow is not entrained from ambient air and so the temperature measured by the temperature sensor will not approach the ambient temperature and instead will be at (or near) the (delivered) target temperature or be at (or near) the temperature of the exhaled patient gas.

During inspiration if the delivered flow rate is in excess of the inspiratory demand, the excess delivered flow will not be inhaled by the patient and instead will flow back past the sensor. In this case the temperature sensor will measure a temperature at, or near the delivered gas temperature. During expiration the delivered gas will be forced back towards the interface by the force of the patient's exhaled breath and the measured gas temperature will be a mix of the delivered temperature, and the patient's naturally conditioned expiratory gas. It is desirable that the blended temperature of these two gases is distinguishable from ambient temperature, so as to detect when the measured temperature is caused by entrainment. Alternatively, a breath detection algorithm may be used where it is possible to determine the separate periods of inspiration and expiration. In this case it is only necessary to detect entrainment during the inspiratory phase and the expiratory temperature may be disregarded. For this it is only necessary that the delivered temperature and ambient temperatures are significantly different as the blended delivered temperature and naturally conditioned expiration temperature will not be taken into account.

FIGS. 21 to 27 show the temperature measured (at different flow rates) over time by the temperature sensor in in-vivo tests that were performed on a 28 year old male. These graphs, by way of example, demonstrate the observations that the present invention is based on. The delivered (target) gasflow temperature from the flow generator to the patient is approximately 37° C. Ambient temperature is approximately 20 to 24°. Referring to the Figures, troughs represent where cooler room air may have been entrained as the measured temperature is lower than target temperature and/or approaches the ambient temperature. As the flow rate is increased, the successive Figures show fewer troughs (ambient air entrainment), until the point where the inspiratory flow demand is met, such as demonstrated in FIG. 27, which in this example may be greater than 35 L/min Here the Figures show no troughs above 35 L per minute, which indicates that at that flow rate or above there is sufficient gas flow to meet inspiratory demand (including peak inspiratory demand) so no room air has been entrained.

Based on this observation, in one embodiment, the temperature at a particular time can be taken, passed to the controller 13 and compared in the controller to a threshold, e.g. related to the ambient air temperature and/or delivered gas (e.g. air and/or oxygen) target temperature, and based on that entrainment or otherwise, ambient air is detected, thus indicating whether inspiratory demand is met. The respiratory flow functions can then be implemented by the controller 13 in conjunction with the apparatus 10.

In an alternative embodiment, the average temperature can be logged/determined in the controller 13 from a plurality of temperature readings. If the average temperature approaches or exceeds the target temperature of the delivered flow (see FIG. 27), then it can be an indication that inspiratory demand is being met by the apparatus. If the average temperature approaches the temperature of the ambient air and/or is below the target temperature, then it can be an indication that entrainment of ambient air is occurring and inspiratory demand is not being met.

Based on this observation, in one embodiment, to determine if the inspiratory demand has been met, the average temperature from the temperature sensor measurements can be compared by the controller 13 to a range of the delivered flow target temperature (and/or ambient air temperature) at the interface. If average temperature falls within a particular range, then it can be determined that inspiratory demand has been met. An example uses in-vivo tests on a 28 year old male to show that in this case the range may be within ±0.5° C. of the set point (of delivered gas (e.g. air/oxygen) flow temperature) and may plateau at the set point between 30-35 L/min, which can indicate the inspiratory demand falls within this range. These approaches are not limited to the above examples and may be used to determine, display and/or meet the inspiratory demand of a patient and/or determine and display that entrainment is occurring and/or adjust the flow to prevent entrainment For this 'average case' the delivered and expiration temperatures would ideally be similar (that is: both 37° C.), and different from ambient, in order to make it obvious when there are deviations from the delivered expiratory temperature.

Alternatively, the invention could also work if both the delivered and expiratory temperatures are (significantly) greater than the ambient temperature and the delivered temperature is the lower temperature out of the delivered and the expiratory temperatures). In this case, any reduction from the delivered temperature can be sure to be from entrained air, not from a lower expired gas temperature being blended in. The invention could also work if both the delivered and expiratory temperatures are (significantly) less than the ambient temperature and the delivered temperature is the higher temperature out of the delivered and the expiratory temperatures). In this case, any increase from the delivered temperature can be sure to be from entrained air, not from a lower expired gas temperature. If inspiration only was measured, the measured (inspiratory) temperature could be directly compared to the target temperature to check for entrainment during inspiration and the expiratory temperature could be ignored.

Using these approaches, the temperature may be periodically or continuously monitored (and optionally use an averaged or instantaneous figure) so that the flow rate of the apparatus can be adjusted by the controller 13 with the patient's inspiratory demand and/or an indication provided to the user so that they can manually control the apparatus to adjust the flow rate, or take other action. The patient's inspiratory temperature can be averaged over any number of breaths between 3-720 breaths, or any time period between 5 seconds-1 hour. These ranges serve as examples of possible ranges that could be used to determine monitoring intervals and are in no way limiting to the scope of the patent. Monitoring optionally allows the flow rate to be periodically changed based on any changes in the temperature of the patient. For example, if greater than a threshold value, for example 50% or more than 5, of the measured inspiratory breaths showed a temperature less than the delivered temperature (and the ambient temperature is below the delivered temperature), the flow rate may be increased by 5 L/min. The threshold may be a percentage between 1-100% or may be an absolute number of breaths for example 1-720 breaths. When a threshold is crossed the increase in flow rate may be between 1-20 L/min.

Figure 20:
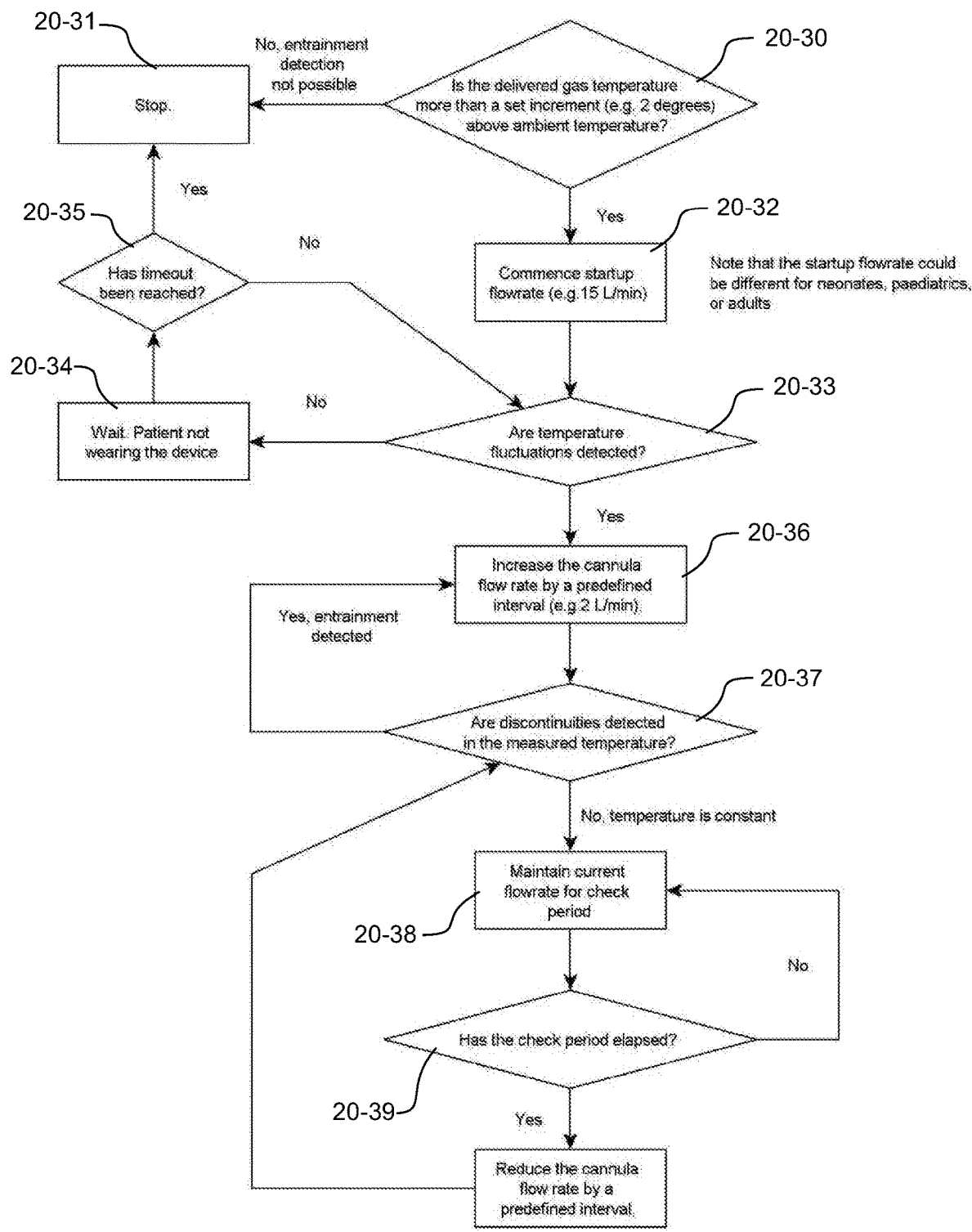
FIG. 20 is a flow diagram showing operation of a high flow therapy apparatus according to one embodiment.

A (non limiting) exemplary embodiment is shown with respect to FIGS. 1, 19 and 20.

A patient uses a flow therapy breathing apparatus 10 such as that shown in FIG. 1, connected to a cannula 17 shown in FIGS. 1, 19 with a thermocouple temperature sensor 20. Upon operation, temperature readings from the thermocouple 20 are transmitted (wired or wirelessly) to the controller 13 and logged to either create instantaneous temperature readings and/or an average temperature record. Upon initial start-up, step 20-30, the controller 13 first determines if the delivered gas temperature is above a set increment (e.g. 2°) above the ambient temperature. If it is not, step 20-31, there is not sufficient difference between ambient temperature and delivered gasflow temperature for the method to work, and detection stops. Otherwise, step 20-32, the flow therapy apparatus 10 commences delivery of gasflow to the patient, e.g. at 15 L per minute or a flow rate that is unlikely to meet the peak inspiratory demand of the patient.

Temperature readings (or readings indicating temperature) from the temperature sensor 20 are transmitted to and logged by the controller 13 and analysed. If temperature fluctuations are not detected, step 20-33, it is determined by the controller that the patient is not wearing the device, step 20-34. If a timeout is reached, step 20-35, then the monitoring process stops. Otherwise, step 20-33, the test is carried out again. Otherwise, step 20-33, if temperature fluctuations are detected by the controller 13, the controller operates the flow generator 11 of the flow therapy apparatus to increase the flow rate of gas delivered to the patient by a predefined level, e.g. 2 L per minute, step 20-36. The controller analyses the temperature readings it receives, and if fluctuations/discrepancies in the temperature are detected by the controller 13, step 20-37, then it is determined that entrainment has occurred of ambient air, indicating that inspiratory demand is not being met by the flow therapy apparatus. As a result, the controller 13 operates flow generator 11 the flow therapy apparatus to increase the flow rate delivered to the patient, step 20-36, to try to meet inspiratory demand. Otherwise, if the temperature remains constant, this is an indication that there is no ambient gasflow entrainment and therefore the flow therapy apparatus is providing sufficient gasflow to meet inspiratory demand and no action is taken by the controller. The controller 13, step 20-38, maintains the current flow rate for a period. Once that period has elapsed, step 20-39, the controller 13 operates the flow generator 11 of the flow therapy apparatus to drop the flow rate and carry out the check again, step 20-37, to determine if there is a fluctuation/discrepancy in the temperature. The determined inspiratory demand of the patient could be displayed to the user, or entrainment, or the flow could be automatically adjusted etc. This process could be carried at the start of operation or throughout the operation of the flow therapy apparatus.

This embodiment on the flow chart assumes a delivered temperature approximating 37° C. by way of example, but this should not be limiting to the scope of the invention. Because of this the expiratory and delivered temperatures will be approximately the same and so any temperature fluctuations/discontinuities must be caused by entrainment. Entrainment detection could also be considered as any temperature deviation from the delivered/expiratory temperature and towards the ambient temperature. In non-37° C. cases, measurements would occur during inspiration only so that direct comparison with the delivered temperature can be made. Or as above, the expiratory and delivered temperatures would both need to be greater than ambient, and delivered temperature less than the expiratory. For this case, entrainment could also be considered as any temperature deviation below the delivered temperature and towards the ambient temperature. Another possible method could be to check for the number of measured temperature levels. The presence of three temperature levels would represent the delivered, expiration and entrained ambient temperatures, indicating inadequate flow rate. Two temperature levels would indicate adequate flow to meet inspiratory demand (delivered and expiratory temperatures measured only).

At suitable times, based on the outcome of the process, the process can involve the controller and apparatus carrying out one or more of these inspiratory flow functions:
- determining a parameter indicative of ambient air entrainment and/or insufficient generated gasflow to meet inspiratory demand,
- determining if ambient entrainment and/or insufficient generated gasflow to meet inspiratory demand is occurring,
- determining the (peak) inspiratory demand
- determining the amount of entrained flow
- providing an indication (e.g. on a display) of the entrainment parameter, and/or whether entrainment and/or insufficient generated gasflow to meet inspiratory demand is occurring,
- providing an indication (e.g. on a display) of the (peak) inspiratory demand or entrained flow
- controlling the flow generator to meet inspiratory demand,
- providing an indication (e.g. on a display) of inspiratory demand compliance to a user in order to manually control (e.g. through the user interface) the flow generator to meet inspiratory demand,
- providing a recommendation to the user of a flow rate that meets or exceeds the measured peak inspiratory flow.

That will be appreciated that the above description relates to just one embodiment and variations. The controller in the flow therapy apparatus can utilise the measured temperature information from the temperature sensor to assist in providing flow to the patient that meets in the inspiratory demand. That can be by way of the controller using the temperature information and the observation described above and doing any one or more of the inspiratory flow functions.

Some embodiments may deliver the instantaneous demand of a patient across their inspiratory demand. This may be a continuously monitored and variable flow rate that may match or exceed the inspiratory flow rate of a patient at any point of the inspiratory phase. This may improve patient comfort as the delivered flow rate may be reduced when not required.

Figure 12:
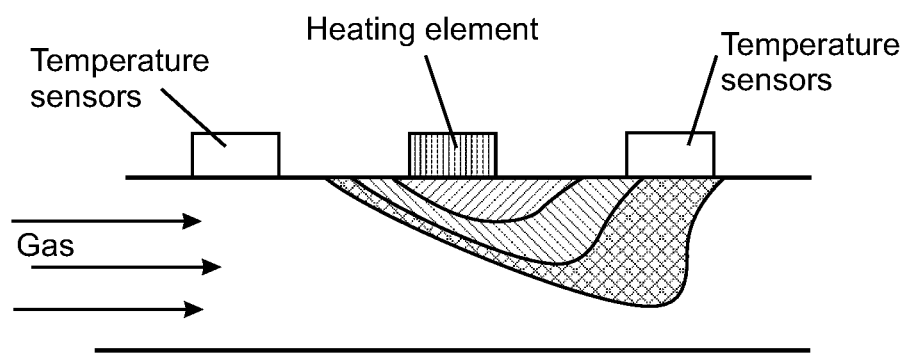
FIG. 12 is an example of a calorimetric flow sensor.

1.6 Determining if Peak Inspiratory Flow Rate (Demand) is Met Using a Calorimetric Flow Meter In one embodiment a calorimetric flow meter may be used to determine nasal flow, which may include two or more temperature sensors separated by a short distance and located either side of a small heating element and positioned on the cannula (FIG. 12). By measuring the difference in temperature detected by the sensors, both the direction and the magnitude of the flow may be measured. Flow direction is determined to be in the direction of the temperature sensor that measures a higher temperature since the heat emitted from the heater is carried in the upstream direction, as illustrated in FIG. 12. The magnitude of the flow is determined by calibrating flow with the difference in temperature between the two sensors. With nasal flow measured and cannula flowrate otherwise known or similarly measured, this may provide an estimation that the peak inspiratory demand may have been exceeded, or that the flow may be short of supplying the patient with their peak inspiratory demand. It may also estimate the difference between the flow delivered and the peak inspiratory demand that may be required for that patient. This approach does not require a calibration step as the patient peak demand may be met accurately and instantly, or may be exceeded by a defined amount, based on the temperature data. The entrained flow may be continuously monitored to enable the delivered flow rate to be adjusted as the patient's inspiratory demand changes. Or alternatively monitoring may occur but is not limited to occurring anywhere in a range of 3-720 breaths, or a range of 5 seconds-1 hour, and the flow rate may be periodically changed based on any changes.

1.7 Determining if Peak Inspiratory Flow Rate (Demand) is Met Using a Flow Sensor In one embodiment a flow direction sensor may be positioned at the cannula (FIG. 13) and used to detect the direction of flow into the nares. If the inspiratory demand is not met, entrainment of room air may be detected as the entrained air flows past the sensor. As a result the flow rate may be increased until this entrainment may no longer be detected.

A flow speed sensor may determine if inspiratory demand is not met as the flow speed between the end of expiration and the peak of inspiration may equal zero at some point as the flow changes direction. Increasing the flow rate so the flow speed into the nares does not fall below zero may prevent entrainment of flow as the flow may travel only in one direction (out of the nose), and thus flow may not be entrained. The apparatus could respond by informing the user of the presence, or not, of entrainment, recommend a change in flow rate in order to meet inspiratory demand, or automatically change the flow to meet inspiratory demand/a % of inspiratory demand A mechanical signal positioned on the interface may provide a clear indication of whether or not room air is being entrained by the patient. A mechanical signal may be embodied by but is not limited to a tell-tale structure, miniature wind-vane or the like. An example of a tell-tale structure may be but is not limited to a piece of yarn, string, or length of flexible material that may move in line with the flow direction. In this way, if entrainment is occurring the mechanical signal may be sucked towards or into the nose, and if entrainment is not occurring it may be blown out of the nose. A miniature wind vane may be coloured, for example, it may be red on one side or at one end to indicate entrainment and may be green on the other side or at the other end if the flow is moving out of the nose. The above example is in no way limiting, as any number or combination of colour or colours may be used. The user could be informed of the status of the mechanical signal that would ensure entrainment does not occur/inspiratory demand is met.

1.8 Determining if Peak Inspiratory Flow Rate (Demand) is Met Using Electromechanical Switch Another embodiment uses an electromechanical switch positioned on the interface which may either connect or disconnect with an electrical circuit if air is entrained, and may then be monitored to determine whether the patient is entraining room air. As a patient entrains room air a negative pressure may be generated in their nose. This negative pressure may cause the switch to elevate on entrainment of room air which may enable the connection or disconnection with an electrical circuit. If the inspiratory demand of a patient is met, they may not be entraining room air and the flow may be directed downwards, out of the nose. Thus a negative pressure may not be generated in the nose if entrainment is not occurring and therefore the switch may not elevate and the connected or disconnected state of the electrical circuit will be maintained. The connection or disconnection state of the circuit may be monitored to determine if the patient is entraining room air and thus it may indicate if inspiratory demand is being met.

Figure 14:
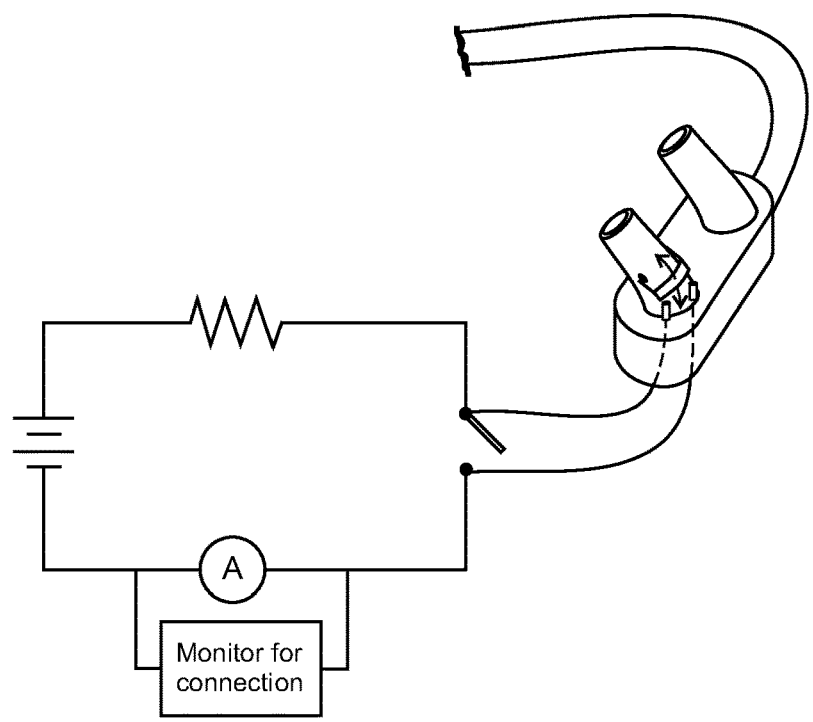
FIG. 14 is a cannula connected to an electrical circuit.

An example of this approach is shown in FIG. 14 where a switch is positioned on the outside of a cannula prong and if the switch is in a normal closed position it may be contacting the connecting pins located under the switch and completing the circuit (where the natural weight of the switch holds the switch against the pins). If entrainment of room air occurs the switch may be elevated due to negative pressure that may be present in the nose of a patient which may (overcome the weight of the switch and) cause a break in the circuit as the switch may disconnect from the pins. Any break in a circuit may be detected, for example by an ammeter and may indicate that entrainment of room air is occurring which may indicate that inspiratory demand is not being met. In this case increasing the delivered flow rate may prevent further entrainment of room air and may help to meet inspiratory demand. A visual aid may be added to increase usability. A visual aid may refer to but is in no way limited to a light that may be added to the circuit. The light state may indicate if entrainment is occurring. The light state as herein described refers to the light being on or off and this may be an indication of whether or not entrainment is occurring. The light may be off as the circuit is disconnected and may be on if the circuit is connected. Thus if the circuit disconnects during entrainment of room air which may be due to elevation of the switch it may be expected that the light may also be off as a visual indicator to the user that entrainment is occurring and therefore the patient may not be receiving a flow that meets their inspiratory demand. On the other hand, if the circuit connects when the switch is elevated due to entrainment of room air, it may be expected that the light may be on as a visual indicator that the patient may not be meeting their inspiratory demand.

In these approaches which may determine if entrainment is occurring, it may be possible to deliver the inspiratory demand of a patient by increasing the flow rate until entrainment is eliminated. Periodically monitoring the delivered flow rate may be useful to determine if this continues to deliver the inspiratory demand of the patient. It may also be useful to periodically decrease the flow rate and to monitor the senses output to reassess the patient's inspiratory demand. In this way, delivery of excess flow to the patient may be minimised to maintain patient comfort.

Some embodiments may deliver the instantaneous demand of a patient across their inspiratory demand. This may be a continuously monitored and variable flow rate that may match or exceed the inspiratory flow rate of a patient at any point of the inspiratory phase. This may improve patient comfort as the delivered flow rate may be reduced when it may not be required.

1.9 Determining Inspiratory Flow Rate (Demand) Using Airway Pressure 1.9.1 General Description In some embodiments, airway pressure monitoring is utilised to carry out one or more of the inspiratory flow functions above. An apparatus and method are provided that implement pressure monitoring for this purpose. This embodiment relates to continual monitoring for making continual/instantaneous flow rate changes to meet inspiratory demand, but the embodiment could also work in a constant flow rate situation where the flow rate is set to meet (such as exceed or deliver a percentage of the) peak inspiratory demand.

In one embodiment the airway pressure may be monitored continuously. During natural breathing a negative pressure is created in the patient's airway as they inhale. An increasing flow rate may mean the patient may not inhale as much room air, reducing the negative pressure generated in the patient's airway during inspiration. If the flow being received is not sufficient to meet the patient's inspiratory demand, the pressure in the patient's airway may fall below zero and the patient may begin to entrain room air. If the patient's inspiratory demand is met their airway pressure may be above zero and it may prevent further entrainment of room air. A pressure line may be connected to the interface which may measure the pressure at the entrance to the patient's nose which may be located as the flow sensor in FIG. 13. To determine the flow rate at which inspiratory demand may be met, the flow rate may be increased and the pressure at the nostrils monitored until it is greater than zero. By monitoring the nose pressure a flow rate may be delivered that may cause the nose pressure to be greater than zero, which may satisfy the inspiratory demand of the patient. An example may be if the inspiratory demand of a patient is 30 L/min (FIG. 3). The pressure at the nose may exceed zero when the flow rate is at or greater than 30 L/min, for example 32.5 L/min or 35 L/min.

The airway pressure may be continuously monitored to adjust the flow rate with regards to the patient's instantaneous inspiratory flow demand.

Figure 15:
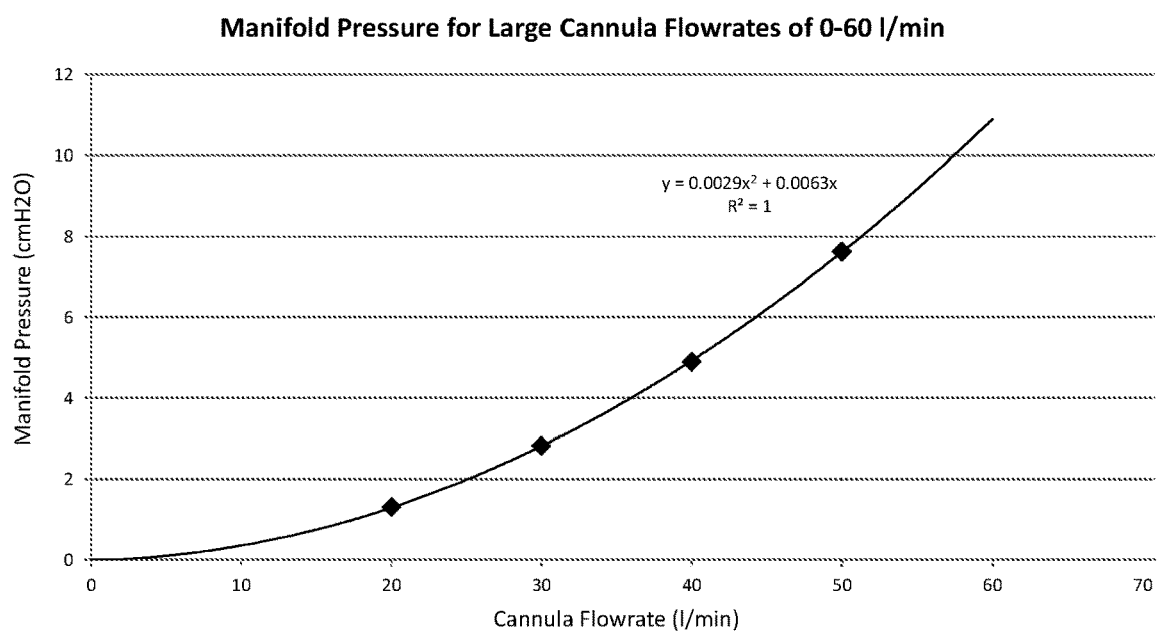
FIG. 15 is a graphical depiction of the relationship between pressure and flow.
Figure 16:
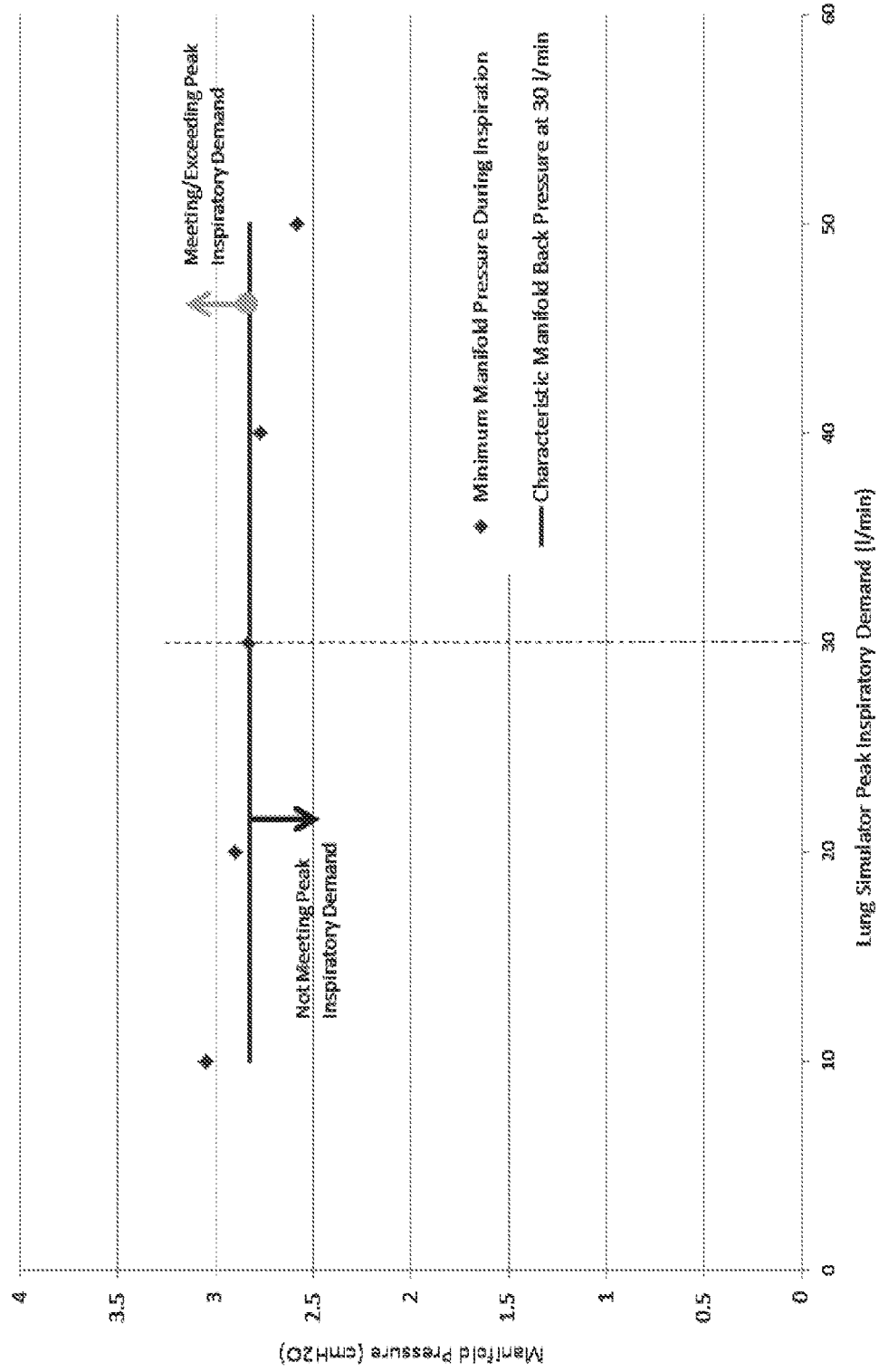
FIGS. 16-18 are graphical depictions of inspiratory demand with relation to pressure at the manifold and backpressure.
Figure 17:
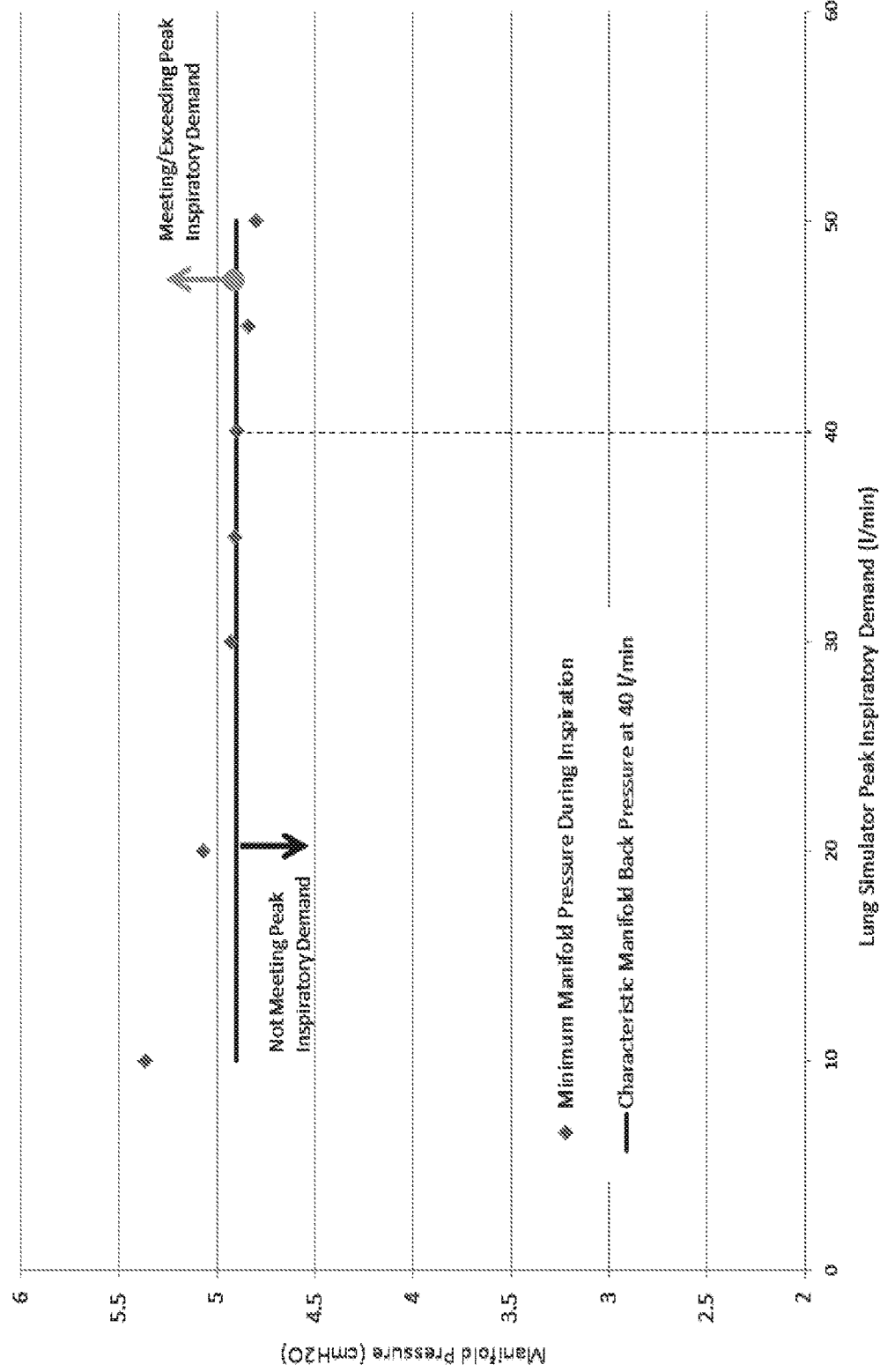
Figure 18:
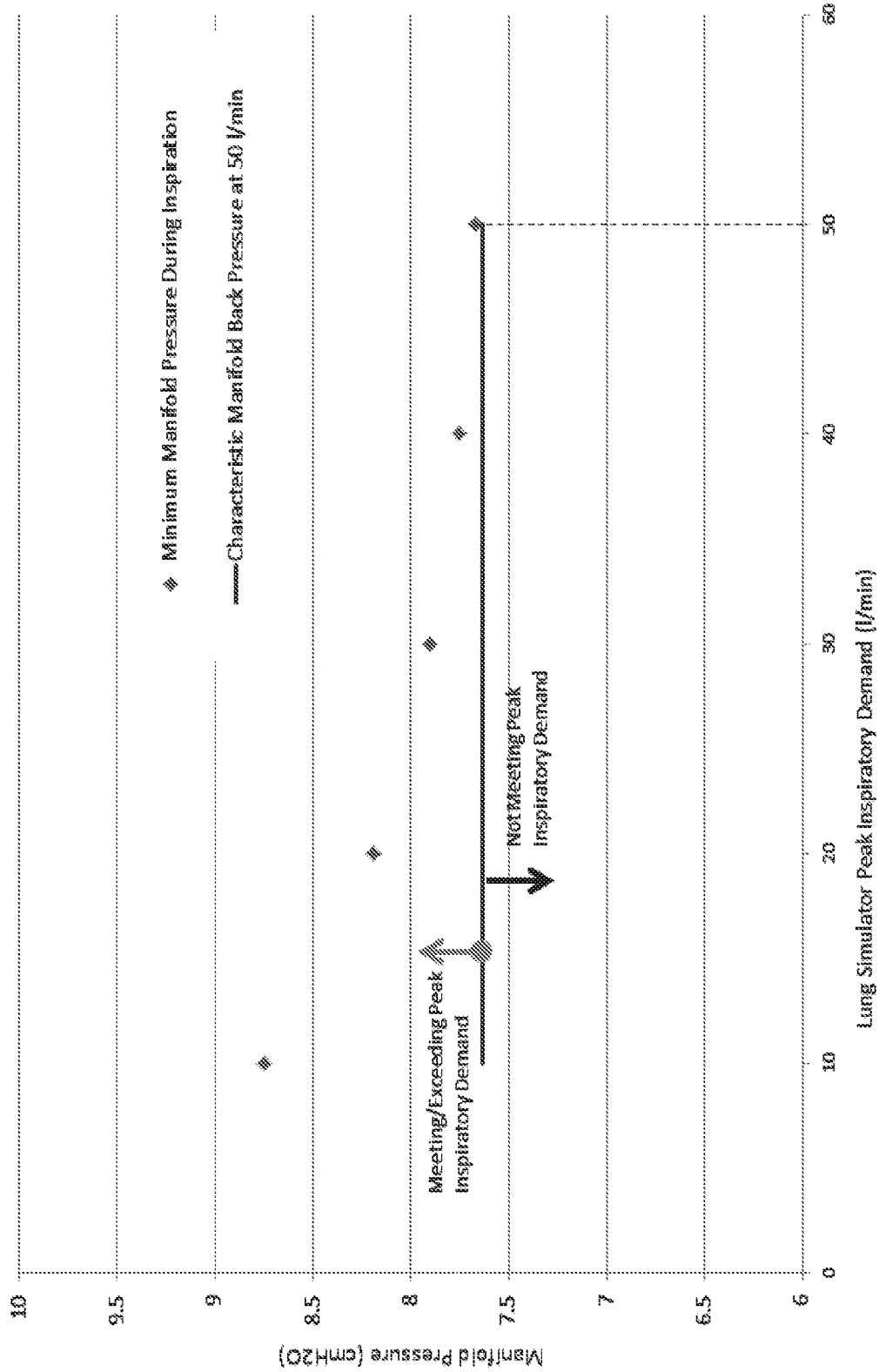

It is possible to measure the characteristic backpressure generated at a location in the system, when a patient is not wearing the interface (FIG. 15). System pressure monitoring during use, when a patient is wearing the interface, may enable comparison of the measured system pressure to the known, characteristic pressure. This comparison may estimate if inspiratory demand is met. When the patient is wearing the device, the pressure at the system may be monitored continuously. If inspiratory demand is met, the instantaneous system pressure may be greater than the characteristic backpressure for the delivered flow rate. However if inspiratory demand is not met, the instantaneous system pressure may be less than the characteristic back pressure for the delivered flow rate. This may occur because the patient may be generating a negative pressure to entrain additional room air. FIGS. 16-18 show test results conducted on an in-vitro lung simulator where the system pressure is the pressure measured in the cannula manifold, the instantaneous manifold pressure is less than the characteristic backpressure for delivered flow rates that are less than the inspiratory demand. This may indicate that entrainment is occurring. As a result the flow rate may be adjusted to meet the inspiratory demand of the patient, and the instantaneous manifold pressure may be greater than the characteristic backpressure for the delivered flow rate.

To determine which characteristic back pressure to use in the estimation, it may be necessary for the device to determine which interface is connected. A device may detect which interface is connected, the size of the interface connected, or the like, by measuring the backpressure at least one known flow rate, either with a patient during use or without a patient during a calibration step. It may also detect the interface by electronic identification, mechanical identification, user input or the like.

This approach may be controlled by measuring and monitoring the pressure at any number of places along the interface, including the manifold as described above, as well as at the chamber. By continuously monitoring the pressure, the flow rate may responsively adjust to any changes in the patient's inspiratory demand during their inspiratory cycle.

1.9.2 Detailed Description of One Embodiment Using Airway Pressure Continuous Monitoring (for Instantaneous Flow Rate Adjustment)

Figure 13:
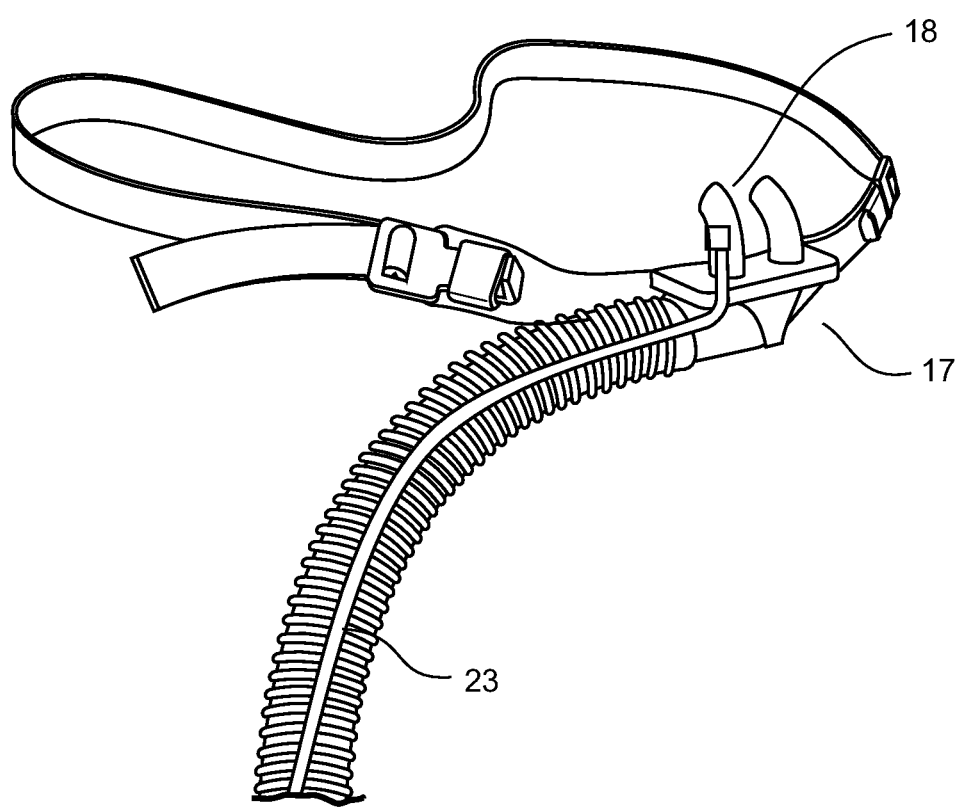
FIG. 13 shows a flow sensor, pressure line and pressure sensor located on a nasal cannula.

Referring to FIGS. 1 and 13, the patient interface 17 of the flow therapy breathing apparatus 10 is a cannula or similar, and a pressure sensor 24 (optionally used with a pressure line 23) is coupled to the interface 17 in a manner (such as near one of the nasal prongs 18) to measure pressure just inside the airways (such as nares) of the patient when the apparatus is being used. The pressure line 23 can be coupled between the cannula and the housing 4 of the apparatus 10, where a pressure sensor or similar is provided 24. The pressure sensor is coupled to and transmits its output to the controller 13. In some embodiments, the airway pressure measured by the pressure sensor 24 via the pressure line 23 can be monitored continuously in the controller 13. Analysis of the pressure measurements enables the controller to carry out one or more of the inspiratory flow functions, based on the observed details described below. In alternatives, an electronic connection (e.g.: wire relaying electronic pressure signal) or wireless transmission (i.e.: no pressure line) could be provided to the pressure sensor instead of a pressure line. A pressure line is particularly characteristic of a differential pressure sensor. Reference herein to a pressure sensor can relate to any suitable pressure arrangement.

Figure 29:
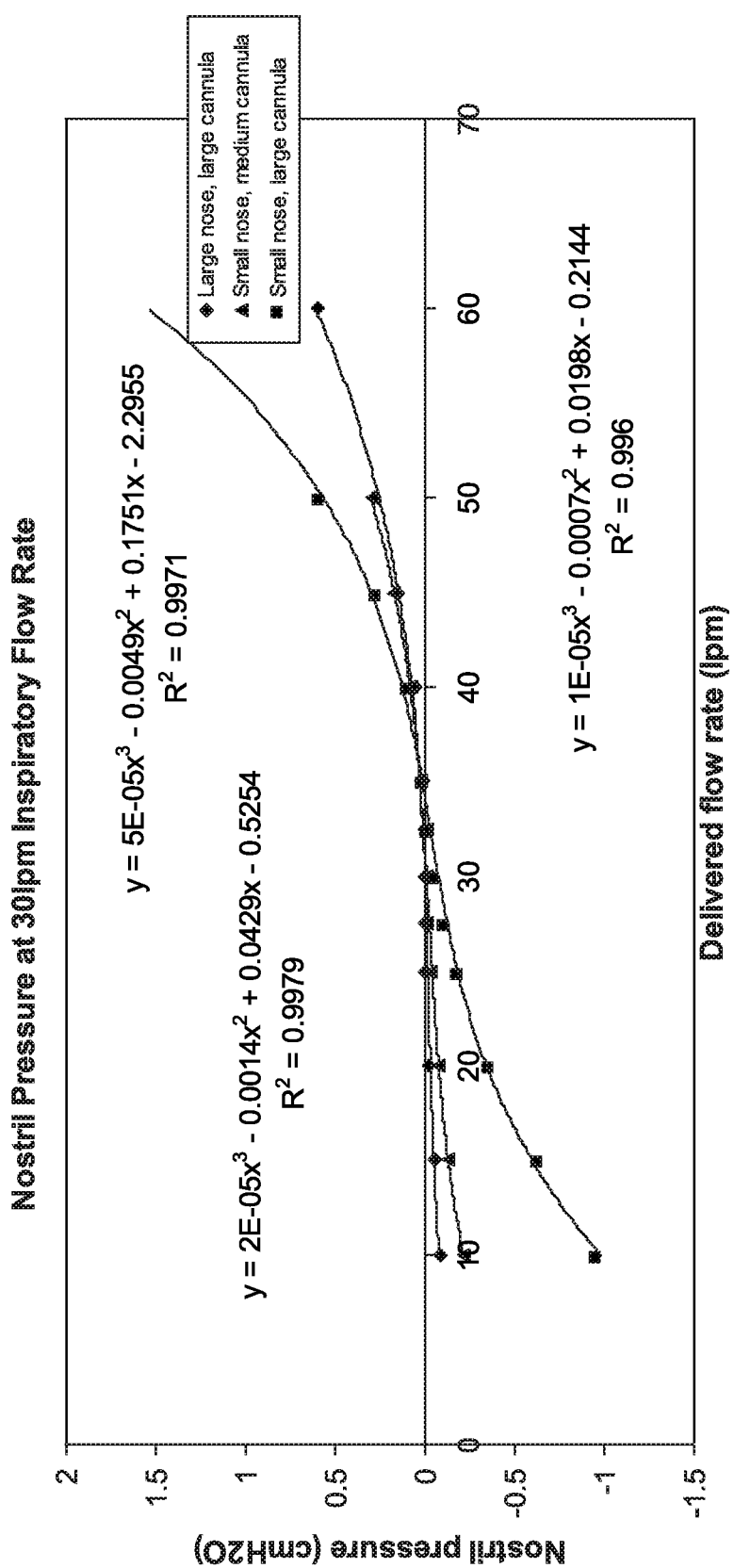
FIG. 29 is a graph showing the pressure and flow at which inspiratory demand is met.

When we inspire the inspiratory muscles create a pressure in the lungs that is negative with respect to ambient pressure to draw ambient air in though the airways. The pressure throughout the airway is negative over inspiration. The magnitude of the negative pressure reduces distally as the resistance to flow of the airway is overcome until the pressure at the nostrils is at ambient pressure. During a natural inspiration the location just inside the nostrils in the nasal vestibule where the cannula prongs would terminate is slightly negative. A cannula worn without any delivered flow causes this slightly negative pressure to be more negative since the cannula prong occludes a proportion of the nares and hence increases flow resistance into the nose. Where the flow therapy breathing apparatus 10 does not provide a sufficient flow rate of gas flow to meet peak inspiratory demand, the pressure at the termination of the prongs will remain negative and the negative pressure will draw in (entrain) ambient air to make up the shortfall gas flow—therefore a negative pressure indicates air entrainment, in turn indicating inspiratory demand is not met. If the flow rate of gas flow provided by the flow breathing apparatus 10 increases, this reduces the negative pressure during inspiration, and reduces the level of entrained ambient air. If the gas flow rate provided by the breathing apparatus 10 increases to meet inspiratory demand, the airway pressure increases to zero or above, and entrainment of ambient air stops. Therefore, increasing flow rate to keep the airway pressure above zero means that ambient air is not being entrained and so inspiratory demand is met. More generally, observing the airway pressure indicates whether entrainment is occurring or not, and therefore whether respiratory demand is being met The pressure line 23 connected to the interface measures the pressure at the entrance to the patient's nose which may be located as the flow sensor in FIG. 13. To determine the flow rate at which inspiratory demand may be met, the flow rate may be increased and the pressure at the nostrils monitored until it is greater than zero. By monitoring the nose pressure a flow rate may be delivered that may cause the nose pressure to be greater than zero, which may satisfy the inspiratory demand of the patient. An example may be if the inspiratory demand of a patient is 30 L/min (FIG. 29).

The pressure at the nose may exceed zero when the flow rate is at or greater than 30 L/min, for example 32.5 L/min or 35 L/min. This information can be used to control the apparatus to deliver a flow rate that meets inspiratory demand, determine what the inspiratory demand (including peak) is, or both.

Figure 28:
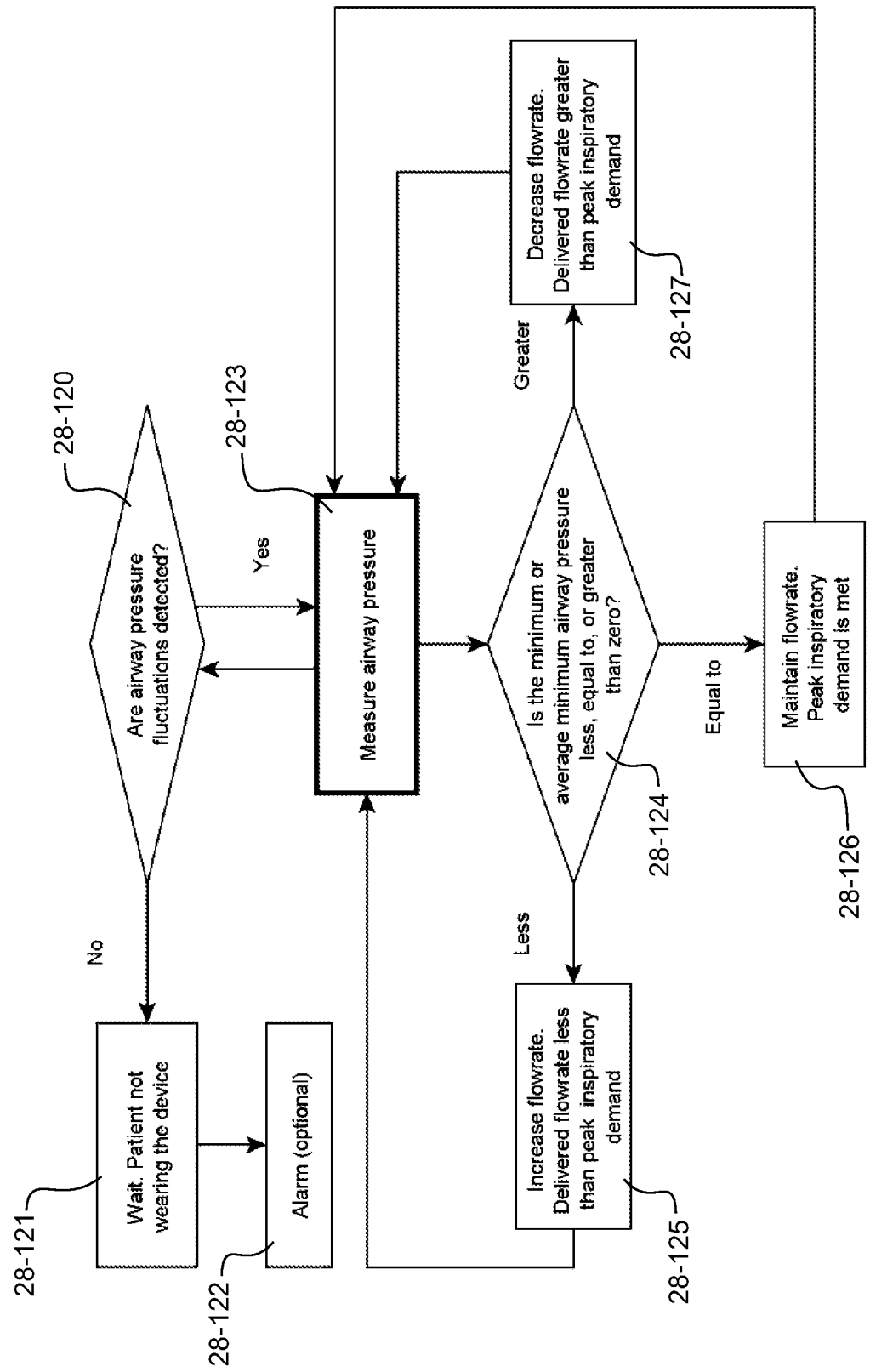
FIGS. 28 and 30 are flow diagrams showing operation of a high flow therapy apparatus according to the second embodiment.

A (non-limiting) exemplary embodiment is shown with respect to FIGS. 1, 13 and 28. A patient uses a flow therapy breathing apparatus 10 with a cannula flow rate such as that shown in FIG. 1, 13, connected to a cannula 17 with a pressure line 23 coupled near the nasal and returning to a sensor 24 in the housing that is connected to the controller 13. Upon operation, the controller 13 receives pressure readings from the pressure sensor 24 and determines if airway pressure fluctuations are detected, step 28-120. If not, the patient is not wearing the interface and optionally an alarm sounded, steps 28-121, 28-122. If airway pressure fluctuations are detected, it is presumed that the patient is using the apparatus 10 and airway pressure measurements are taken by the pressure sensor 24 and transmitted to the controller 13, step 28-123. If the minimum or average airway pressure is less than zero, step 28-124, it is determined that peak inspiratory demand is not being met. The controller 13 controls the flow generator 11 to increase the flow rate to try to meet respiratory demand, step 28-125, e.g. at 5 litre per minute intervals. If the minimum or average airway pressure is zero, step 124, it is determined that inspiratory demand is being met. The controller 13 maintains the flow rate, step 28-126. If the minimum or average airway pressure is above zero, step 28-124, it is determined that inspiratory demand is being met and in fact exceeded. The controller 13 controls the flow generator 11 to reduce the flow rate, step 28-127. Airway pressure is then measured again, step 28-123. Alternatively to control the flow rate, the controller could provide an indication of whether respiratory demand is or is not being met, and/or enable user manual control to adjust the flow rate as required. The average could be taken over similar intervals as in the above method. The minimum pressure could be the single absolute minimum value over a time period, or there could be a threshold for the number of allowable measurements above/below zero, or there could be a threshold for the percentage of allowable measurements above/below zero over a period of time or there could be an 'average' minimum calculated, where the trough of each breath cycle is detected and the minimum pressure value for each detected trough is measured and averaged over a time period.

Figure 30:
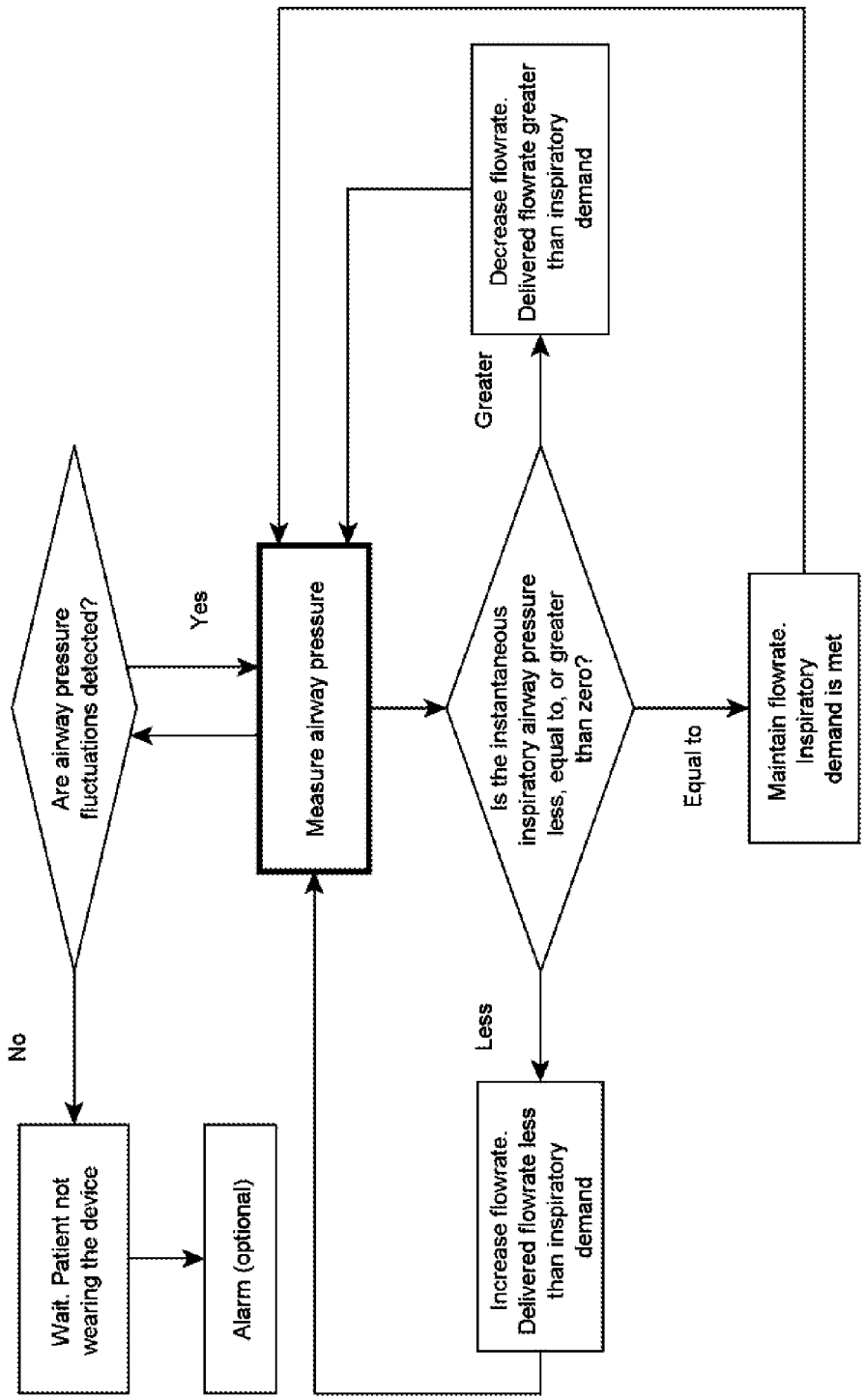

An alternative method is shown in FIG. 30 using a variable cannula flow rate. For instantaneous demand the measurements would be a lot more frequent, and the algorithm would use only instantaneous pressure measurements, not averages. Alternatively, it may be possible to measure several sampled breath cycles and then 'match' the flow rate to the average of these patterns. Then the flow pattern could be maintained for a set period of time, before re-sampling.

1.10 Determining if Peak Inspiratory Flow Rate (Demand) is Met Using Fan Power Motor Consumption In some embodiments fan power monitoring is an approach that may monitor the power consumption of the device so that it may responsively adjust to changes in the inspiratory demand of the patient. A certain amount of power may be required to deliver a specific flow rate. The baseline power as described herein refers to the fan power that may be used to deliver a specific flow rate when an interface is attached to the device but not worn by a patient. When the patient wears the interface the backpressure at the airway may change the amount of power necessary to deliver a specific flow rate. The patient may need to entrain room air if a delivered flow rate is less than a patient's inspiratory demand, which may cause the power required during inspiration to decrease. As a result the power supplied may be less than a baseline power level. If however the flow rate increases to above inspiratory demand, the backpressure at the airway may increase as the patient may not be entraining room air. Thus the power consumption required to maintain the delivered flow rate may increase above the baseline power level. Therefore by monitoring the motor power consumption with increasing flow rates it may be possible to determine when inspiratory demand has been met by determining when the required power for a given flow rate may exceed the baseline power. Continuous monitoring of the power consumption may enable the flow rate to responsively adjust to changes in the inspiratory demand of a patient during their breathing cycle. As the resistance offered by different interfaces or circuit configurations may vary, the baseline power for each interface or circuit configuration may also vary. Interface type, size, or the like, may be detected by, but not limited to, measuring the power consumption for a given flow rate, using electronic identification, mechanical identification, user input, or the like. Size detection may occur but is not limited to occurring during an initial calibration step before the interface is applied to a patient or when the interface is applied to a patient. Different embodiments of this approach may monitor the current through the motor, motor torque, motor speed, or the like.

1.11 Determining Inspiratory Flow Rate (Demand) Using System Pressure Continuous Monitoring (for Instantaneous Flow Rate Adjustment)

In some embodiments, system back pressure monitoring is utilised to carry out one or more of the inspiratory flow functions above. An apparatus and method are provided that implement pressure monitoring for this purpose. This embodiment relates to continual monitoring which could be used to make continual/instantaneous flow rate changes to meet inspiratory demand, but the embodiment could also work in a constant flow rate situation where the flow rate is set to meet peak inspiratory demand.

Referring to FIG. 1, the patient interface 17 of the flow therapy breathing apparatus 10 is a cannula or similar, and a pressure sensor 25 is disposed in the manifold 19 (or other suitable location) to measure system back pressure created in the manifold. The pressure sensor 25 is connected via a wire or other suitable conductor 9 to an input of the controller 13 for transmitting output from the pressure sensor 20 to the controller. Alternatively, the pressure sensor 25 could have or be connected to a transmitter for wireless transmission 8 of output from the pressure sensor to the controller 13, via a transceiver 15 coupled to the controller. In some embodiments, the system back pressure measured by the pressure sensor 25 can be monitored continuously in the controller. Analysis of the pressure measurements with respect to a characteristic system back pressure determined prior to use enables the controller to carry out one or more of the inspiratory flow functions, based on the observed as described below.

Figure 31:
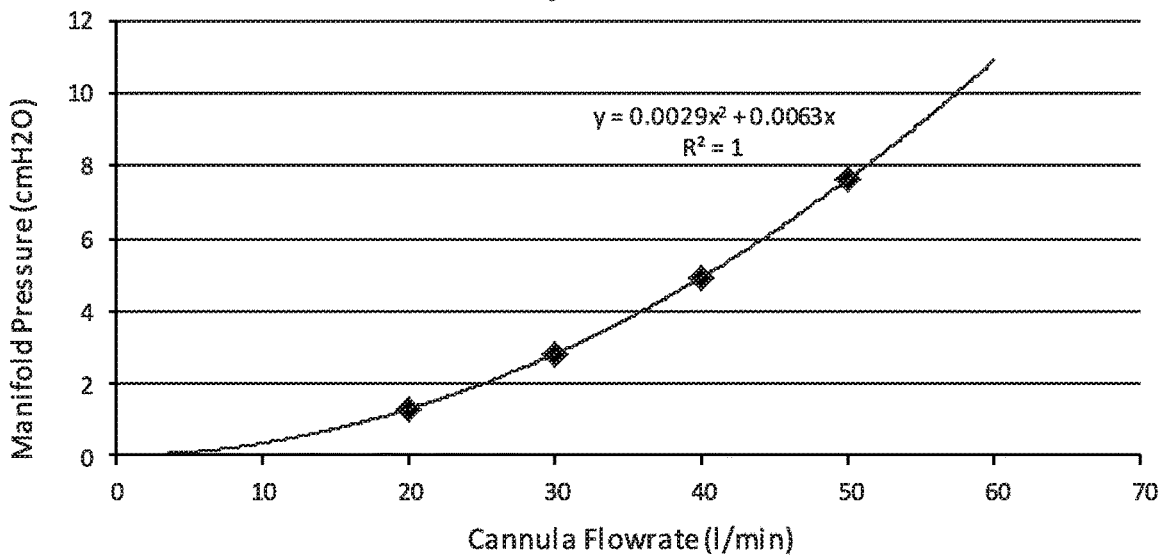
FIG. 31 is a graph showing manifold pressure.

It is possible to measure the characteristic system back pressure generated in the manifold by each interface, when a patient is not wearing the interface (FIG. 31) to establish a non-use characteristic pressure across a range of flow rates. When the apparatus 10 is in use, system back pressure (e.g. manifold) monitoring can take place when a patient is wearing the interface, to enable comparison of the measured system (e.g. manifold) back pressure to the known, characteristic pressure at the delivered flow. This comparison can estimate if inspiratory demand is met. When the patient is wearing the interface, the pressure at the manifold can be monitored continuously. If inspiratory demand is met, the instantaneous manifold pressure is greater than the characteristic system back pressure for the delivered flow rate. However, if inspiratory demand is not met, the instantaneous manifold pressure is less than the characteristic system back pressure for the delivered flow rate. This occurs because the patient is generating a negative pressure to entrain additional room air, in a manner described in the previous embodiment.

Figure 32:
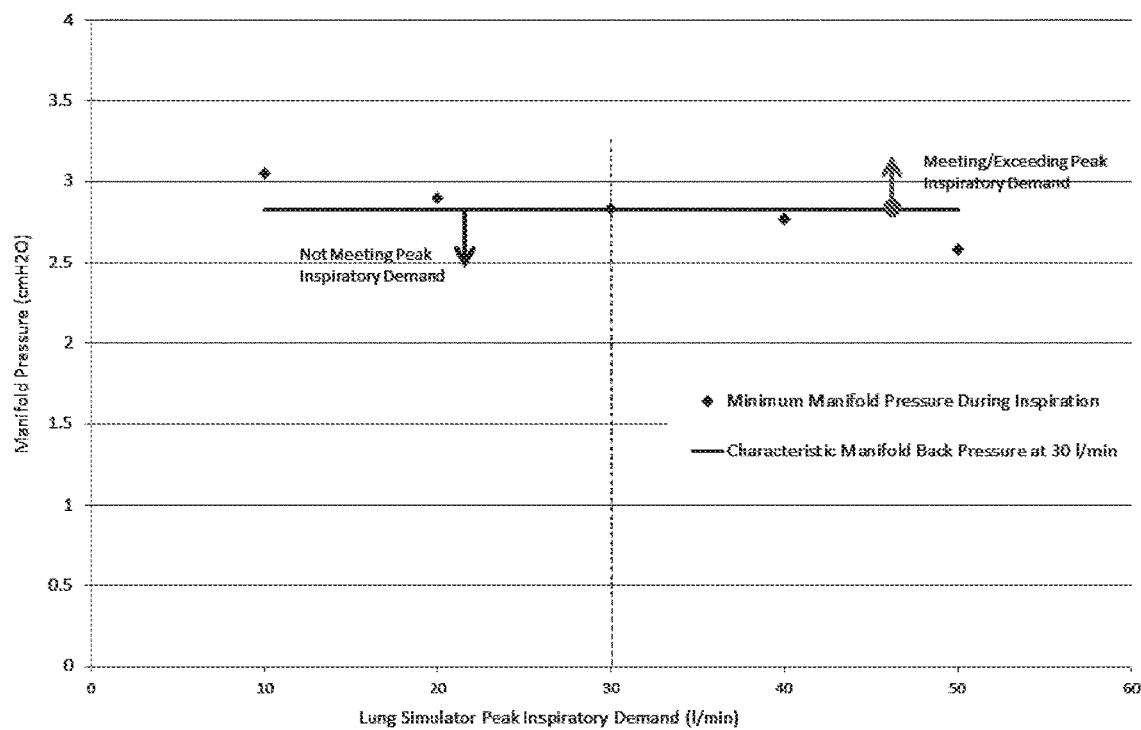
FIGS. 32 to 34 show graphs of whether or not inspiratory demand is met at various flow rates.
Figure 33:
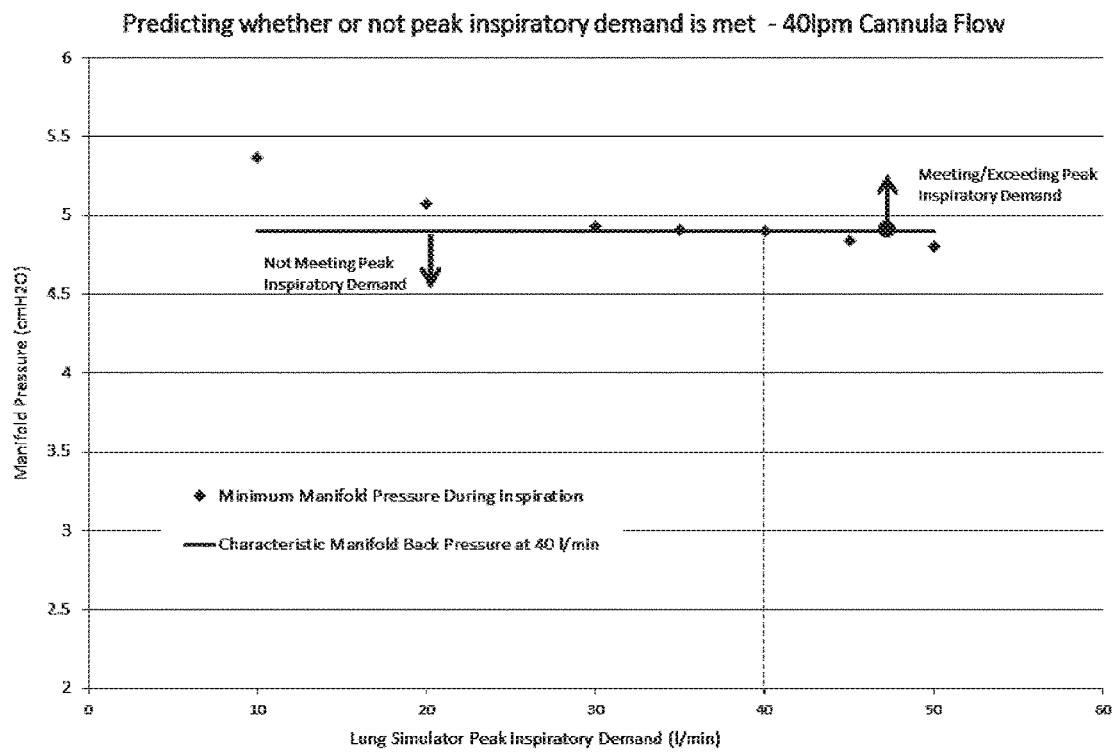
Figure 34:
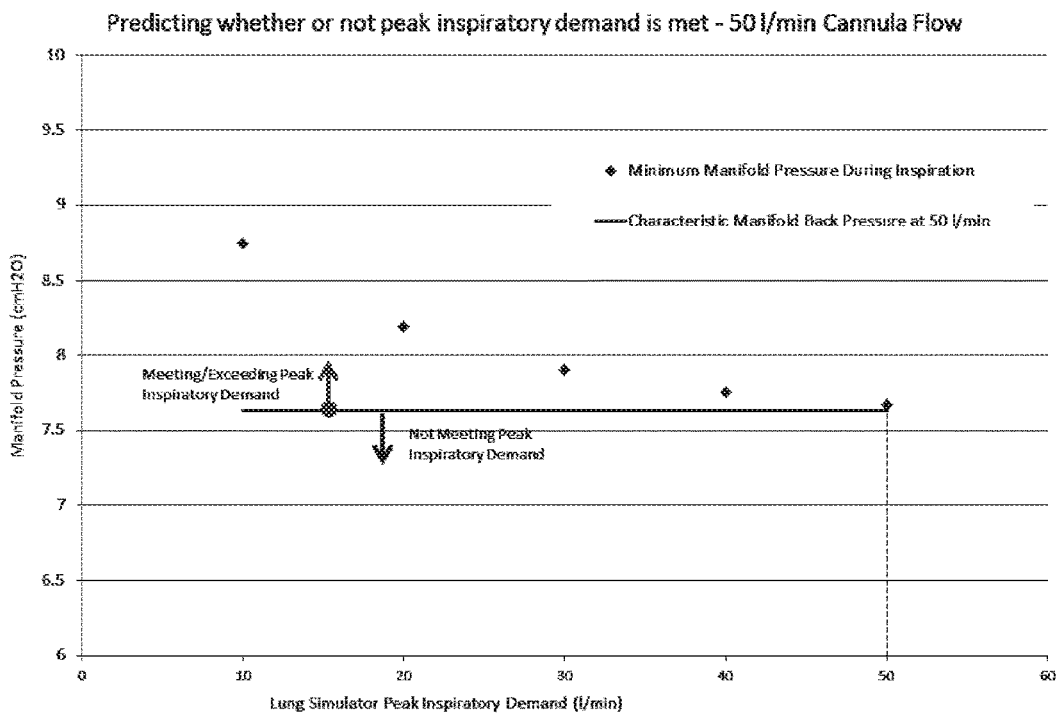

FIGS. 32-34 show test results conducted on an in-vitro lung simulator. For a set inspiratory demand, the manifold pressure is less than the characteristic backpressure for delivered flow rates that are less than the set inspiratory demand. This indicates that entrainment is occurring. As a result the flow rate can be adjusted to meet the inspiratory demand of the patient, and the instantaneous manifold pressure may be equal to or greater than the characteristic backpressure for the delivered flow rate.

To determine which characteristic system back pressure to use in the estimation, it may be necessary for the apparatus to determine which interface is connected. The apparatus 10 can detect which interface is connected, the size of the interface connected, or the like, by measuring the backpressure at a known flow rate, either with a patient during use or without a patient during a calibration step. It can also detect the interface by electronic identification, mechanical identification, user input or the like.

This approach can be controlled by measuring and monitoring the pressure at any number of places in the system, including the manifold as described above, as well as at the chamber. By continuously monitoring the pressure, the flow rate can be responsively adjusted to any changes in the patient's inspiratory demand during their inspiratory cycle.

Figure 35:
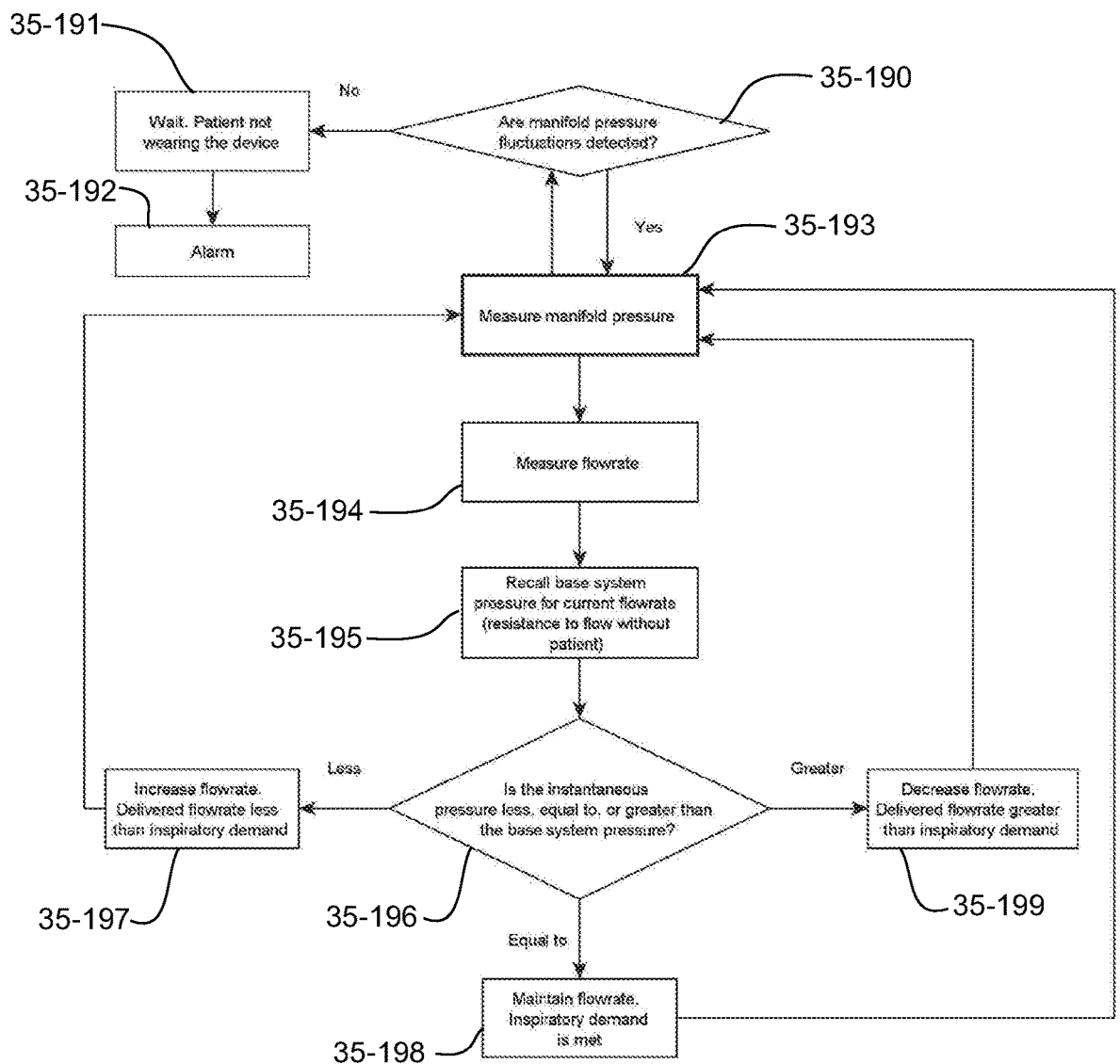
FIGS. 35 and 36 are flow diagrams showing operation of a high flow therapy apparatus according to a third embodiment.

A non-limiting exemplary embodiment shown with respects to FIGS. 1 and 35.

A patient uses a flow therapy breathing apparatus 10 such as that shown in FIG. 1, connected to a cannula 17 with a pressure sensor 25 coupled to the manifold 19 or other suitable location, the pressure sensor 25 being coupled to the controller 13 in a suitable manner to enable wired or wireless transmission of output. A characteristic system back pressure for the particular patient interface being used is taken prior to use. Upon operation, the controller 13 receives pressure readings from the pressure sensor 25 and determines if system (e.g. manifold) pressure fluctuations are detected, step 35-190. If not, the patient is not wearing the interface and optionally an alarm sounded, steps 35-191, 35-192. If system back pressure fluctuations are detected, it is presumed that the patient is using the apparatus 10 and pressure measurements are taken by the pressure sensor 25 and transmitted to the controller 13, step 35-192. The flow rate is also measured using a suitable flow sensor or similar, and this is transmitted to the controller 13, step 35-194. Characteristic pressure changes with flow rate, thus a different characteristic pressure is associated with each delivered flow rate.

The controller 13 then obtains the characteristic system back pressure previously obtained, step 35-195, and compares this to the measured manifold pressure, step 35-196. If the minimum or average manifold pressure or average inspiratory pressure is less than the characteristic pressure, step 35-197, or a certain number of breaths over a period of time give pressure values less than the characteristic pressure, it is determined that inspiratory demand is not being met. The controller 13 controls the flow generator 11 to increase the flow rate to try to meet respiratory demand, step 35-197. If the minimum or average airway pressure above the characteristic pressure, step 35-199, it is determined that peak inspiratory demand is being met and in fact exceeded. The controller 13 controls the flow generator 11 to reduce the flow rate, step 35-199. If the minimum or average manifold pressure is equal to the characteristic pressure, step 35-198, it is determined that inspiratory demand is being met. The controller 13 controls the flow generator 11 to maintain the flow rate, step 35-198. The manifold pressure is then measured again, step 35-193 to 35-196. If the minimum or average airway pressure above the characteristic pressure, step 35-199, it is determined that inspiratory demand is being met and in fact exceeded. The controller 13 controls the flow generator 11 to reduce the flow rate, step 35-199. The manifold pressure is then measured again, step 35-193 to 35-196. Alternatively to control the flow rate, the controller could provide an indication of whether respiratory demand is or is not being met, and/or enable the user to manually control to adjust the flow rate as required.

Figure 36:
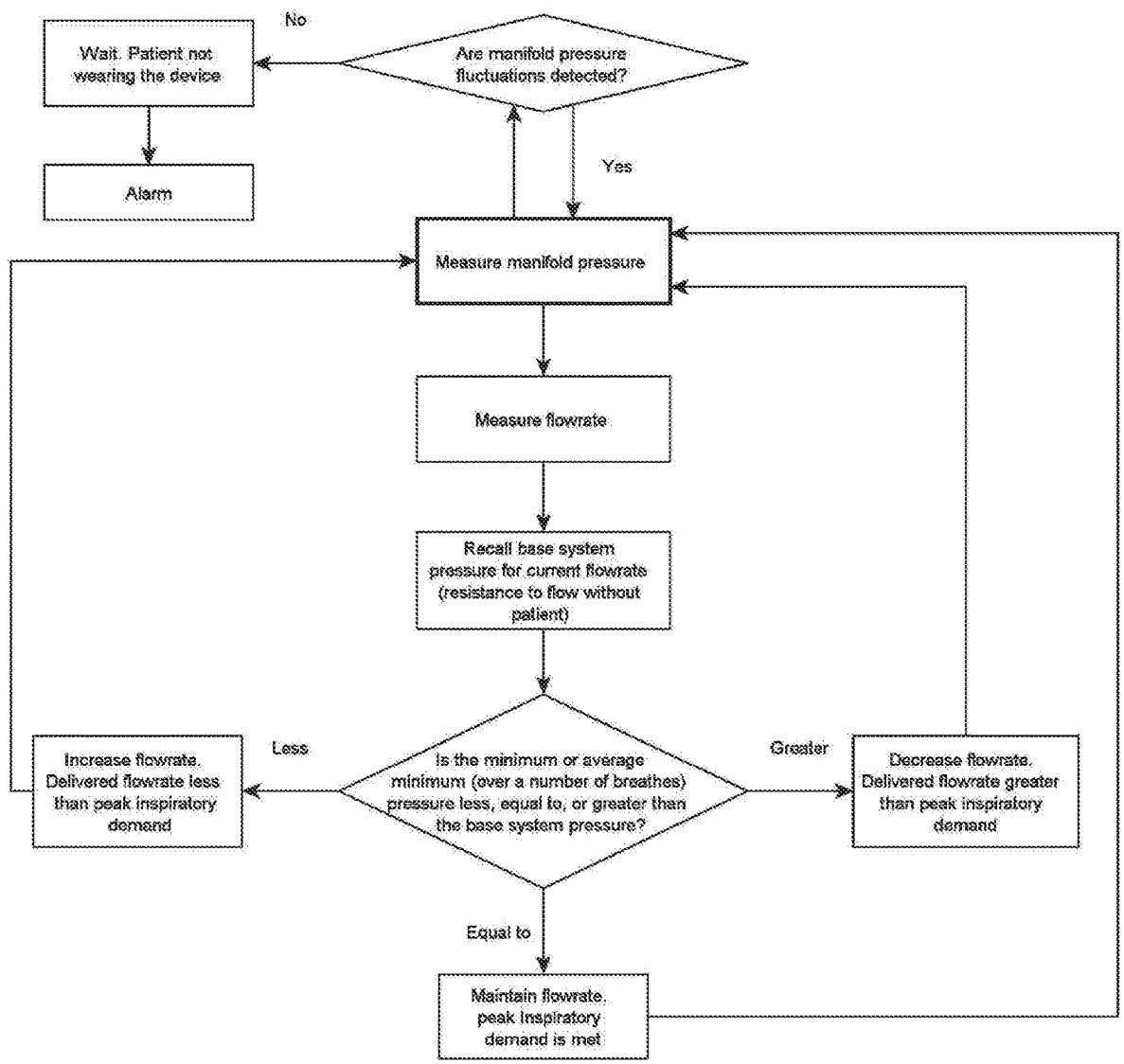
Figure 37:
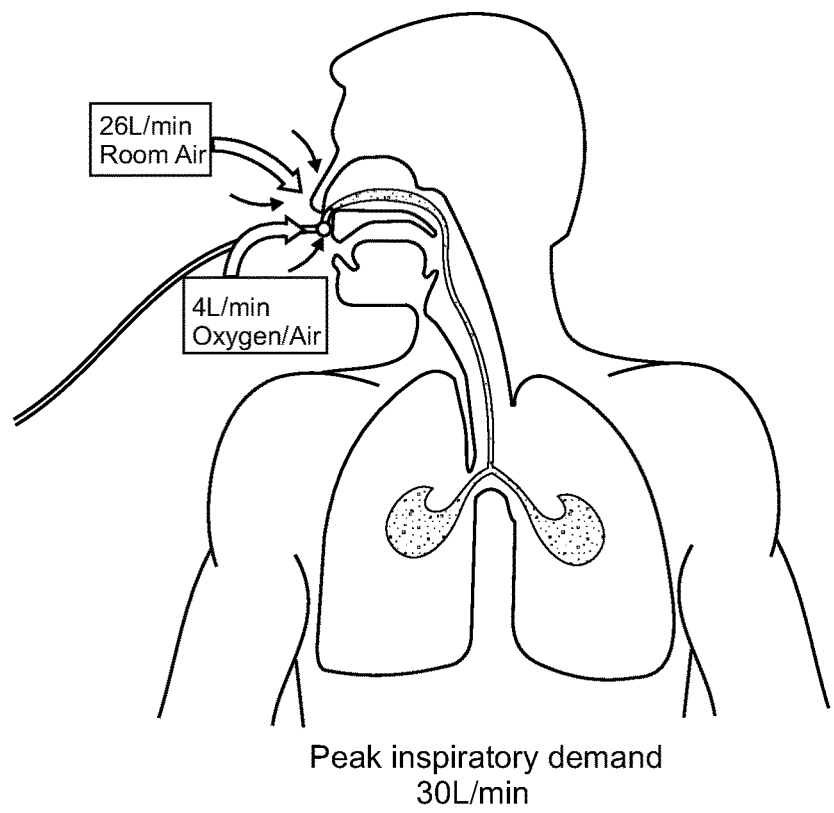
FIG. 37 shows the difference between low and high flow gas delivery.
Figure 37:
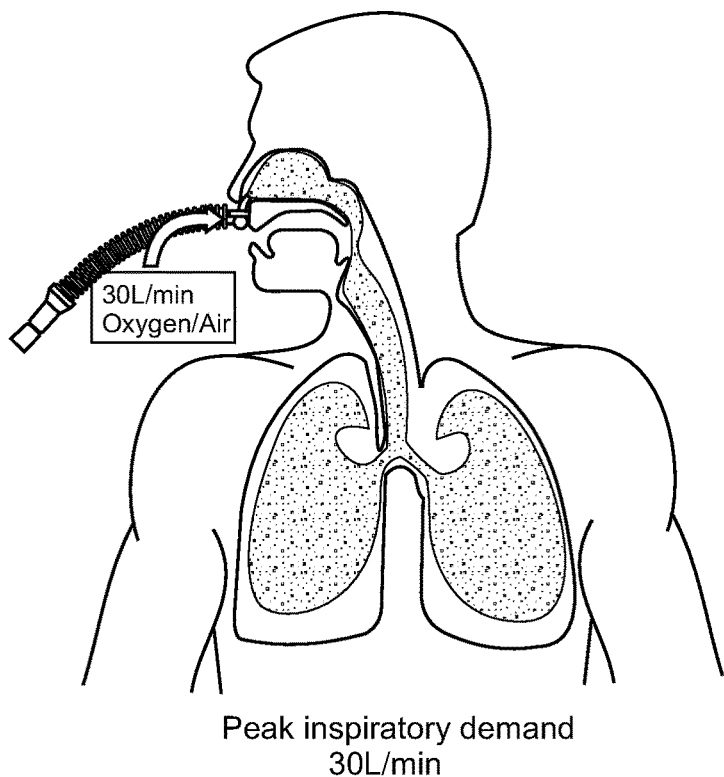

The above description relates to meeting inspiratory demand with a constant cannula flow rate. In an alternative embodiment shown in FIG. 36, a similar method can be undertaken with a variable cannula flow rate. All methods could be implemented with variable cannula flow rate, to meet instantaneous demand.

In the methods, it may be desirable that the user wishes to know the patient's inspiratory demand but also wishes to set the delivered flow rate at a value that exceeds, or is less than the patient's inspiratory demand. In this case the apparatus can go through a calibration step where the flow rate is increased or decreased in increments to a value that approaches the inspiratory demand. When the device measures that inspiratory demand has been met this value is displayed to the user and the apparatus flow rate returns to the set value. This calibration step could be performed automatically at pre-defined intervals. The interval may be between 10 minutes to 24 hours, or the interval may be set by the user. Or it may be possible for the user to manually trigger a calibration to take place.

It may also be possible to determine the inspiratory demand with relatively few measurements. FIG. 29 shows that pressure measurements taken in the nose over a flow range follow a polynomial curve. If the characteristic shape of the curve is known (relationship between delivered flow rate and airway pressure) relatively few measurements may be taken around the user-set delivered flow rate and these measurements used to extrapolate the inspiratory demand. This would enable the device to calculate and display the inspiratory demand without having to change the delivered flow rate too substantially from the user's desired level or reduce it below, or increase it to above the inspiratory demand (depending on the user's flow setting). This technique may also be applied to the system pressure monitoring method if a characteristic pressure-flow curve is determined once the device has been applied.

As an extension to this, if a more complete pressure flow curve can be established at some point during the patient's therapy then their inspiratory demand could be calculated more accurately. Subsequent measurements, after a time period, could then be taken at certain points along this curve to determine if the patient's flow-pressure characteristics had changed significantly. If their characteristics had not it could be assumed their inspiratory demand had also not changed. If they had changed it may be necessary to re-calculate the curve, take several measurements around the user-set delivered flow rate and extrapolate for the demand (as above), or increment the flow rate, to determine the new inspiratory demand.

2 Determining Respiratory Flow Rate

Some embodiments will now be described that relate to methods and apparatus for determining respiratory flow rate being the flow rate at any point in the breath cycle. In some embodiments, that can comprise determining inspiratory flow rate and/or using that information. In some embodiments that can comprise determining expiratory flow rate and/or using that information. In other embodiments respiratory flow rate is determined irrespective of whether it is expiratory or inspiratory flow.

For example, some embodiments relate to a flow therapy apparatus (such as a high flow therapy apparatus) and/or its method of use and/or methods for providing information and control of the apparatus in relation to the inspiratory demand of a patient using the apparatus. Other embodiments work with flow therapy apparatus. Embodiments will now be described relating to methods and apparatus for determining/estimating inspiratory flow rate (demand) and/or determining whether inspiratory demand is being met, exceeded or not met. These embodiments can be used to provide information to users and/or enable users and/or the apparatus to be configured with a flow rate that meets inspiratory demand, or a flow rate that is based on knowledge of inspiratory demand. Other embodiments relate to expiratory flow determination.

2.1 Flow Therapy Apparatus for Respiratory Flow Rate Determination Embodiments

A general description of a flow therapy apparatus (typically a high flow therapy apparatus) will be provided, and particular embodiments of the apparatus and its use will then be described. In general terms, the method and apparatus of the present invention utilise system pressure and/or other parameters (being a pressure at some point in the high flow therapy apparatus) to determine respiratory flow rate. Particular embodiments of the invention comprise determined peak inspiratory or expiratory flow rate, and determining the pressure in the manifold/cannula of the patient interface, as described below. These are non-limiting examples.

Figure 38:
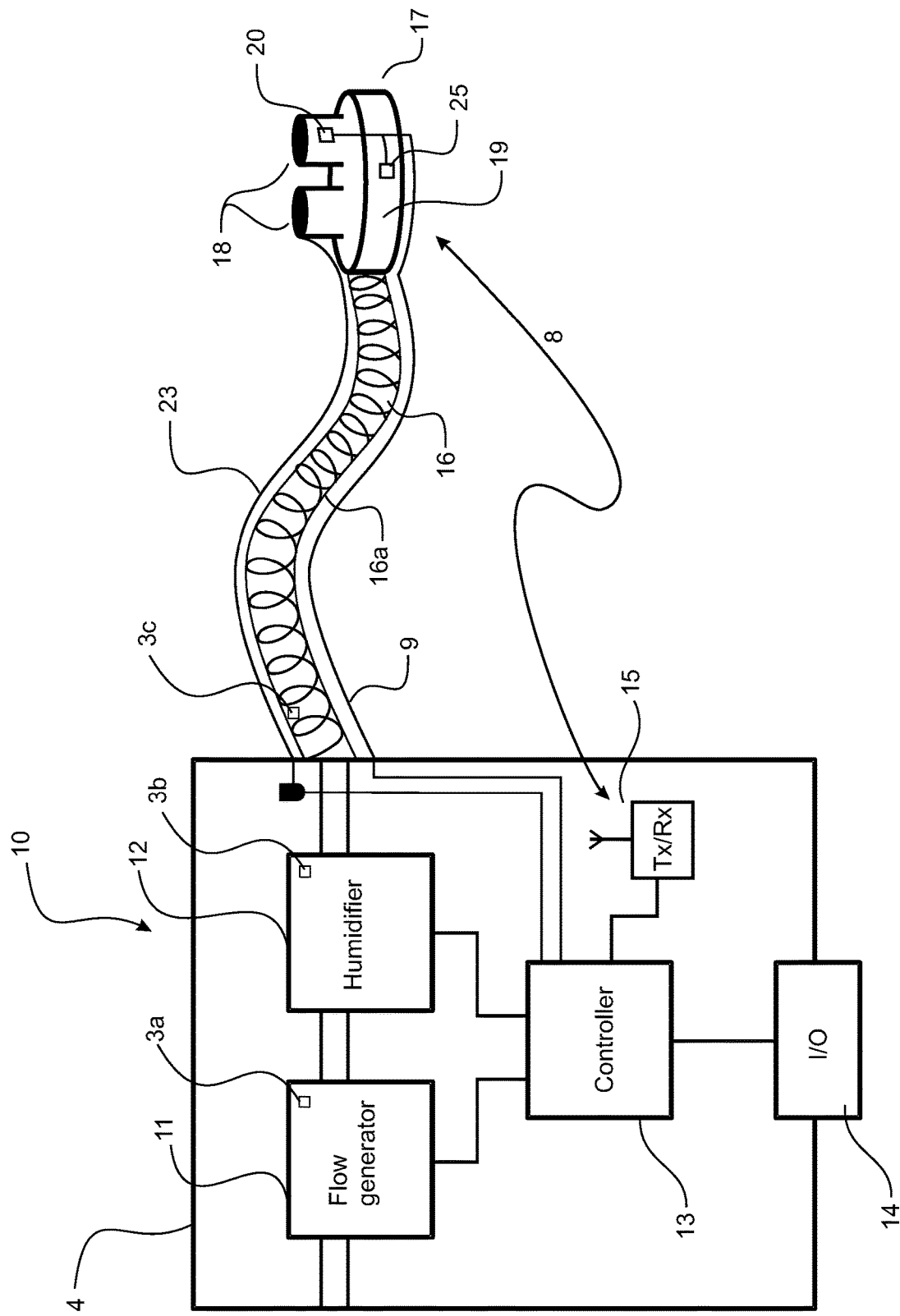
FIG. 38 is a (e.g. high) flow therapy apparatus adapted to provide or assist to provide high flow therapy that meets inspiratory demand of a patient.

A flow therapy apparatus 10 is shown in FIG. 38 for respiratory flow determination. It is similar to that shown in FIG. 1 and will keep the same reference numerals. It can be used for any of the embodiments described, including those for inspiratory demand estimation and expiratory flow estimate. It comprises a housing 4 that contains a flow generator 11, humidifier 12, controller 13 and user I/O interface 14 (comprising, for example, a display and input devices such as buttons or the like). The controller 13 is programmed to control the components of the apparatus, including: operating the flow generator 11 to create a flow of gas (gas flow) for delivery to a patient, operating the humidifier 12 to humidify and/or heat the generated gas flow, adjust the flow rate of other introduced gases, e.g. oxygen, receive user input from the user interface 14 for reconfiguration and/or user-defined operation of the apparatus 10, output information (for example on the display) to the user. The user could be a patient, healthcare professional or anyone else interested in using the apparatus.

A patient breathing conduit 16 is coupled to a gas flow output in the housing 4 of the high flow therapy apparatus 10, and is coupled to a patient interface 17, such as a nasal cannula with a manifold 19 and nasal prongs 18. The humidified gas flow that is generated by the high flow therapy apparatus is delivered to the patient via the patient conduit 16 through the cannula 17. The patient conduit 16a can have a heater wire to heat gas flow passing through to the patient, under control of the controller 13. The patient conduit 16 and/or patient interface can be considered part of the high flow therapy apparatus 10, or alternatively peripheral to it. Use of the term "(high) flow therapy apparatus" can be utilised for either alternative.

General operation of a flow therapy breathing apparatus 10 will be known to those skilled in the art, and need not be described in detail here. However, in general terms the controller 13: controls the flow generator 11 to generate a gas flow of the desired flow rate (generated gas flow), and controls the humidifier 12 to humidify the gas flow and/or heat it. The gas flow is directed out through the patient conduit 16 and cannula 17 to the patient. The controller 13 can also control heating elements 16a in the humidifier and/or patient conduit to heat the gas to a desired temperature (also termed "target temperature" or "set point") that achieves the required level of therapy and/or comfort for the patient. The controller 13 can be programmed with or determine a suitable target temperature.

Operation sensors, such as flow, temperature, humidity, gas concentration and/or pressure sensors can be placed in various locations in the flow therapy apparatus and/or the breathing conduit and/or cannula. Output from the sensors can be received by the controller 13, to assist it to operate the flow therapy apparatus in a manner that provides optimal therapy, including meeting inspiratory demand.

2.2 Estimating Inspiratory Flow Rate (Demand) Using Patient Pressure, System Pressure and Characteristic Pressure 2.2.1 General Overview The embodiments described herein relate to estimating or otherwise determining respiratory flow rate—either being inspiratory or expiratory flow rate as the case may require, and then using that information to assist in providing high flow therapy.

For example, determining inspiratory flow rate can assist in providing therapy that meets inspiratory demand. This is just one possible application of the embodiments described. Although flows of gas delivered via a patient interface exist in the prior art, an aspect of at least one of the embodiments disclosed herein includes the realisation that there are problems with the implementation and use of these high flow systems in the prior art. Nasal high flow systems in the prior art may not meet the inspiratory demand of a patient. Inspiratory demand as herein described may refer to the amount of gas (flow rate) a patient may require during inspiration. Prior art systems may not measure or calculate this inspiratory demand, or may not determine inspiratory demand for individual patients. Thus the flow rate delivered to patients may not reflect their specific respiratory condition or individual demand, which may provide inadequate respiratory support and/or may compromise the effectiveness of the therapy. Flows delivered to a patient that are below their inspiratory demand may cause entrainment of room air during inspiration as the patient may require more gas to meet their inspiratory demand. Entrainment of room air may dilute the humidity, temperature, oxygen concentration, or other gases mixed into the delivered gas to the patient compromising the treatment and preventing effective control of the therapy. It may also be desirable for a clinician to know that they are exceeding a patient's inspiratory demand, and by how much. Flows delivered to a patient that are above inspiratory demand may cause undesired physiological outcomes, discomfort to the patient and may be associated with excess noise generation. Currently clinicians (e.g. doctors, nurses or other healthcare professionals) may be unsure as to the specific inspiratory demand of their patients, thus to prescribe a flow rate may be difficult and may not reflect the flow rate that best meets their patients' needs.

The present specification relates to embodiments of a flow therapy apparatus (typically called a high flow therapy apparatus) and its method of use. In some embodiments, the apparatus and its method of use enable operation to provide gas flow (the more general term for "airflow") at a flow rate that meets inspiratory demand (or at some level relative to inspiratory demand), or at least provides assistance (e.g. through provision of information) to achieve this, or at least provides the information regarding inspiratory demand (such as a number or an indication of inspiratory demand being met/not met) even if the existing delivered flow rate is maintained. Meeting inspiratory demand means to supply a flow of gas through a patient interface at a rate that approximates, equals or exceeds the flow rate of gas desired by a patient's normal or augmented inspiratory breath pattern such that little or no ambient air is required or entrained to supplement the supplied flow rate. In the case of providing a constant flow, providing gas flow that meets inspiratory demand will mean providing a gas flow that meets peak inspiratory demand, although this is not essential in other cases. Peak inspiratory demand is a special case of inspiratory demand (that is, at the peak of inspiration), and is covered by any reference to inspiratory demand.

In embodiments, apparatus and methods are disclosed that may calculate or measure the inspiratory demand of a patient or measure some parameter indicative of whether inspiratory demand is being met. Determining the inspiratory demand of a patient or some parameter indicative of whether it is being met may enable a flow to be delivered to the patient which may equal or exceed the determined inspiratory demand. The inspiratory demand may be met by delivering a constant flow rate corresponding to the determined peak demand of a patient that may be similar to, equal or exceed the peak inspiratory demand of the patient over a time period, number of breaths or the like. The inspiratory demand may also be continuously monitored and thus a variable flow that may match or exceed the instantaneous demand of the patient during the inspiratory phase may be supplied by the device. Other ways of delivering inspiratory demand may also be possible. Delivering inspiratory demand may prevent entrainment of room air during inspiration which may prevent dilution of the humidity delivered to the patient and may increase the efficacy of the therapy. Clinicians may also have more confidence that accurate levels of inhaled oxygen concentration may be delivered to the patient as less dilution of flow may occur.

Apparatus and methods can display the determined inspiratory demand or parameter indicative of whether inspiratory demand is being met to the user. This may allow the user to manually adjust the therapy or the device may automatically adjust the therapy to meet the particular demand of a patient. The device may provide feedback to the user regarding the flow being delivered to the patient and may indicate if inspiratory demand is being met which may allow the user to alter the flow to better meet inspiratory demand. The flow may be increased until it is sufficient to meet inspiratory demand, or it may be decreased so that excess flow may not be delivered to the patient, which may increase patient comfort. In other embodiments the device may automatically adjust the delivered flow rate in a way that may satisfy the inspiratory demand of the patient. The display may include information to the user regarding whether the device is meeting the inspiratory demand of the patient. An automated apparatus may have upper and lower limits set by the user for the flow or these limits may be determined by the device. Alternatively, the delivered flow rate may be set to automatically deliver some fraction/percentage of the measured inspiratory demand (including percentage >100%), or exceed, or be less than the inspiratory demand by some absolute amount. For example, it may be desirable to deliver as low as 10% of or more 500% of inspiratory demand. In one possibility, 100 L/min is delivered in order to generate a higher level of inspiratory pressure—if inspiratory demand was 20 L/min, this would be 5 times the level. The algorithm that defines the delivered flow rate as a function of the measured peak inspiratory demand (PID) (or more generally inspiratory demand) could be programmed as one or more default settings into the device or the algorithm could be customised by the user.

Humidifiers are used to provide humidified respiratory gases to a patient. Gases are delivered to a patient via a patient interface. Patient interfaces as herein described refer to, but are not limited to, a face mask, an oral mask, a nasal mask, a nasal cannula (often called a "cannula"), a combination of oral and nasal mask, or the like. Gases delivered to patients at 100% relative humidity and 37° C. mimic the transformation of air that occurs as it passes through the nose to the lungs. This promotes efficient gas exchange and ventilation in the lungs, aids defense mechanisms in the airways and increases patient comfort during treatment. Nasal high flow is a therapy that typically delivers a high flow of humidified gas to a patient through a patient interface. It is a therapy that may deliver the inspiratory demand of a patient. Inspiratory demand as herein described refers to the amount of air that may satisfy a patient's need during inspiration. Meeting inspiratory demand is not limited to being achieved with a nasal cannula, but may be achieved using patient interfaces such as a face mask, oral mask, nasal mask, nasal cannula, combination of oral and nasal mask, or the like, as described above. If inspiratory demand is met the patient may not entrain room air during inspiration. This is beneficial as entrainment of air may dilution of the inspired gas which may compromise the therapy. Inspiratory demand may vary between patients or with patient condition and therefore may require constant or regular monitoring.

Figure 21:
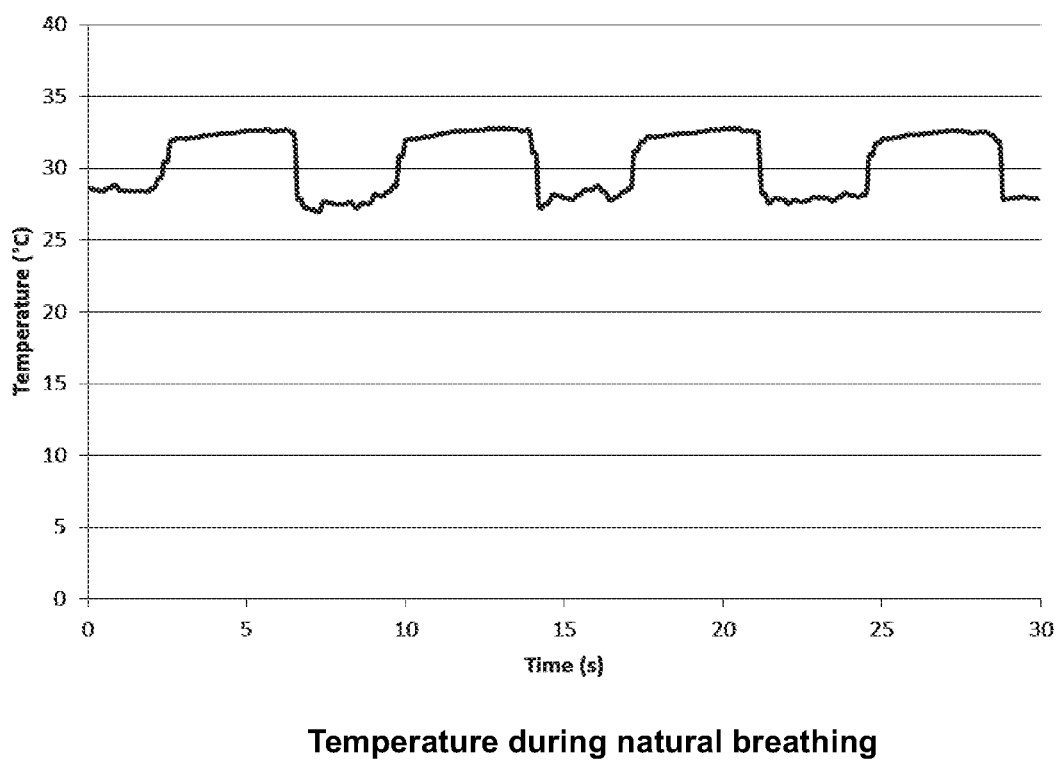
FIGS. 21 to 27 show graphs of measured temperature at different flow rates during operation of the high flow therapy apparatus according to one embodiment.
Figure 22:
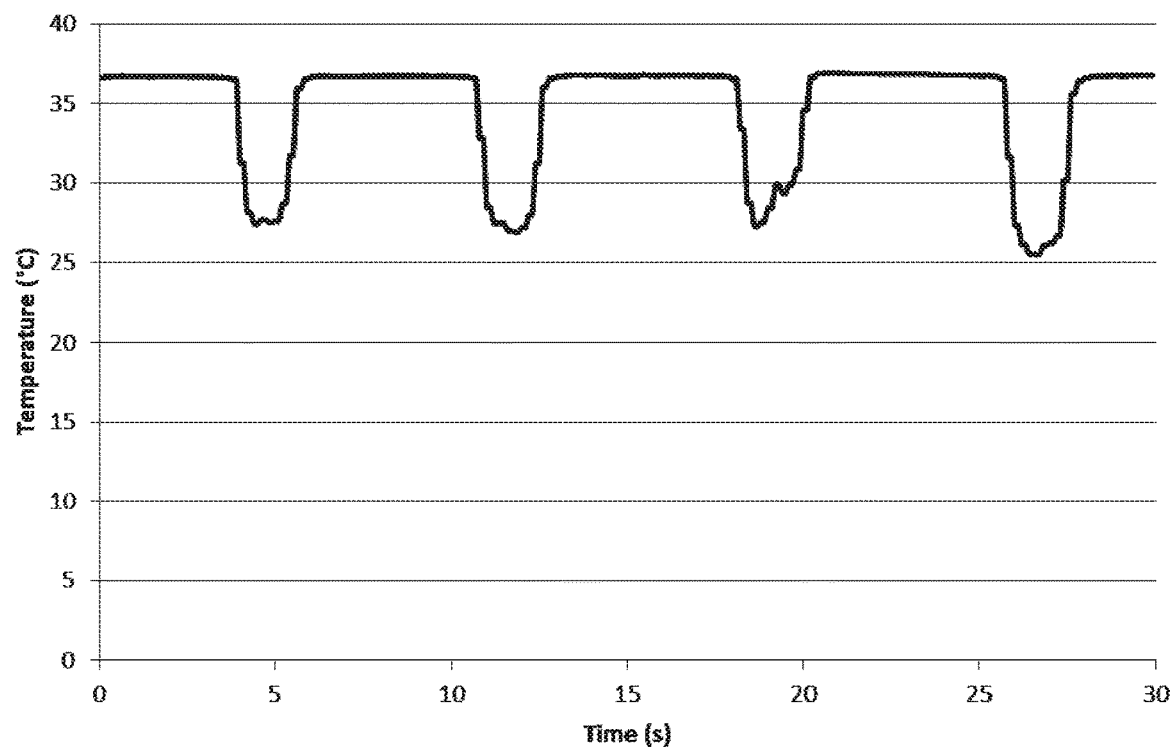
Figure 23:
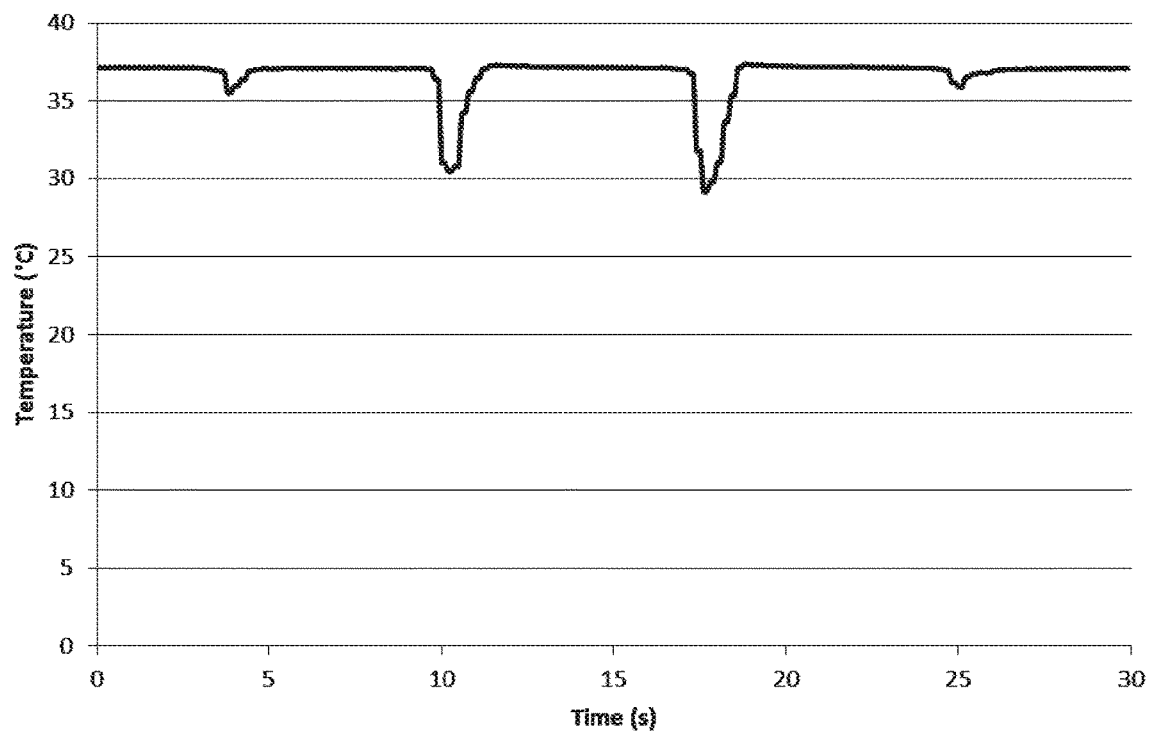
Figure 24:
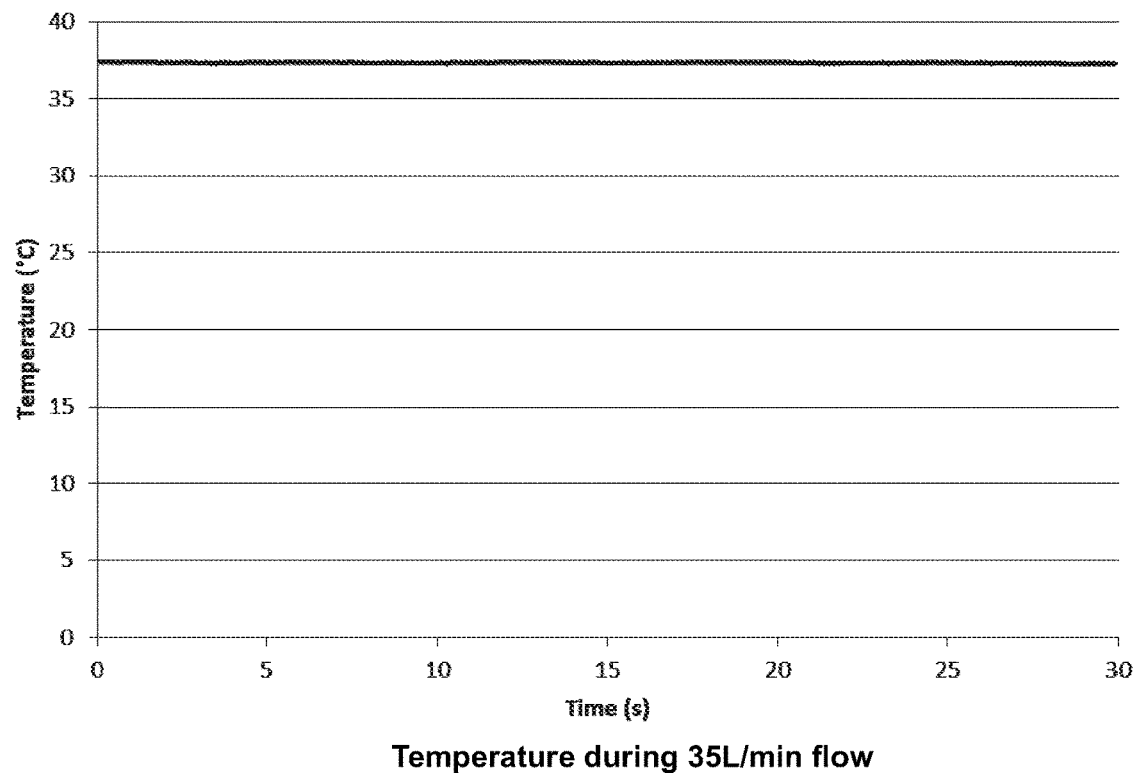
Figure 25:
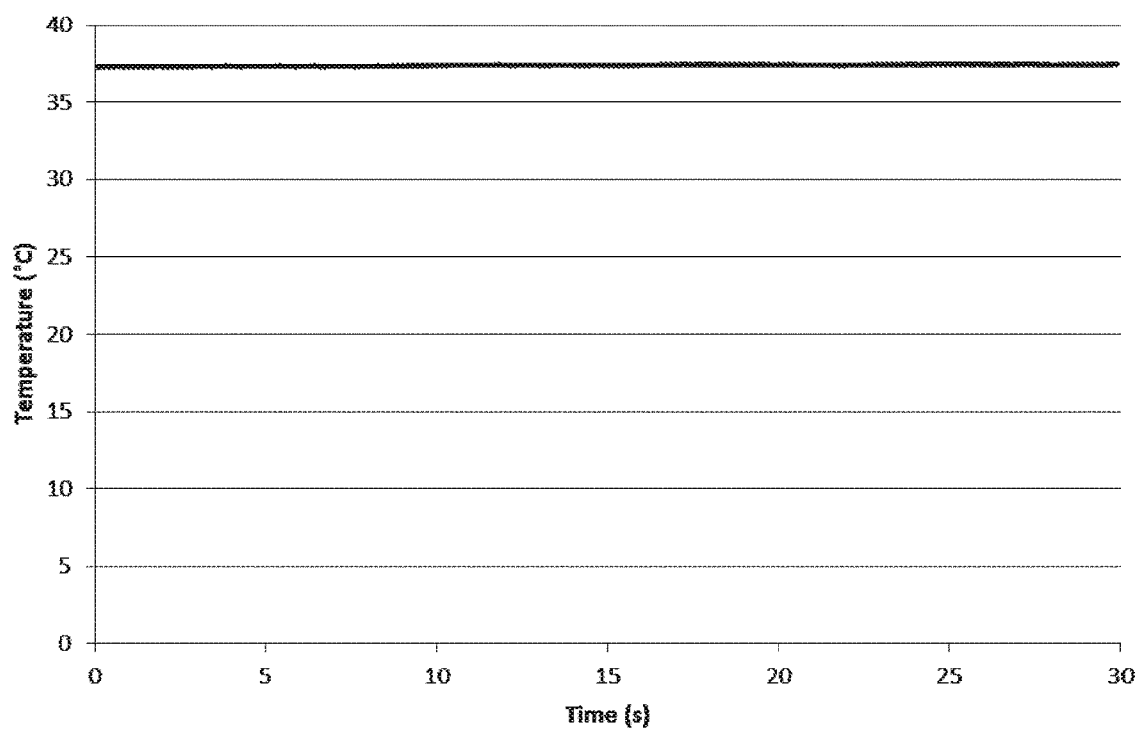
Figure 26:
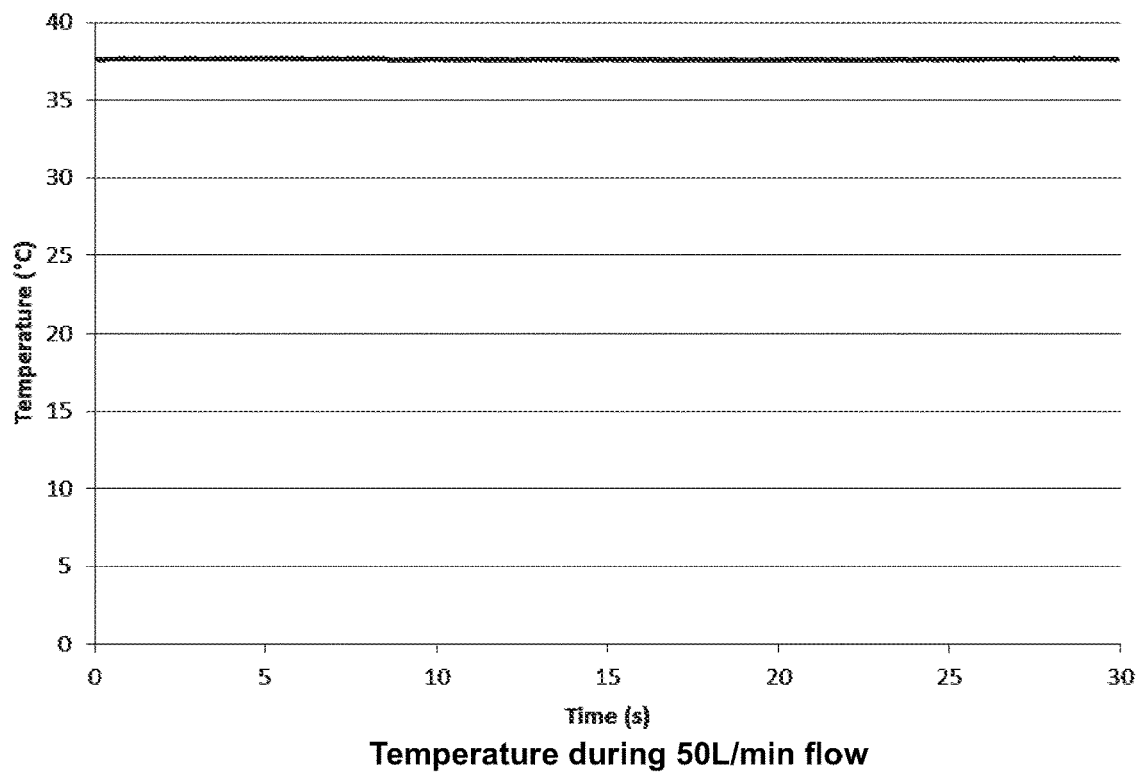
Figure 27:
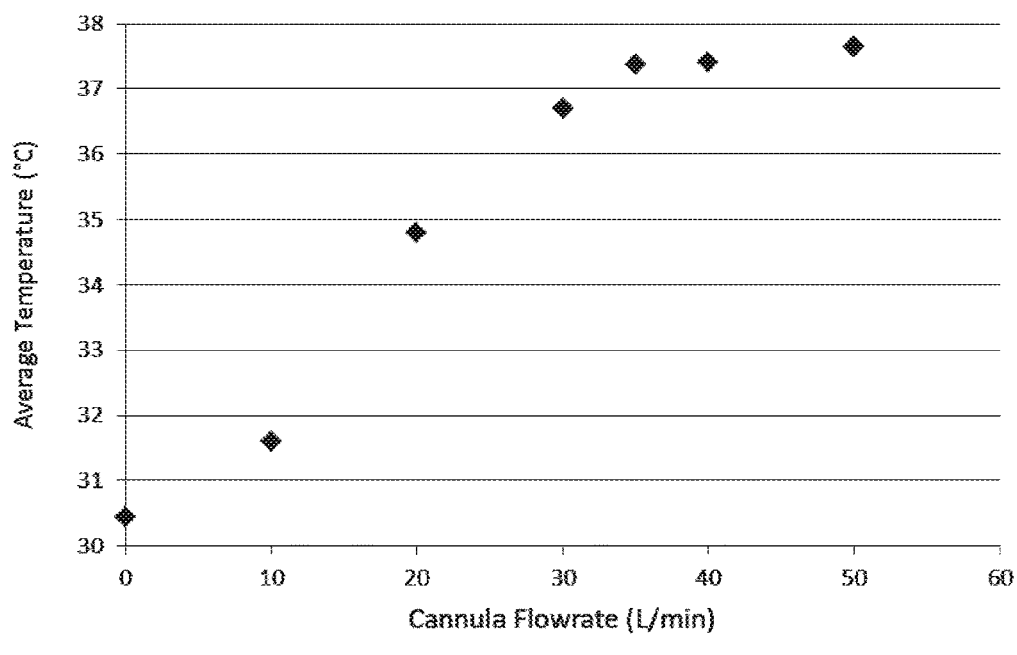

In embodiments, the inspiratory demand may be met by delivering a constant flow rate corresponding to the determined peak demand of a patient that may be similar to, equal or exceed the peak inspiratory demand of the patient over a time period, number of breaths or the like. This flow, while constant for a period of time, can be changed based on the latest measurements and may be re-adjusted at e.g. set intervals or after a number of breaths etc. The inspiratory demand may also or alternatively be continuously monitored and thus a variable flow that may match or exceed the instantaneous inspiratory demand of the patient during the inspiratory phase may be supplied by the device. Over a period of time or a number of breathing cycles this peak inspiratory flow rate may change and may be delivered as the average of the peak flow rates over the previous cycles or time period. By matching or exceeding the peak flow demand of the patient, it may be possible to reduce the entrainment of room air that may occur during inspiration at delivered flow rates (FIG. 21). In this way the delivered therapy may not be diluted, and the correct humidity, oxygen, or both, may be delivered to the patient. Accurate oxygen delivery is important because it may be necessary to deliver high concentrations of oxygen to a patient if entrainment of room air is occurring. This may cause the user to increase the flow rate of the therapy to ensure accurate oxygen delivery is met. By continuously monitoring a patient inspiratory demand may be met by delivering a flow that may reflect the instantaneous inspiratory flow rate of the patient. In this way the flow being delivered may meet the inspiratory demand of a patient across a breathing cycle, may improve patient comfort and may reduce the delivered flow rate when it may not be required.

In embodiments, the apparatus may calculate and display information regarding the inspiratory flow rate to the user. This information may include but is not limited to, an estimation of the patient's (peak or instantaneous) inspiratory demand, whether the demand is being met by the current delivered flow, the parameters that describe the current flow, the change in inspiratory demand over time, any combination of these, or the like. This may be displayed but is not limited to a visual or light indicator to indicate if inspiratory demand has been met. A visual indicator may refer to but is not limited to a display that may use colour such as, red to indicate inspiratory demand is not being met, and green to indicate that inspiratory demand is being met. Any colours or combination of colours may be used, a single colour may be used, or more than two colours may be used. The display may also be used to indicate the proportion of the patient's inspiratory demand is being met. The display may allow a user to alter the delivered flow rate. Alterations may increase the delivered flow rate so it may match or exceed inspiratory demand, or they may decrease the delivered flow rate so that the flow being delivered to the patient may not cause noise or patient discomfort.

In one embodiment the user may set a constant flow rate to be delivered to a patient. This flow rate may sufficiently meet the peak inspiratory demand of a patient or may be a flow rate that is a proportion of the estimated inspiratory demand. An example of a flow rate that may be a proportion of the estimated inspiratory demand of a patient may be but is not limited to 0-200% or even 500% of the peak inspiratory demand of a patient. A user may also set a delivered flow that may have a different inspiratory and expiratory flow rate, where either or both flow rates may vary over the breathing cycle. The inspiratory flow rate may be used to provide feedback to the user regarding the current flow being delivered and may provide an indication of whether this is a sufficient flow using a display, coloured indicators, or the like. This may allow the user to manually alter the settings of the device, or they may be able to manually monitor the inspiratory demand of the patient. In some embodiments the device may automatically adjust the delivered flow rate, in a way that may meet the inspiratory demand of the patient. In another embodiment, if the device detects the inspiratory demand of the patient is not met, it may provide a recommendation for the delivered flow rates to the user, who may then accept or reject the recommendation. If the recommendation is accepted, the recommended flow rates are implemented. If it is rejected the user may then choose to manually alter the delivered flow rates. This feedback mechanism may be combined with automatic adjustment, or any other combinations not limited to the above, may be formed.

In other embodiments, apparatus and methods are disclosed that may calculate or measure the expiratory flow rate of a patient. This information can be provided to a clinician and used by the clinician and/or by the apparatus to provide improved high flow therapy and/or other therapies.

2.2.2 First General Embodiment of Inspiratory Demand Estimation Using Patient Pressure, System Pressure and Characteristic Pressure Referring to FIGS. 38, to 41, 42a to 44a, a first general embodiment of the apparatus and method is now described. A flow rate is delivered using the apparatus and the flow rate is sensed using a flow rate sensor, step 39-30. A system pressure is then determined, step 39-31. The system pressure refers to a pressure parameter indicative of or being the pressure at any point in the breathing apparatus 10 (including any of the peripheral components) that can be used to determine inspiratory demand. The system pressure is determined using a sensor placed at a suitable part of the apparatus where pressure is being measured, such as the flow generator 3a, the humidifier 3b or the patient conduit 3c or in the cannula 25/20, or at a mixing chamber where $O_2$ and ambient air mix or in any other suitable part of the system. Where peak inspiratory demand is being estimated, the minimum system pressure is determined, and in the more general case of estimating inspiratory demand at any point in the breath cycle, the system pressure at that point in the breath cycle is determined.

Once the system pressure is measured, the pressure characteristic of the relevant components of the system (up to the point where pressure is being measured) is determined, step 39-32. The pressure characteristic takes into account the pressure caused by the resistance to the flow of the system components at a particular flow rate due to the physical characteristics of the system components at that flow rate. That is, the characteristic pressure indicates the contribution to pressure made by the system due to its physical characteristics at that flow rate. For example, if the system pressure is taken at the flow generator 11, the pressure contributions of the patient interface 17, patient conduit 23, humidifier 12, an internal ducting would contribute to the pressure characteristic. The characteristic pressure is determined using the measured flow rate as an input along with knowledge of the characteristics of the system, or it can be determined from a look up table, relationship, graph or the like that correlates the pressure contribution of particular system components at particular flow rates to the system pressure. The controller 13 next determines a patient pressure, being the pressure contribution by the patient, step 39-33. The controller determines this by subtracting the characteristic pressure from the system pressure. Patient pressure indicates a relationship between the delivered gas flow rate and the inspiratory demand. If patient pressure is based on a minimum system pressure, then it indicates a relationship between the delivered gas flow rate and peak inspiratory demand.

From the patient pressure the controller 13 then determines a flow rate offset from the inspiratory demand flow rate that the patient pressure represents, step 39-34. The flow rate offset (also termed "$Q_{offset}$" later in the description) is the flow that escapes through the nares 70 around the patient interface to atmosphere and is more generally referred to as an instance of "nasal flow". Flow rate offset is the difference (offset) between the gas flow rate delivered by the apparatus and the inspiratory demand (flow rate) of the patient at a point in time. Flow rate offset is a special case of nasal flow that occurs during inspiration—the term "nasal flow" can cover the more general case of flow during inspiration or expiration. When the delivered gas flow rate exceeds inspiratory demand, nasal flow/offset flow is a leakage flow rate (also termed "leakage flow"). When the delivered gas flow rate is less than inspiratory demand, nasal flow/offset flow is an entrained flow (rate).

This flow rate offset may be calculated by using the patient pressure as an input. Alternatively, the flow rate offset can be determined from a look up table, mathematical relationship, graph or the like that correlates the offset flow rate to patient pressure. The relationship can be calculated or determined empirically. Once the offset flow rate is calculated, it can be used in any suitable manner. In one example, the offset flow rate and/or inspiratory demand flow rate (if calculated) is displayed on a screen (e.g. on the I/O 14) or otherwise conveyed, step 39-35. This can be viewed by a clinician and then used to adjust the operating parameters of the apparatus, step 39-36, for example, to meet inspiratory demand (or meet a level relative to inspiratory demand using a percentage thereof or deliver a flow rate that is offset from the inspiratory demand by an absolute amount—ensuring accurate delivered oxygen fraction or for weaning the therapy). Alternatively, the controller 13 could utilise the offset flow rate to automatically adjust the gas flow rate provided by the apparatus commensurate with the offset flow rate to meet inspiratory demand, step 39-36. The above actions can refer to peak inspiratory demand if the patient pressure has been determined using minimum system pressure in the apparatus.

More generally, the patient pressure is indicative of inspiratory demand (or peak inspiratory demand if based on a minimum apparatus pressure). (Peak) inspiratory demand can be determined or inferred, and action taken in, any suitable manner using the patient pressure. It is not necessary to find (peak) inspiratory demand using a flow rate offset. This information could be obtained in other manners from patient pressure, or patient pressure or some parameter derived from it could be used to inform a user and/or operate flow therapy.

2.2.3 Peak Inspiratory Demand Estimation According to First General Embodiment Using Patient Pressure, System Pressure and Characteristic Pressure One particular non-limiting embodiment will now be described for determining the peak inspiratory demand (PID) of a patient, and/or subsequently utilising PID information. Once determined, an indication of the PID for the patient can be displayed for consideration by a physician for determining delivered gas flow rate (also termed "flow rate") or other setting for the apparatus; or alternatively, the PID can be used by the apparatus to adaptively alter the delivered gas flow rate to meet peak inspiratory demand. Inspiratory demand is the gas flow rate required/demanded by a patient at a particular (instantaneous) point in time, and peak inspiratory demand is the peak gas flow rate required/demanded by the patient during the peak inspiration point of the breath cycle. The phrase "peak inspiratory demand" refers to a flow rate and can be used interchangeably with the phrase "peak inspiratory demand flow rate"

The method and apparatus will be described with reference to FIGS. 38, to 41, 42*a* to 44*a*, wherein the apparatus of FIG. 38 can be configured to carry out the method to determine and utilise PID, as set out in the flow chart of FIG. 39. For example, the controller 13 can be programmed to carry out the method in the flow chart of FIG. 39 using as inputs information from sensors in the apparatus. A cannula is shown in FIG. 38 and will be described with reference to the embodiments below, but it will be appreciated that the embodiments described are not restricted to the use of a cannula and in fact the embodiments described would work with any type of suitable patient interface. Any references herein to cannula could be generalised to refer to any suitable patient interface.

The apparatus delivers gas flow and has a flow sensor placed just after the flow generator, in or around the cannula (or other patient interface) or at some other suitable point for sensing the gas flow rate delivered to the patient, step 39-30. Where an additional $O_2$ source is provided, the flow sensing can be provided after the mixing of $O_2$ with ambient gas. The output from the flow sensor is communicated to the controller 13. The controller can determine the current/instantaneous delivered gas flow rate, or a value representative of that flow rate over a number of breath cycles. The apparatus 10 also has a pressure sensor 25 or 20 placed in or around the cannula (such as inside or proximate the manifold of the cannula or inside or proximate the prongs) for sensing the system pressure (in this case the cannula/manifold pressure) or sensing a pressure parameter indicative of that pressure, step 39-31. (As noted earlier, alternatively, the pressure sensor could be placed in any other suitable location in the circuit, such as in or after the flow generator 3*a*, humidifier 3*b*, or patient breathing conduit 3*c*, or at a mixing chamber where $O_2$ and ambient air mix.)

More generally, reference to pressure in this embodiment means any pressure parameter/value being or indicative of actual pressure in the manifold (or more generally the cannula). The cannula has a manifold, so in this embodiment pressure can alternatively be termed "manifold pressure" as a cannula is used. The manifold pressure will comprise pressure contributions from or due to the apparatus, patient and cannula (more generally the patient interface). The output of the pressure sensor 20/25 is communicated to the controller 13. From that output, the controller 13 determines a minimum manifold pressure in the cannula, step 39-31. The minimum manifold pressure may be a single or instantaneous pressure relating to (that is, indicative of or being) the minimum pressure of the cannula in a particular breath cycle (that is, at peak inspiration), or the minimum manifold pressure may be or indicative of a representative pressure of several breath cycles, such as a mean or average minimum, or median minimum pressure in the cannula over each of e.g. five breaths cycles.

An example of a method that could be used to determine a minimum pressure is to continuously monitor the instantaneous pressure readings storing any values that are less than all other previous values. The minimum pressure found within this set of stored values is the minimum system pressure used in the PID calculation, or is used as a component of the average/median minimum pressure. The set of stored values is refreshed when the instantaneous pressure reading exceeds a certain threshold value e.g.: increases by a set absolute value, or percentage from the previous reading or exceeds the mean pressure, indicating a new breath.

Figure 41:
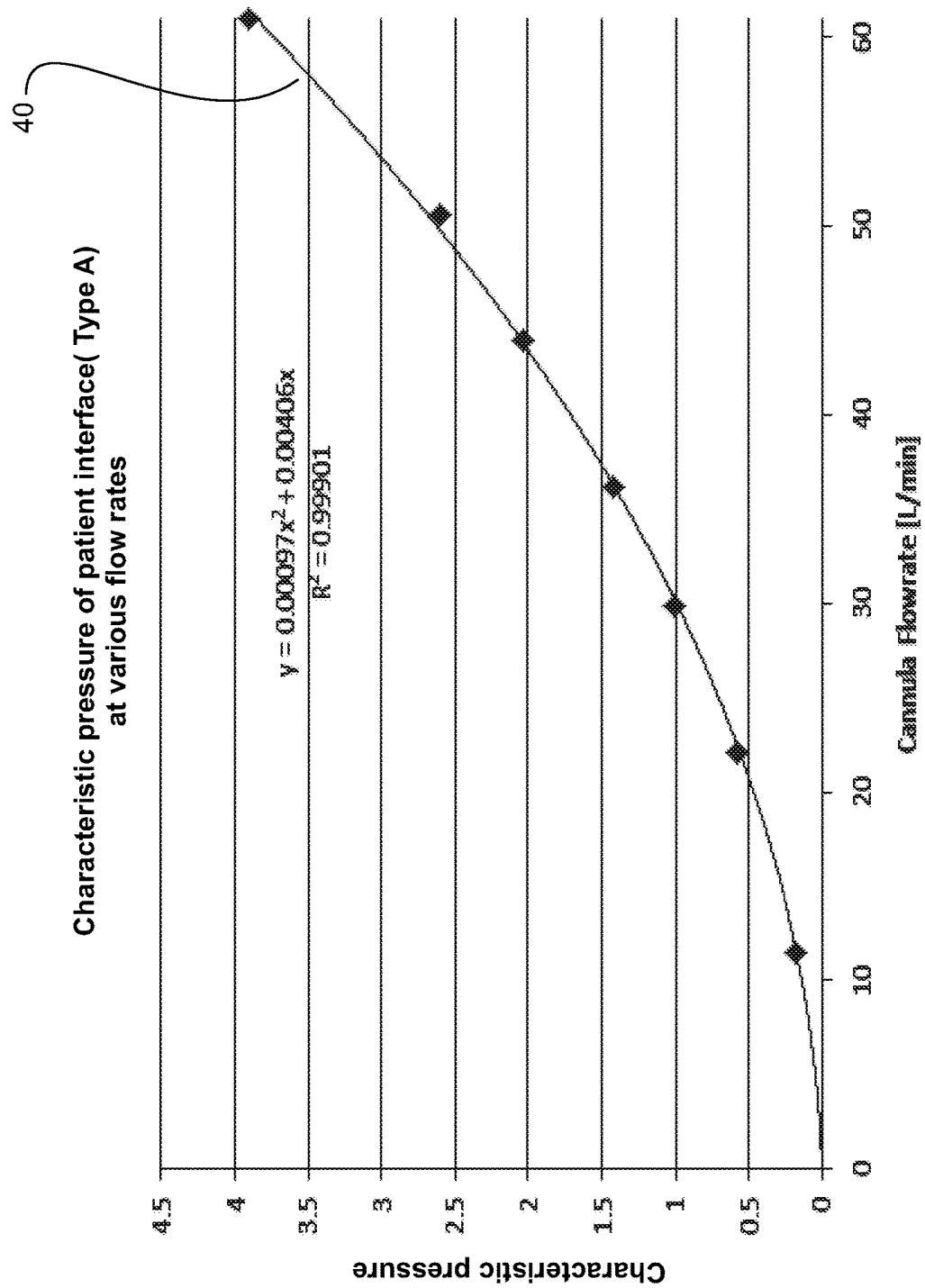
FIG. 41 is a graph showing an indicative characteristic pressure curve for a patient interface at various flow rates.

Next, step 39-32, the controller 13 obtains a characteristic pressure 40 of the cannula at the flow rate determined by the controller. The characteristic pressure 40 is the pressure caused by the resistance to the flow of the cannula at a particular flow rate due to the physical characteristics of the cannula at that flow rate. That is, the characteristic pressure indicates the contribution to pressure made by the cannula due to its physical characteristics at that flow rate. This characteristic pressure 40 may be calculated by using the measured flow rate as an input along with knowledge of the characteristics of the cannula, or it can be determined from a look up table, relationship, graph or the like that correlates the pressure contribution of a particular cannula at particular flow rates to the manifold pressure. A generic such relationship and graph is shown in FIG. 41 for a hypothetical cannula termed "Type A". Alternatively, the characteristic pressure could be determined in a calibration step at the time of measurement for that particular patient/set-up by taking a pressure measurement when the cannula has been removed from the patient for a time. Note, if a pressure sensor is used at another location in the circuit (such as at locations 3*a*, 3*b* or 3*c*), then the characteristic pressure will be the pressure caused by resistance to the flow by all components in the circuit that affect the pressure, such as the patient conduit, flow generator, humidifier and/or internal ducting. In such cases, the pressure measured will not be the manifold or cannula pressure, but the pressure of the relevant location/component in the circuit.

The controller 13 next determines a patient pressure, being the pressure contribution by the patient to the manifold pressure, step 39-33. The controller determines this by subtracting the characteristic pressure 40 from the minimum manifold pressure. That is, $$P_{pmin} = P_{mmin} - P_{char} \quad (1)$$

where
  $P_{pmin}$=(minimum) patient pressure
  $P_{char}$=characteristic pressure
  $P_{mmin}$=minimum manifold pressure As the patient pressure in this case is determined from minimum manifold pressure, it can termed a "minimum patient pressure"—although hereinafter will just be referred to the as the more general "patient pressure". The patient pressure (when determined from minimum manifold pressure) indicates a relationship between the delivered gas flow rate and the peak inspiratory demand. If the patient pressure is zero (at a particular instant in time), this indicates that the gas flow rate being supplied (delivered) to the cannula (at that time) is meeting the inspiratory demand. If the patient pressure is below zero, this indicates that the flow rate being supplied to the cannula is insufficient to meet inspiratory demand and that ambient air has been entrained into the breath flow.

Conversely, a patient pressure above zero indicates that the gas flow rate being provided (delivered) to the cannula is above what is required by the patient. From the patient pressure, and based on the above, the controller 13 then determines the flow rate offset 42-41 (which can also be termed nasal flow) from the peak inspiratory demand flow rate that the patient pressure represents, step 39-34. This flow rate offset 42-41 may be calculated by using the patient pressure as an input.

Alternatively, the flow rate offset can be determined from a look up table, mathematical relationship, graph or the like that correlates the offset flow rate 42-41 to patient pressure.

Figure 42A:
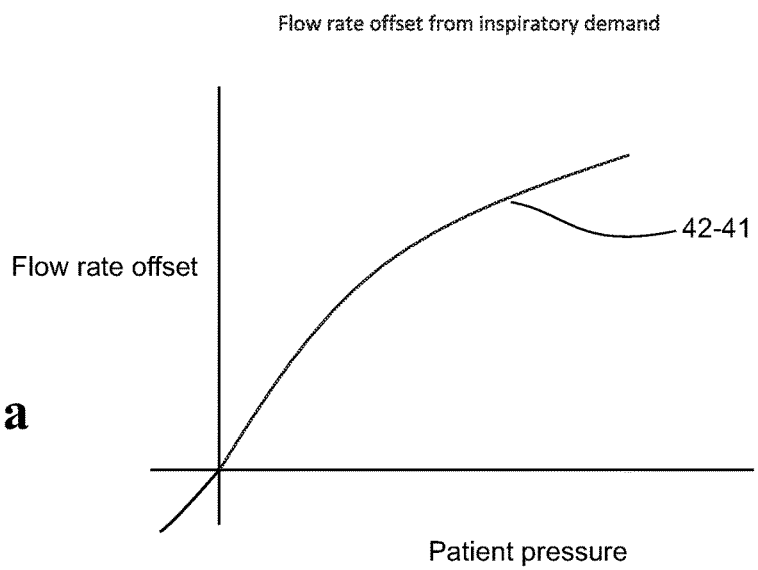
FIG. 42a is a graph showing an indicative flow rate offset from inspiratory demand.

A generic relationship showing flow rate offset 42-41 from peak inspiratory demand is shown in FIG. 42a. The relationship can be calculated or determined empirically. An empirical derivation can be determined by taking a population average which is stored in the controller and accessed as required via a look-up table, calculation from the relationship equation or similar, or by creating a relationship for each individual patient as part of a calibration step/learning period. An individual patient relationship could be found by taking patient pressure measurements over a range of flow rates allowing for a stabilisation period of say 5 breaths, or several minutes at each flow rate. The recorded data would be analysed to find the flow rate at which the patient pressure equalled zero, and this would be taken as an estimate of the patient's inspiratory demand. The flow rate offset at all other tested flow rates could be calculated by finding the difference between the delivered flow rate and the estimated patient inspiratory demand. In this way the flow rate offsets could be matched to the patient pressures measured across the tested flow rate range, and a patient specific relationship could be found. This calibration could be performed at the onset of therapy and/or at intervals throughout the therapy and/or when initiated by the user or the device, for example when the patient has moved causing a change in the arrangement of the device tubing and thus its characteristic resistance to flow. The range of tested flow rates may be set by the device or may be chosen by the user based on the expected delivered flow rates throughout the patient's treatment.

The relationship 42-41 depicted by the graph in FIG. 42a shows the relationship between the patient pressure and flow rate offset (from the PID flow rate). If the offset flow rate is positive, this indicates that the gas flow rate being delivered is more than the peak inspiratory demand. If the offset flow rate is negative in that indicates that insufficient gas flow rate is being delivered to the patient and will not meet their peak inspiratory demand flow rate. Optionally, the actual PID flow rate can be calculated by subtracting the offset flow rate from the delivered gas flow rate.

Once the offset flow rate is calculated, it can be used in any suitable manner. In one example, the offset flow rate and/or PID flow rate (if calculated) is displayed on a screen (e.g. on the I/O 14) or otherwise conveyed, step 39-35. This can be viewed by a clinician and then used to adjust the operating parameters of the apparatus, step 39-36, for example, to meet PID (or meet a level relative to a percentage of PID or deliver a flow rate that is offset from the PID by an absolute amount—ensuring accurate delivered oxygen fraction or for weaning the therapy). For example, if there is a negative offset flow rate indicating that the apparatus is not providing sufficient gas flow breath rate to meet PID of the patient, then the clinician can increase the delivered gas flow rate by that (offset flow rate) amount to meet the demand. Alternatively, the controller 13 could utilise the offset flow rate to automatically adjust the gas flow rate provided by the apparatus commensurate with the offset flow rate to meet PID, step 39-36.

Figure 39:
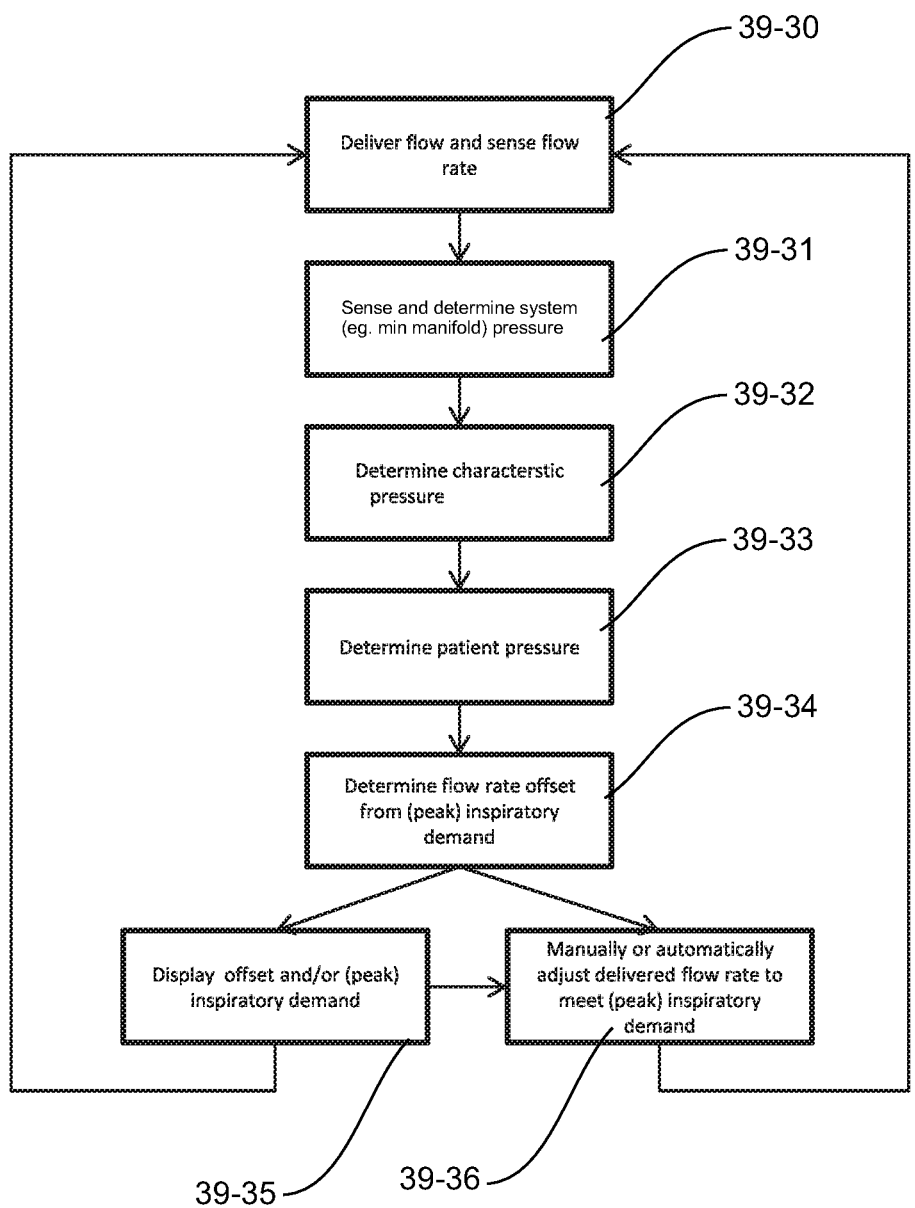
FIG. 39 is a flow diagram of one method of estimating inspiratory demand according to a first general embodiment.

FIG. 39 shows one operation of determining flow rate offset. The peak inspiratory demand of a patient can vary continuously, and the method of FIG. 39 can be continually or periodically carried out to re-determine the flow rate offset continually/periodically to obtain an updated PID indication.

A particular non-limiting example will now be described with reference to FIGS. 38, 39 and 43a. The delivered gas flow rate is measured using the flow rate sensor as previously described, step 39-30. In this example the delivered flow rate is 40 litres per minute. The minimum manifold pressure is then measured using the pressure sensor 20/25 as previously described, step 31. The characteristic pressure caused by the resistance to flow of the cannula at 40 litres per minute is determined by the controller (e.g. in this example 1.71cmH$_2$O) and then is subtracted from the minimum manifold pressure (measured as 2.45cmH$_2$O in this example) to give the patient pressure, steps 39-32, 39-33. In this example the resultant patient pressure is 0.74 cmH2O. The controller 13 then determines the offset flow rate of 15.7 litres per minute (L/min) using the following mathematical relationship 50, which is also depicted in graphical form in FIG. 5, step 39-34. The estimated PID is therefore 15.7 L/min below the current flow rate of 40 L/min, that is, 24.3 L/min.

$$y = 1.4374x^3 - 8.8912x^2 + 27.204x - 0.1115 \quad (2)$$

Where
  y=offset flow rate (litres per minute), and
  x=patient pressure (pressure difference in cm H$_2$0)

Figure 43A:
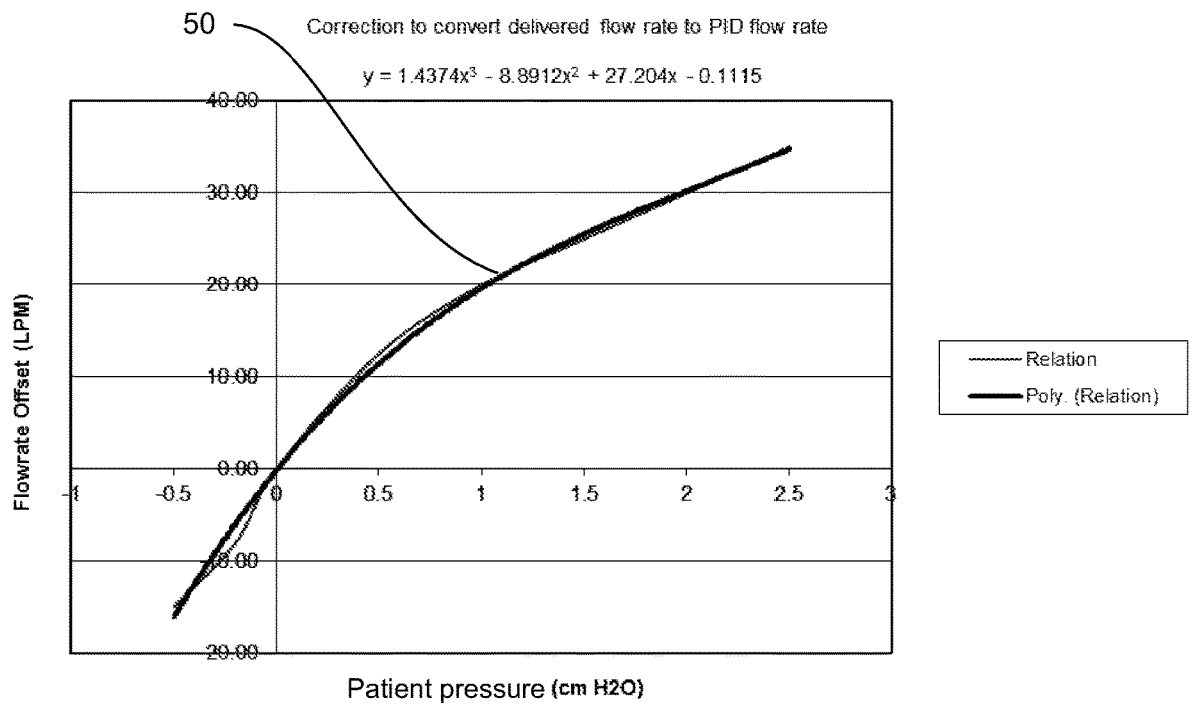
FIG. 43a is a graph showing the relationship between flow rate offset from (peak) inspiratory demand and patient pressure.

The relationship in FIG. 43a is determined empirically, over which is superimposed a polynomial best fit (as per the equation above)—see FIG. 44a and the explanation below. The example values used above are indicative only to demonstrate how the offset pressure is calculated. It is not critical to have values to the level of accuracy shown.

As can be calculated from the equation above, and visually determined from the graph in FIG. 43a, a patient pressure of 0.74 cm $H_2O$ equates to a flow rate offset of 15.7 litres per minute, step 34. Optionally, the actual PID estimate can then be calculated as 24.3 litres per minute being the delivered flow rate 40 litres/minute less the offset flow rate of 15.7 litres per minute, step 34. The offset flow rate and/or the PID estimate can be displayed, step 39-35 and/or used, step 39-36, by a clinician to adjust the apparatus to deliver the PID, or used by the controller to automatically adjust the delivered flow rate to meet PID.

More generally, the table below shows the calculated offset flow rate as determined from the relationship, and the resulting PID estimate using the method described above for various cannula flow rates. As can be seen, the PID estimate varies between 22.8 L/min and 26.6 L/min for delivered cannula flow rates of 10-60 Litres per minute, which is within an acceptable margin of error. Also, PID will not necessarily be the same at all flow rates—PID can change with cannula flow rate. That is, with most patients, PID is slightly higher with higher cannula flows. The variation shown in the table is at least in part due to true variation in PID due to breathing being a dynamic system.

TABLE 1

| Cannula Flow rate | Patient Pressure (Minimum Manifold Pressure - Characteristic Pressure) | Flow rate Offset | Peak Inspiratory Demand Estimate |
|---|---|---|---|
| 10 | −0.41 | −12.8 | 22.8 |
| 15 | −0.24 | −7.3 | 22.3 |
| 20 | −0.08 | −2.5 | 22.5 |
| 25 | 0.08 | 2.1 | 22.9 |
| 30 | 0.27 | 6.6 | 23.4 |
| 35 | 0.48 | 11.1 | 23.9 |
| 40 | 0.74 | 15.7 | 24.3 |
| 45 | 1.04 | 20.2 | 24.8 |
| 50 | 1.40 | 24.5 | 25.5 |
| 55 | 1.84 | 28.8 | 26.2 |
| 60 | 2.35 | 33.4 | 26.6 |

The mathematical relationships and graphs, such as those shown in FIG. 43a can be determined by measuring, for a sample of patients, the manifold pressure at each of a range of delivered cannula gas flow rates, and then obtaining a representative measure, such as the mean. It will be appreciated that FIG. 43a and the accompany equation is illustrative only, and should not be considered limiting. Other variations could be derived/devised that still implement the invention.

Figure 44A:
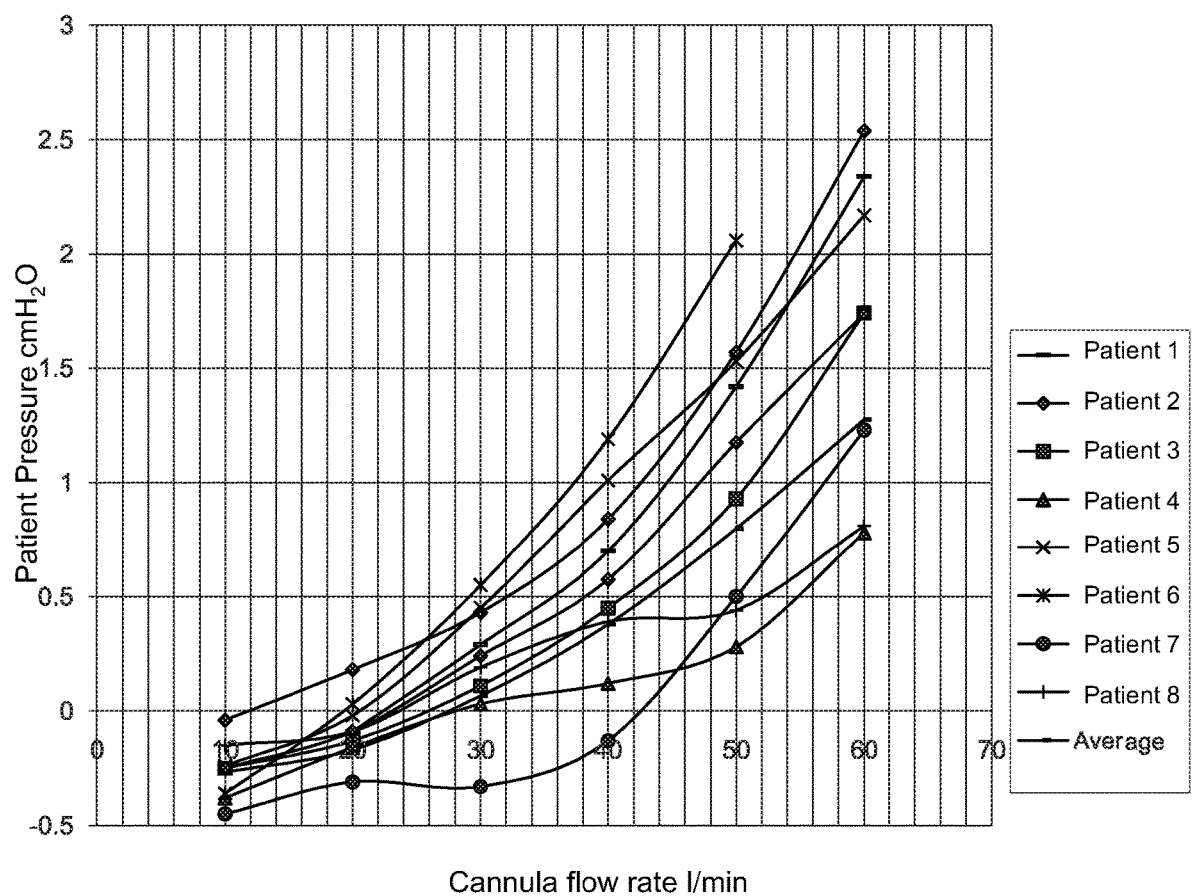

FIG. 44a shows empirical data used to generate the relationship of FIG. 43a. The patient pressure at various flow rates is measured for a range of patients. The flow rate at the zero patient pressure points correlates to the representative PIDs of the patients that were measured. The offset flow rate for each patient can be found by subtracting the determined inspiratory flow from each delivered cannula flow rate. The patient pressure/offset flow curves can thus be plotted for each patient. A representative trend/best fit line is found for the population of patient pressure/offset flow curves using a suitable statistical method. Using the trend line, a representative plot of the patient pressure versus the flow rate offset from the PID flow rate results in the graph of FIG. 43a, and the best fit line function can be calculated (that is, equation 2 above).

2.2.4 Instantaneous Inspiratory Demand Estimation According to First General Embodiment Using Patient Pressure, System Pressure and Characteristic Pressure The embodiments above relate to finding a peak inspiratory demand flow rate, or some indication thereof. This is the flow rate demand of the patient at the peak of their inspiration Minimum manifold pressure (or in the more general case a system pressure) is used to obtain this, the minimum manifold pressure correlating to the point in time at which there is peak inspiration. More generally, the method can be utilised to find the instantaneous demand of a patient, at any point of the respiratory cycle. The method is the same as described previously, but rather than measuring the minimum manifold pressure (which corresponds to a point in time of peak inspiratory flow) the manifold pressure can be taken at any instantaneous time (or a representative value of the same point of the breath cycle across multiple breath cycles). Any references to peak inspiratory demand and/or minimum (manifold) pressure in the description above and related drawings can be generalised to "inspiratory demand" and "(manifold) pressure" respectively. Once that manifold pressure is obtained, the characteristic pressure is subtracted from it to give the patient pressure. This will be the patient pressure correlating to the point of the respiration cycle at which the manifold pressure was taken. A flow rate offset is then determined from the relationship or graph, such as shown in FIG. 43a, and from that a flow rate offset determined being the flow rate offset from the instantaneous inspiratory demand at that point in time. This can be displayed and/or utilised to determine that the instantaneous inspiratory demand, and/or used by clinician or by the controller for controlling the flow rate to meet the instantaneous inspiratory demand.

In this more general case of measuring inspiratory demand, the phase of the breath cycle is determined (and the patient pressure is determined during that phase) as the relationship described in FIG. 43a only applies to the inspiratory phase of a breath cycle. The breath phase can be determined by calculating a mean patient pressure or a mean system pressure over several breath periods and assigning all pressure measurements below this mean value to be part of the inspiratory phase (and all measurements above this mean value to be part of the expiratory phase). The mean value can be re-calculated at regular intervals (e.g. every 5 breaths) and each calculated mean value may be used retrospectively only for the period of breaths over which it was calculated, and/or may be used as the comparison value for future measurements. The mean pressure may be also re-calculated according to an IIR median filter or other such algorithm. If the patient's breathing is deemed sufficiently stable (for example by taking a number of mean pressure measurements over a longer period of time and noting that all measurements fall within an acceptable range) the period over which that mean pressure applies may be extended, or the weighting within a filter algorithm may be altered.

It would also be possible to calculate other parameters related to the patient's inspiratory demand such as their mean inspiratory demand. These values could be communicated to the user through the display and may allow the user to set delivered flow rates relative to these values, or in combined consideration with the PID.

In the general case and referring again to FIG. 38, the controller 13 measures a manifold pressure (or more generally a system pressure at any point in the apparatus) during some point in an inspiration phase, and then determines the corresponding patient pressure being the pressure contribution by the patient to the manifold pressure (or, more generally, system pressure), step 39-33. The controller determines this by subtracting the characteristic pressure 40 from the manifold pressure (or more generally system pressure). That is, $$P_p = P_{sys} - P_{char} \quad (3)$$

where
- $P_p$ = patient pressure
- $P_{char}$ = characteristic pressure
- $P_{sys}$ = system pressure The remainder of the method is as described above to provide the inspiratory demand (and/or offset therefrom) at the point in the inspiratory breath phase that the manifold pressure was measured. This information can then be displayed and/or used as previously described for PID.

The embodiments above refer to manifold pressure. The minimum manifold pressure (relating to the pressure at peak inspiration) or the general case manifold pressure (relating at another point in the breath cycle) correspond to the pressure in or proximate the cannula (or other patient interface) for a particular breath cycle or plurality of cycles. The manifold pressure may therefore not be the actual pressure in the manifold, but something indicative of it. More generally, the minimum manifold pressure or general case manifold pressure is a pressure parameter indicative of or being the pressure in the patient interface (in this case a cannula) at a point of the breath cycle over one or more cycles, and may comprise a pressure value(s) from outside, inside or proximate the patient interface that is not necessarily the pressure in the patient interface, but is indicative of it.

Even more generally, the pressure can be measured at any point in the system. If a pressure is measured at another location in the circuit/system (such as at sensor locations 3a, 3b or 3c), then the characteristic pressure will be the pressure caused by resistance to the flow by all components in the circuit that affect the pressure, such as the patient conduit, flow generator, humidifier and/or internal ducting. In such cases, the pressure measured will not be the manifold or cannula pressure, but the pressure of the relevant location/component in the circuit.

In another alternative, a pressure might not be measured by a sensor, but determined by another means, such as by looking at the power demand of the flow generator.

Instantaneous inspiratory flow rate can be displayed and/or used (by a clinician or the apparatus) to control the apparatus to meeting inspiratory demand. For example, the apparatus could be controlled to continually adapted the output flow rate to meet inspiratory demand throughout that entire portion of the breath cycle.

2.3 Estimating Expiratory Flow Rate Using Patient Pressure, System Pressure and Characteristic Pressure 2.3.1 First General Embodiment of Expiratory Flow Rate Estimation Using Patient Pressure, System Pressure and Characteristic Pressure Referring to FIGS. 38, 40, 41, 42b-44b, a first general embodiment of the apparatus and method is now described for determining expiratory flow rate. The above method and apparatus can also be utilised to determine expiratory flow rate—both peak and instantaneous. Much of the description for determining inspiratory flow rate applies also for determining expiratory flow rate, so the following description will not describe all aspects of the embodiment, but instead rely on the previous description for features common to both embodiments.

Figure 40:
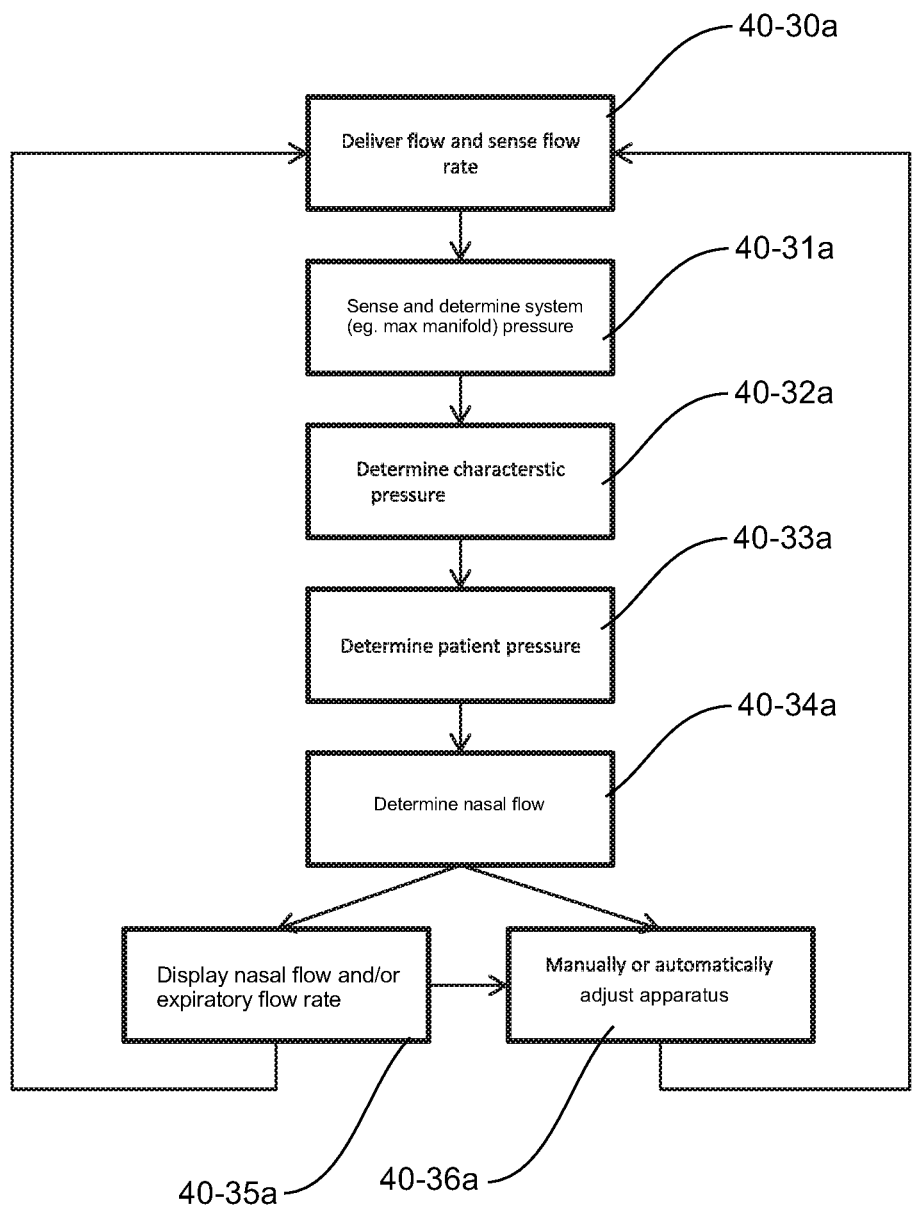
FIG. 40 is a flow diagram of one method of estimating expiratory flow rate according to a first general embodiment.

Referring to FIG. 40 a flow rate is delivered using the apparatus and the flow rate is sensed using a flow rate sensor, step 40-30a. A system pressure is then determined, step 40-31a. The system pressure is determined using a sensor placed at a suitable part of the apparatus where pressure is being measured, such as the flow generator 3a, the humidifier 3b or the patient conduit 3c or in the cannula 25/20, or at a mixing chamber where $O_2$ and ambient air/gas mix or in any other suitable part of the system. Where peak expiratory flow rate is being estimated, the maximum system pressure is determined, and in the more general case of estimating expiratory flow rate at any point in the breath cycle, the system pressure at that point in the breath cycle is determined.

Once the system pressure is measured, the pressure characteristic of the relevant components of the system (up to the point where pressure is being measured) is determined, step 40-32a, using any technique described for inspiratory flow. The controller 13 next determines a patient pressure, being the pressure contribution by the patient, step 40-33a. The controller determines this by subtracting the characteristic pressure from the system pressure. Patient pressure indicates a relationship between the delivered gas flow rate and the expiratory flow rate. If patient pressure is based on a maximum system pressure, then it indicates a relationship between the delivered gas flow rate and peak expiratory flow rate.

From the patient pressure the controller 13 then determines a nasal flow rate or leakage flow rate from the expiratory flow rate that the patient pressure represents, step 40-34a. This nasal or leakage flow is the flow that escapes through the nares 70 around the patient interface to atmosphere. Nasal flow is combination of the gas flow rate delivered by the apparatus and the expiratory flow rate of the patient at a point in time. Nasal flow (also termed "leakage flow") is the expiratory flow "equivalent" of the flow rate offset during inspiration. Nasal flow can also be used interchangeably with "nasal flow rate" and likewise "leakage flow" can be used interchangeably with "leakage flow rate".

This nasal flow rate may be calculated by using the patient pressure as an input. Alternatively, the nasal flow rate can be determined from a look up table, mathematical relationship, graph or the like that correlates the nasal flow rate to patient pressure. The relationship can be calculated or determined empirically. Once the nasal flow rate is calculated, it can be used in any suitable manner. In one example, the nasal flow rate and/or expiratory flow rate (if calculated) is displayed on a screen (e.g. on the I/O 14) or otherwise conveyed, step 40-35a. This can be viewed by a clinician and then used to adjust the operating parameters of the apparatus, step 40-36a. Alternatively, the controller 13 could utilise the nasal flow rate to automatically adjust the apparatus operating parameters, step 40-36. The above actions can refer to peak expiratory flow rate if the patient pressure has been determined using maximum system pressure in the apparatus.

More generally, the patient pressure is indicative of expiratory flow rate (or peak expiratory flow rate if based on a maximum apparatus pressure). (Peak) expiratory demand can be determined or inferred, and action taken in, any suitable manner using the patient pressure. It is not necessary to find (peak) expiratory flow rate using a nasal flow rate. This information could be obtained in other manners from patient pressure, or patient pressure or some parameter derived from it could be used to inform a user and/or operate flow therapy.

2.3.2 Peak Expiratory Estimation According to First General Embodiment Using Patient Pressure, System Pressure and Characteristic Pressure One particular non-limiting embodiment will now be described for determining the peak expiratory flow rate of a patient. Once determined, an indication of the peak expiratory flow rate for the patient can be displayed for consideration by a physician for determining any suitable setting for the apparatus; or alternatively, the peak expiratory flow rate can be used by the apparatus to adaptively alter the operating parameters.

The apparatus delivers gas flow and has a flow sensor placed just after the flow generator, in or around the cannula (or other patient interface) or at some other suitable point for sensing the gas flow rate delivered to the patient, step 40-30a. Where an additional gas (such as $O_2$) source is provided, the flow sensing can be provided after any gas mixing. The output from the flow sensor is communicated to the controller 13. The controller can determine the current/instantaneous delivered gas flow rate, or a value representative of that flow rate over a number of breath cycles. The apparatus 10 also has a pressure sensor 25 or 20 placed in or around the cannula (such as inside or proximate the manifold of the cannula or inside or proximate the prongs) for sensing the system pressure (in this case the cannula/manifold pressure) or sensing a pressure parameter indicative of that pressure, step 31a. The output of the pressure sensor 20/25 is communicated to the controller 13. From that output, the controller 13 determines a maximum manifold pressure in the cannula, step 40-31a. The maximum manifold pressure may be a single or instantaneous pressure relating to (that is, indicative of or being) the maximum pressure of the cannula in a particular breath cycle (that is, at peak expiration), or the maximum manifold pressure may be or indicative of a representative pressure of several breath cycles, such as a mean or average maximum, or median maximum pressure in the cannula over each of e.g. five breaths cycles.

An example of a method that could be used to determine a maximum pressure is to continuously monitor the instantaneous pressure readings storing any values that are less than all other previous values. The maximum pressure found within this set of stored values is the maximum system pressure used in the expiratory flow calculation, or is used as a component of the average/median maximum pressure. The set of stored values is refreshed when the instantaneous pressure reading falls below a certain threshold value e.g.: decreases by a set absolute value, or percentage from the previous reading or falls below the mean pressure, indicating a new breath.

Next, step 40-32a, the controller 13 obtains a characteristic pressure 40 of the cannula at the flow rate determined by the controller, this can be done is a similar way as described for inspiratory demand.

The controller 13 next determines a patient pressure, being the pressure contribution by the patient to the manifold pressure, step 40-33a. The controller determines this by subtracting the characteristic pressure 40 from the maximum manifold pressure. That is, $$P_{pmax} = P_{mmax} - P_{char} \qquad (1')$$

where
$P_{pmax}$=(maximum) patient pressure
$P_{char}$=characteristic pressure
$P_{mmax}$=maximum manifold pressure As the patient pressure in this case is determined from maximum manifold pressure, it can termed a "maximum patient pressure"—although hereinafter will just be referred to the as the more general "patient pressure". The patient pressure (when determined from maximum manifold pressure) indicates a relationship between the delivered gas flow rate and the peak expiratory flow rate.

Figure 42B:
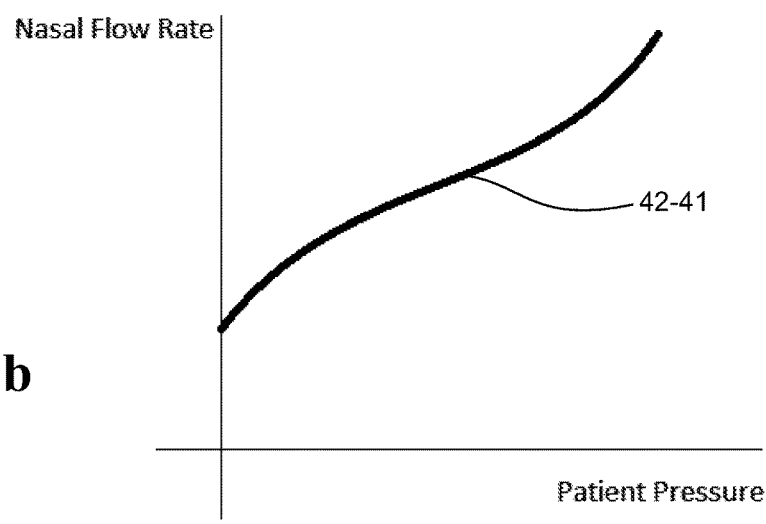
FIG. 42b is a graph showing an indicative nasal flow rate.

The relationship 42-41a depicted by the graph in FIG. 42b shows a relationship between the patient pressure and flow rate offset (from the expiratory flow rate). If the offset flow rate is positive, this indicates that the gas flow rate being delivered is more than the peak inspiratory demand. If the offset flow rate is negative in that indicates that insufficient gas flow rate is being delivered to the patient and will not meet their peak inspiratory demand flow rate. Optionally, the actual expiratory flow rate can be calculated by combining the delivered gas flow rate and the offset flow rate.

Once the nasal flow rate is calculated, step 40-34a, it can be used in any suitable manner. In one example, the nasal flow rate and/or peak expiratory flow rate (if calculated) is displayed on a screen (e.g. on the I/O 14) or otherwise conveyed, step 40-35a. This can be viewed by a clinician and then used to adjust the operating parameters of the apparatus, step 40-36a

FIG. 40 shows one operation of determining nasal flow rate. The peak expiratory flow rate of a patient can vary continuously, and the method of FIG. 40 can be continually or periodically carried out to re-determine the nasal flow rate continually/periodically to obtain an updated peak expiratory flow rate indication.

A particular non limiting example will now be described with reference to FIGS. 38, 40, and 43b. The delivered gas flow rate is measured using the flow rate sensor as previously described, step 40-30. In this example the delivered flow rate is 40 litres per minute. The maximum manifold pressure is then measured using the pressure sensor 20/25 as previously described, step 40-31. The characteristic pressure caused by the resistance to flow of the cannula at 40 litres per minute is determined by the controller (e.g. in this example 4.26 $cmH_2O$) and then is subtracted from the maximum manifold pressure (measured as 13.99 $cmH_2O$ in this example) to give the patient pressure, steps 40-32, 40-33. In this example the resultant patient pressure is 9.73 $cmH_2O$. The controller 13 then determines the nasal flow rate of 67.10 litres per minute using the following mathematical relationship 50, which is also depicted in graphical form in FIG. 43b, step 40-34. The estimated peak expiratory flow rate is therefore 67.11 litres per minute minus the current flow rate of 40 L/min, this is, 27.10 litres per minute.

$$y = 0.023x^3 - 0.802x^2 + 12.13x + 3.813 \qquad (2')$$

Where y=nasal flow rate (litres per minute), and
x=patient pressure (in $cmH_2O$)

Figure 43B:
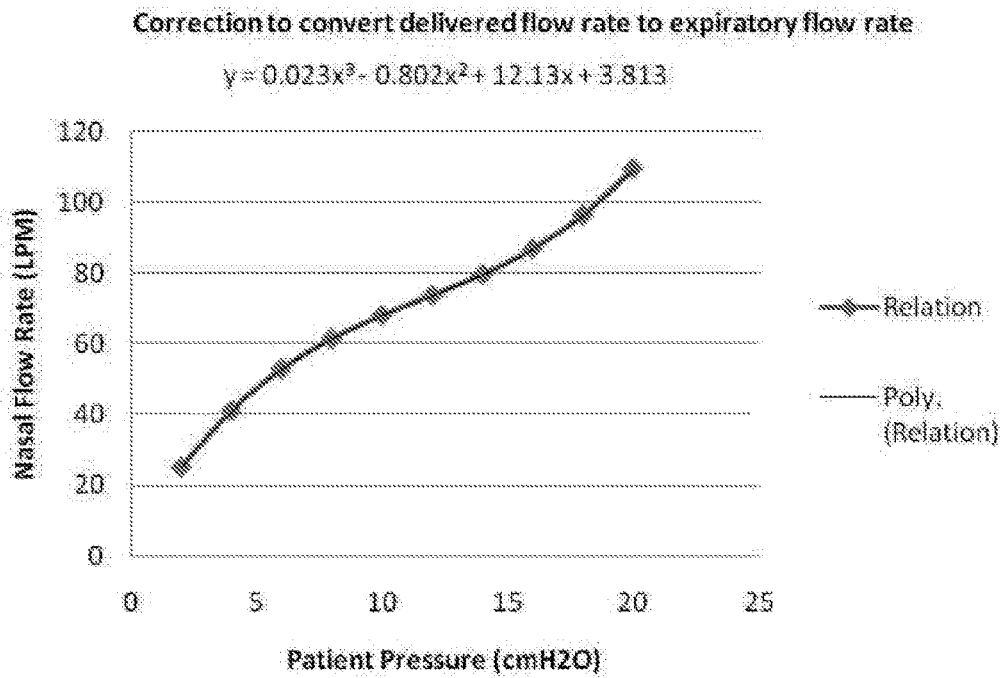
FIG. 43b is a graph showing the relationship between nasal flow rate from (peak) expiratory flow rate and patient pressure.

The relationship in FIG. 43b is determined empirically from a set of population data, over which is superimposed a polynomial best fit (as per the equation above)—see FIG. 44b and the explanation below. The example values used above are indicative only to demonstrate how the offset pressure is calculated. It is not critical to have values to the level of accuracy shown.

As can be calculated from the equation above, and visually determined from the graph in FIG. 43b, a patient pressure of 9.73 cm $H_2O$ equates to a nasal flow rate of 67.10 litres per minute, step 40-34. Optionally, the actual peak expiratory flow rate estimate can then be calculated as 27.10 litres per minute being the nasal flow rate 67.10 litres/minute less the cannula flow rate of 40 litres per minute, step 40-34. The nasal flow rate and/or the peak expiratory flow rate estimate can be displayed, step 40-35 and/or used, step 40-36, by a clinician to adjust the apparatus parameters, or used by the controller to automatically adjust the delivered flow rate or apparatus parameters.

More generally, the table below shows the calculated nasal flow rate as determined from the relationship in the equation above, and the resulting peak expiratory flow rate estimate using the method described above for various cannula flow rates. As can be seen, the peak expiratory flow rate estimate varies between 26.16 L/min and 30.80 L/min for delivered cannula flow rates of 10-60 Litres per minute, which is within an acceptable margin of error.

TABLE 1

| Cannula Flow rate | Patient Pressure (Maximum Manifold Pressure - Characteristic Pressure) | Nasal Flow Rate | Peak Expiratory Flow Rate Estimate |
|---|---|---|---|
| 10 | 3.97 | 40.80 | 30.80 |
| 20 | 5.60 | 50.63 | 30.63 |
| 30 | 7.27 | 58.44 | 28.44 |
| 40 | 9.73 | 67.11 | 27.11 |
| 50 | 12.74 | 75.72 | 25.72 |
| 60 | 15.85 | 86.16 | 26.16 |

The mathematical relationships and graphs, such as those shown in FIG. 5a can be determined by measuring, for a sample of patients, the manifold pressure at each of a range of delivered cannula gas flow rates, and then obtaining a representative measure, such as the mean. It will be appreciated that FIG. 43b and the accompany equation is illustrative only, and should not be considered limiting. Other variations could be derived/devised that still implement the invention.

Figure 44B:
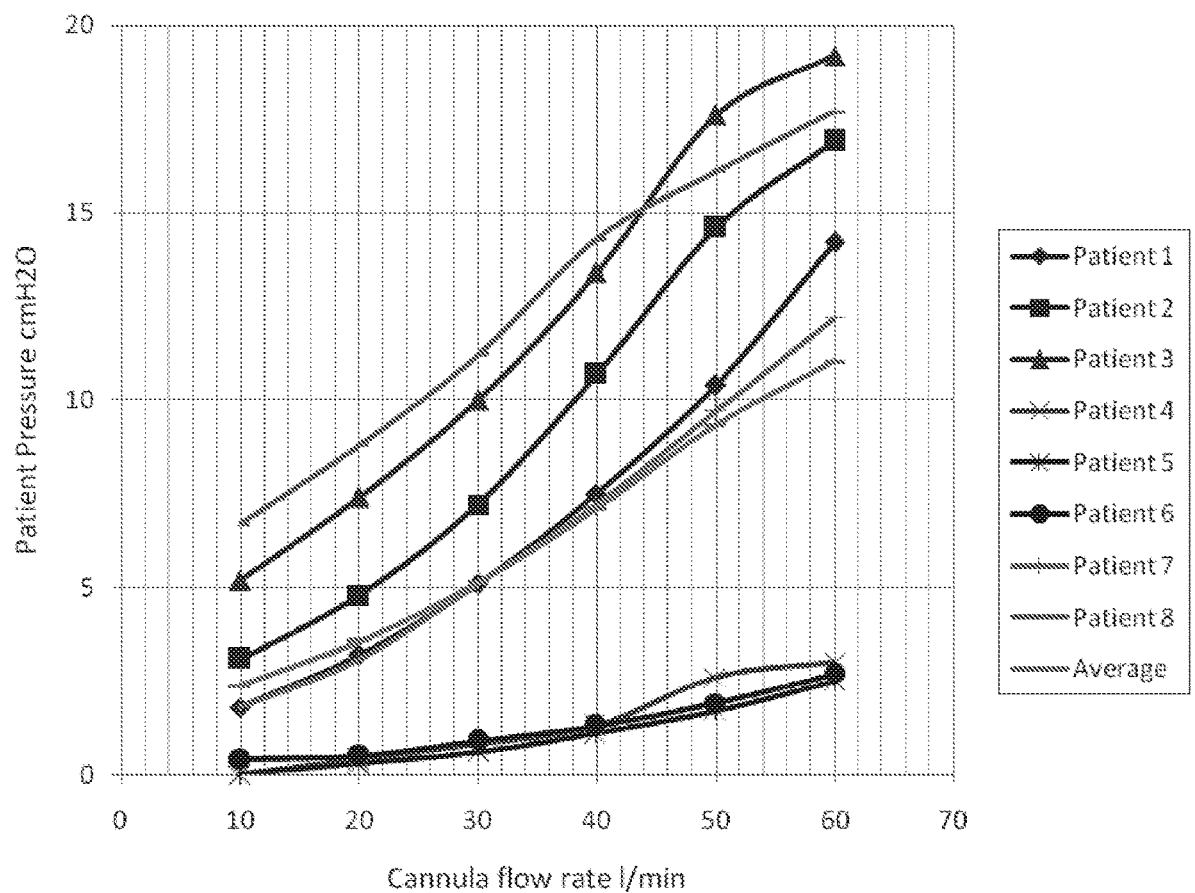
FIG. 44b shows graphs of patient flow rate versus pressure curves for determining the relationship in FIG. 5b.

FIG. 44b shows empirical data used to generate the relationship of FIG. 43b. The patient pressure at various flow rates is measured for a range of patients. The expiratory flow for each patient can be measured regularly, at certain time intervals, or at the start of treatment, for example using a sealed system and a flow measuring device such as those that can be found in a ventilator. Or the data may be collected by in vitro methods such as using a lung simulator with a set expiratory flow rate. The nasal flow rate for each patient case can be found by adding the determined expiratory flow to each delivered cannula flow rate. The patient pressure/nasal flow curves can thus be plotted for each patient case. A representative trend/best fit line can be found for the population of patient pressure/nasal flow curves using a suitable statistical method. Using the trend line, a representative plot of the patient pressure versus the nasal flow rate for peak expiratory flow results in the graph of FIG. 5a, and the best fit line function can be calculated (that is, equation 2' above).

2.3.3 Instantaneous Expiratory Flow Estimation According to First General Embodiment Using Patient Pressure, System Pressure and Characteristic Pressure The embodiments above relate to finding a peak expiratory flow rate, or some indication thereof. More generally, the method can be utilised to find the instantaneous expiratory flow rate of a patient, at any point of the (expiration portion of) respiratory cycle. The method is the same as described previously, but rather than measuring the maximum manifold pressure (which corresponds to a point in time of peak expiratory flow) the manifold pressure can be taken at any instantaneous time (or a representative value of the same point of the breath cycle across multiple breath cycles). Any references to peak expiratory flow rate and/or maximum (manifold) pressure in the description above and related drawings can be generalised to "expiratory flow rate" and "(manifold) pressure" respectively. Once that manifold pressure is obtained, the characteristic pressure is subtracted from it to give the patient pressure. This will be the patient pressure correlating to the point of the respiration cycle at which the manifold pressure was taken. A nasal flow rate is then determined from a relationship or graph such as FIG. 5b, and from that a nasal flow rate determined being the nasal flow rate from the instantaneous expiratory flow rate at that point in time. This can be displayed and/or utilised to determine that the instantaneous expiratory flow rate, and/or used by clinician or by the controller for controlling the operating parameters of the apparatus.

In this more general case of measuring expiratory flow rate, the phase of the breath cycle is determined (and the patient pressure is determined during that phase). The breath phase can be determined by calculating a mean patient pressure or a mean system pressure over several breath periods and assigning all pressure measurements below this mean value to be part of the inspiratory phase (and all measurements above this mean value to be part of the expiratory phase). The mean value can be re-calculated at regular intervals (e.g. every 5 breaths) and each calculated mean value may be used retrospectively only for the period of breaths over which it was calculated, and/or may be used as the comparison value for future measurements. The mean pressure may be also re-calculated according to an IIR median filter or other such algorithm. If the patient's breathing is deemed sufficiently stable (for example by taking a number of mean pressure measurements over a longer period of time and noting that all measurements fall within an acceptable range) the period over which that mean pressure applies may be extended, or the weighting within a filter algorithm may be altered.

It would also be possible to calculate other parameters related to the patient's expiratory flow such as their mean expiratory flow. These values could be communicated to the user through the display and may allow the user to set operation of the apparatus.

In the general case and referring again to FIG. 40, the controller 13 measures a manifold pressure (or more generally a system pressure at any point in the apparatus) during some point in an expiration phase, and then determines the corresponding patient pressure being the pressure contribution by the patient to the manifold pressure (or, more generally, system pressure), step 33a.

The controller determines this by subtracting the characteristic pressure 40 from the manifold pressure (or more generally system pressure). That is, $$P_p = P_{sys} - P_{char} \tag{3'}$$

where $P_p$=patient pressure
$P_{char}$=characteristic pressure
$P_{sys}$=system pressure The remainder of the method is as described above to provide the expiratory flow rate (and/or offset therefrom) at the point in the expiratory breath phase that the manifold pressure was measured. This information can then be displayed and/or used as previously described for peak expiratory flow rate.

The embodiments above refer to manifold pressure. The maximum manifold pressure (relating to the pressure at peak expiration) or the general case manifold pressure (relating at another point in the breath cycle) correspond to the pressure in or proximate the cannula (or other patient interface) for a particular breath cycle or plurality of cycles. The manifold pressure may therefore not be the actual pressure in the manifold, but something indicative of it. More generally, the maximum manifold pressure or general case manifold pressure is a pressure parameter indicative of or being the pressure in the patient interface (in this case a cannula) at a point of the breath cycle over one or more cycles, and may comprise a pressure value(s) from outside, inside or proximate the patient interface that is not necessarily the pressure in the patient interface, but is indicative of it.

Even more generally, the pressure can be measured at any point in the system. If a pressure is measured at another location in the circuit/system (such as at sensor locations 3a, 3b or 3c), then the characteristic pressure will be the pressure caused by resistance to the flow by all components in the circuit that affect the pressure, such as the patient conduit, flow generator, humidifier and/or internal ducting. In such cases, the pressure measured will not be the manifold or cannula pressure, but the pressure of the relevant location/component in the circuit.

In another alternative, a pressure might not be measured by a sensor, but determined by another means, such as by looking at the power demand of the flow generator.

2.3.4 Identifying Expiratory or Inspiratory Flow Rate, and Estimating Respiratory Flow Rate During Breath Flow In the embodiments discussed, either inspiratory flow or expiratory flow rate is determined for display and/or operation of the apparatus. The equations described determine the flow rate at any time during the breath flow, irrespective of whether it is an inspiration portion or expiration portion. Therefore, if the flow rate for a particular breath portion (that is, either inspiration or expiration) is required this can be determined in a suitable manner. In one example, the breath flow can be monitored and transitions detected so that the processor determines whether the breath is in the inspiration phase or expiration phase. If an inspiratory flow rate is required, then the microprocessor determines when inspiratory part of the breath occurs, and takes the required measurements and calculations during that inspiration portion. Likewise, if and expiratory flow rate as required, then the microprocessor determines when expiratory part of the breath occurs, and takes the required measurements and calculations during that expiration portion. In an alternative, the microprocessor does not determine which part of the breath is occurring. Rather, the microprocessor takes required measurements and calculations to determine the flow rate and ascertains whether that flow rate pertains to expiration or inspiration by measuring the patient pressure and then comparing it to the mean patient pressure over a period of time. If the patient pressure is above the mean patient pressure, then the calculated flow rate relates to and expiratory flow rate; and conversely if the patient pressure is below the mean patient pressure, then the calculated flow rate relates to an inspiratory flow rate.

In further embodiments using patient pressure, system pressure and characteristic pressure, rather than determining the flow rate specifically during inspiration or expiration, the flow rate is determined using the same techniques above at any time, regularly and/or continuously during the breath cycle. This would give periodic or continuous information of respiration flow rate at any point of the breath cycle, irrespective of whether it is inspiratory or expiration. It may not be necessary to know which part of the breath cycle is occurring to carry out the estimation and/or it might not be necessary for the output flow rate to indicate whether the flow rate is inspiration or expiration—although one or both of these might be desirable.

Figure 50:
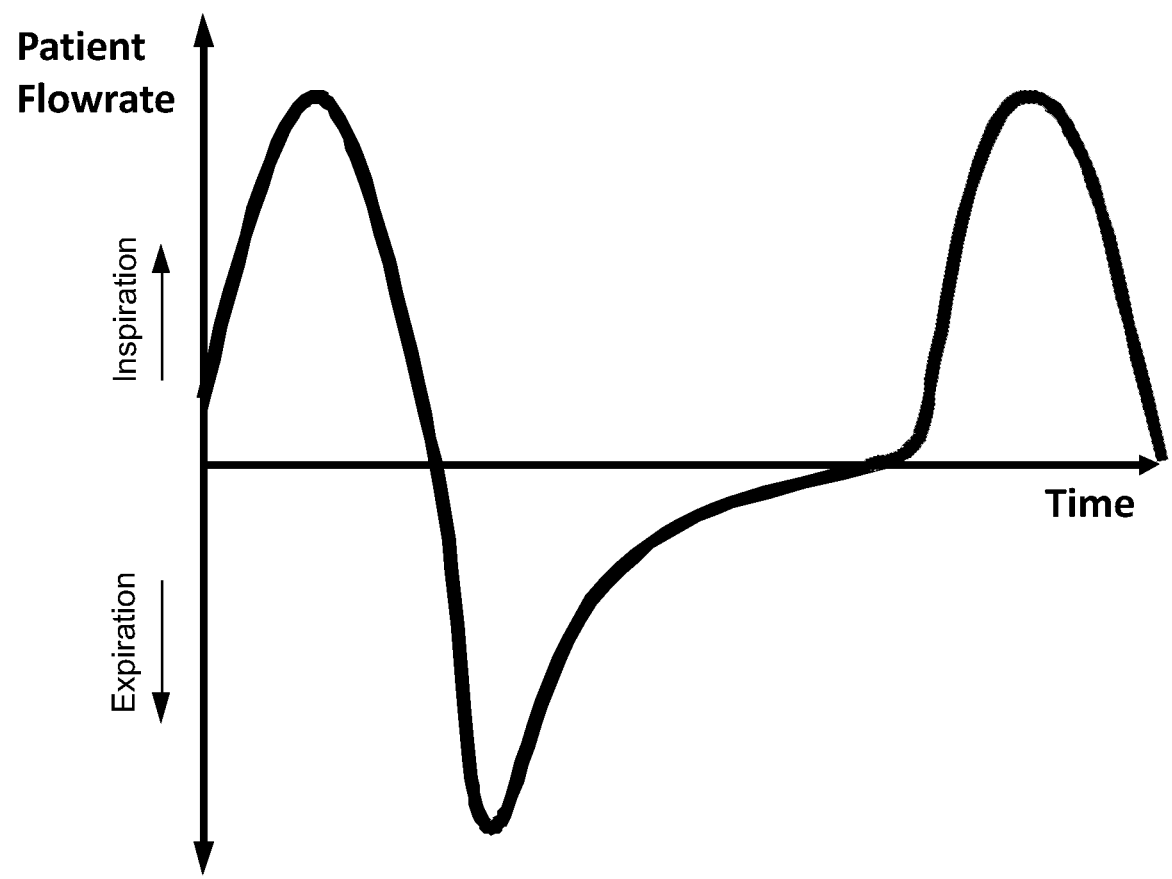
FIG. 50 is a graph showing display of a breath flow rate as determined by embodiments.

It is then possible to display on the apparatus or elsewhere an indication of the respiratory flow rate. This might be, for example an instantaneous or real time numerical or graphical indication of flow rate, either continuously or periodically. Alternatively, or in addition could be a numerical or graphical display of periodic or continuous historical respiratory flow rate. FIG. 50 shows a graphical display in schematic form of breath flow rate as determined by the embodiments described and which could be displayed on the user interface.

Figure 45:
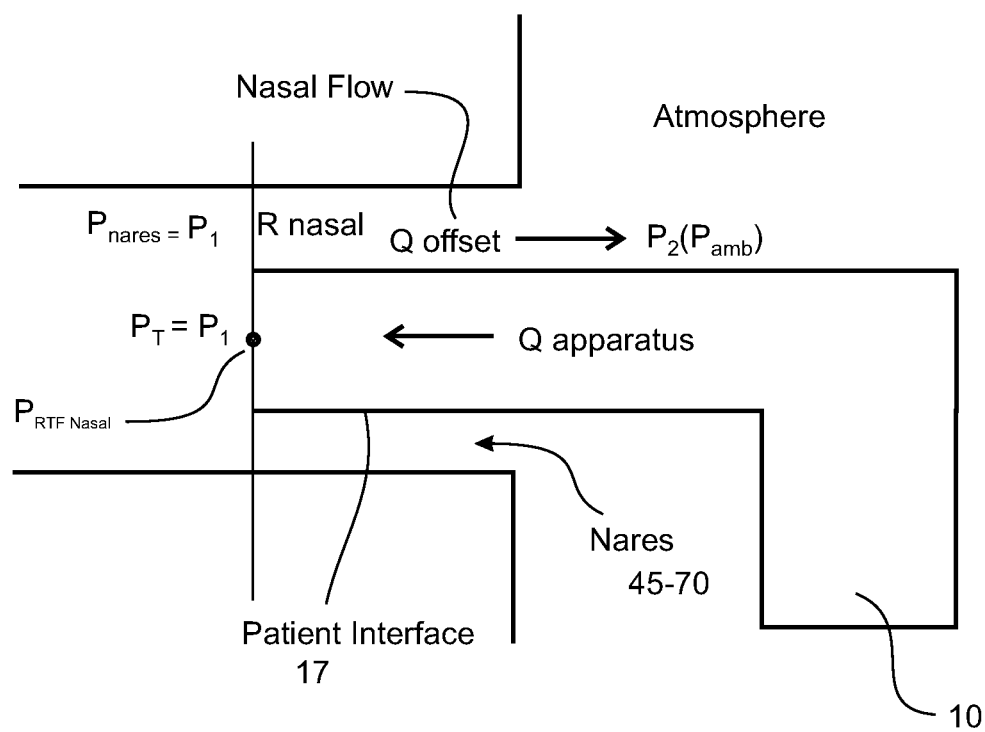
FIG. 45 is a schematic diagram showing the nasal passage being supplied with airflow from a flow therapy apparatus.
Figures 46A, 46B:
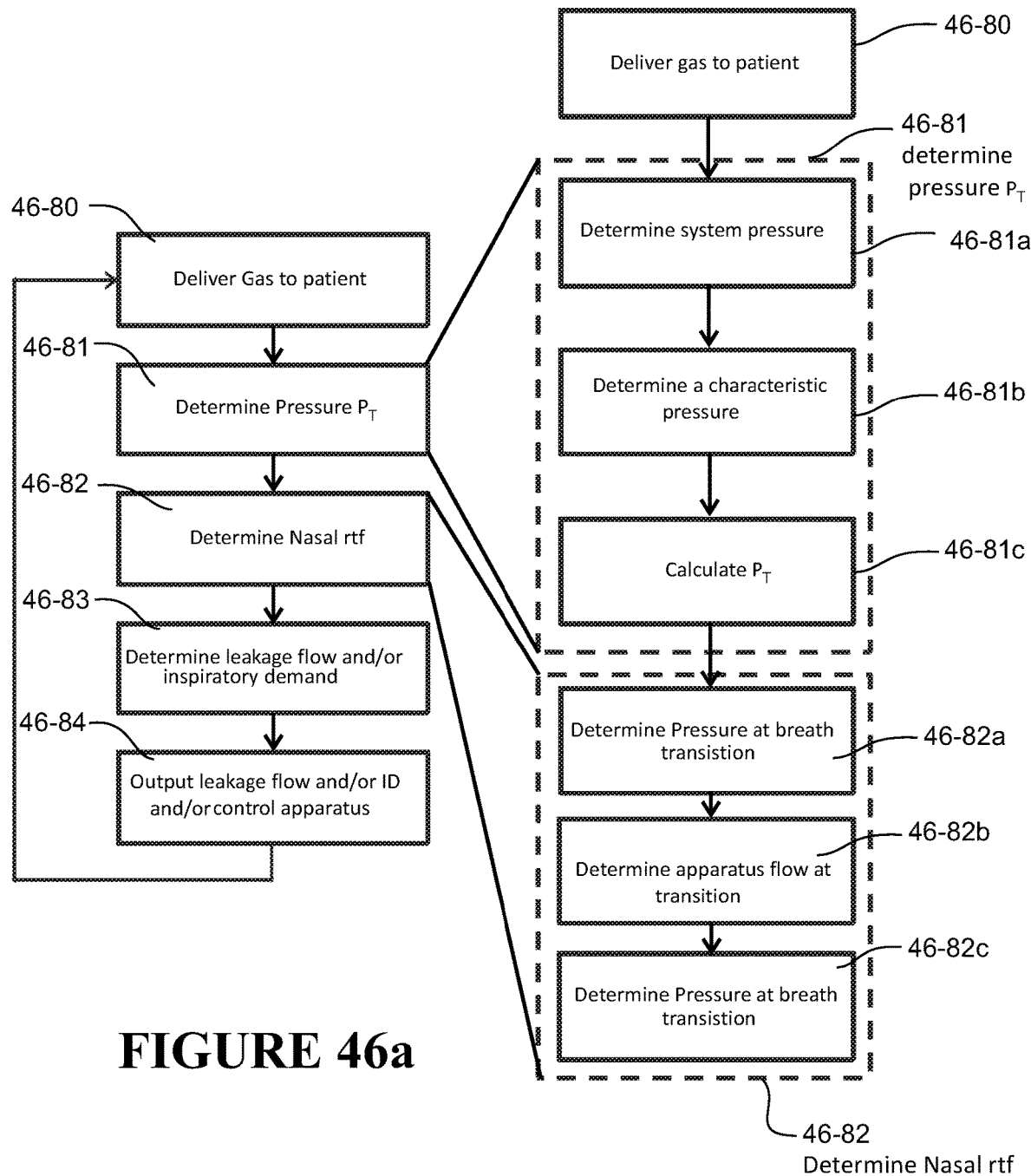
FIG. 46a is flow diagram showing a second general embodiment of estimating inspiratory demand.
FIG. 46b is a flow diagram showing one method of estimating inspiratory demand according to the second general embodiment.

2.4 Estimating Inspiratory Flow Rate (Demand) Using Nasal Flow 2.4.1 Second General Embodiment of Inspiratory Demand Estimation Using Nasal Flow Referring to FIGS. 38, 45 and 46a, a second general embodiment of the apparatus and method is now described. FIG. 45 shows diagrammatically an apparatus delivering gas flow at a flow rate ("$Q_{apparatus}$") to the nares 45-70 of a patient, and nasal gas flow at a flow rate ("$Q_{offset}$") through the nares 70. $Q_{offset}$ (more generally "nasal flow") is the flow that escapes through the nares 45-70 around the patient interface to atmosphere. $Q_{offset}$ is the difference (offset) between the gas flow rate $Q_{apparatus}$ delivered by the apparatus and the inspiratory demand (flow rate) of the patient at a point in time. $Q_{offset}$ is a special case of nasal flow that occurs during inspiration—the term "nasal flow" can cover the more general case of flow during inspiration or expiration. When the gas flow rate $Q_{apparatus}$ exceeds inspiratory demand, $Q_{offset}$ is a leakage flow rate (also termed "leakage flow"). When the gas flow rate $Q_{apparatus}$ is less than inspiratory demand, $Q_{offset}$ is an entrained flow (rate). In general terms, the apparatus 10 administers/delivers gas at a flow rate ($Q_{apparatus}$) to the patient via the patient interface 17 into the nares 45-70. It determines a pressure $P_1$ at the point where the gas flow is delivered and from that and knowledge of a nasal resistance to flow ($R_{nasal}$) determines the leakage flow ($Q_{offset}$), from which inspiratory demand can be determined. $P_1$ is the nasal pressure due to the resistance to flow of $Q_{offset}$ passing through $R_{nasal}$—and can also be termed patient pressure. $P_T$ is the terminal pressure, which is the pressure at the outlet of the patient interface, such as the prongs of the cannula. When the patient interface is worn, the terminal pressure $P_T$ equals the patient pressure $P_1$ (also termed "$P_P$"). This is the case in FIG. 45, so $P_1$ and $P_T$ are the same. Reference will now be made to $P_T$. The time where $P_T$ is at a minimum during a breath cycle corresponds to the nasal flow at peak inspiratory demand. Therefore, when $P_T$ is at a minimum, the associated nasal flow indicates peak inspiratory demand. Nasal flow can be determined continuously or periodically to provide an updated indication of (peak) inspiratory demand. This information can be used to control the apparatus and/or provide information to a user and/or physician.

Referring now to FIG. 46a, the general embodiment will be described. The controller 13 uses inputs to determine the nasal flow according to the equation:

$$Q_{offset} = \sqrt{\frac{|P_T|}{R_{nasal}}} \qquad (4)$$

Where:

$Q_{offset}$ is the nasal flow at a point in time $P_T$ is Terminal pressure (also being $P_p$ or patient pressure) being a pressure in, at or proximate the outlet of the patient interface and/or or in, at or proximate the nares of the patient at a point in time $R_{nasal}$ is the nasal resistance to flow.

$P_T$ could be positive or negative during inspiration. (It will always be positive during expiration.) So the numerator for $Q_{offset}$ has an absolute sign to avoid having a square root of a negative number.

The controller operates the apparatus and determines the parameters according to the embodiment.

A gas at a flow rate ($Q_{apparatus}$) is delivered/administered to the patient using the apparatus, step 46-80. A pressure at $P_T$ is determined, step 46-81, being a terminal pressure in, at or proximate the outlet of the patient interface or in, at or proximate the nares of the patient. A nasal resistance to flow ($R_{nasal}$) is also determined, step 46-82. A nasal flow parameter being or being indicative of the nasal (leakage or entrainment) flow rate is then determined, step 46-83, based on the terminal pressure $P_T$ and nasal resistance to flow (RTF). The nasal flow $Q_{offset}$ is a flow rate that is indicative of inspiratory demand, as it is the flow rate offset between flow rate provided by the apparatus 10 and the inspiratory demand flow rate. Therefore, if nasal flow is zero, then inspiratory demand is being met—that is, the apparatus is providing gas at a flow rate that meets inspiratory demand (flow rate). If nasal flow is positive flow through the nares to atmosphere (leakage), then inspiratory demand is being exceeded, as the gas flow rate being provided by the apparatus is greater than inspiratory demand. If nasal flow is negative flow from the atmosphere through to the nares (entrainment), then inspiratory demand is not being met, as the gas flow rate being provided by the apparatus is less than inspiratory demand. The magnitude and direction of offset of the nasal flow rate can therefore be used to determine inspiratory demand to provide an indication (such as an estimation) thereof. The nasal flow (and the corresponding inspiratory demand) relates to the nasal flow (and inspiratory demand) at the point in time that the pressure $P_T$ is measured or otherwise determined. If the pressure $P_T$ determined is the minimum pressure of a breath cycle, then the nasal flow relates to and can indicate peak inspiratory demand.

The controller 13 operates the output 14 to provide an indication of nasal flow and/or inspiratory demand, step 46-84. Alternatively, or additionally, the controller 13 operates the apparatus 10 based on the nasal flow and/or inspiratory demand that has been determined. In one example, the offset flow rate and/or PID flow rate (if calculated) is displayed on a screen (e.g. on the I/O 14) or otherwise conveyed. This can be viewed by a clinician and then used to adjust the operating parameters of the apparatus, for example, to meet PID (or meet a level relative to a percentage of PID or deliver a flow rate that is offset from the PID by an absolute amount—ensuring accurate delivered oxygen fraction or for weaning the therapy). For example, if there is a negative offset flow rate indicating that the apparatus is not providing sufficient gas flow breath rate to meet PID of the patient, then the clinician can increase the delivered gas flow rate by that (offset flow rate) amount to meet the demand. Alternatively, the controller 13 could utilise the offset flow rate to automatically adjust the gas flow rate provided by the apparatus commensurate with the offset flow rate to meet PID. The above actions can refer to peak inspiratory demand if the terminal pressure has been determined using minimum system pressure in the apparatus.

More generally, the terminal pressure is indicative of inspiratory demand (or peak inspiratory demand if based on a minimum apparatus pressure). (Peak) inspiratory demand can be determined or inferred, and action taken in, any suitable manner using the terminal pressure. It is not necessary to find (peak) inspiratory demand using a flow rate offset. This information could be obtained in other manners from terminal pressure, or some parameter derived from it could be used to inform a user and/or operate flow therapy.

These are just some examples and are not exhaustive of the uses of nasal flow and/or respiratory demand.

2.4.2 Peak Inspiratory Demand Estimation According to Second General Embodiment Using Nasal Flow One particular non-limiting embodiment will now be described for determining a) the nasal flow (rate) $Q_{offset}$ at the point/time of peak inspiratory demand (PID) of a patient, b) subsequently utilising nasal flow, and/or c) determining and using PID information. Once determined, an indication of the nasal flow and/or PID for the patient can be displayed 14 for consideration by a physician for determining delivered gas flow rate or other setting for the apparatus; or alternatively, the nasal flow and/or PID can be used by the apparatus to adaptively alter the delivered gas flow rate to meet peak inspiratory demand.

The method and apparatus will be described with reference to FIGS. 38 and 45 to 48, wherein the apparatus of FIG. 38 can be configured to carry out the method to determine and utilise nasal flow and/or PID, as set out in the flow chart of FIGS. 46a/46b. For example, the controller 13 can be programmed to carry out the method in the flow chart of FIG. 46b using as inputs information from sensors in the apparatus 10. A cannula 17 is shown in FIG. 38 and will be described with reference to the embodiments below, but it will be appreciated that the embodiments are not restricted to the use of a cannula and in fact the embodiments would work with any type of suitable patient interface. Any references herein to cannula could be generalised to refer to any suitable patient interface.

FIG. 8b shows a more detailed embodiment of the general embodiment shown in FIG. 46a. In this embodiment, the controller 13 in the apparatus 10 uses inputs to determine the nasal flow at peak inspiration according to the equation:

$$Q_{offset} = \sqrt{\frac{|P_{min} - P_{char}|}{R_{nasal}}} \qquad (5)$$

Where:

$Q_{offset}$ is the nasal flow at peak inspiration $P_{min}$ is the system pressure at peak inspiration at a location in the apparatus $P_{char}$ is the characteristic pressure at the delivered gas flow rate (also it can be described as the pressure due to resistance to flow)

$R_{nasal}$ is the nasal resistance to flow.

$P_{min} - P_{char}$ could be positive or negative during inspiration. (It will always be positive during expiration.) So the numerator for $Q_{offset}$ has an absolute sign to avoid having a square root of a negative number.

Equation 5 is a special case of equation 4 as it determines $Q_{offset}$ at peak inspiration, where $P_{min} - P_{char} = P_T$ in equation 4 at peak inspiration.

It can be useful to retain information about the direction of $Q_{offset}$ (that is, is it leakage flow or entrainment), which is lost by the absolute sign in the equation above. Therefore, alternatively, the following could be used, where, in the case of the second equation, the sign and hence direction of offset flow is retained.

If $P_{min} - P_{char} \geq 0$ $$Q_{offset} = \sqrt{\frac{P_{min} - P_{char}}{R_{nasal}}} \qquad (5a)$$

Else if $P_{min} - P_{char} < 0$ $$Q_{offset} = -\sqrt{\frac{|P_{min} - P_{char}|}{R_{nasal}}} \qquad (5b)$$

Determining nasal flow according to equation 5 will now be described in more detail with reference to FIG. 46*b*. Note, the description below sets out one possible sequence in which the steps of the method would be carried out, but this should not be considered limiting and the steps could be carried out in a different order still resulting in a leakage flow parameter in accordance with equation 5.

The apparatus 10 delivers gas at a flow rate $Q_{apparatus}$ to the patient via the patient interface, step 46-80. This is delivered at a flow rate that can be determined by a flow sensor positioned at some location in the apparatus flow path, such as previously described. The controller 13 then determines the pressure $P_T$, step 46-81. To do this, first the controller determines system pressure (which could be a parameter being or being indicative of system pressure) at a location in the apparatus 10 using at least one pressure sensor at that location, step 46-81*a*. The pressure sensor 25 or 20 could be placed in or around the cannula (such as inside or proximate the manifold of the cannula or inside or proximate the prongs) or could be placed in any other suitable location in the circuit, such as in or after the flow generator 3*a*, humidifier 3*b*, or patient breathing conduit 3*c*, or at a mixing chamber where $O_2$ and ambient air mix.

For determining a nasal flow related to peak inspiratory demand, it is the minimum pressure during a breath cycle that is determined, as this point in time correlates to the peak inspiratory demand point of the breath cycle for the patient. The output of the pressure sensor is communicated to the controller 13, and from that output, the controller 13 determines the minimum pressure at the location. This minimum pressure could be a single or instantaneous pressure relating to (that is, indicative of or being) the minimum pressure in a particular breath cycle (that is, at peak inspiration), or the minimum pressure may be or indicative of a representative pressure of several breath cycles, such as a mean or average minimum, or median minimum pressure over each of e.g. five breaths cycles. An example of a method that could be used to determine a minimum pressure is to continuously or periodically monitor the instantaneous pressure readings storing any values that are less than all other previous values. The minimum pressure found within this set of stored values is the minimum system pressure used, or is used as a component of the average/median minimum pressure. The set of stored values is refreshed when the instantaneous pressure reading exceeds a certain threshold value e.g.: increases by a set absolute value, or percentage from the previous reading or exceeds the mean pressure, indicating a new breath.

Figure 47:
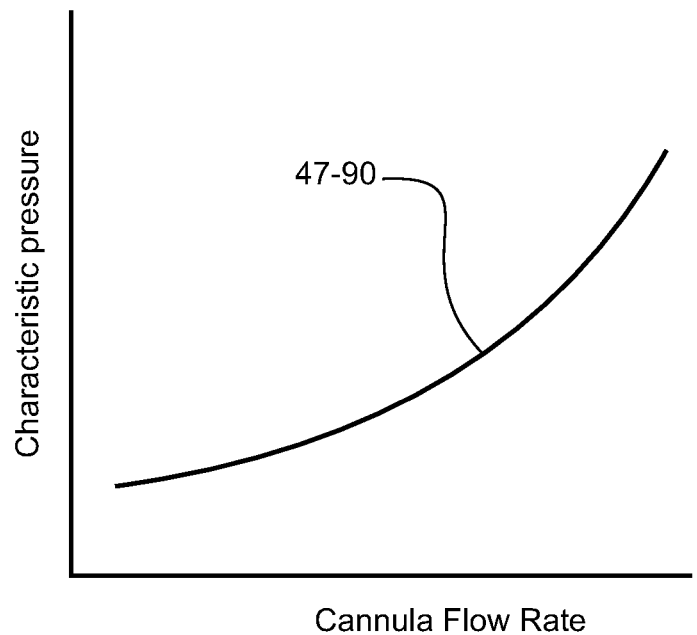
FIG. 47 is a flow versus characteristic pressure curve.

The controller 13 obtains, step 46-81*b*, a characteristic pressure ($P_{char}$) of the apparatus 10 for the location (that is, the location where the pressure is being measured by the pressure sensor) at the flow rate $Q_{apparatus}$ that the apparatus delivers gas to the patient. FIG. 47 shows a generic characteristic pressure curve versus flow rate for a hypothetical location in the apparatus. As described previously, the characteristic pressure 47-90 is the pressure caused by the resistance to the flow of the apparatus components (such as the patient conduit, flow generator, humidifier and/or internal ducting) forming the flow path at a particular flow rate due to the physical characteristics of the components at that flow rate. That is, the characteristic pressure indicates the contribution to pressure made by the apparatus components due to the physical characteristics at that flow rate. This characteristic pressure 47-90 may be calculated by using the measured flow rate as an input along with knowledge of the characteristics of the apparatus flow path components, or it can be determined from a look up table, relationship, graph or the like that correlates the pressure contribution of a particular cannula at particular flow rates to the system pressure. Alternatively, the characteristic pressure could be determined in a calibration step at the time of measurement for that particular patient/set-up by taking a pressure measurement when the cannula has been removed from the patient for a time.

Once the minimum pressure and the characteristic pressure are found, then $P_T$ can be calculated according to the following, step 46-81*c*:

$$P_T = P_{min} - P_{char} \qquad (6)$$

where
  $P_T$=terminal pressure
  $P_{char}$=characteristic pressure at the location in the apparatus
  $P_{min}$ (=$P_{system@tPI}$) system pressure at minimum at the location in the apparatus at time tPI As can be seen, equation 6 is mathematically equivalent to equation 1, so $P_T$ is a patient pressure, being the pressure at the patient that is calculated from the system pressure less the contribution by the apparatus to that system pressure.

Figure 48:
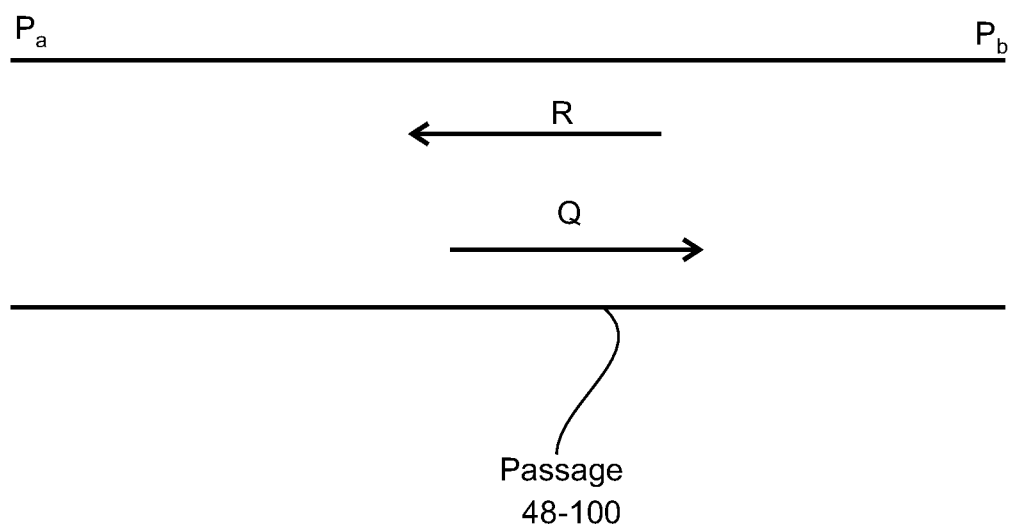
FIG. 48 is a schematic diagram of flow in a passage causing resistance to flow.

The nasal resistance to flow ($R_{nasal}$) is calculated at step 46-82. Resistance to flow is the intrinsic characteristic that resists flow in a passage. Referring to FIG. 48, flow Q occurs in a passage 100 when there is a pressure differential between $P_a$ and $P_b$ at two locations in the passage, where $P_a > P_b$. The resistance to flow in FIG. 48 for a turbulent flow condition is defined by:

$$R = \frac{Pa - Pb}{Q^2} \qquad (7)$$

Where:
  R is resistance to flow in cmH$_2$O/litres per minute
  Q is flow in litres per minute
  and assuming that flow through the patient interface is not laminar. If it is laminar, the denominator term is Q not $Q^2$ Referring to FIG. 45, in determining nasal resistance to flow ($R_{nasal}$), the nasal passage outside the cannula 17 can be considered the flow passage of FIG. 10, the leakage flow $Q_{offset}$ is the flow Q and the pressure differentials at two locations can be $P_{nares}$, $P_{amb}$, correspond to $P_a$, $P_b$ where $P_{nares}$ can be approximated by $P_T/P_P$ and $P_{amb}$ is the ambient pressure $P_2$. Therefore, nasal resistance to flow can be defined by:

$$R_{nasal} = \frac{P_{nares} - P_{amb}}{Q_{offset}^2} \quad (8)$$

At the breath transition between inspiration and expiration, there is no flow to or from the lungs of the patient ($Q_{patient}=0$), and therefore all flow from the apparatus ($Q_{apparatus}$) through the cannula 17 will escape as nasal flow $Q_{offset}$. Therefore at the transition, the nasal flow equals the gas flow rate delivered by the apparatus, that is $Q_{offset}=Q_{apparatus}$. From this information, and information relating to the pressure at the transition of inspiration/expiration, $R_{nasal}$ can be calculated or otherwise determined according to the following equation:

$$R_{nasal} = \frac{P_{trans} - P_{char}}{Q_{offset}^2} \quad (9)$$

Where:
$P_{trans}$ is the pressure at inspiration/expiration transition
$Q_{offset}=Q_{apparatus}$
Or, in the case of laminar flow, the following is used.

$$R_{nasal} = \frac{P_{trans} - P_{char}}{Q_{offset}} \quad (9a)$$

$P_{trans}$ in the equation above is taken at the same location as the system pressure. $P_{trans}$ can be measured at a different location, but in that case a different $P_{char}$ must be used corresponding to the location where $P_{trans}$ is measured.

Figure 49:
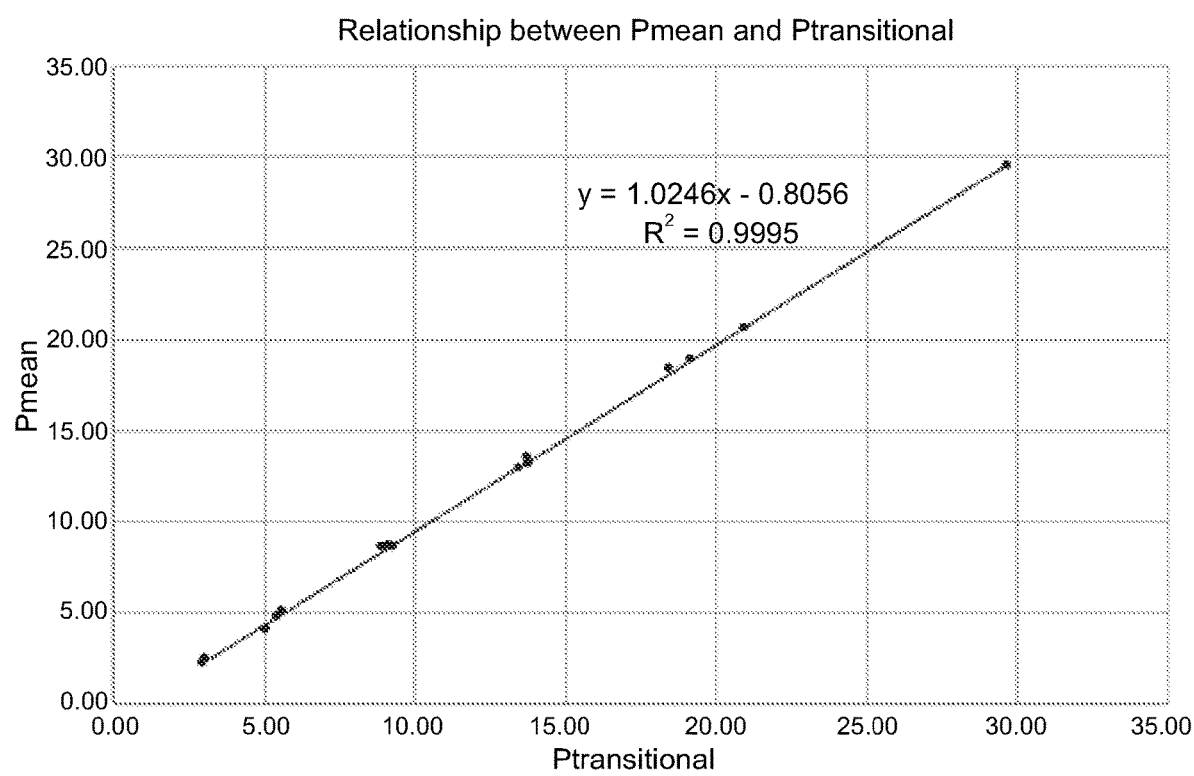
FIG. 49 is a graph showing the relationship between the mean pressure and the transitional pressure.

It has been determined, that the pressure at the transition of inspiration/expiration is approximately equal to the mean pressure throughout the breath cycle. To determine this, the transitional pressure was measured from the known point of expiration/inspiration transition using a lung simulator and compared to the mean pressure—a graph demonstrating this is shown in FIG. 49. The relationship is approximately 1:1. Therefore, $R_{nasal}$, step 82, can be determined from the mean pressure, step 46-82a, and the apparatus flow at the breath transition, step 46-82b.

At this point, nasal flow can be determined according to equation 5, step 46-83:

$$Q_{offset} = \sqrt{\frac{|P_{min} - P_{char}|}{R_{nasal}}} \quad (5)$$

Or

If $P_{min} - P_{char} \geq 0$ $$Q_{offset} = \sqrt{\frac{P_{min} - P_{char}}{R_{nasal}}} \quad (5a)$$

Else if $P_{min} - P_{char} < 0$ $$Q_{offset} = -\sqrt{\frac{|P_{min} - P_{char}|}{R_{nasal}}} \quad (5b)$$

If retaining information about the direction of nasal flow

Once nasal flow is determined, it provides an indication of peak inspiratory demand, step 46-83. Peak inspiratory demand is the gas flow rate provided by the apparatus less the leakage flow. Furthermore, if nasal flow is positive, then it indicates that peak inspiratory demand is being exceeded; if nasal flow is negative, then it indicates that peak inspiratory demand is not being met; and if nasal flow is zero, this indicates that peak inspiratory demand is being met. Nasal flow can be continuously or periodically recalculated using the method of FIG. 46b to provide updated estimates.

The information can be displayed and/or used as described previously, step 46-84.

Two examples for determining peak inspiratory flow follow:

Example 1

Cannula Flow Rate Greater than PID

Cannula Flow Rate ($Q_{apparatus}$)=40 L/min
Characteristic Pressure ($P_{char}$)=4.26 cmH2O
Mean Pressure (equivalent to $P_{trans}$)=8.93 cmH2O
Minimum Pressure ($P_{min}$)=5.26 cmH2O $$R_{nasal} = \frac{P_{trans} - P_{char}}{Q_{offset}^2} = 0.00292 \text{ cmH2O/L}^2/\text{min}^2$$

$$Q_{offset} = \sqrt{\frac{P_{min} - P_{char}}{R_{nasal}}} = 18.51 \text{ L/min}$$

So estimated PID=$Q_{apparatus}$−$Q_{offset}$=21.5 L/min
where actual PID=23.4 L/min Example 2

Cannula Flow Rate Below PID

Cannula Flow Rate ($Q_{apparatus}$)=20 L/min
Characteristic Pressure ($P_{char}$)=1.06 cmH2O
Mean Pressure (equivalent to $P_{trans}$)=3.00 cmH2O
Minimum Pressure ($P_{min}$)=0.65 cmH2O $$R_{nasal} = \frac{P_{trans} - P_{char}}{Q_{offset}^2} = 0.00521 \text{ cmH2O/L}^2/\text{min}^2$$

$$Q_{offset} = \sqrt{\frac{P_{min} - P_{char}}{R_{nasal}}} = 8.91 \text{ L/min}$$

So estimated PID=$Q_{apparatus}$−$Q_{offset}$=28.2 L/min
where actual PID=33.7 L/min 2.4.3 Inspiratory Demand Estimation According to Second General Embodiment Using Nasal Flow The embodiment above relates to finding a peak inspiratory demand flow rate, or some indication thereof. This is the flow rate demand of the patient at the peak of their inspiration. More generally, the method can be utilised to find the instantaneous inspiratory demand of a patient, at any point of the respiratory cycle. The method is the same as described previously, but rather than measuring the minimum pressure (which corresponds to a point in time of peak inspiratory flow) the system pressure can be taken at any instantaneous time (or a representative value of the same point/time of the breath cycle across multiple breath cycles). Any references to peak inspiratory demand and/or minimum pressure in the description above and related drawings can be generalised to "inspiratory demand" and "system pressure" respectively.

The process for determining an inspiratory demand will be briefly be described, as it follows the same steps as for finding peak respiratory demand.

Referring to FIG. 46a, 46b, the controller 13 in the apparatus 11 uses inputs to determine the leakage flow at peak inspiration according to the equation:

$$Q_{offset} = \sqrt{\frac{|P_{(t)} - P_{char}|}{R_{nasal}}} \quad (10)$$

Where Qoffset is the nasal flow at time t

P(t) is the system pressure at time t $P_{char}$ is the characteristic pressure at the delivered gas flow rate $R_{nasal}$ is the nasal resistance to flow.

Equation 10 is the more general case of equation 5.

$P_{(t)}$–$P_{char}$ could be positive or negative during inspiration. (It will always be positive during expiration.) So the numerator for $Q_{offset}$ has an absolute sign to avoid having a square root of a negative number.

It can be useful to retain information about the direction of Qoffset (that is, is it leakage flow or entrainment), which is lost by the absolute sign in the equation above. Therefore, alternatively, the following could be used, where, in the case of the second equation, the sign and hence direction of offset flow is retained.

If $p(t) - p_{char} \geq 0$ $$Q_{offset} = \sqrt{\frac{p(t) - p_{char}}{R_{nasal}}} \quad (10a)$$

Else if $p(t) - p_{char} < 0$ $$Q_{offset} = \sqrt{\frac{|p(t) - p_{char}|}{R_{nasal}}} \quad (10b)$$

The apparatus delivers gas at a flow rate $Q_{apparatus}$ to the patient via the patient interface, step 46-80. The controller 13 then determines the pressure $P_T$, step 46-81. To do this, first the controller determines system pressure (which could be a parameter being or being indicative of system pressure) at a location in the apparatus using at least one pressure sensor at that location, step 46-81a. The pressure is taken at the point in time for which inspiratory demand is being estimated, so a minimum pressure is not necessarily determined. The controller 13 obtains, step 46-81b, a characteristic pressure of the apparatus for the location at the flow rate that the apparatus delivers gas to the patient.

$P_T$ can be calculated according to equation 6, step 46-81c and $R_{nasal}$ is determined according to equation 9. At this point, leakage flow can be determined according to equation 10.

Nasal flow, once determined, provides an indication of (instantaneous) inspiratory demand. Inspiratory demand is the gas flow rate provided by the apparatus less the nasal flow. Furthermore, if nasal flow is positive, then it indicates that inspiratory demand is being exceeded; if nasal flow is negative, then it indicates that inspiratory demand is not being met; and if nasal flow is zero, this indicates that inspiratory demand is being met. Nasal flow can be continuously or periodically recalculated using the method of FIG. 46b to provide updated estimates.

The information can be displayed and/or used as described previously.

In one possible embodiment, both the first embodiment and the second embodiment (or variations of them) could be utilised in cooperation. When $Q_{offset}$<5 litres/minute, the first embodiment is more accurate and could be used. When $Q_{offset}$>5 litres/minute, the second embodiment is more accurate and could be used. The controller could be configured with both embodiments and configured to select whether to utilise the first embodiment or the second embodiment based on the flow rate.

2.5 Estimating Expiratory Flow Rate Using Nasal Flow 2.5.1 Second General Embodiment of Expiratory Flow Rate Estimation Using Nasal Flow The above method and apparatus can also be utilised to determine expiratory flow rate—both peak and instantaneous. Much of the description for determining inspiratory flow rate applies also for determining expiratory flow rate, so the following description will not describe all aspects of the embodiment, but instead rely on the previous description.

Referring to FIGS. 38, 45 and 46c, 46d, a second general embodiment of the apparatus and method is now described. FIG. 45 shows diagrammatically an apparatus delivering gas flow at a flow rate ("$Q_{apparatus}$") to the nares 70 of a patient, and nasal gas flow at a flow rate ("$Q_{nasal}$") through the nares 45-70. $Q_{nasal}$ (nasal flow or nasal flow rate) is the flow that escapes through the nares 45-70 around the patient interface to atmosphere. During the expiratory phase, the nasal flow is the combination of the expiration and the gas flow $Q_{apparatus}$, so $Q_{nasal}$ is the addition (of the gas flow rate $Q_{apparatus}$ delivered by the apparatus and the expiratory flow rate of the patient at a point in time. Nasal flow (also termed "leakage flow) is expiratory flow "equivalent" of the flow rate offset during inspiration. Nasal flow can also be used interchangeably with "nasal flow rate" and likewise "leakage flow" can be used interchangeably with "leakage flow rate". Note, that the flow at $P_T/P_1$ could be into the patient (inspiration) or out of the patient (expiration)—the latter is the case for this embodiment In general terms, the apparatus 10 administers/delivers gas at a flow rate ($Q_{apparatus}$) to the patient via the patient interface 17 into the nares 45-70. It determines a pressure $P_1$ at the point where the gas flow is delivered and from that and knowledge of a nasal resistance to flow ($R_{nasal}$) determines the leakage flow ($Q_{nasal}$), from which expiratory flow can be determined. $P_1$ is the nasal pressure due to the resistance to flow of $Q_{nasal}$ passing through $R_{nasal}$—and can also be termed patient pressure. $P_T$ is the terminal pressure, which is the pressure at the outlet of the patient interface, such as the prongs of the cannula. When the patient interface is worn, the terminal pressure $P_T$ equals the patient pressure $P_1$ (also termed "$P_P$". This is the case in FIG. 7, so $P_1$ and $P_T$ are the same. Reference will now be made to $P_T$ The time where $P_T$ is at a maximum during a breath cycle corresponds to the nasal flow at peak expiratory flow rate. Therefore, when $P_T$ is at a maximum, the associated nasal flow indicates peak expiratory flow rate. Nasal flow can be determined continuously or periodically to provide an updated indication of (peak) expiratory flow rate. This information can be used to control the apparatus and/or provide information to a user and/or physician.

Figures 46C, 46D:
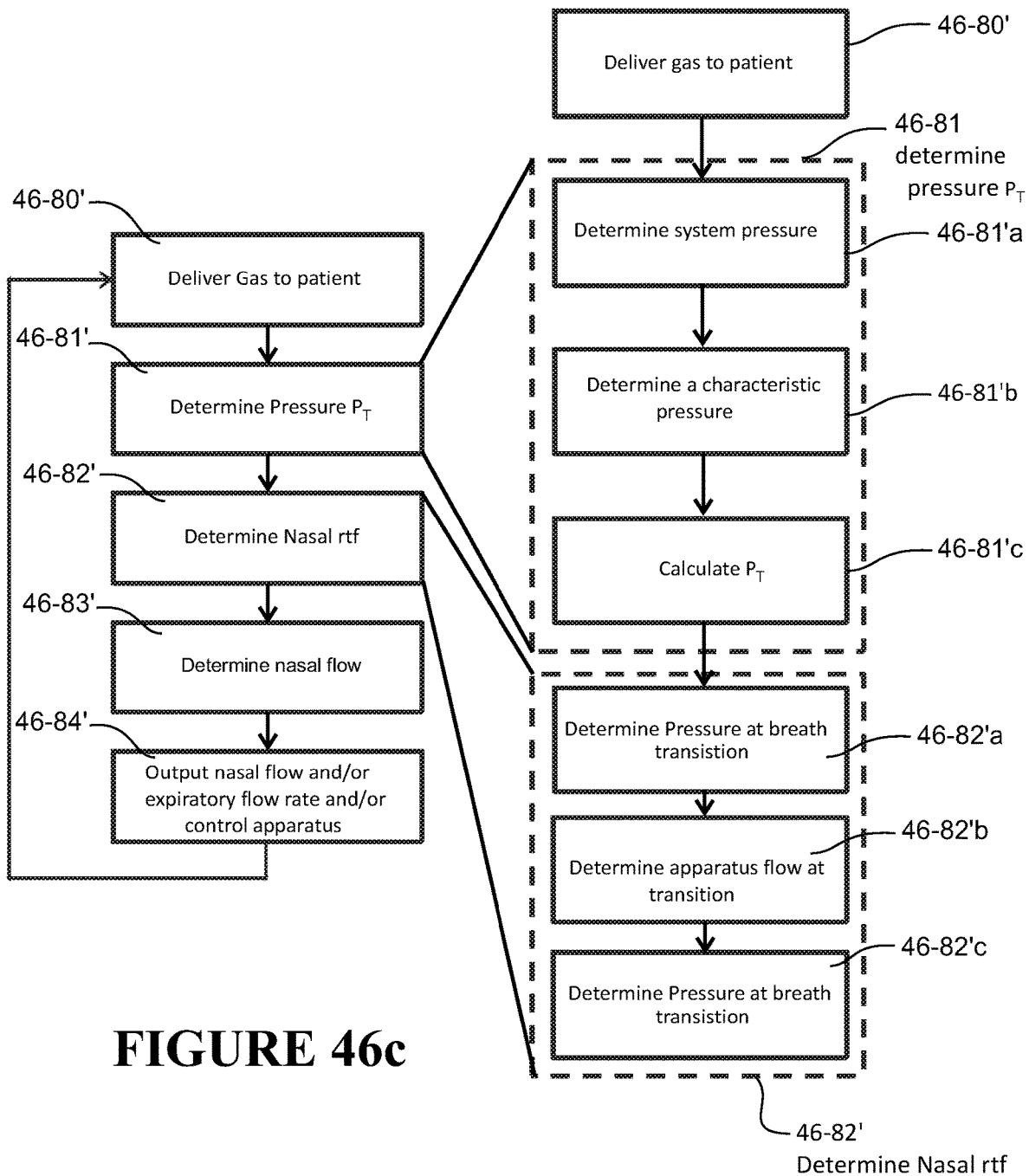
FIG. 46c is flow diagram showing a second general embodiment of estimating expiratory flow rate.
FIG. 46d is a flow diagram showing one method of estimating expiratory flow rate according to the second general embodiment.

Referring now to FIG. 46c, the general embodiment will be described. The controller 13 in the apparatus uses inputs to determine the nasal flow according to the equation:

$$Q_{nasal} = \sqrt{\frac{|P_T|}{R_{nasal}}} \qquad (4')$$

Where:
- $Q_{nasal}$ is the nasal flow at a point in time
- $P_T$ is Terminal pressure (also being $P_p$ or patient pressure) being a pressure in, at or proximate the outlet of the patient interface and/or or in, at or proximate the nares of the patient at a point in time
- $R_{nasal}$ is the nasal resistance to flow.

This equation is mathematically equivalent to equation (4') but with the term $Q_{nasal}$ (nasal flow) used rather than $Q_{offset}$ as the more general term nasal flow is the more appropriate term during expiration. $P_T$ will always be positive during expiration. So the absolute sign for the numerator for is not strictly necessary, but is provided for the more general case where the equation could be used to determine flow rate at any point in the breath flow, including during inspiration where sometimes $P_T$ could be negative.

The controller operates the apparatus and determines the parameters according to the embodiment.

A gas at a flow rate ($Q_{apparatus}$) is delivered/administered to the patient using the apparatus, step 46-80'. A pressure at $P_T$ is determined, step 46-81', being a terminal pressure in, at or proximate the outlet of the patient interface or in, at or proximate the nares of the patient. A nasal resistance to flow ($R_{nasal}$) is also determined, step 46-82'. A nasal flow parameter being or being indicative of the nasal (leakage) flow rate is then determined, step 46-83', based on the terminal pressure $P_T$ and nasal resistance to flow (RTF). The nasal flow $Q_{nasal}$ is a flow rate that is indicative of expiratory flow rate, as it is the flow rate combination of the flow rate provided by the apparatus 10 and the expiratory flow rate. The magnitude of the nasal flow rate can therefore be used to determine expiratory flow rate to provide an indication (such as an estimation) thereof. The nasal flow (and the corresponding expiratory flow) relates to the nasal flow (and expiratory flow rate) at the point in time that the pressure $P_T$ is measured or otherwise determined. If the pressure $P_T$ determined is the maximum pressure of a breath cycle, then the nasal flow relates to and can indicate peak expiratory flow rate.

The controller 13 operates the output 14 to provide an indication of nasal flow and/or expiratory flow rate, step 46-84'. Alternatively, or additionally, the controller 13 operates the apparatus 10 based on the nasal flow and/or expiratory demand that has been determined. In one example, the nasal flow rate and/or expiratory flow rate (if calculated) is displayed on a screen (e.g. on the I/O 14) or otherwise conveyed. This can be viewed by a clinician and then used to adjust the operating parameters of the apparatus. Alternatively, the controller 13 could utilise the nasal flow rate to automatically adjust the gas operation parameters of the apparatus. The above actions can refer to peak expiratory flow rate if the terminal pressure has been determined using maximum system pressure in the apparatus.

More generally, the terminal pressure is indicative of expiratory flow rate (or peak expiratory flow rate if based on a maximum apparatus pressure). (Peak) expiratory flow rate can be determined or inferred, and action taken in, any suitable manner using the terminal pressure. It is not necessary to find the actual (peak) expiratory flow rate using a nasal flow rate. This information could be obtained in other manners from terminal pressure, or some parameter derived from it could be used to inform a user and/or operate flow therapy.

These are just some examples and are not exhaustive of the uses of nasal flow and/or respiratory flow rate.

2.5.2 Peak Expiratory Estimation According to Second General Embodiment Using Nasal Flow One particular non-limiting embodiment will now be described for determining a) the nasal flow (rate) $Q_{nasal}$ at the point/time of peak expiratory flow of a patient, b) subsequently utilising nasal flow, and/or c) determining and using peak expiratory flow rate information. Once determined, an indication of the nasal flow and/or peak expiratory flow rate for the patient can be displayed 14 for consideration by a physician for determining delivered gas flow rate or other setting for the apparatus; or alternatively, the nasal flow and/or expiratory flow rate can be used by the apparatus to adaptively alter the delivered gas flow rate or other operation parameters.

The method and apparatus will be described with reference to FIGS. 38 and 45 to 48, wherein the apparatus of FIG. 38 can be configured to carry out the method to determine and utilise nasal flow and/or peak expiratory flow rate, as set out in the flow chart of FIG. 46c For example, the controller 13 can be programmed to carry out the method in the flow chart of FIG. 46d using as inputs information from sensors in the apparatus 10.

FIG. 46d shows a more detailed embodiment of the general embodiment shown in FIG. 46c. In this embodiment, the controller 13 in the apparatus 10 uses inputs to determine the nasal flow at peak expiration according to the equation:

$$Q_{nasal} = \sqrt{\frac{|P_{max} - P_{char}|}{R_{nasal}}} \qquad (5')$$

Where:
- $Q_{nasal}$ is the nasal flow at peak expiration
- $P_{max}$ is the system pressure at peak expiration at a location in the apparatus
- $P_{char}$ is the characteristic pressure at the delivered gas flow rate (also it can be described as the pressure due to resistance to flow)
- $R_{nasal}$ is the nasal resistance to flow.

This equation is mathematically equivalent to equation (5') but with the term $Q_{nasal}$ (nasal flow) used rather than $Q_{offset}$ as the more general term nasal flow is the more appropriate term during expiration. It also uses $P_{max}$ rather than $P_{min}$ as it is the maximum pressure that is used for determining peak expiratory flow. $P_{max}-P_{char}$ will always be positive during expiration. So the absolute sign for the numerator for is not strictly necessary, but is provided for the more general case where the equation could be used to determine flow rate at any point in the breath flow, including during inspiration where sometimes $P_{max}-P_{char}$ could be negative.

Equation 5' is a special case of equation 4' as it determines $Q_{nasal}$ at peak expiration, where $P_{max}-P_{char}=P_T$ in equation 4' at peak expiration.

Determining nasal flow according equation 5' will now be described in more detail with reference to FIG. 8d. Note, the description below sets out one possible sequence in which the steps of the method would be carried out, but this should not be considered limiting and the steps could be carried out in a different order still resulting in a leakage flow parameter in accordance with equation 5'.

The apparatus 10 delivers gas at a flow rate $Q_{apparatus}$ to the patient via the patient interface, step 46-80'. This is delivered at a flow rate that can be determined by a flow sensor positioned at some location in the apparatus flow path, such as previously described. The controller 13 then determines the pressure $P_T$, step 46-81'. To do this, first the controller determines system pressure (which could be a parameter being or being indicative of system pressure) at a location in the apparatus 10 using at least one pressure sensor at that location, step 46-81'a. The pressure sensor 25 or 20 could be placed in or around the cannula (such as inside or proximate the manifold of the cannula or inside or proximate the prongs) or could be placed in any other suitable location in the circuit, such as in or after the flow generator 3a, humidifier 3b, or patient breathing conduit 3c, or at a mixing chamber where $O_2$ and ambient air mix.

For determining a nasal flow related to peak expiratory flow, it is the maximum pressure during a breath cycle that is determined, as this point in time correlates to the peak expiratory flow point of the breath cycle for the patient. The output of the pressure sensor is communicated to the controller 13, and from that output, the controller 13 determines the minimum pressure at the location. This maximum pressure could be a single or instantaneous pressure relating to (that is, indicative of or being) the maximum pressure in a particular breath cycle (that is, at peak expiration), or the maximum pressure may be or indicative of a representative pressure of several breath cycles, such as a mean or average minimum, or median maximum pressure over each of e.g. five breaths cycles. An example of a method that could be used to determine a maximum pressure is to continuously or periodically monitor the instantaneous pressure readings storing any values that are greater than all other previous values. The maximum pressure found within this set of stored values is the maximum system pressure used, or is used as a component of the average/median maximum pressure. The set of stored values is refreshed when the instantaneous pressure reading is below a certain threshold value e.g.: decreases by a set absolute value, or percentage from the previous reading or is below the mean pressure, indicating a new breath.

The controller 13 obtains, step 46-81'b, a characteristic pressure ($P_{char}$) of the apparatus 10 for the location (that is, the location where the pressure is being measured by the pressure sensor) at the flow rate $Q_{apparatus}$ that the apparatus delivers gas to the patient. FIG. 47 shows a generic characteristic pressure curve versus flow rate for a hypothetical location in the apparatus. Once the maximum pressure and the characteristic pressure are found, then $P_T$ can be calculated according to the following, step 46-81'c:

$$P_T = P_{max} - P_{char} \tag{6'}$$

where $P_T$=terminal pressure $P_{char}$=characteristic pressure at the location in the apparatus $P_{max}$ (=$P_{system@tPI}$)=system pressure at maximum at the location in the apparatus at time tPI As can be seen, equation 6 is mathematically equivalent to equation 1, so $P_T$ is a patient pressure, being the pressure at the patient that is calculated from the system pressure less the contribution by the apparatus to that system pressure.

The nasal resistance to flow ($R_{nasal}$) is calculated at step 46-82' using equation (9), as described previously.

As previously described, $R_{nasal}$ step 46-82'c, can be determined from the mean pressure, step 46-82'a, and the apparatus flow at the breath transition, step 46-82'b.

At this point, nasal flow can be determined according to equation 5', step 46-83:

$$Q_{nasal} = \sqrt{\frac{|P_{max} - P_{char}|}{R_{nasal}}} \tag{5'}$$

This equation is mathematically equivalent to equation (5') but with the term $Q_{nasal}$ (nasal flow) used rather than $Q_{offset}$ as the more general term nasal flow is the more appropriate term during expiration. It also uses $P_{max}$ rather than $P_{min}$ as it is the maximum pressure that is used for determining peak expiratory flow Once nasal flow is determined, it provides an indication of peak expiratory flow, step 46-83'. Peak expiratory flow is the leakage/nasal flow less the gas flow rate provided by the apparatus. Nasal flow can be continuously or periodically recalculated using the method of FIG. 8d to provide updated estimates.

The information can be displayed and/or used as described previously, step 46-84'.

2.5.3 Instantaneous Expiratory Flow Estimation According to First General Embodiment Using Nasal Flow The embodiment above relates to finding a peak expiratory flow rate, or some indication thereof. More generally, the method can be utilised to find the instantaneous expiratory flow rate of a patient, at any point of the expiration portion of the respiratory cycle. The method is the same as described previously, but rather than measuring the maximum pressure (which corresponds to a point in time of peak expiratory flow) the system pressure can be taken at any instantaneous time (or a representative value of the same point/time of the breath cycle across multiple breath cycles). The process for determining an expiratory flow rate will be briefly be described, as it follows the same steps as for finding peak expiratory flow rate.

Referring to FIG. 44c/44d the controller 13 in the apparatus 11 uses inputs to determine the leakage flow at peak expiration according to the equation:

$$Q_{nasal} = \sqrt{\frac{|P_{(t)} - P_{char}|}{R_{nasal}}} \tag{10'}$$

Where $Q_{nasal}$ is the nasal flow at time t $P_{(t)}$ is the system pressure at time t $P_{char}$ is the characteristic pressure at the delivered gas flow rate $R_{nasal}$ is the nasal resistance to flow.

This equation is mathematically equivalent to equation (10') but with the term $Q_{nasal}$ (nasal flow) used rather than $Q_{offset}$ as the more general term nasal flow is the more appropriate term during expiration. $P_T - P_{char}$ will always be positive during expiration. So the absolute sign for the numerator for is not strictly necessary, but is provided for the more general case where the equation could be used to determine flow rate at any point in the breath flow, including during inspiration where sometimes $P_T - P_{char}$ could be negative.

Equation 10' is the more general case of equation 5'.

The apparatus delivers gas at a flow rate $Q_{apparatus}$ to the patient via the patient interface, step 46-80'. The controller 13 then determines the pressure $P_T$, step 46-81'. To do this, first the controller determines system pressure (which could be a parameter being or being indicative of system pressure) at a location in the apparatus using at least one pressure sensor at that location, step 46-81'a. The pressure is taken at the point in time for which expiratory flow rate is being estimated, so a maximum pressure is not necessarily determined. The controller 13 obtains, step 46-81'b, a characteristic pressure of the apparatus for the location at the flow rate that the apparatus delivers gas to the patient.

$P_T$ can be calculated according to equation 6, step 46-81'c and $R_{nasal}$ is determined according to equation 9. At this point, leakage flow can be determined according to equation 10'

Nasal flow, once determined, provides an indication of (instantaneous) expiratory flow rate. Expiratory flow rate is the nasal flow less the gas flow rate provided by the apparatus. Nasal flow can be continuously or periodically recalculated using the method of FIG. 44d to provide updated estimates.

The information can be displayed and/or used as described previously.

2.5.4 Identifying Expiratory or Inspiratory Flow Rate, and Estimating Respiratory Flow Rate During Breath Flow In the embodiments discussed, either inspiratory flow or expiratory flow rate is determined for display and/or operation of the apparatus. The equations described determine the flow rate at any time during the breath flow, irrespective of whether it is an inspiration portion or expiration portion. Therefore, if the flow rate for a particular breath portion (that is, either inspiration or expiration) is required this can be determined in a suitable manner. In one example, the breath flow can be monitored and transitions detected so that the processor determines whether the breath is in the inspiration phase or expiration phase. If an inspiratory flow rate is required, then the microprocessor determines when inspiratory part of the breath occurs, and takes the required measurements and calculations during that inspiration portion. Likewise, if and expiratory flow rate as required, then the microprocessor determines when expiratory part of the breath occurs, and takes the required measurements and calculations during that expiration portion. In an alternative, the microprocessor does not determine which part of the breath is occurring. Rather, the microprocessor takes required measurements and calculations to determine the flow rate. At any ascertains whether that flow rate pertains to expiration or inspiration by measuring the patient pressure and then comparing it to the mean patient pressure over a period of time. If the patient pressure is above the mean patient pressure, then the calculated flow rate relates to and expiratory flow rate; and conversely if the patient pressure is below the mean patient pressure, then the calculated flow rate relates to an inspiratory flow rate.

In further embodiments using nasal flow, rather than determining the flow rate specifically during inspiration or expiration, the flow rate is determined using the same techniques above at any time, regularly and/or continuously during the breath cycle. This would give periodic or continuous information of respiration flow rate at any point of the breath cycle, irrespective of whether it is inspiratory or expiration. It may not be necessary to know which part of the breath cycle is occurring to carry out the estimation and/or it might not be necessary for the output flow rate to indicate whether the flow rate is inspiration or expiration—although one or both of these might be desirable. The equations and description for determining expiratory flow are general enough to be used for determining respiratory flow at any point of the breath cycle.

It is then possible to display on the apparatus or elsewhere an indication of the respiratory flow rate. This might be, for example an instantaneous or real time numerical or graphical indication of flow rate, either continuously or periodically. Alternatively, or in addition could be a numerical or graphical display of periodic or continuous historical respiratory flow rate. FIG. 50 shows a graphical display in schematic form of breath flow rate as determined by the embodiments described and which could be displayed on the user interface.

2.6 Other Embodiments for Determining Respiratory Flow Rate, Including Inspiratory Demand and Expiratory Flow Rate In any embodiment where flow rate is measured using flow sensor, an alternative flow could be determined in another ways—such as by user input, or motor signal/power. It is not necessarily essential that a flow sensor is used to obtain the flow rate.

Monitoring/estimating the patient's inspiratory and expiratory flow rate (more general respiratory flow) also has implications for diagnostics. A relatively high inspiratory demand for a patient of a certain height/weight can indicate to the user a high metabolic requirement. Inspiratory and expiratory flow can be used as an indicator for work of breathing. An increase in the patient's inspiratory demand may also represent an increase in metabolic demand and hence an increase in respiration in order to meet this demand. A display of the trend in a patient's inspiratory or expiratory flow rate (for example in tabular form, graphically or by some other means on the input/output interface 14) could help to provide information on this. It may also be possible to provide alarms around this information using the input/output interface 14. For example the device could detect when the inspiratory or expiratory flow rate exceeds a certain pre-defined limit, or when the inspiratory or expiratory flow rate increases faster than a pre-defined rate. The device could alarm, automatically change the delivered flow rate and/or oxygen, provide a treatment recommendation to the user based on this information, or provide a recommendation that the user change the patient treatment to a higher or lower level of respiratory support. The inspiratory or expiratory flow rate could also be used to inform the patient's weaning process, for example a decreasing inspiratory demand could indicate a decreasing metabolic requirement and in response the device could automatically reduce the delivered flow rate and/or oxygen or provide a recommendation to the user based on this information. These outcomes could be implemented using the estimated inspiratory and expiratory flow rate as described above.

A change in expiratory flow can also indicate changes in patient condition and trends/rates of change can be useful to display to the clinician as information.

In the embodiments described above, the methods and/or apparatus for estimating inspiratory flow rate and/or expiratory flow rate form part of a breathing apparatus, such as flow therapy apparatus, that delivers a flow of gas to a patient. In alternative embodiments, the methods and apparatus are not performed on and/or do not form part of such breathing apparatus but instead form part of a separate apparatus. For example, a monitoring apparatus with a processor or similar may be programmed with the methods described and can be coupled to a breathing apparatus that delivers a flow of gas to a patient. For example, the monitoring apparatus maybe coupled to the sensors and/or controller/data storage of a breathing apparatus, to obtain information for estimating a respiratory flow rate (either inspiratory and/or expiratory flow rate) and may also be coupled to the controller and/or display of the breathing apparatus to control the breathing apparatus and/or display information relating to the respiratory (inspiratory and/or expiratory) flow rate. Alternatively, the information could be displayed on the monitoring apparatus itself. In other embodiments, the monitoring apparatus itself may comprise the required sensors for obtaining information to estimate the respiratory (expiratory and/or inspiratory) flow rate. The breathing apparatus may simply be a source of gas flow, such as a hospital gas source. Other embodiments are also envisaged. What this demonstrates is that it is not essential for the embodiments to be integrated with a breathing apparatus and they could be implemented in an apparatus, so long as some type of flow of gas from a suitable source is provided to the patient.

Any of the calibration routines can be conducted at the start of operation or at regular periods through treatment, when initiated by used or the apparatus or on a patient condition change.

A gas source could be any suitable source (e.g. compressed gas), not just a motor and blower.

In any embodiment, the method and/or apparatus can be arranged to:
Display/indicate on or more of:
  whether inspiratory demand is met or not,
  the inspiratory demand flow rate
  expiratory flow rate, or
  more generally respiratory flow
  whether entrainment is occurring or not
  the entrained flow rate
  the change in inspiratory demand, expiratory flow rate and/or respiratory flow rate
  the rate of change in inspiratory demand, expiratory flow rate and/or respiratory flow
  how much the delivered flow should be changed by to achieve:
    meeting inspiratory demand
    meeting a % of inspiratory demand or delivering a % of expiratory flow
    eliminating entrainment
    a flow target defined by the user with respect to entrainment or inspiratory demand or expiratory flow rate or respiratory flow rate
    recommending the delivered flow rate or a change in flow that would achieve any of the above
    automatically changing the flow to achieve any of the above 3. Flow and/or Pressure Oscillation to Provide Improved Gas Exchange 3.1 Overview In many respiratory conditions, for example chronic obstructive pulmonary disease or COPD, a patient can have difficulty effecting a sufficient exchange of gases with his/her environment. This difficulty may be the result of a variety of physiological faults, including a breakdown of lung tissue, dysfunctions of the small airways, excessive accumulation of sputum, or cardiac insufficiency. With such conditions, it is useful to provide the patient with a therapy that can improve the ventilation and/or gas exchange of the patient. In some situations, the patient may be provided with a respiratory therapy system that includes a gas source, an interface or mask that can be used to transmit gas to the patient, and a conduit extending between the gas source and the interface or mask. The gas source may, for example, be a bulk supply of a gas suitable for inspiration, e.g. air or oxygen, a mechanical blower capable of propelling a gas through the conduit to the interface, or some combination of both. The system may include one or more means for heating and/or humidifying gases passing through the system to improve patient comfort and/or improve the prognosis of the respiratory condition.

The volume of air in the anatomical dead space, consists of exhaled CO2 captured in the patient's airways that is rebreathed upon inspiration A patient suffering from respiratory conditions may benefit from reducing the amount of CO2 in the anatomical deadspace that is rebreathed upon inspiration. To reduce the amount of CO2 in the anatomical deadspace, the patient can be treated with high flow therapy, which can involve use of a gas in a respiratory device that is propelled through the system at a relatively high flow rate. The high flow of gases reaching the patient's airways can be beneficial for flushing out the patient's airways, which can reduce the CO2 in the anatomical deadspace by flushing the airways with fresh gas. As a mechanical dead space volume may be present if the patient uses a relatively low flow rate and a relatively large interface, e.g. a full face mask, it is beneficial to use a relatively small interface, e.g. a nasal cannula, and use a relatively high flow rate to minimize mechanical dead space and thereby further minimize the amount of CO2 rebreathed.

The airways comprise conducting airways and respiratory airways. That said, typically, the term "airways" can refer to the entire respiratory tract, both inside and outside of the lungs. Anatomical dead space is the volume of gas in the conducting airways that remains at the end of expiration to be re-breathed in the following inspiration. The conducting airways typically are considered to comprise the region from the mouth/nose through to the trachea, bronchi and terminal bronchioles. This region is only used to conduct air to the lungs and is the anatomical dead space. Respiratory airways typically are considered to comprise the lungs. The explanation of conducting and respiratory airways above is indicative only and should not be considered limiting—each term could possibly cover different aspects of the airways according to alternative definitions. The term "airway" itself is typically used to cover both conducting and/or respiratory airways, but again is indicative only and should not be considered limiting. The term "airway" could also be considered to cover the airspace within the airway.

A reduction in airway $CO_2$ concentration is desirable to assist some patients who have any number of respiratory conditions that lead to impaired respiratory systems and may have high $CO_2$ levels or require control over the amount of inspired CO2. Also or alternatively, an increase in $O_2$ is desirable to assist some patients who have any number of respiratory conditions.

Figure 51:
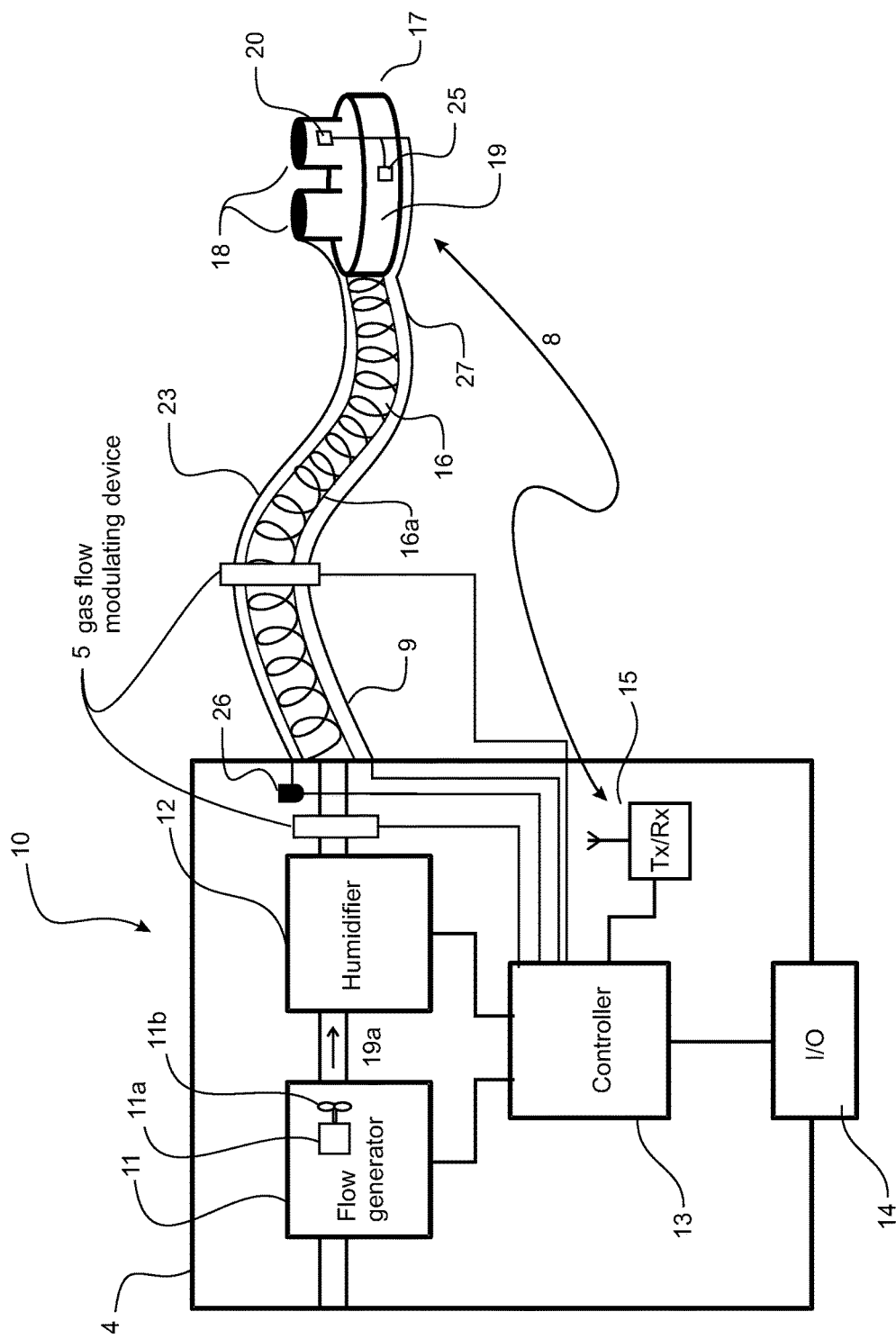
FIG. 51 is a schematic drawing of a flow therapy machine that can provide $CO_2$ washout and/or provide increased $O_2$.

3.2 General Overview of Embodiments for Gas Flow and Pressure Modulation to Promote Gas Exchange With reference to FIG. 51, a respiratory therapy system for providing respiratory therapy is shown. The respiratory therapy system may comprise a blower or flow generator comprising an gases inlet through which gases may be pulled by, for example, the rotation of an impeller or other rotary element (not shown) in or on the blower and a gases outlet through which gas may pass into a conduit. Preferably the blower comprises a controller (not shown) that in use may increase, decrease, modulate, or otherwise control the output of the blower. The gases passing through the conduit may enter a humidification system comprising a humidification chamber through a chamber inlet. In some configurations, the humidification chamber may in use contain a quantity of water that may be heated by heating element so that some of the water evaporates and moistens air passing through the humidification system. Air may then pass out of the humidification chamber through the chamber outlet and through a conduit, where it eventually reaches an interface that may communicate gases to a patient. The interface may be any device that may convey gases to a patient, including full face masks, nasal masks, oral masks, nasal pillows, and nasal cannulas, and the like.

Although the above paragraph discloses one possible respiratory therapy system, many configurations and variations of the respiratory therapy system are possible. For example, the blower may comprise a user interface or control system comprising levers, dials, buttons, touch screens, or other means of adjusting the flow rate and/or pressure of gases leaving the blower. In some configurations, the blower 100 may be controlled remotely using a remote user interface. In some configurations, the flow source may instead be a pressurized gas container that may be used to propel gas through the respiratory therapy system. The gas container may comprise or be used with a valve that may be used to adjust the flow rate of gases passing out the container and through the respiratory therapy system. In some configurations, the blower may be used in tandem with a gas container to provide a flow of gas through the respiratory therapy system. In some configurations, oxygen or other breathable gases may be added anywhere along the circuit of the respiratory therapy system, and may be mixed with the gases propelled by the blower. In some configurations, the humidification system may be inactive, or may be absent all together. In some configurations, the two conduits could be a single continuous conduit. In some configurations, the blower and the humidification system may be an integrated unit with a single housing. The humidification system may comprise a user interface or control system that may be used to adjust the heat and/or humidity modulation of the gases passing through the system. In some configurations, the humidification system may be controlled remotely using a remote user interface. In some configurations, the conduits may be heated using one or more conduit heaters. In some such configurations, the conduit heaters may be resistive wires that may heat up upon the application of electrical energy, and may be on, in, or within the conduits, (e.g. between two or more walls of the conduits). Preferably, if the respiratory therapy system is used to deliver a high gas flow therapy, a nasal cannula is used as the interface.

Attention is now given to the details of high flow therapy. Possible therapeutic benefits of the use of high flow therapy include reduced the effect of anatomical and/or mechanical dead space, which can reduce the breathing of CO2. Improving the turbulence of the flow used in the therapy may further improve gas mixing and reduce dead space. Accordingly, the flow rate of the flow used in high flow therapy may be oscillated between two or more different flow rates at a given frequency. For example, the flow rate delivered in the therapy may alternate between 25 and 26 L/minute at a frequency of 15 HZ. Alternatively, or in addition to the introduction of an oscillation to the flow rate of the flow, the pressure of the flow may be oscillated between two or more different pressures at a given frequency. For example, a flow delivered in therapy may alternate between pressures of 6 cm H2O and 6.5 cm H2O at a frequency of 15 HZ. Advantageously, by adding high frequency oscillations to a high flow therapy, in which there is already a positive net flow of gas towards a patient, improved CO2 clearance can be realized. In some preferred configurations, the flow oscillations are imparted by superimposing a second flow on top of a base unidirectional first flow towards a patient. This unidirectional base flow may be delivered at a constant rate or may be varied over the course of a therapy session, for example in response to a detected breathing cycle of a patient or according to some pattern or algorithm determined by a respiratory therapy system and/or user.

An oscillation may be imparted to a flow in a multitude of different ways. In some configurations, a flow may be oscillated by controlling the motor of the blower in such a way that the motor speed of the motor undergoes rapid variations. In some configurations, a flow may be modulated to have oscillations by an inline electroacoustic transducer (e.g. a speaker) or other frequency-producing device. In some such configurations, advantageously, the frequency-producing device could also simultaneously or at times be used to generate audible sounds, such as audible music or radio broadcasts. In some configurations, a flow may be modulated through the use of an inline valve (e.g. a solenoid-actuated diaphragm valve). In some configurations, a linear actuator may be used to cause a flow to oscillate by, for example, cutting off a portion of the flow path from the blower to the interface. The linear actuator may be, for example, a pump or piston, and may be pneumatically driven, hydraulically driven, and/or electrically driven. In some configurations, an inline rotary flow chopper (operating similarly to an optical chopper) may be used to impart an oscillation to a flow. In some configurations, an aerodynamic or mechanical flutter valve may impart an oscillation to a flow. In some configurations, a source of compressed gas with a control valve may provide additional bursts of gas to a flow to impart an oscillation. Such methods and arrangements for producing oscillations in a flow used for respiratory therapy should not be taken to be limiting.

Any physical object comprises one or more resonant frequencies at which there is a tendency for the object to vibrate or oscillate at a relative maximum amplitude. Likewise, volumes of airspace within the body of a patient, e.g. within the lungs, trachea, and/or alveoli, or volumes of air in a patient interface, e.g. a nasal cannula, may resonate if an oscillating flow is provided to the volumes at one or more resonant frequencies. Advantageously, providing flow therapy with an oscillating flow rate at such resonant frequencies (hereon referred to as a 'resonant' therapy) can introduce several therapeutic benefits relative to providing oscillatory flow therapy at frequencies that are not resonant frequencies. In some cases, providing a resonant therapy may greatly improve gas mixing, decreasing the effect of anatomical and/or mechanical dead spaces. Thus, for a given flow rate, improved CO2 clearance may be realized, or stated in another way, a lower flow rate may be necessary to achieve a desired CO2 clearance or patient pressure relative to the flow rate necessary under a default therapy. Therapy with a reduced flow rate may be perceived as more comfortable for the patient, which may improve the patient's adherence to therapy and long-term prognosis.

Various volumes of airspace within a patient's airways, for example, may resonate at different frequencies, and as noted above, there may be several frequencies for each volume that may correspond to optimal frequencies for several specific therapeutic benefits. The resonant frequencies are a function of the volumes of airspace in the patient, which may be estimated, for example, by tidal volume or by the height of the patient as an indicator if tidal volume. In some configurations, the oscillation frequency of the therapeutic flow may be controlled manually by a user through the input of variables such as the patient height or tidal volume into, for example, a controller in the respiratory therapy system. In some configurations, the user may input the desired oscillation frequency, oscillation amplitude, flow rate, and/or pressure directly. In some configurations, the resonant frequencies may be found automatically by a controller in the respiratory therapy system. In some configurations, a controller in the respiratory therapy system may implement an automatic frequency sweep testing routine, wherein the controller searches for one or more resonant frequencies to be used with a patient. In such a routine, the controller may, for example, cause the respiratory therapy system to deliver a flow with an oscillation at a given test frequency and determine one or more variables related to a therapy session, including airway CO2 or $O_2$ or other gas concentration, expired air CO2 concentration, transcutaneous CO2 concentration, respiratory rate, and/or other breathing performance indicators. The controller could then measure the one or more variables using one or more different test frequencies and compare the variable sets to find effective resonant frequencies for a given patient. In some configurations, the controller may also implement an automatic frequency sweep testing routine to find one or more flow and/or pressure amplitudes for a given oscillation that are most effective for a given frequency. The testing routine may be similar to that described above, and may be used to find the most therapeutically beneficial amplitude for a given resonant frequency. In any of these automatic frequency, pressure, amplitude, and/or flow rate finding methods, the controller may automatically implement the optimal found frequency, pressure, amplitude, and/or flow rate in the therapy or may provide recommendations to the user through the use of a display or other output device on the respiratory therapy system. In some configurations, the controller may be used to automatically find the frequencies, pressures, flow rates, amplitudes etc. that are optimal for therapy, but may also be limited to searching a range of parameter settings defined by the user. The automated sweeps may be conducted on top of a user-defined or default base flow rate/pressure, or could be conducted over a range of base flow rate/pressures to determine the optimum combination. The user may fix one or more, or none of the frequency, pressure, amplitude, and/or flow rate and the controller may determine the optimum combination of the remaining, or all of the other parameters Certain features, aspects and advantages of some configurations of the present disclosure have been described with reference to use by a patient or user. However, certain features, aspects and advantages of the use of the system as described may be advantageously practiced by other people on behalf of the patient, including medical professionals, medical device dealers, or medical device providers. Certain features, aspects and advantages of the methods and apparatus of the present disclosure may be equally applied to usage by other people.

3.2.1 Overview of Flow Therapy Apparatus and Operation

A flow therapy apparatus 10 is shown in FIG. 51. It is similar to FIG. 1 and the same reference numerals will be used. It comprises a housing 4 that contains a flow generator 11, humidifier 12, controller 13 and user I/O interface 14 (comprising, for example, a display and input devices such as buttons or the like). The flow generator 11 comprises a fan 11b or similar that is rotated by a motor 11a to create a gas flow (note, in alternatives other sources of gas could be used—e.g. a compressed gas source). The controller 13 is programmed to control the components of the apparatus, including: operating the flow generator 11 to create a flow of gas 19a (gas flow) for delivery to a patient (by controlling the motor 11a to rotate the fan 11b), operating the humidifier 12 to humidify and/or heat the generated gas flow 19b, receive user input from the user interface 14 for reconfiguration and/or user-defined operation of the apparatus 10, output information (for example on the display) to the user. The user could be a patient, healthcare professional or anyone else interested in using the apparatus. The gas flow could be a flow of air, a flow of 02, or any other suitable breathing gas or mix of breathing gases.

A patient breathing conduit 16 is coupled to a gas flow output in the housing 4 of the high flow therapy apparatus 10, and is coupled to a patient interface 17, such as a nasal cannula with a manifold 19 and nasal prongs 18. Note, the interface may be any device that may convey gases to a patient, such as full face masks, nasal masks, oral masks, nasal pillows, and nasal cannulas, and the like. The humidified gas flow 19b that is generated by the (preferably high) flow therapy apparatus 10 is delivered to the patient via the patient conduit 16 through the cannula 17. The patient conduit 16 can have a heater wire 16a to heat gas flow 19b passing through to the patient, under control of the controller 13. The patient conduit 16 and/or patient interface 17 can be considered part of the flow therapy apparatus 10, or alternatively peripheral to it. Use of the term "(high) flow therapy apparatus" can be utilised for either alternative.

General operation of a flow therapy breathing apparatus 10 will be known to those skilled in the art, and need not be described in detail here. However, in general terms the controller 13: controls the flow generator 11 to generate a gas flow of the desired flow rate (generated gas flow), controls the humidifier 12 to humidify the gas flow and/or heat it. The gas flow is directed out through the patient conduit 16 and cannula 17 to the patient. The controller 13 can also control heating elements e.g. 16a in the humidifier and/or patient conduit 16 to heat the gas to a desired temperature (also termed "target temperature" or "set point") that achieves the required level of therapy and/or comfort for the patient. The controller 13 can be programmed with or determine a suitable target temperature.

Operation sensors e.g. 20, 25, 26, such as flow, temperature, humidity and/or pressure sensors can be placed in various locations in the flow therapy apparatus and/or the breathing conduit and/or cannula. Output from the sensors can be received by the controller 13 via wired 27 or wireless transmission 8, to assist it to operate the flow therapy apparatus in a manner that provides desired therapy. A pressure line 23 could be provided with a pressure sensor 26 in the apparatus 10 to measure gas flow pressure.

Figure 52:
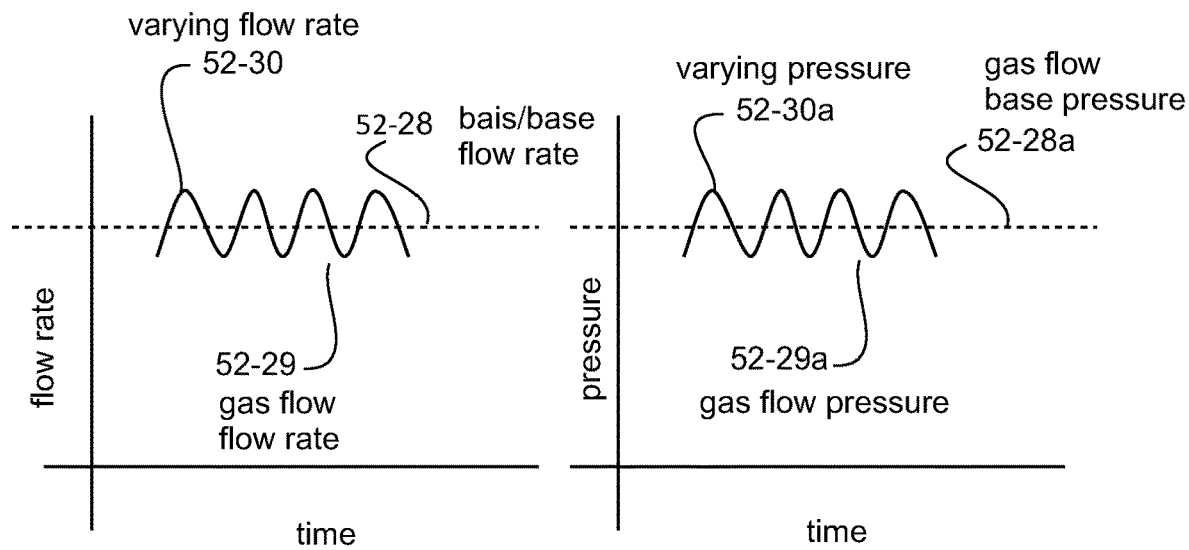
FIG. 52 shows a drawing of the varying gas flow produced by an apparatus configured and/or operated according to the present invention.

Referring to FIG. 52, in addition to providing usual flow therapy, in accordance with the present invention, the flow therapy apparatus 10 can be adapted with further apparatus and/or operated to provide gas flow oscillation in order to provide $CO_2$ washout (flushing) of the patient's airway and/or increase in $O_2$ using the apparatus 10. In one option, the apparatus 10 comprises or is coupled to a gas flow modulating device 5 that varies the gas flow flow rate 52-29 around a base or bias flow rate 52-28 (bias in the sense of an offset from zero, equivalent to a DC bias analogy). In an alternative option, the apparatus 10 does not have a modulating device but is operated to vary the gas flow rate around the base or bias flow rate. Either option provides a (preferably high frequency e.g. 10 Hz) oscillating gas flow 52-29 around a (preferably although not necessarily constant) base flow rate 52-28 that assists with $CO_2$ washout and/or increase in $O_2$. As an example, the frequency could be in the range of 2-250 Hz, although the frequency could fall outside this range. As an example the base flow rate could be configured to meet the patient's inspiratory demand, or a percentage of. In either option, the oscillation/variation might not have a single frequency, but might comprise multiple (including a range of) frequencies. It will be appreciated that the invention herein could relate to any sort of flow rate/pressure variation/oscillation with one or more frequencies. Reference in this specification to an oscillation frequency should not be considered limiting and should be considered to cover oscillation comprising two or more frequencies.

3.2.2 Gas Exchange Including $CO_2$ Washout and/or Increase $O_2$

Anatomical dead space is the volume of gas in the conducting airways that remains at the end of expiration to be re-breathed in the following inspiration. The high flow rates and jetting from a patient interface such as a cannula flush the dead space of end expiratory gases that are high in $CO_2$ with fresh gas. A reduction in airway $CO_2$ concentration is desirable to assist patients who have any number of respiratory conditions that lead to impaired respiratory systems and/or high CO2 levels.

It has been determined that anatomical dead space $CO_2$ concentration may be reduced and/or $O_2$ increased by causing the delivered flow rate to oscillate about a base flow rate. This reduces the effect of anatomical dead space. They have also determined that the minimisation of dead space/$CO_2$ and/or increase of $O_2$ when using such oscillatory therapy is greatest when the frequency of the oscillation is one that resonates with one or more volumes of space within the conducting airway and/or respiratory airway (e.g. lungs) of the patient.

The addition of (preferably high frequency) flow oscillations to gas flows in accordance with embodiments described provide improved $CO_2$ washout and/or increased $O_2$. Application of a varying gas flow that oscillates around a base/bias flow rate increases mixing of the contained gases that facilitates $CO_2$ washout and/or increased $O_2$. Every volume of patient airspace (e.g. lung) has a resonant frequency. The airspace is the volume of air within an airway, such as a lung. The physical airway (such as lungs, trachea etc.) might also have a resonant frequency.

Any physical object comprises one or more resonant frequencies at which there is a tendency for the object to vibrate or oscillate at a relative maximum amplitude. Likewise, volumes of airspace within the body of a patient, e.g. within the lungs, trachea, and/or alveoli, or volumes of air in a patient interface, e.g. a nasal cannula, may resonate if an oscillating flow is provided to the volumes at one or more resonant frequencies. Advantageously, providing flow therapy with an oscillating flow rate at such resonant frequencies (also referred to as a 'resonant' therapy) can introduce several therapeutic benefits relative to providing oscillatory flow therapy at frequencies that are not resonant frequencies (also referred to as a 'default' therapy). In some cases, providing a resonant therapy may greatly improve gas mixing, decreasing anatomical and/or apparatus dead spaces. Thus, for a given mean flow rate, improved $CO_2$ clearance may be realised, or stated in another way, a lower mean flow rate may be necessary to achieve a desired $CO_2$ clearance or patient pressure relative to the flow rate necessary under a default therapy. Therapy with a reduced flow rate may be perceived as more comfortable for the patient, which may improve the patient's adherence to therapy and long-term prognosis. A reduced therapy mean flow rate/pressure may also be beneficial for patients with barotrauma or hyper-inflation concerns Various volumes of airspace within a patient's airways, such as in the lungs, for example, may resonate at different frequencies, and as noted above, there may be several frequencies for each volume that may correspond to optimal frequencies for several specific therapeutic benefits. The resonant frequencies are a function of the volumes of airspace in the patient, which may be estimated, for example, by tidal volume or by the height of the patient. The airways themselves might also have a resonant frequency. Therefore, reference to a resonant frequency of an airway can refer to a resonant frequency of the airspace within the airway and/or the physical aspects of the airway.

Figure 53:
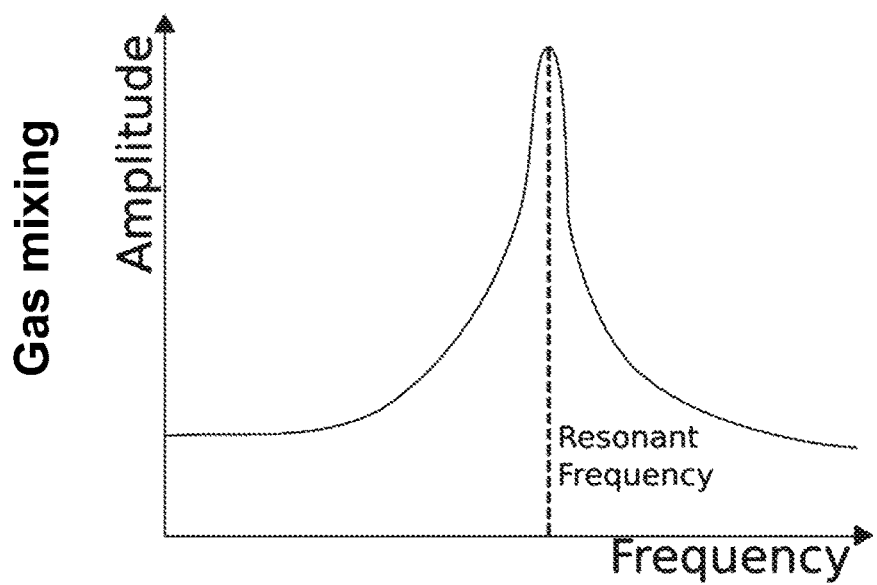
FIG. 53 shows gas mixing peak at the resonant frequency of a patient airspace.

Therefore, gas mixing increases dramatically if the varying gas flow oscillates at the resonant frequency of the airspace. FIG. 53 illustrates how amplitude or in this case the level of gas mixing, may increase dramatically at the resonant frequency. Delivering an oscillating gas flow at a frequency that matches the resonant frequency of the lungs as a whole, or a spectrum of frequencies that encompass the resonant frequencies of the various compartments of the lungs will encourage mixing and removal of $CO_2$ from the lung.

Figure 54:
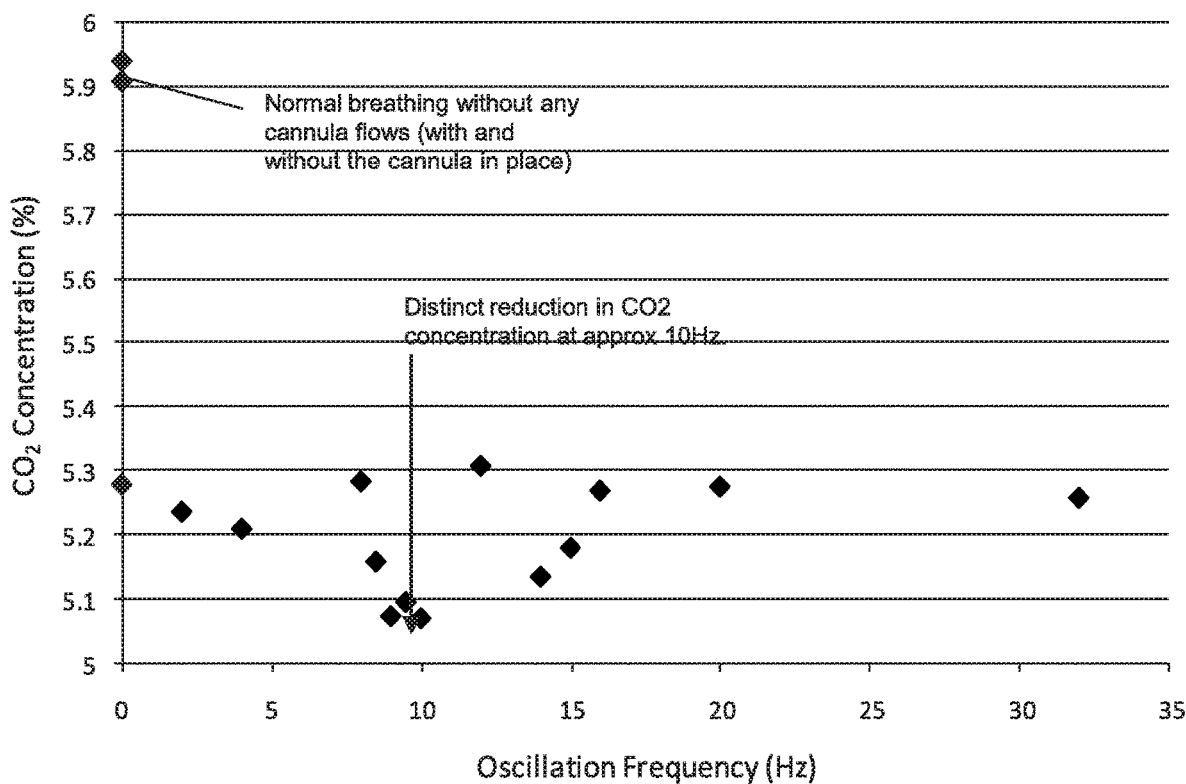
FIG. 54 shows the relationship between gas flow oscillation frequency and $CO_2$ concentration in a patient's airway.
Figure 55:
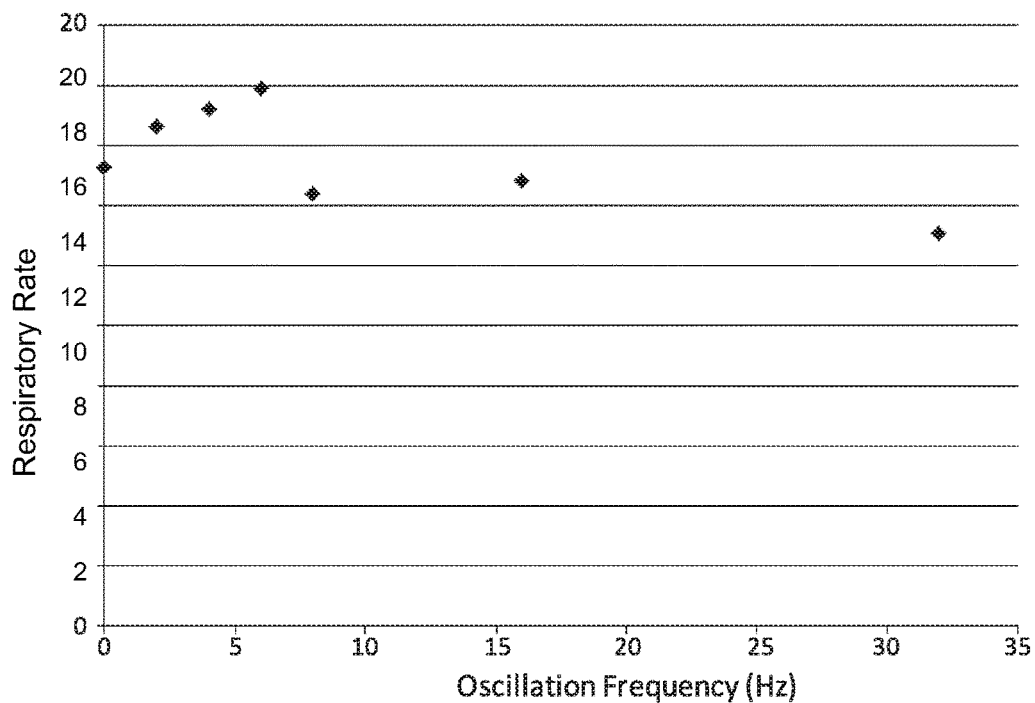
FIG. 55 shows the relationship between gas flow oscillation frequency and respiratory rate.

Preliminary experimental measurements have shown improved $CO_2$ clearance with a gas flow that varies about a base flow rate. It could be assumed that the average $O_2$ concentration would have also increased due to the displacement of $CO_2$. Measurements taken in a physiologically accurate model of the human airways and in a live subject are shown in FIGS. 54 and 55 respectively. In FIG. 54, at the airspace (e.g. lung) resonant frequency of 10 Hz, there is a drop off in $CO_2$ concentration, indicating good $CO_2$ washout. Note that here an increase in mixing at resonance has led to a reduction in $CO_2$ concentration. A corresponding drop in respiratory rate is shown at 10 Hz in FIG. 55. The in-vivo test measured respiratory rate instead of $CO_2$ concentration since it was easier to measure, and $CO_2$ concentration and respiratory rate are directly related (lower $CO_2$ concentrations lead to reduced respiratory rates). Therefore the reduction in respiratory rate here is likely due to a reduction in $CO_2$ concentration from an increase in mixing at resonance. The peaks in FIGS. 54 and 55 are therefore inverted when compared to FIG. 52. Both in-vitro and in-vivo results infer that there is a reduction in $CO_2$ concentration at certain frequencies. The resonant (optimal) frequency may be different for each patient. Automatic detection of each patient's resonant frequency with respiratory performance feedback could be desirable. Without identification of the resonant frequency specific to each patient, a population averaged optimal frequency or frequencies could be used as a default, or the frequency may be manually elected by the user.

3.2.3 Methods and Apparatus for Gas Flow Oscillation to Promote Gas Exchange

The embodiments described relate to apparatus and/or control methods for facilitating gas flow oscillation to facilitate/promote (improved) gas exchange (e.g. mixing) such as improved $CO_2$ washout (flushing) and/or increase in $O_2$. Referring to FIG. 52 and as mentioned above, embodiments of the present invention provide an apparatus and/or method of operation that provides a varying gas flow rate 52-29 that oscillates at a frequency about a base flow rate 52-28 such as shown in FIG. 52. The base flow rate 28 provides bulk flow of gas to the patient to provide the usual flow therapy treatments, and the oscillation 52-30 provides improved gas exchange such as $CO_2$ washout/increase in $O_2$. Alternatively or additionally, embodiments provide an apparatus and/or method of operation that provides a varying gas flow pressure 52-29a that oscillates 52-30a at a frequency about a base pressure 52-28a, which provides a varying gas flow flow rate 52-30 that oscillates at a frequency about a base flow rate 52-28, also such as shown in FIG. 52. The base flow rate 52-28 provides bulk flow of gas to the patient to provide the usual flow therapy treatments, and the oscillation 52-30a/30 provides $CO_2$ washout/increase in $O_2$. In any embodiment, the base flow rate and/or pressure and the flow rate and/or pressure variation could be specified by a user/clinician using the user interface 14. They could, for example, stipulate one or more of: a) the base flow rate and flow rate oscillation, b) the base flow rate and pressure oscillation, c) the base pressure and flow rate oscillation, and/or d) the base pressure and pressure oscillation, Possible therapeutic benefits of the use of high flow therapy include a reduced effect of anatomical and/or apparatus dead space, which can reduce the breathing of CO2. Improving the turbulence of the flow used in the therapy further improves gas mixing and reduces dead space. Accordingly, the flow rate of the flow used in high flow therapy is oscillated between two or more different flow rates at a given frequency about a base flow rate. For example, the flow rate delivered in the therapy may have a mean of 30 Litres/min and an oscillatory flow rate of +/−5 Litres/min at a frequency of 15 HZ. Alternatively, or in addition to the introduction of an oscillation to the flow rate of the flow, the pressure of the flow may be oscillated between two or more different pressures at a given frequency. For example, a flow delivered in therapy may deliver a mean pressure of pressure of 6 cm $H_2O$ with an oscillatory pressure of 4 cm $H_2O$ at a frequency of 15 HZ. Advantageously, by adding high frequency oscillations to a high flow therapy, in which there is a positive net flow of gas (base flow) towards a patient, improved CO2 clearance can be realized. In some preferred configurations, the flow oscillations are imparted by superimposing a second flow on top of a base unidirectional first (base) flow towards a patient. This unidirectional base flow may be delivered at a constant rate or may be varied over the course of a therapy session, for example in response to a detected breathing cycle of a patient or according to some pattern or algorithm determined by a respiratory therapy system and/or user. It may also be varied on a more frequent basis, such as every breath cycle in response to expiratory and inspiratory transitions, for example.

In one embodiment, the controller 10 is configured to operate the fan 11b in the blower at a base speed to provide gas flow 52-29 at the base flow rate 52-28 and/or pressure. The controller is further configured to modulate the gas flow 52-29 with an oscillation frequency 52-30 by varying the fan speed 11b around the base speed. For example, it might do this by providing a modulated motor speed control signal to the motor 11a that comprises a bias voltage correlating to a speed that provides the desired base flow rate 52-28 and/or pressure, and an oscillating modulating voltage at a frequency that oscillates the motor speed around the base speed to provide the desired gas flow flow rate oscillation (either by varying flow rate and/or pressure). Gas flow flow rate oscillation promotes gas exchange, and this is the desired outcome irrespective of whether flow rate modulated and/or pressure modulation are used. In effect, pressure modulating can cause flow rate oscillation.

Figure 56:
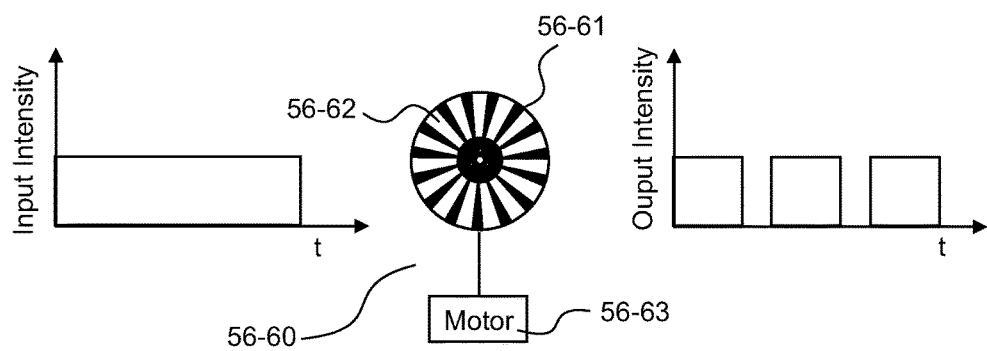
FIGS. 56 to 67 show possible gas flow modulating devices.

Referring to FIG. 56, in other embodiments, the flow therapy apparatus comprises or is attached to or used with a modulating device 5. In these embodiments, the controller 13 controls the motor 11a speed to operate the blower to provide a (preferably constant) base flow rate 52-28. The gas flow modulating device 5 is placed in a suitable location in the gas flow path from the blower, such as after the humidifier outlet 12 or in the patient conduit 16. The modulating device 5 is controlled with the controller 13 to vary the gas flow 19a from the blower to provide the oscillating gas flow 29/19a. This could be by way of modulating the gas flow flow rate and/or pressure.

Referring to FIG. 56, in one such embodiment the modulating device 5 is a chopper wheel 56-60 placed in the gas flow path at a suitable location, such as inside the flow therapy apparatus between the outlet of the humidifier 12 and the patient conduit 16 or in the conduit 16 itself. The chopper wheel comprises a circular disc 56-61 with openings spaced e.g. 56-62 around the disc, and a motor 56-63 to drive the disc. Chopper wheel motor 56-63 is coupled to the controller 13. The controller 13 is configured to operate the fan 11b at the required rate to provide gas flow at the base flow rate 52-28—this may be provided via a separate conduit or through some continuous aperture located in the disc, or next to the disc. It would also be possible to have two flow sources 67-170a, 67-170b converging to a single patient supply flow 67-170c such as in FIG. 67.

The controller 13 is further configured to operate the chopper wheel motor 56-63 to spin the disc 56-61 in the gas flow path 19b at the required rpm. Spinning the disc 56-61 alternately blocks the gas flow path 19b and then opens the path to allow gas flow through again as each successive aperture 56-62 passes through the gas flow path 19b (although noting there might be a continuous aperture—e.g. concentric aperture—to allow for base flow rate). This creates a variation in the gas flow flow rate and/or pressure to create the oscillation 52-30 around the base flow rate 52-28. The controller is configured to operate the chopper wheel motor 56-63 to spin the disc 56-61 at the required rpm to get the desired frequency of oscillation 30. For example, to get an oscillation frequency fHz the disc 56-61 is rotated at an rpm of f/no. of apertures.

Figure 57:
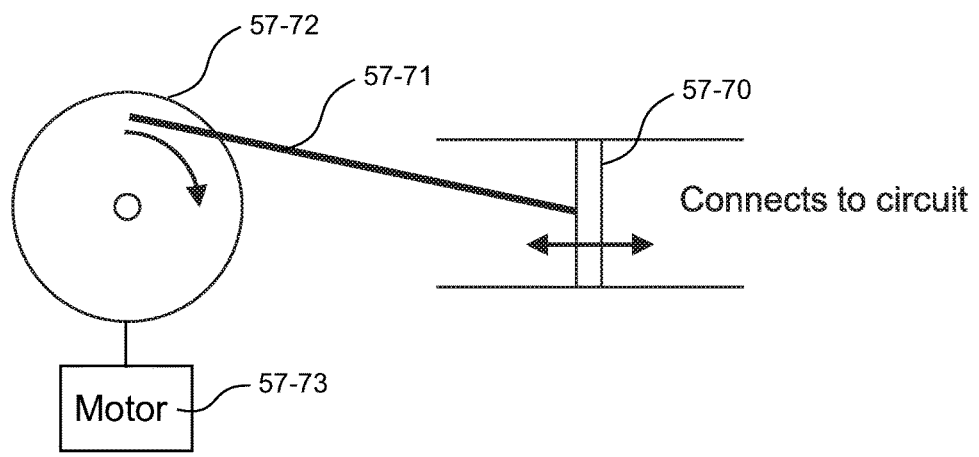
Figure 67:
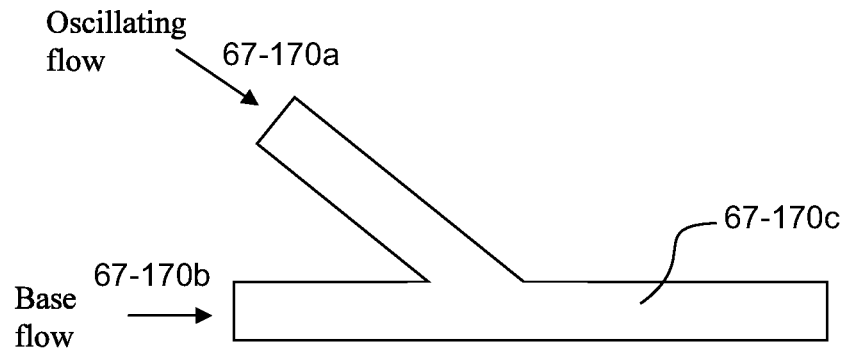

Referring to FIG. 57, in another embodiment the modulating device 5 is a piston 57-70 placed in the gas flow path 19b at a suitable location, such as inside the flow therapy apparatus between the outlet of the humidifier 12 and the patient conduit 16, or in the conduit 16 itself. The piston 57-70 is connected via a crankshaft 57-71 to a disc 57-72 or other rotating member, which itself is coupled to a motor 57-73 to drive the disc. The motor 57-73 is coupled to the controller 13. Rotation of the motor 57-73 oscillates the piston 57-70 in the gas flow path 19b by way of the crankshaft 57-71. The controller 13 is configured to operate at the fan 11b of the blower 11 at the required rate to provide the base flow rate 52-28. The controller 13 is further configured to operate the piston motor 57-70 to spin the disc 57-72 at the required rpm to oscillate the piston 57-70 in the flow path 19b at the desired frequency. Oscillating the piston 57-70 alternately creates pressure waves in the gas flow path that are superimposed on the base gas flow 52-28. This creates a variation 52-30 in the gas flow 19b/29 to create the oscillation 30 around the base flow rate 52-28. The controller is configured to operate the piston motor 57-73 to spin the disc 57-72 at the required rpm to get the desired frequency of piston oscillation to create the required variation frequency in the gas flow. An alternative flow source or other flow path (such as an aperture) to provide base flow is also provided, such as shown in FIG. 67.

As is evident from the above embodiments, an oscillation may be imparted to a flow in a multitude of different ways. In some configurations, a flow can be oscillated by controlling the motor of the blower 11 in such a way that the motor speed of the motor undergoes rapid variations. In some configurations, a flow can be modulated to have oscillations by an inline electroacoustic transducer (e.g. a speaker) or other frequency-producing device. In some such configurations, advantageously, the frequency-producing device could also simultaneously or at times be used to generate audible sounds, such as audible music or radio broadcasts. In some configurations, a flow can be modulated through the use of an inline valve (e.g. a solenoid-actuated diaphragm valve). In some configurations, a linear actuator may be used to cause a flow to oscillate by, for example, cutting off a portion of the flow path from the blower 11 to the interface 17. The linear actuator can be, for example, a pump or piston, and may be pneumatically driven, hydraulically driven, and/or electrically driven. In some configurations, an inline rotary flow chopper (operating similarly to an optical chopper) may be used to impart an oscillation to a flow. In some configurations, an aerodynamic or mechanical flutter valve imparts an oscillation to a flow. In some configurations, a source of compressed gas with a control valve may provide additional bursts of gas to a flow to impart an oscillation. Such methods and arrangements for producing oscillations in a flow used for respiratory therapy should not be taken to be limiting.

Therefore, many other modulation devices could be envisaged by those skilled in the art. Some further examples are shown in more detail in FIGS. 58 to 67. For example, referring to FIG. 64, in another embodiment an oscillatable diaphragm device (such as a speaker) 64-140 is placed in the gas flow path 64-141 at a suitable location. That would work in much the same way as the piston. The diaphragm is oscillated backwards and forwards by magnet 64-142 activated by an AC electrical signal sent from the controller 13 at the desired frequency to create pressure waves in the base gas flow at the desired frequency. An alternative flow source or other flow path (such as an aperture) to provide base flow is also provided.

Figure 58:
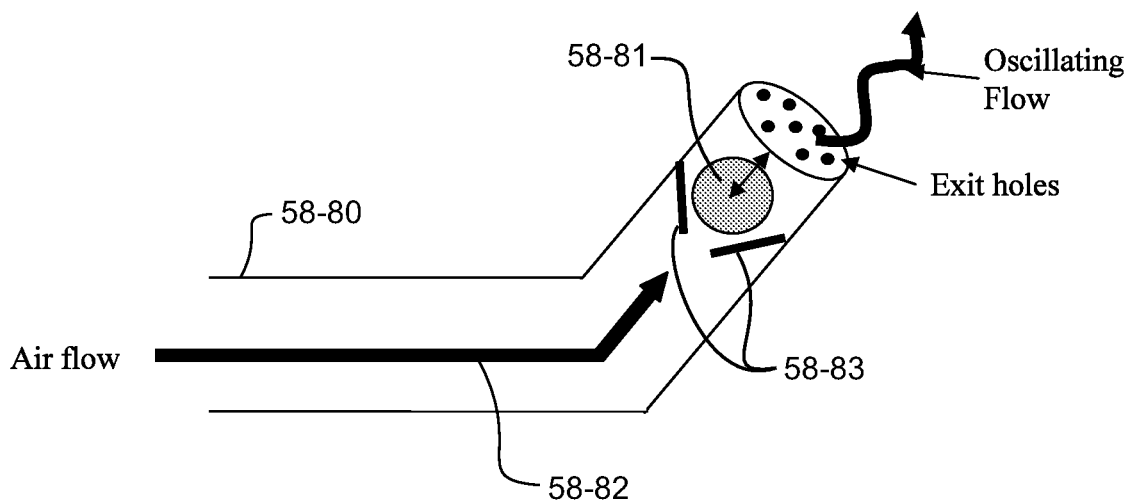
Figure 59:
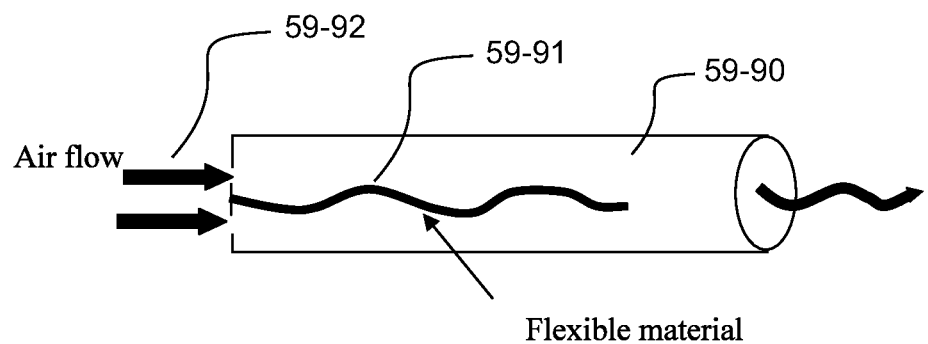
Figure 60:
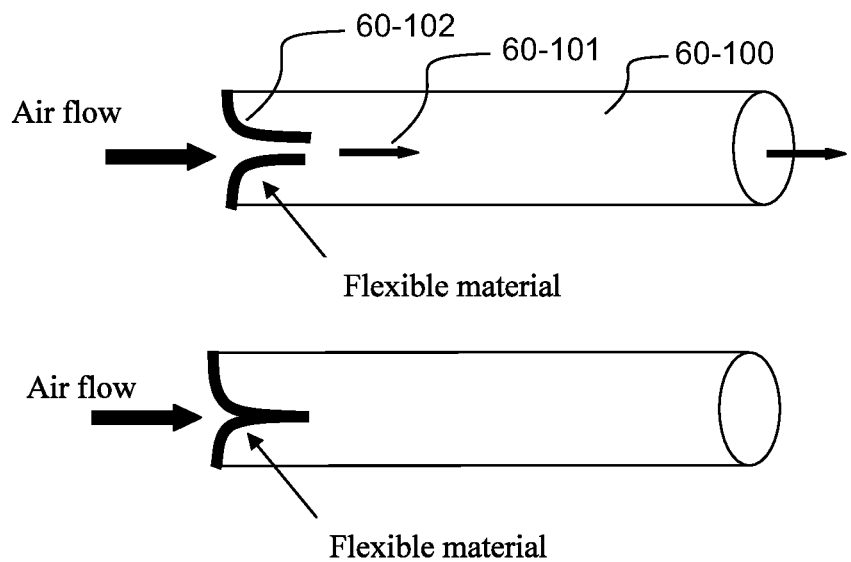
Figure 61:
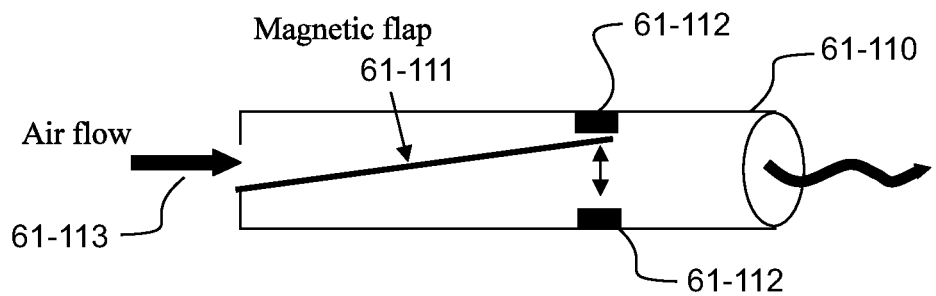
Figure 62:
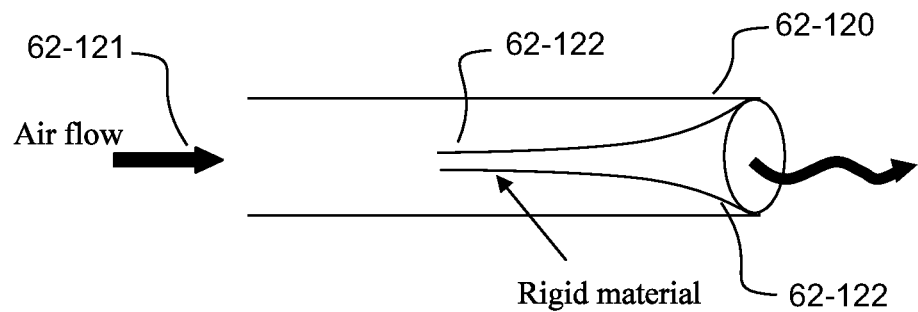

Similarly, referring to FIGS. 58 to 62, various aerodynamic or mechanical flutter valve arrangements could be placed in the gas flow path and operated in the same manner. In FIG. 58, a ball flutter valve 58-80 is provide in which air flow 58-82 causes a ball 58-81 to oscillate between the end of the tube and angled supports 58-83 inside tube. In FIG. 59, a flutter valve 59-90 is provided in which air flow 59-92 above and/or below a strip 59-91 of material causes material to flutter creating oscillations in flow. Depending on the design this may need alternative air source—for example, if air flow was insufficient through apertures to provide enough base flow, or if material occluded outlet or inlets too much during movement. In FIG. 60, a flutter valve 60-100 is provided in which air flow 60-101 into strips 60-102 of material cause them to open, permitting air flow. Air flow through the gap lowers pressure causing the strips to close back together. As the pressure builds up behind them they are forced open again. This cycle repeats creating the oscillations in the flow. The embodiment uses an alternative air source to provide a base flow rate as the strips 60-102 occlude flow. FIG. 61 shows a magnetic hinge valve 61-110 in which a flap 61-111 is alternately attracted to each magnet 61-112, permitting or blocking air flow to outlet. Polarity is controlled by the controller. The embodiment uses an alternative air source to provide a base flow rate as the flap 61-111 will block the inlet. FIG. 62 shows a reed valve 120 in which air flow 62-121 between strips 62-122 of material causes the material to flutter. This is similar to the air flow through a needed instrument. This embodiment does not require additional base flow, unless pressure from delivered air flow causes the reeds to occlude completely.

Figure 63:
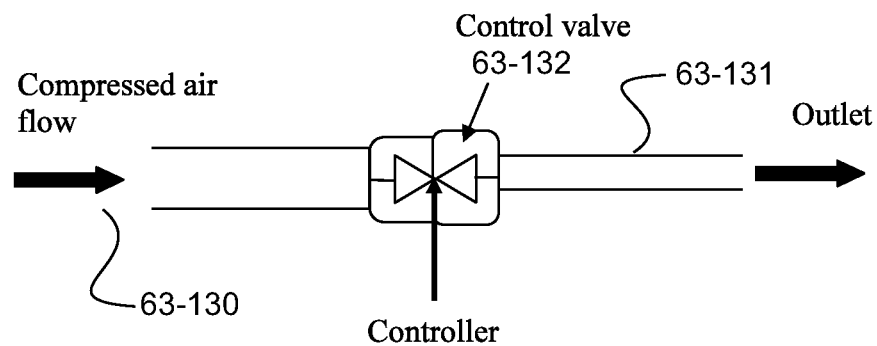
Figure 64:
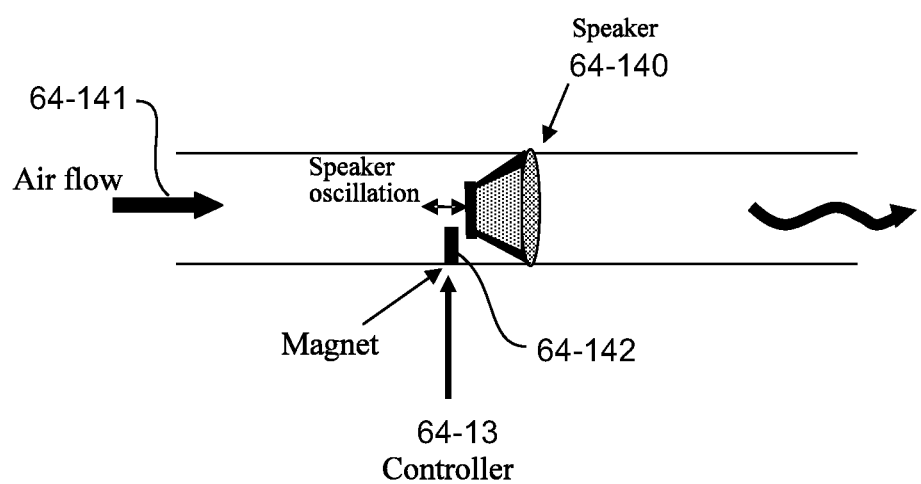
Figure 65:
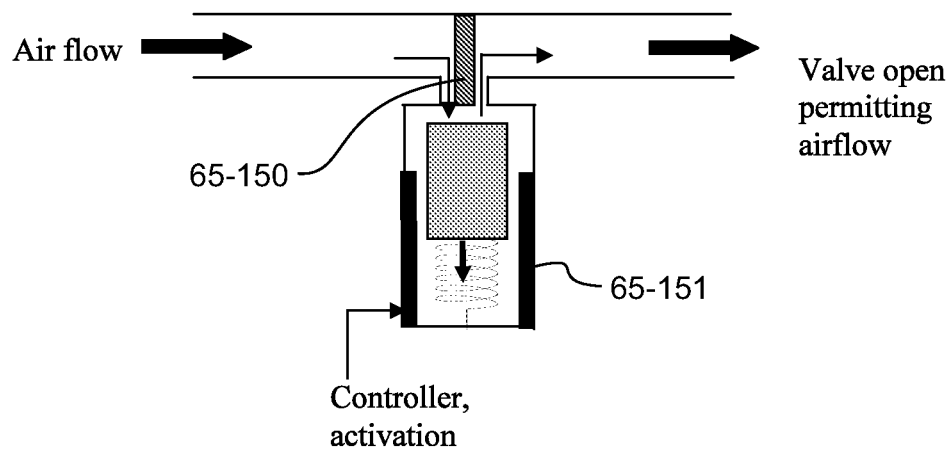
Figure 65:
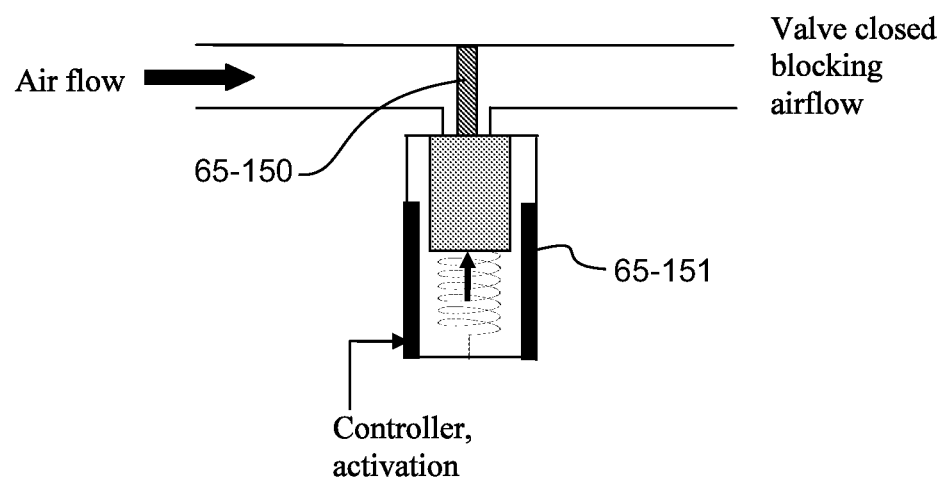
Figure 66:
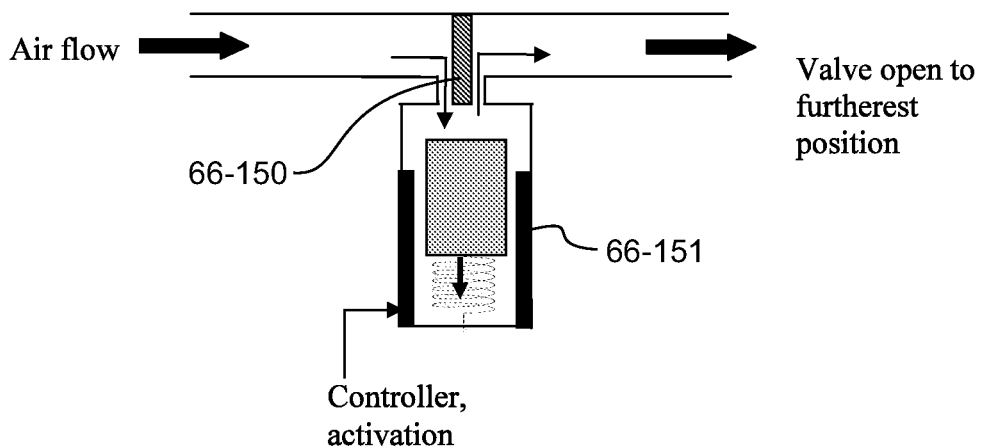
Figure 66:
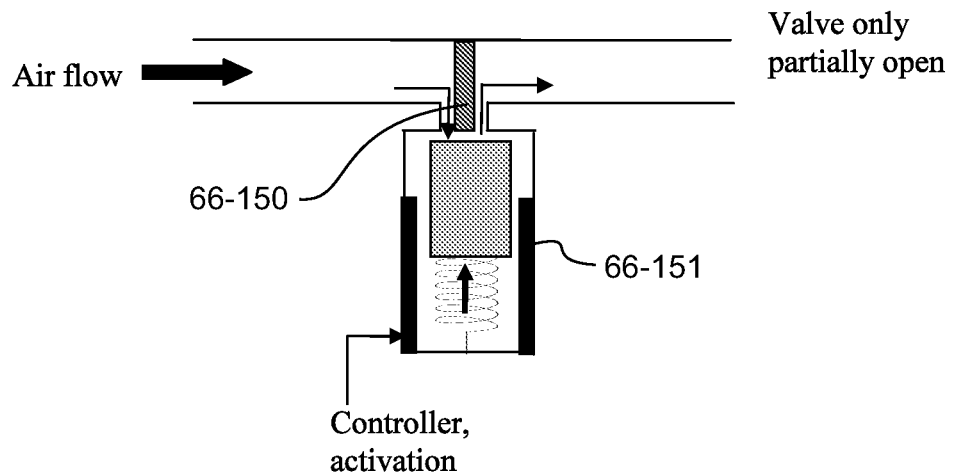

In FIG. 63, a gas source 63-130 could be fed into the gas flow line 63-131 and a valve 132 operated by the controller to provide pulses of gas to create pressure fluctuations at the desired frequency. In FIG. 65, an in-line linear actuator could be provided also. A solenoid actuated valve 65-150 is provide in which the solenoid 65-151 is alternately activated and deactivated by controller to open/close a valve 65-150, to create flow oscillations. The embodiment uses an alternative air source to provide a base flow rate. Alternatively in FIG. 65-56, a solenoid actuated valve with base flow is provided in which the solenoid 65-151 is alternately activated and deactivated to move position of a plunger 65-150 back and forth, creating flow oscillations, but still providing base flow at all times.

In cases where base flow is provided by a separate source, the arrangement in FIG. 67 could be used, by way of example.

The modulation devices shown in the Figures are not exhaustive of the possibilities. Other options would be envisaged by those skilled in the art.

In all embodiments, preferable the modulating frequency is at least one of the resonant frequencies of the patient airspace, although this is not essential. In alternatives, the modulating frequency that creates the oscillation is not a single frequency but rather a range or band of frequencies, which preferably, although not necessarily, comprises the resonant frequencies of the patient airspace. Or the band of frequencies could be a wide spectrum of frequencies such as those seen in white noise. The use of the term "frequency" in this specification can cover the case where multiple frequencies are used.

There are many possible ways in which the required modulating frequency(ies) is(are) determined and there are many possible ways in which the apparatus can be operated to control gas flow modulation to provide the required oscillation. For example, the oscillation frequency of the therapeutic flow can be controlled manually by a user through the input of variables such as the patient height or tidal volume into, for example, the controller 13 in the respiratory therapy system using the user interface. In some configurations, the user may input the desired oscillation frequency, oscillation amplitude, flow rate, and/or pressure directly. It may be possible for the device to automatically select the oscillatory frequency for an individual patient. This could be achieved by an auto-detection algorithm where the device applies a range of frequencies to the patient and records the expired $CO_2$ concentration and/or respiratory rate of the patient in response to each frequency. In this way it may be possible for the device to determine the frequency that promotes the most $CO_2$ clearance for that patient. It can be considered that this frequency corresponds to the resonant frequency of the patient's airspace. This algorithm may be run at the initiation of therapy (that is, a calibration step), at periods throughout the therapy or may be initiated manually by the user. In another embodiment the device may apply a combination of flow rate amplitudes as well as frequencies to determine both the optimal frequency and flow rate amplitude.

In some configurations, the resonant frequencies may be found automatically by a controller in the respiratory therapy system. In some configurations, a controller in the respiratory therapy system may implement an automatic frequency sweep testing routine, wherein the controller searches for one or more resonant frequencies to be used with a patient. In such a routine, the controller may, for example, cause the respiratory therapy system to deliver a flow with an oscillation at a given test frequency and determine one or more variables related to a therapy session, including airway $CO_2$ or $O_2$ or other gas concentration, expired air $CO_2$ concentration, transcutaneous $CO_2$ concentration, respiratory rate, and/or other breathing performance indicators. The controller could then measure the one or more variables using one or more different test frequencies and compare the variable sets to find effective resonant frequencies for a given patient. In some configurations, the controller may also implement an automatic frequency sweep testing routine to find one or more amplitudes for a given oscillation that are most effective for a given frequency and/or pressure. The testing routine may be similar to that described above, and may be used to find the most therapeutically beneficial amplitude for a given resonant frequency and/or pressure. In any of these automatic frequency, pressure, amplitude, and/or flow rate finding methods, the controller may automatically implement the optimal found frequency, pressure, amplitude, and/or flow rate in the therapy or may provide recommendations to the user through the use of a display or other output device on the respiratory therapy system. In some configurations, the controller may be used to automatically find the frequencies, pressures, flow rates, etc. that are optimal for therapy, but may also be limited to searching a range of parameter settings defined by the user. Or, the user could fix some parameters and allow the apparatus to automatically determine others Although the above embodiment discloses one possible respiratory therapy system, many configurations and variations of the respiratory therapy system are possible. For example, the user interface 14 and/or control system 13 can comprise comprising levers, dials, buttons, touch screens, or other means of adjusting the flow rate and/or pressure of gases leaving the blower 11. In some configurations, the blower 11 may be controlled remotely using a remote user interface. In some configurations, the blower 11 may instead be a pressurized gas container that may be used to propel gas through the respiratory therapy system. The gas container may comprise or be used with a valve that may be used to adjust the flow rate of gases passing out the container and through the respiratory therapy system. In some configurations, the blower 11 may be used in tandem with a gas container to provide a flow of gas through the respiratory therapy system.

In some configurations, oxygen or other breathable gases may be added anywhere along the circuit of the respiratory therapy system, and may be mixed with the gases propelled by the blower 11. In some configurations, the humidifier 12 may be inactive, or may be absent all together. In some configurations, the two conduits 23, 16 could be a single continuous conduit. In some configurations, the blower 11 and the humidification system 12 are an integrated unit with a single housing, and in others they can be separate units. The humidification system 12 can comprise a user interface or control system (the same or different to 14, 13) that can be used to adjust the heat and/or humidity modulation of the gases passing through the apparatus 10. In some configurations, the humidifier 12 may be controlled remotely using a remote user interface. In some configurations, the conduits 23, 16 may be heated using one or more conduit heaters 16a. In some such configurations, the conduit heaters may be resistive wires that may heat up upon the application of electrical energy, and may be on, in, or within the conduits (e.g. between two or more walls of the conduits). Preferably, if the respiratory therapy system is used to deliver a high gas flow therapy, a nasal cannula is used as the interface 17. Oscillations could be imparted during only a part of the respiratory cycle, for example just during expiration, or a portion thereof. The portion could be defined by the user.

4. Determining Patient Airway Pressure 4.1 Overview

Flow therapy is used to deliver gas flow to a patient at a delivered flow rate to assist with respiration. The therapy is delivered using a flow therapy apparatus To assist with control of the apparatus, existing apparatus measure pressure—but the measured pressure is either: static pressure only (and not total delivered patient pressure), or is measured using a patient interface that seals on a patients nose and/or mouth. High flow therapy delivers pressure to the patient that has a significant dynamic pressure component and does so in a non-sealed system where air flows are freely available to exhaust to the atmosphere. Presently available means of pressure measurement are therefore inaccurate when used on high flow therapy.

4.2 Flow Therapy Apparatus

A flow therapy apparatus 10 is used shown in FIG. 38. It provides gas flow to a patient through a non-sealing interface. It comprises a housing 4 that contains a flow source 11 (such as a flow generator/blower), humidifier 12, controller 13 and user I/O interface 14 (comprising, for example, a display and input devices such as buttons or the like). The controller 13 is programmed to control the components of the apparatus, including: operating the flow generator 11 to create a flow of gas (gas flow) for delivery to a patient, operating the humidifier 12 to humidify and/or heat the generated gas flow, adjust the flow rate of other introduced gases, e.g. oxygen, receive user input from the user interface 14 for reconfiguration and/or user-defined operation of the apparatus 10, output information (for example on the display) to the user. The user could be a patient, healthcare professional or anyone else interested in using the apparatus. In an alternative, the flow source could be another source of flow such as compressed gas (e.g. $O_2$). Further, the flow source need not actually be in the housing but instead could be outside the housing. The flow source could be controlled in the apparatus and/or at the source.

A patient breathing conduit 16 is coupled to a gas flow output in the housing 4 of the high flow therapy apparatus 10, and is coupled to a patient interface 17, such as a nasal cannula with a manifold 19 and nasal prongs 18. The humidified gas flow that is generated by the high flow therapy apparatus is delivered to the patient via the patient conduit 16 through the cannula 17. The patient conduit 16a can have a heater wire to heat gas flow passing through to the patient, under control of the controller 13. The patient conduit 16 and/or patient interface can be considered part of the high flow therapy apparatus 10, or alternatively peripheral to it. Use of the term "(high) flow therapy apparatus" can be utilised for either alternative.

General operation of a flow therapy breathing apparatus 10 will be known to those skilled in the art, and need not be described in detail here. However, in general terms the controller 13: controls the flow generator 11 to generate a gas flow of the desired flow rate (generated gas flow), and controls the humidifier 12 to humidify the gas flow and/or heat it. The gas flow is directed out through the patient conduit 16 and cannula 17 to the patient. The controller 13 can also control heating elements 16a in the humidifier and/or patient conduit to heat the gas to a desired temperature (also termed "target temperature" or "set point") that achieves the required level of therapy and/or comfort for the patient. The controller 13 can be programmed with or determine a suitable target temperature.

Operation sensors, such as flow, temperature, humidity, gas concentration and/or pressure sensors can be placed in various locations in the flow therapy apparatus and/or the breathing conduit and/or cannula. Output from the sensors can be received by the controller 13, to assist it to operate the flow therapy apparatus in a manner that provides optimal therapy, including delivering a set pressure.

4.3 Determining an Estimate of Patient Airway Pressure

Figure 68:
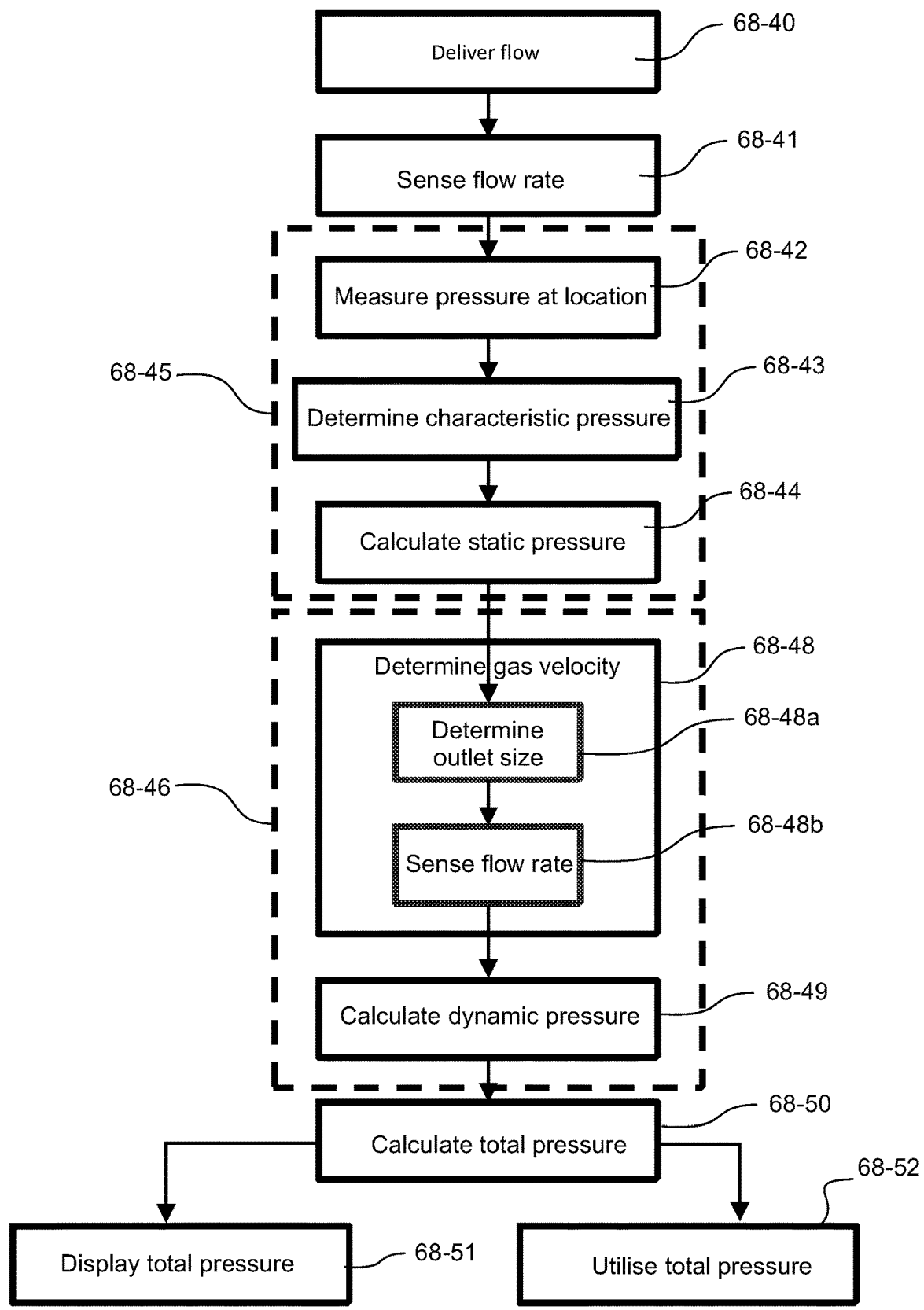
FIG. 68 is a flow diagram of a method for determining total delivered patient pressure.
Figure 69:
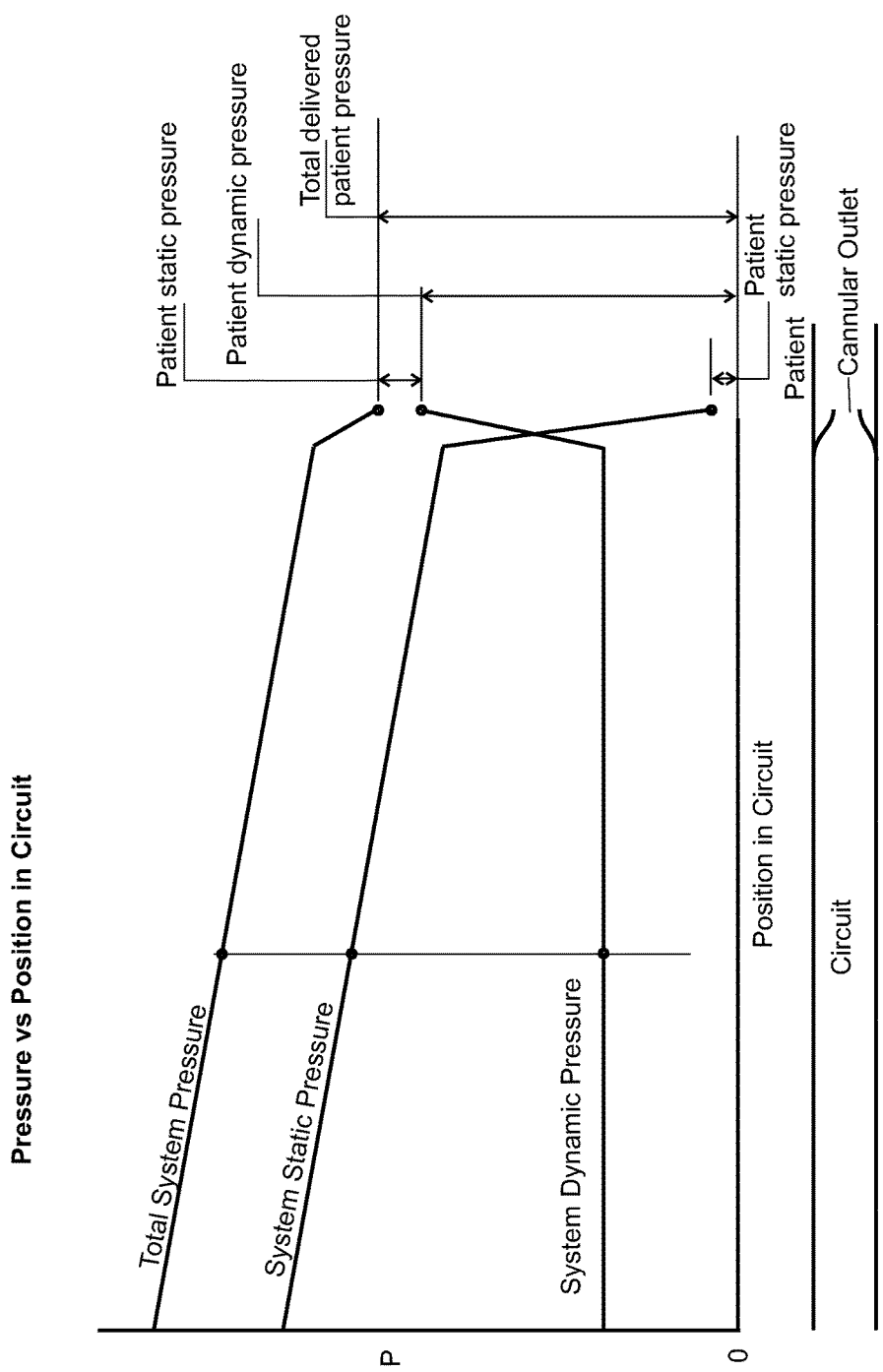
FIG. 69 is a plot of various pressures at various positions in a breathing circuit.

A general embodiment of the present invention will be described with reference to FIGS. 38 and 68, 69. FIG. 68 shows a method of operation of the apparatus in FIG. 38, and FIG. 69 shows the pressures at various points in the apparatus circuit, which assists in illustrating the model that is implemented in the method of operation. The embodiment described in these Figures refers to a cannula as the patient interface, but this is exemplary only and should not be considered limiting. Any suitable type of patient interface could be used. It will also be appreciated that the steps described need not necessarily happen in the order described.

In general terms, the flow therapy apparatus and in particular, but not necessary exclusively, controller 13 is configured to non-invasively determine a total delivered patient pressure in the flow therapy apparatus 10, where the apparatus comprises the patient interface 17 and delivery conduit 16 as well as the housing 4 and its internal hardware. The total delivered patient pressure estimates or otherwise indicates the pressure delivered to a patient's airway. The total delivered patient pressure could be found (as an example) by determining a pressure parameter at some point in the apparatus circuit, being a parameter that indicates or can be used to indicate total delivered patient pressure.

Total delivered patient pressure ($P_{TDPP}$) can be modelled as a function to obtain an estimate. The model can be defined as:

$$P_{TDPP} = f(P_{System\ Static}, P_{Characteristic}, v, Q, P_{System\ Static(0)}, \varrho, \text{Outlet size}) \quad (1)$$

where
- $P_{TDPP}$ is the total delivered patient pressure
- $P_{System\ Static}$ is the system static pressure at a location of measurement
- $P_{characteristic}$ is the contribution of the apparatus to system static pressure at a location of measurement
- v is the velocity of gas flow
- Q is the delivered flow rate
- $P_{System\ Static\ (0)}$ is the system static pressure at the location of measurement when flow rate (Q) is zero.
- $\varrho$ is the gas density
- 'Outlet size' is the size of a patient interface outlet, such as cannula prongs.

$P_{system\ Static\ (0)}$ is the system static pressure measured when the flow rate is decreased to zero but the patient is still wearing the interface and communicating the time varying pressures generated by their breathing into the cannula (not ideal as it requires a pause in therapy).

$P_{system\ Static}$ and $P_{system\ Static\ (0)}$ variables could be the minimum, mean, maximum, or instantaneous values of a breath cycle, or a combination of these.

The controller is configured with the model to operate the apparatus to determine total delivered patient pressure.

In one model, the total delivered patient pressure is calculated from and/or defined by a static patient pressure and dynamic patient pressure according to the following equation.

$$P_{TDPP} = P_{Patient\ Static} + P_{Patient\ Dynamic} \quad (2)$$

where
- $P_{TDPP}$ is as defined previously
- $P_{Patient\ Static}$ is the static patient pressure (component)
- $P_{Patient\ Dynamic}$ is the dynamic patient pressure (component)

$P_{Patient\ Dynamic}$ relates to v in equation (1) as per equation (4) below, while $P_{Patient\ Static}$ relates to $P_{characteristic}$ and $P_{system\ static}$ in equation (1) as per equation (3) below.

The total delivered patient pressure estimates the patient airway pressure, which is representative of the delivered pressure (that is, the pressure at the beginning of the respiratory tract). The dynamic pressure component takes into account the additional pressure that the patient receives due to the momentum of the air.

The total delivered patient pressure can be determined by:
a) a single sensor (which sits in a flow path in the apparatus at the location) that measures total delivered patient pressure, or,
b) measuring static patient pressure using a pressure sensor at a measurement location, then determining dynamic patient pressure through another method and then adding the static and dynamic pressures.

The information can then be displayed and/or used to control the apparatus.

For explanatory purposes, various pressures in an apparatus circuit that contribute to and are used to estimate total delivered patient pressure are shown in FIG. 69. The term "circuit" can refer to the entire circuit flow path circuit of an apparatus, including inlet, blower, humidifier, internal ducting, breathing conduit and the patient interface. FIG. 69 for simplicity however just refers to the breathing conduit and patient interface. This should not be considered limiting and the pressures shown could apply to any part of the apparatus circuit.

Referring to FIG. 69, at any point in the breathing conduit, there is a system static pressure ($P_{System\ static}$), which can be measured at any location in the system. The patient static pressure at one measurement location is indicated. System static patient pressure has a component due to the contribution of the physical characteristics of the system ($P_{characteristic}$) to static pressure and also a component due to the contribution of the patient ($P_{Patient\ static}$) to static pressure. Characteristic pressure at a location can be determined experimentally by measuring pressures at that location in the apparatus at various flow rates but before actual use on a patient. There is also a patient dynamic pressure ($P_{Patient\ Dynamic}$), which is caused by the flow of gas. The static and dynamic pressures are added to give the total delivered patient pressure ($P_{TDPP}$). As can be seen in FIG. 69, the static pressure drops as you travel towards the patient, due to physical characteristics of the circuit. Dynamic pressure remains constant as the cross-sectional area of the circuit remains constant. At the patient interface (e.g. cannula) the outlet area narrows (is smaller than the conduit area) and increases the velocity of the gas. This increases the dynamic patient pressure and results in a greater loss of system static pressure to overcome the resistance to flow of the narrowing. The outlet area (end of prongs) provides an indication of delivered patient dynamic pressure and thus total delivered patient pressure, which the present invention estimates. Therefore, the total system pressure ($P_{System\ Static} + P_{System\ Dynamic}$) at the end of prongs can give an indication of total delivered patient pressure. The present invention, in one embodiment, models the end of prongs system pressure to determine total delivered patient pressure.

Referring back to FIGS. 38 and 68, the controller (and apparatus generally) are configured with the model and method described below to operate the apparatus to determine total delivered patient pressure in accordance with the method described below. To determine total delivered patient pressure according to option b), first the apparatus is operated to deliver a gas flow to the patient at a delivered gas flow rate using the flow generator as operated by the controller, step 68-40. This method could also be device independent, as long as you had knowledge of/measured the flow rate and knew the interface outlet size. A flow sensor placed in a suitable location in the apparatus. This could be just after the flow generator, in or around the cannula (or other patient interface) or at some other suitable point for sensing the gas flow rate delivered to the patient, step 68-41. Where an additional gas source is provided, the flow sensing can be provided after the mixing of the additional gas with ambient gas. The output from the flow sensor is communicated to the controller 13. The controller can determine the current/instantaneous delivered gas flow rate, or a value representative of that flow rate over a number of breath cycles.

A patient static pressure is then determined, step 68-45. First, a system static pressure is then measured, step 68-42, at the location in the apparatus using a pressure sensor placed at a suitable location in the apparatus, such as at the flow generator 3a, the humidifier 3b or the patient conduit 3c or in the cannula 25/20, or at a mixing chamber where the additional gas and ambient air mix or in any other suitable part of the system.

As noted above with reference to FIG. 69, the measured system static pressure contains contributions from the patient and also the system itself, according to the following equations.

$$P_{Patient\ Static} = P_{System\ Static} - P_{Characteristic} \quad (3)$$

where $P_{Patient\ Static}$ = patient static pressure at the measurement location $P_{System\ Static}$ = system static pressure at the measurement location $P_{Characteristic}$ = characteristic static pressure at the measurement location Because of this, once the system static pressure is measured, the pressure characteristic of the relevant components of the system (up to the point where pressure is being measured) is determined, step 68-43. The pressure characteristic takes into account the pressure caused by the resistance to the flow of the system components at a particular flow rate due to the physical characteristics of the system components at that flow rate. That is, the characteristic pressure indicates the contribution to pressure made by the system due to its physical characteristics at that flow rate. For example, if the system pressure is taken at the flow generator 11, the pressure contributions of the patient interface 17, patient conduit 23, humidifier 12, and internal ducting would contribute to the characteristic pressure. The characteristic pressure for a given flow rate is determined using the current flow rate as an input along with knowledge of the characteristics of the system, or it can be determined from a look up table, relationship, graph or the like that correlates the pressure contribution of particular system components at particular flow rates to the system pressure. Or it can be measured at the time of treatment if the interface is removed from the patient covered in other methods. The controller 13 next determines the patient static pressure, being the static pressure contribution by the patient. The controller calculates this by subtracting the characteristic static pressure from the system static pressure, according to equation (3), step 68-44.

Next, $P_{dyn}$ is ascertained, step 68-46. The dynamic pressure component is related to the flow density and velocity as shown in equation (4). Equation (4) is derived from Bernoulli's theorem, which is typically limited in application to laminar flows. The optional empirically derived constant or function 'f' may be added to account for turbulence at higher cannula flow rates.

The dynamic pressure component is defined (approximated) by the following equation.

$$P_{Patient\ Dynamic} = \tfrac{1}{2} f \varrho\, v^2, \quad (4)$$

where v is the velocity of the gas at the delivered flow rate.

$\varrho$ is the density of the gas f is an empirically derived constant or function (which is optional)

The patient dynamic pressure component takes into account the additional pressure that the patient receives due to the momentum of the air. To determine dynamic pressure, the velocity of gas at the delivered flow rate is determined, which can be ascertained in a number of ways. For example, where the location is in a patient interface, it can be determined by using the delivered flow rate of gas and the outlet size of the patient interface, according to the following equation.

$$v = Q/A$$

where v is the velocity of the gas at the delivered flow rate in m/s

Q = the flow rate of delivered gas in m³/s

A = the outlet area in m²

Once patient dynamic pressure is ascertained, it is added to patient static pressure as per in equations (2), (3) to obtain the total delivered patient pressure, step 68-50.

The total delivered patient pressure estimates the patient airway pressure, (for example, at the patient interface outlet), which is representative of the delivered pressure (that is, the pressure at the beginning of the respiratory tract). It can be displayed, step 68-51 and/or used to control the apparatus or for other uses, step 52. For example, an estimate of total delivered patient pressure can (non-invasively)

- provide an additional parameter for controlling/monitoring the treatment of high flow
- aid understanding of the clinical outcomes of high flow on an individual patient
- create an easily identifiable comparison with more traditional pressure based therapies (as opposed to flow based).
- Assist in diagnostics—detection of patient deterioration, improvement and stability, for example via monitoring of trends and/or changes in pressure 4.4 Exemplary Embodiment An exemplary embodiment will now be described in more detail. In this case, the location in the apparatus at which the system total pressure is determined is the outlet of the nasal prongs of the cannula. The total delivered patient pressure is determined by finding patient static and dynamic pressures and using equation (2).

The method and apparatus will be described with reference to FIGS. 38 and 68, wherein the apparatus of FIG. 38 can be configured to carry out the method to determine total delivered patient pressure, non-invasively, as set out in the flow chart of FIG. 68. For example, the controller 13 can be programmed to carry out the method in the flow chart of FIG. 68 using as inputs information from sensors in the apparatus. A cannula is shown in FIG. 38 and will be described with reference to the embodiment below, but it will be appreciated that the invention is not restricted to the use of a cannula and in fact the invention would work with any type of suitable patient interface. Any references herein to cannula could be generalised to refer to any suitable patient interface.

The apparatus delivers gas flow, step 68-40, and has a flow sensor placed just after the flow generator (or other flow source), in or around the cannula (or other patient interface) or at some other suitable point for sensing the gas flow rate delivered to the patient, step 41. Where an additional $O_2$ or other gas source is provided, the flow sensing can be provided after the mixing of $O_2$ or other gas with ambient gas. The output from the flow sensor is communicated to the controller 13. The controller can determine the current/instantaneous delivered gas flow rate, or a value representative of that flow rate over a number of breath cycles. In an alternative, flow can be determined from blower power or some other indicator of flow. Alternatively, it could be determined from the controller. For example, one can assume that the apparatus is delivering the flow the user has input.

Next, system static pressure is ascertained, step 45. The apparatus 10 has a pressure sensor 25 or 20 placed in or around the cannula (such as inside or proximate the manifold of the cannula or inside or proximate the prongs) for sensing the system static pressure (in this case the cannula/manifold pressure) or sensing a pressure parameter indicative of that static pressure, step 42. (As noted earlier, alternatively, the pressure sensor could be placed in any other suitable location in the circuit, such as in or after the flow generator 3a, humidifier 3b, or patient breathing conduit 3c, or at a mixing chamber where $O_2$ and ambient air mix.) More generally, reference to "system static pressure" in this embodiment means any system static pressure parameter/value being or indicative of system static pressure in the manifold (or more generally the cannula). The system static pressure will comprise pressure contributions from or due to the apparatus, patient and cannula (more generally the patient interface). The output of the pressure sensor 20/25 is communicated to the controller 13.

Figure 70:
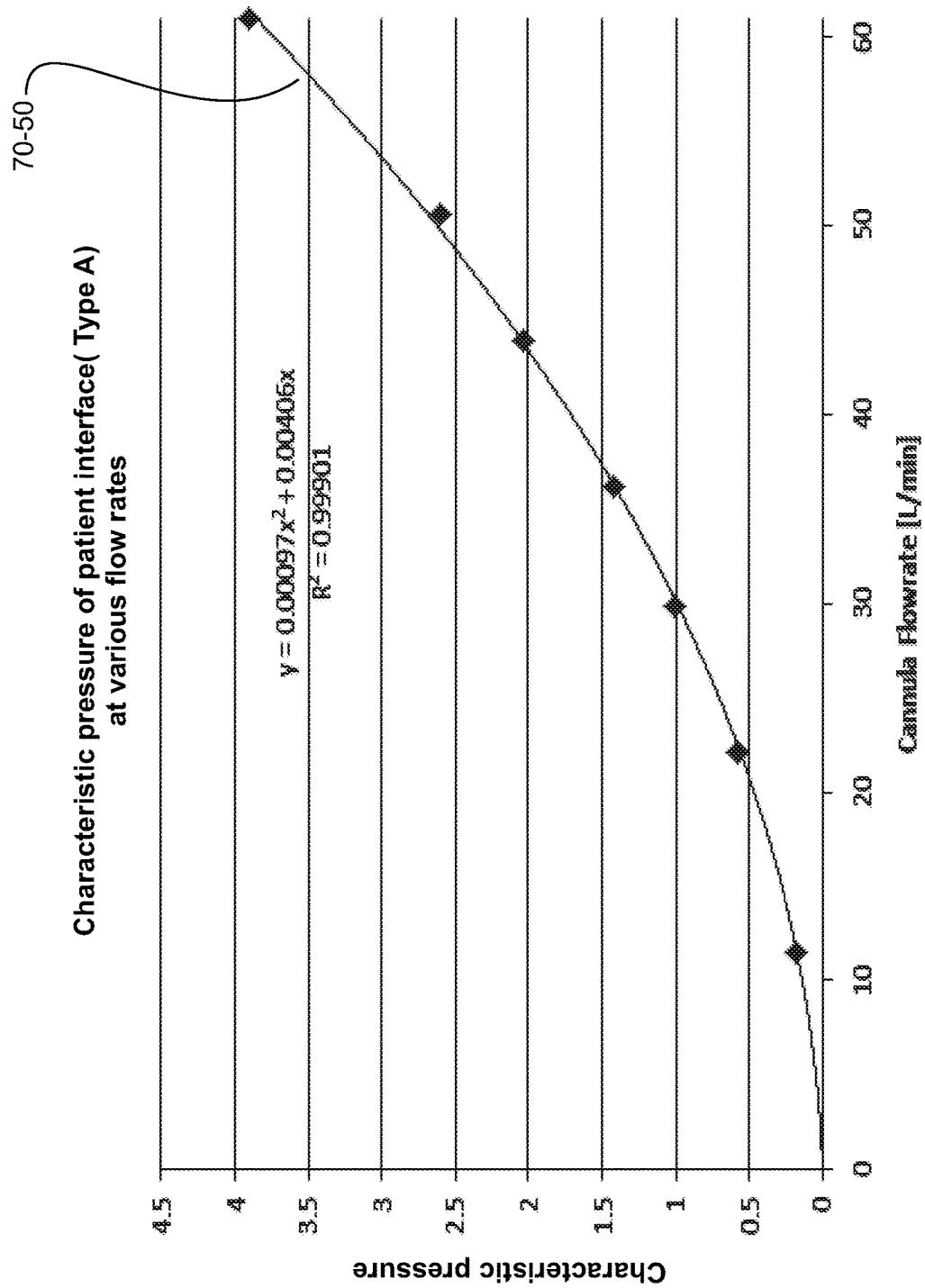
FIG. 70 is a graph showing an indicative characteristic pressure curve for a patient interface at various flow rates.

The controller 13 receives the system (cannula) pressure measurements from the pressure sensor which could be in the cannula, which is disposed in or proximate the nasal prong of the cannula near the nasal passage of a patient. The pressure measurement received has contributions from the patient and characteristics of the system itself. The patient static pressure is determined from the system static pressure as measured at the particular location minus the characteristic pressure of the apparatus at that location, as per equation (3). To do this, next, step 68-43, the controller 13 obtains a characteristic static pressure of the cannula at the flow rate determined by the controller 13. The patient static pressure at a location in the apparatus/system, such as the cannula is a function of the system static pressure measured at that location (that is, system pressure) and the characteristic pressure of the system at that location, as per the equation below.

$$P_{Patient\ Static} = P_{System\ Static} - P_{Characteristic} \quad (3)$$

where $P_{Patient\ Static}$=patient static pressure at the measurement location $P_{System\ Static}$ system static pressure at the measurement location $P_{Characteristic}$ characteristic static pressure at the measurement location The characteristic static pressure is the "baseline" pressure caused by the resistance to the flow of the cannula at a particular flow rate due to the physical characteristics of the cannula at that flow rate, without any contribution by the patient. That is, the characteristic static pressure indicates the contribution to static pressure made by the cannula due to its physical characteristics at that flow rate. This characteristic static pressure 70-50 may be calculated by using the measured flow rate as an input along with knowledge of the characteristics of the cannula, or it can be determined from a look up table, relationship, graph or the like that correlates the pressure contribution of a particular cannula at particular flow rates to the manifold pressure. A generic such relationship and graph is shown in FIG. 70 for a hypothetical cannula termed "Type A". Alternatively, the characteristic pressure could be determined in a calibration step at the time of measurement for that particular patient/set-up by taking pressure measurements when the cannula has been removed from the patient for a time at that location for various flow rates.

Note, if a pressure sensor is used at another location in the circuit (such as at locations 3a, 3b or 3c), then the characteristic static pressure will be the pressure caused by resistance to the flow by all components in the circuit that affect the pressure, such as the patient conduit, flow generator, humidifier and/or internal ducting. In such cases, the pressure measured will not be the manifold or cannula pressure, but the pressure of the relevant location/component in the circuit.

The controller 13 calculates the patient static pressure $P_{Patient\ Static}$, step 68-44, using equation (3) and knowledge of the characteristic pressure and measured static pressure.

Next the controller determines dynamic pressure, step 68-46, according to the equation:

$$P_{Patient\ Dynamic} = \tfrac{1}{2} Q\ v^2, \quad (4)$$

where v is the velocity of the gas at the delivered flow rate.

As stated previously, the dynamic pressure component takes into account the additional pressure that the patient receives due to the momentum of the air. $v^2$ is a function of delivered gas flow rate and the prong size (outlet area) of the cannula (or other outlet of the patient interface being used), as per the following equation.

$$v = Q/A \quad (5)$$

where v=the velocity of the gas at the delivered flow rate in m/s

Q=the flow rate of delivered gas in $m^3/s$

A=the outlet size in $m^2$

To determine dynamic patient pressure, the velocity has to be determined, step 68-48. First the controller determines the prong outlet size, step 68-48a. In one embodiment, the cannula is identified so that the prong size can be ascertained. The identification might be of the particular cannula itself, or the type of cannula. In one variation, the cannula has an RFID tag or other electronic identification circuit or element that the controller can detect. Alternatively, a user can provide input in the user interface 14 identifying the cannula. In yet another alternative, the controller can operate the apparatus to deliver (one or more) or a range or sweep of flow rates before flow therapy is administered to the patient. The controller detects the pressure at each delivered flow rate and then refers to a look-up table or graph that contains pressure values, or a range of pressure values, known to occur at each flow rate in different interfaces. The controller can then match the measured pressures with the stored values/graphs to identify the cannula in use.

Once the interface is identified, a look up table or other source of reference information that correlates various patient interfaces to their various physical characteristics can be used to obtain the outlet size.

In an alternative, the outlet size might be determined in some other manner, other than identifying the cannula. For example, the outlet size might be determined directly by measuring one or more characteristics of the interface.

Once the outlet size has been determined, flow rate is determined, step 68-48b (if not already determined earlier in step 68-41). The gas flow velocity is determined, step 68-48, by the controller from that and/or the previously measured flow rate from the flow sensor using equation (5) and then using that velocity in equation (4) to calculate patient dynamic pressure, step 68-49.

Then, the total delivered patient pressure is calculated from $P_{Patient\ Static}$ and $P_{Patient\ Dynamic}$ using equation (2), step 68-50.

It will be appreciated that the equations define mathematically total delivered patient pressure, but it is not necessary that the controller actually uses those equations, or in that particular order to determine total pressure. The controller can use any suitable algorithm, equations, look up tables or similar to obtain a total pressure that is mathematically equivalent to or an estimation of total delivered pressure as defined by equations (1)-(5).

Once total pressure has been determined, it can be displayed or otherwise communicated to a user via the user interface 14, step 68-51.

Alternatively or in addition, the total pressure information can be used to control the apparatus, either manually (e.g. by a physician reviewing the displayed information and changing apparatus settings) or automatically by the controller, step 68-52.

5. Mechanism Prioritisation

5.1 Overview Mechanism Prioritisation

There are five identified therapy mechanisms of action for which nasal high flow therapy is delivered: 1) Pressure support, 2) $CO_2$ Flushing, 3) Oxygenation, 4) Mucous Clearance, and 5) Humidification. Particular patient conditions gain greater benefit from some of the mechanisms of nasal high flow compared with others. For example, a radiotherapy patient may experience mucositis in the lining of the mouth and throat, resulting in inflammation and sloughing of the mucosal cells and xerostomia, a chronic dry-mouth condition, which is caused by damage to the salivary glands.

Radiotherapy patients may benefit particularly from the humidity that nasal high flow offers, but do not need or want, the other mechanisms. For example, as they do not require any pressure-controlled respiratory support, the delivery of pressure by nasal high flow may be perceived as uncomfortable.

It is currently not possible to isolate and independently control each of the therapy mechanisms or outcomes that nasal high flow is able to deliver via a high flow breathing apparatus. Being able to identify, isolate, and directly apply a particular therapy mechanism of nasal high flow to a patient may not only increase the efficiency of the treatment but may also avoid using an ineffective and potentially uncomfortable therapy mechanism when it is not a priority.

Embodiments described relate to a control system and user interface that enables a user to prioritise one or more of (high) flow therapy mechanisms (such as nasal high flow therapy mechanisms) for a particular patient, while reducing the effect of non-prioritised therapy mechanisms to maximise patient comfort, compliance and/or clinical benefit. By enhancing the functionality of nasal high flow therapy through this control system it may be possible to treat a wider range of patient conditions and acuity levels. Nasal high flow could be used to a greater level of treatment escalation and to a lower level of weaning than the current therapy, reducing the need for the introduction of additional breathing support therapies and hardware.

The apparatus provides the user with the ability to select prioritised therapy mechanisms from a predefined and stored list of therapy mechanisms (therapy mechanism list). The apparatus receives user input control data, via a user interface, indicative of the selected prioritised therapy mechanisms, and then processes that input control data based on pre-programmed or stored operating parameter data to generate a set of operating parameter settings which automatically configure and/or control the apparatus to operate so as to deliver a gasflow having gasflow properties that are customised to deliver or target the prioritised therapy mechanisms for the patient. Optionally, in some embodiments, the apparatus may provide the user with the ability to manually modify, reconfigure or customise one or more of the pre-programmed or stored operating parameter data before or after the prioritised therapy mechanisms have been selected, via the user interface. Optionally, in some embodiments, the apparatus may further provide the user with the ability to manually control or override at any time various apparatus operating parameters, including manually controlling one or more of the gasflow properties of the gasflow.

5.2 Flow Therapy Breathing Apparatus

The control system and user interface may be implemented on any suitable form of flow therapy apparatus. By way of example only, the control system and user interface will be described with reference to one form of suitable flow therapy apparatus that is capable of delivering a heated and humidified gasflow comprising a mixture of atmospheric air and pure oxygen, such that the oxygen concentration or fraction can be controlled. A first form of such an apparatus 10 is shown in FIG. 1A.

In this embodiment, the apparatus 10 comprises a flow generator 11, humidifier 12 (e.g. water filled humidification chamber heated by a heater plate), mixing chamber 707, oxygen controller 5, controller 13, and user I/O interface 14 (comprising, for example, a display and input devices such as buttons or the like). The control system or controller 13 is programmed to control the components of the apparatus via control signals, including: operating the flow generator 11 to create a flow of gas (gasflow) for delivery to a patient, operating the humidifier 12 to humidify and/or heat the generated gasflow, operating the oxygen controller to control the flow rate of oxygen supplied to the mixing chamber 7, receiving user input from the user interface 14 for reconfiguration and/or user-defined operation of the apparatus 10, and outputting information (for example on the display) to the user. The user could be a patient, healthcare professional or anyone else interested in using the apparatus. The user interface 14 may be a touch screen display providing a graphical user interface (GUI), or alternatively or additionally may comprise operable control knobs, dials, buttons, switches or the like, as will be appreciated.

The mixing chamber 7 is configured to receive a pressurised supply or flow of air 70-27 and a supply of oxygen 70-27 for blending or mixing together. The mixed gasflow 70-29 is then output to the humidifier 12. The mixing chamber may be a separate chamber or alternatively simply a junction or conduit path that receives or is coupled to both the air 70-25 and oxygen 70-27 supply conduits. The oxygen controller 5 receives a supply of oxygen from an oxygen supply, which may, for example, be a wall-mounted oxygen supply from a central gases supply in a hospital setting, an oxygen concentrator or an oxygen tank. In one form, the oxygen controller 5 may comprise a valve that is operable to control the flow rate of oxygen being supplied to the mixing chamber 7 to thereby control or vary the oxygen fraction of the mixed gasflow 70-29 output from the mixing chamber 7. The valve may be, for example, a proportional valve electronically controlled by the controller 13 for example.

As will be appreciated, the components of the apparatus may be provided or integrated into a single housing in one form or alternatively the apparatus may comprise two or more housings containing one or more of the components, with the housings being mountable and/or operatively connected to each other.

A patient breathing conduit 16 is coupled to a gasflow output of the humidifier or housing of the apparatus 10, and is coupled to a patient interface 17, such as a nasal cannula with a manifold 19 and nasal prongs 18. The humidified gasflow that is generated by the high flow therapy apparatus is delivered to the patient via the flexible patient breathing conduit 16 through the cannula 17. The breathing conduit 16 can have a heater wire 16a to heat gasflow passing through to the patient, under control of the controller 13. The breathing conduit 16 and/or patient interface 17 can be considered part of the high flow therapy apparatus 10, or alternatively peripheral to it. Use of the term "(high) flow therapy apparatus" can be utilised for either alternative.

Other configurations of the flow therapy apparatus may also be provided. For example, FIG. 1B shows a second form of flow therapy apparatus 10a that has the same components as the first form, but the mixing chamber 70-7 is provided before the flow generator 11. In this second form, the mixing chamber 70-7 may be a chamber prior to the inlet of the flow generator or alternatively an inlet flow path, such as a tortuous conduit path extending from a first end at the inlet of the of flow generator and a second end at the inlet port or opening of the apparatus or flow generator housing.

The inlet port or opening may be open to the surrounding atmosphere and may also couple or connect to a tube or conduit delivering a flow of oxygen.

General operation of the flow therapy breathing apparatus 10 will now be described. In general terms, the controller 13: controls the flow generator 11 to generate a gasflow of the desired flow rate (generated gasflow), controls the oxygen controller 5 to control flow rate of oxygen entering the mixing chamber 70-7 to control the oxygen concentration of the air and oxygen blend, and controls the humidifier 12 to humidify the gasflow and/or heat it. The gasflow is directed out through the patient conduit 16 and cannula 17 to the patient's airways. As mentioned, the controller 13 can control the humidifier and/or heater wire 16a of the patient conduit 16 to heat the gasflow to a desired temperature (also termed "target temperature" or "set point") that achieves the required level of therapy and/or comfort for the patient. By way of example, the controller 13 can control the power delivered to the heater plate 70-12a of the humidifier 12 and/or heater wire 16a of the patient conduit 16 to heat the gasflow to the desired temperature. It will be appreciated that all flow rate settings for the flow generator could be varied as desired between about −250 to 250 lpm, in some apparatus configurations.

Operation sensors, such as flow, temperature, humidity, oxygen concentration, CO2 concentration and/or pressure sensors can be placed in various locations in gasflow path of the flow therapy apparatus and/or the breathing conduit and/or cannula and/or patient airway to measure these characteristics of the gasflow, as will be known to a skilled person. One or more ambient sensors for measuring the ambient temperature, CO2 concentration, oxygen concentration, and/or humidity may also be provided. Output from the sensors can be received by the controller 13, to assist it to operate the flow therapy apparatus in a manner that provides optimal therapy.

The controller 13 comprises a programmable controller, such as a microprocessor, microcontroller or digital signal processor, and has associated memory for storing data. The programmable controller may execute software commands stored in the associated memory. As mentioned, the controller receives input from sources such as the user input interface 14 and any sensors, and controls the system components such as the motor speed of the flow generator, energy level of the heater plate 70-12a in the humidifier 12, patient conduit heater wire 16a, and oxygen controller, to deliver the flow of gases at the desired humidity and/or temperature and/or flow rate and/or oxygen concentration set by the user or in accordance with a configured therapy mode.

5.3 Other Alternative Flow Therapy Apparatus

Figure 70B:
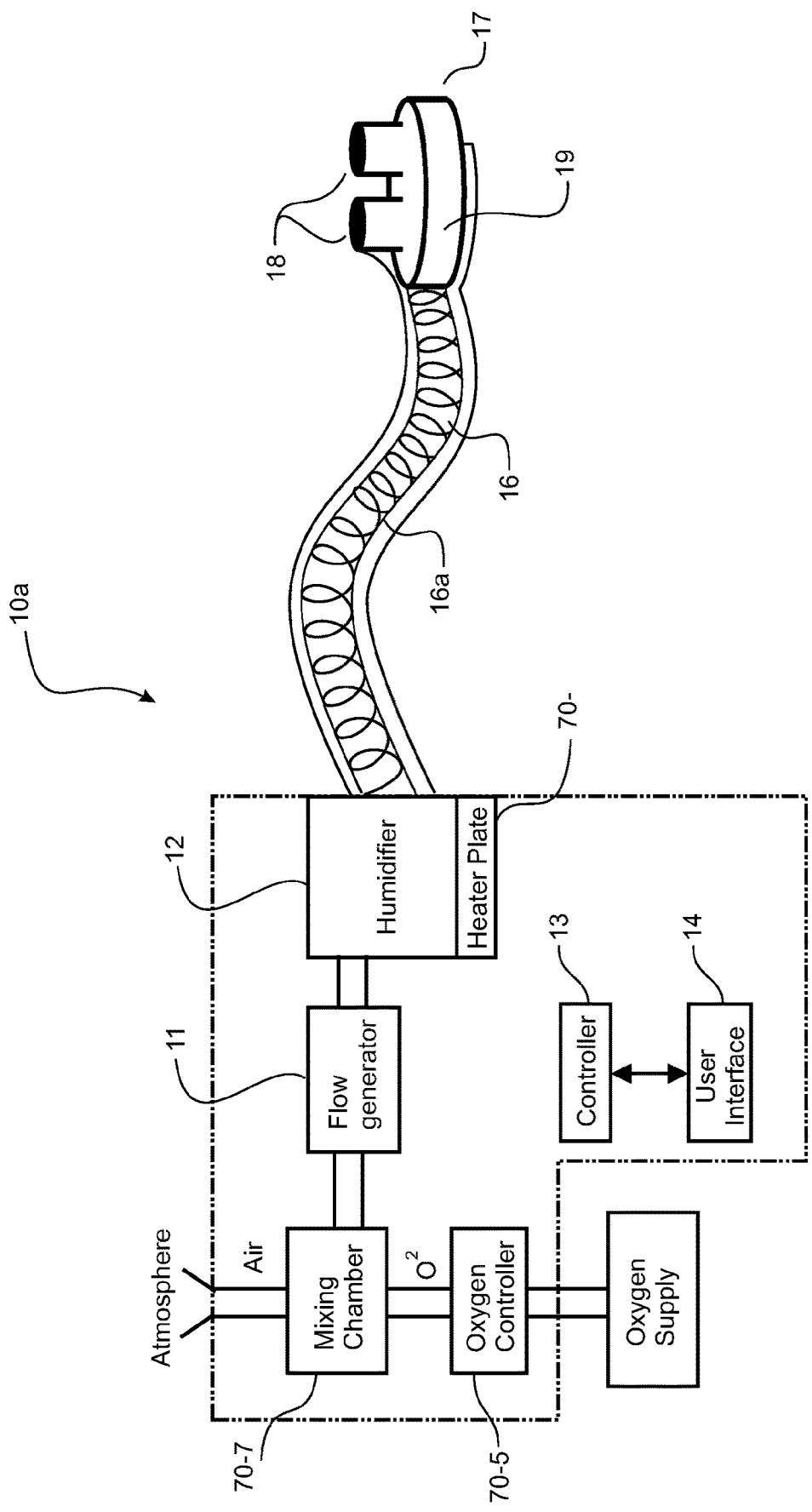
FIG. 70B is a schematic diagram of a flow therapy breathing apparatus in accordance with a second embodiment of the invention in which the mixing chamber for air and oxygen is located before the flow generator.

It will be appreciated that the control system and user interface may also be implemented with other types of flow therapy apparatus, and is not limited to the apparatus types depicted in FIGS. 70A and 70B. By way of example, the control system and user interface may be used with a flow therapy apparatus that does not comprise a humidifier. The apparatus may be part of an overall respiratory system in which a humidifier is connected to or provided at the input of the apparatus to supply it with a pre-humidified gases supply, or it may be connected to or provided at the output of the flow apparatus. Alternatively, a humidifier may be omitted altogether in some embodiments such that the gasflow delivered to the patient is not heated or humidified. The control system and user interface may also be used with a flow therapy apparatus that does not comprise an operable blower or flow generator. For example, such a flow therapy apparatus may receive an air or gases supply from a pressurised gas supply source, for example compressed air or similar, and may control flow rate via an operable valve or similar.

5.4 User Interface

The user interface 14 enables the user to select or prioritise one or more therapy mechanisms from a predefined therapy mechanism list. In this embodiment, the user interface is provided in the form of a touch screen display that the user can interact with via touch input on the screen. Before operation of the apparatus is initiated to generate a gasflow, the user is presented with the predefined therapy mechanism list on the touch screen. The user may then select (with either equal priority or ranked order) which therapy mechanisms to prioritise via interaction with the touch screen, and user input control data indicative of the user selections is then received by the controller 13, which processes the data and automatically generates apparatus operating parameter settings to control the apparatus to generate a gasflow with the desired gas properties based on control system algorithms to be descried later.

Figure 71:
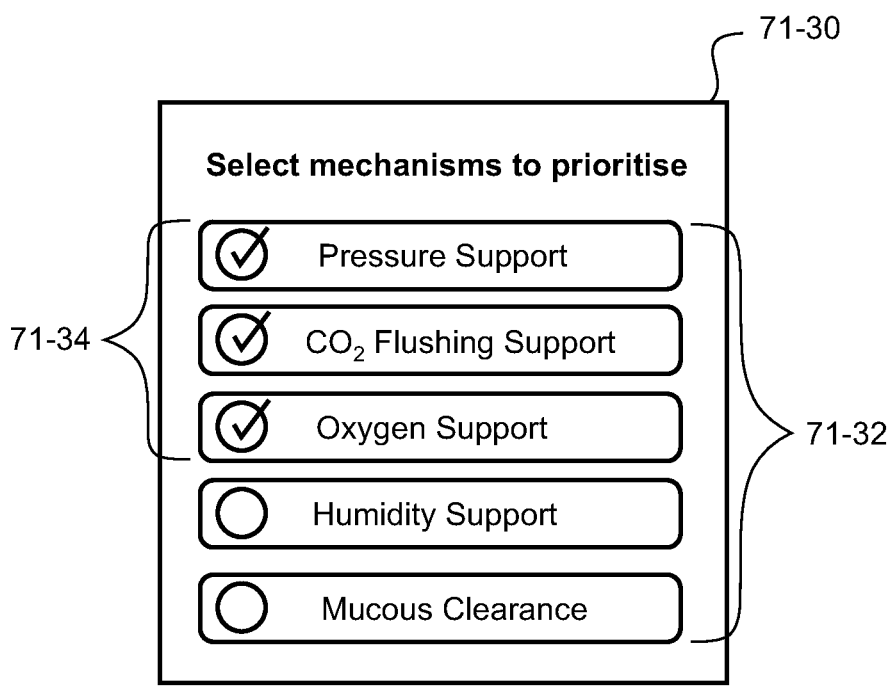
FIG. 71 is a screenshot of a first form user interface for enabling a user to select one or more prioritised therapy mechanisms from a list, with equal priority ranking.

Referring to FIG. 71, a first form of user interface is shown in which the display screen 71-30 depicts a therapy mechanism list 71-32. In this form, the therapy mechanism list 71-32 lists the following five therapy mechanisms that are associated with nasal high flow therapy: Pressure support, $CO_2$ Flushing support, Oxygen support, Humidity support, and Mucous clearance. As shown, the user has selected to prioritise three therapy mechanisms 71-34 from the list, namely Pressure support, $CO_2$ Flushing support, and Oxygen support. In this form, the selected or prioritised therapy mechanisms are non-ranked such that they have an equal priority with respect to each other.

Figure 72:
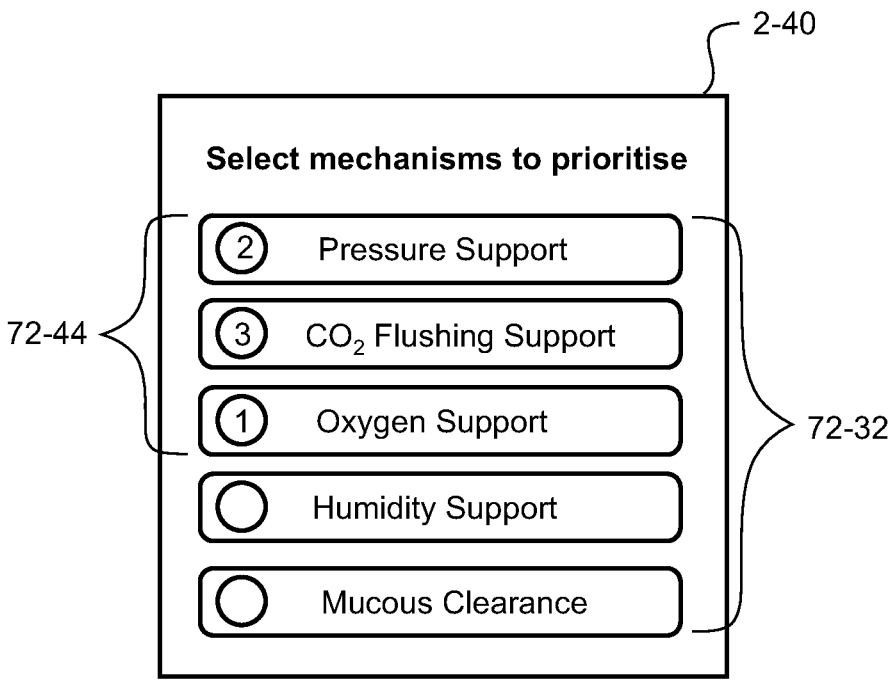
FIG. 72 is a screenshot of a second form of user interface for enabling a user to select prioritised therapy mechanisms from a list, including designating a rank order between the selected prioritised therapy mechanisms.

Referring to FIG. 72, a second form of user interface is shown in which the display screen 72-40 depicts the therapy mechanism list 72-32. In this form, the user is able to designate a ranking order of priority to the selected therapy mechanisms 72-44, and the user input control data indicative of the user selections 72-44 also comprises this ranking order data for processing by the control system.

In one embodiment, the user interface is configured to present the user with every therapy mechanism for selection or deselection as a priority. In this embodiment, the therapy mechanisms may be presented to the user sequentially in a series of screens one at a time or in groups, or all at once on a single screen (as shown in FIGS. 71 and 72). In this embodiment, the user is required to make an active binary decision via the user interface on whether to prioritise each therapy mechanism in the list. For example, in one form, the user selects a tick next to prioritized therapy mechanisms and a cross next to undesired therapy mechanisms. In this embodiment, the input control data generated represents data indicative of which therapy mechanisms have been selected, and which have been deselected.

In another embodiment, the user interface is configured to present the user with all the therapy mechanisms, either sequentially in a series of screens one at a time or in groups, or all at once in a single screen (as shown in FIGS. 71 and 72), and the user is only required to select the desired therapy mechanisms to prioritise, e.g. by selecting a tick next to them, to generate the representative input control data. In this embodiment, it may be assumed that any non-selected therapy mechanisms have been actively deselected.

It will be appreciated that the user interface need not be provided on a touch screen display. In alternative forms, a series of buttons, dials, knobs, toggle switches, or a control pad or the like could be provided for each therapy mechanism to enable the user to select one or more therapy mechanisms to prioritise, and optionally to enable the user to provide a ranking order to the prioritised therapy mechanisms if desired.

5.5 Therapy Mechanisms 5.5.1 Overview of Therapy Mechanisms

In this embodiment, a therapy mechanism list comprising five different therapy mechanisms is presented to the user, as described above. It will be appreciated that in alternative embodiments, any list of two or more desired therapy mechanisms may be presented to the user, and the therapy mechanisms may be any of those previously mentioned or any other additional therapy mechanism associated with flow therapy.

By way of example, five therapy mechanisms are described below, along with example apparatus configurations or operating settings to prioritise such therapy mechanisms if selected by the user for an adult patient. It will be appreciated that the configuration settings will be altered for an infant patient or can be otherwise customised as will be explained later also.

5.5.2 Pressure Support

Patients that have developed atelectasis as a result of say ARDS, pleural effusion or lung compression due to tumours, can benefit from a level of pressure that will reduce or eliminate the likelihood of alveolar collapse. In patients with oxygenation problems, a level of pressure can also help to increase their functional residual capacity (FRC), increasing the surface area for gas exchange to occur and improving Ventilation/perfusion (V/Q) mismatch. V/Q mismatch is common terminology used to represent the ratio between ventilation (air reaching alveoli) and perfusion (blood reaching alveoli to transport the diffused gases around the body). If a patient's ventilation is reduced, the V/Q ratio will be less than optimal. In this case increasing the surface area through delivered pressure can help increase ventilation and thus return the V/Q ratio back to normal levels (reducing V/Q mismatch). V and Q are affected by a number of physiological factors. In one example configuration, if pressure support is prioritised by the user, the apparatus will be automatically configured by the control system to generate a substantially constant flow rate between about 0-250 lpm, such as at about 60 lpm in one embodiment, with the delivered pressure displayed to the user.

If pressure support is not a priority, it can be uncomfortable to the patient. During normal, unassisted breathing the airway pressure cycles over approximately +/−1 cm H2O, i.e., an amplitude of about 2 cmH2O. In one nasal high flow system configuration, pressure support is delivered via a substantially constant flow rate, where increasing flow rates correspond to increasing delivered pressure. A greater level of pressure is felt by the patient during the expiration phase, compared with inspiration as the patient has to breathe out against the applied flow. As a result, this can create a pressure amplitude in the order of about 10 cm H2O. This increased pressure variation can feel unnatural and uncomfortable to a patient, especially if the patient does not physiologically require pressure support.

In this example configuration, if pressure support is not prioritised, the control system will automatically configure or control the apparatus such that the flow rate during expiration is significantly reduced to lower the expiration pressure and thus the magnitude of the pressure amplitude. In one configuration, the expiratory flow rate may be configured to be positive to increase the likelihood of the cannula deadspace being washed out, but comfort is still enhanced. This will improve comfort while enabling the other mechanisms of the therapy to still be delivered during inspiration. Table 1 below gives some example flow rate settings if pressure support is not selected as a priority, and corresponding pressures that may occur in a particular patient. The inspiratory flow rate may be set to meet a high peak inspiratory demand (eg: about 35 lpm) as a default, or set to the patient's inspiratory demand to ensure the therapy is delivered effectively for the majority of patients.

TABLE 1

Example flowrates for minimising pressure amplitude

| | Flowrate (lpm) | Pressure (cmH$^2$O) |
|---|---|---|
| Inspiration | 35 | 0.5 |
| Expiration | 2 | 0.5 |

Patients can also find nasal high flow noisy, particularly at high flow rates. This is most apparent during the expiration phase of the breath cycle as much greater levels of turbulence are created by the opposing flows. For example the average noise level was measured at a 1 m distance from an adult male airway model at about 60 lpm. The noise level was measured at about 46.6 dBA during inspiration and about 55.6 dBA during expiration, resulting in a difference in loudness of about 1.9 times (almost double) between the two. Reducing the flow rate during expiration mitigates this effect and reduces noise significantly. For patients that do not require pressure support and the user wishes to mitigate noise, the user may deselect the pressure support mechanism and the apparatus may decrease the flow rate at expiration as discussed above to assist in reducing noise and improve comfort.

5.5.3 $CO_2$ Flushing

Due to the physiological stress that ICU patients are under, they can have a higher demand for oxygen and often require a much greater level of ventilation compared to a normal, healthy patient. Patients can develop an increased work of breathing trying to meet this demand and ensure adequate ventilation. This increased work means that patients are expending greater metabolic effort and so produce more $CO_2$. To remove the $CO_2$ and keep their gas concentrations at a safe level, this requires even greater ventilation, and therefore work. As patients continually try to increase their effort to breathe and are unable to adequately expire the increasing amounts of $CO_2$ produced, they can experience respiratory muscle fatigue and develop hypercapnia.

Elevated levels of $CO_2$ can also occur in patients that have obstructive diseases such as asthma. Excess mucous in the airway and bronchoconstrictions can inhibit breathing and result in the respiratory muscles being unable to provide sufficient ventilation to meet the patient's metabolic demands.

The types of patients described above others with other respiratory conditions may benefit greatly from $CO_2$ flushing as a way to help regulate $CO_2$ levels.

In one approach, $CO_2$ may be removed from the patient's airways during the expiratory pause, immediately before inspiration, or just at the start if inspiration. At this point, the gas in the airways makes up the initial volume of the following breath so flushing the airways at this point reduces rebreathed $CO_2$. However, high flow rates during expiration can result in uncomfortable pressure and noise (as described in the previous section).

Figure 73A:
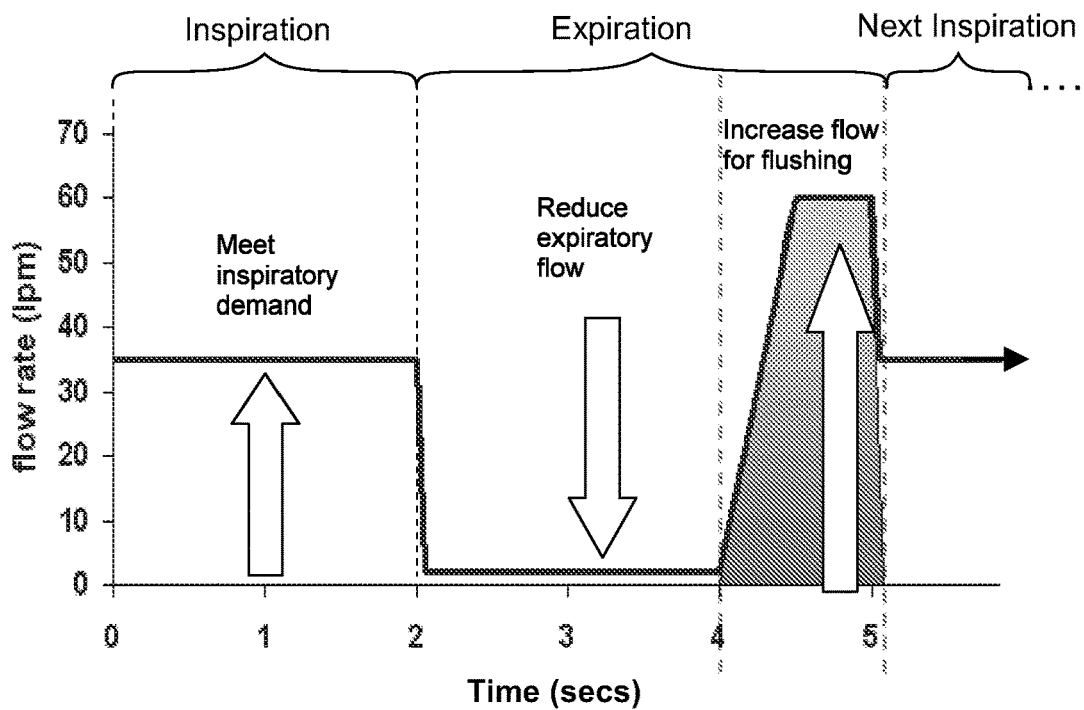
FIGS. 73A and 73B show graphical representations of a $CO_2$ flushing approach in which the flow rate and pressure is varied over the patient's breathing cycle in accordance with an embodiment of the invention.
Figure 73B:
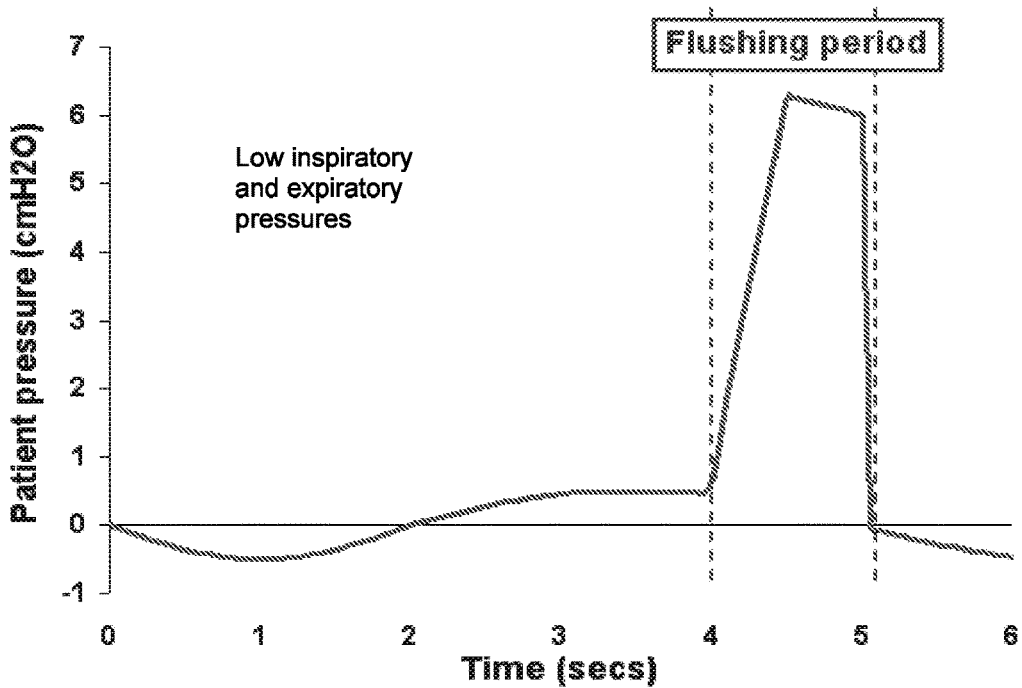

In one example configuration, when $CO_2$ flushing is prioritised by the user, the apparatus may be automatically configured to vary the flow rate over the patient's breathing cycle as follows. Referring to FIGS. 73A and 73B, the apparatus may be configured to deliver an inspiratory flow rate that meets a patient's (peak) inspiratory demand (and so can deliver the other aspects of the therapy), without providing unnecessary additional flow and therefore pressure. The flow rate would then rapidly decrease at the start of expiration to about 2 lpm to aid expiratory effort and reduce the potentially uncomfortable sharp increase in pressure and noise that can be felt at this point. In a 'flushing period', about 1 second before the start of inspiration, the flow rate increases, reaching for example about 60 lpm after about 0.5 seconds, and is held at about 60 lpm for the last about 0.5 seconds of expiration. At the start of the next inspiration, the flow rate drops back to about 35 lpm. This method of varying the flow rate targets flushing at the expiratory pause while reducing or minimising the effect of a rapid pressure increase felt by the patient at the start of expiration. The timing of the flushing and the duration of the flushing period may be determined by measuring and taking the average length of expiration over a number of the previous breaths, and may be customised to the individual patient in some embodiments. In alternative embodiments, the flow rate may be increased in the flushing period to levels lower than 60 lpm, but is typically increased to at least 25 lpm, for adult flow therapy.

As a default, to increase comfort when $CO_2$ flushing is not prioritised by the user, the apparatus may be automatically configured to deliver an inspiratory flow rate that would meet a generally high peak inspiratory demand (eg: 35 lpm), or the patient's measured inspiratory demand and to deliver an expiratory flow rate that is significantly reduced, as in Table 1 above when pressure support is not prioritised. CO2 flushing can also be promoted by simply delivering a higher constant flow rate. However as described above this method may be uncomfortable for some patients.

5.5.4 Oxygen Support

Oxygen may be required in isolation from the other therapy mechanisms for patients such as trauma victims that have sustained a chest injury resulting in reduced lung capacity but have no other co-morbidities. Oxygenation may also be a priority in particular for treating hypoxia due to anaesthetic, hypoventilation or hypotension due to shock. In one example configuration, if oxygen support is prioritised by the user, the apparatus is automatically configured to provide a gasflow having an oxygen concentration of 50%. If oxygen support is not selected as a priority by the user, the apparatus is automatically configured to deliver a gasflow in which the oxygen concentration is about 21% (i.e. the supplemental oxygen supply to the mixing chamber is shut off to provide an atmospheric air gasflow) to reduce or eliminate the likelihood of hyperoxia and save oxygen supply resources.

5.5.5 Humidity Support and Mucous Clearance

As described above it may be desirable to independently prioritise humidity support for a radiotherapy patient. Mucous clearance could also be useful for patients with acute respiratory infection and/or chronic lung disease who have increased bronchial secretions. Pain, narcotic drugs and immobility can also promote the retention of thick secretions and would benefit from mucous clearance aid. One method of promoting mucous clearance is to deliver high levels of humidity. For succinctness, humidity support and mucous clearance will be grouped as one therapy mechanism for the remaining description.

In one example configuration, if humidity support or mucous clearance is selected as a priority by the user, the apparatus is automatically configured to deliver a gasflow with a temperature of about 37° C. and 100% relative humidity. For patients where humidity support or mucous clearance is not a priority, the heat delivered by the elevated temperatures can be uncomfortable. However, at high flow rates, it is uncomfortable to breathe completely dry gas. If humidity or mucous clearance is not prioritised by the user, the temperature is reduced to a level closer to ambient, e.g. about 30° C. in a hospital setting for example, so that only a baseline level of humidity is still delivered. The relative humidity of the delivered gasflow will be held at about 100% in all cases, i.e. whether humidity support or mucous clearance is selected as a priority or not. In this configuration, with the relative humidity maintained at 100%, the change in temperature is used to control the change in absolute humidity of the gasflow.

In an alternative configuration, the absolute humidity of the gasflow may be controlled by varying the relative humidity of the gasflow. The relative humidity may be reduced from 100% by controlling the amount of water vapour delivered into the gasflow path so that the gasflow is not full saturated with humidity. In one form, the temperature may be maintained, say at 37° C. or some other set temperature, while the relative humidity is altered to achieve the desired absolute humidity level. In another form, both the relative humidity and temperature may be altered to achieve the desired absolute humidity level.

5.6 Control Method

5.6.1 Overview

Figure 74:
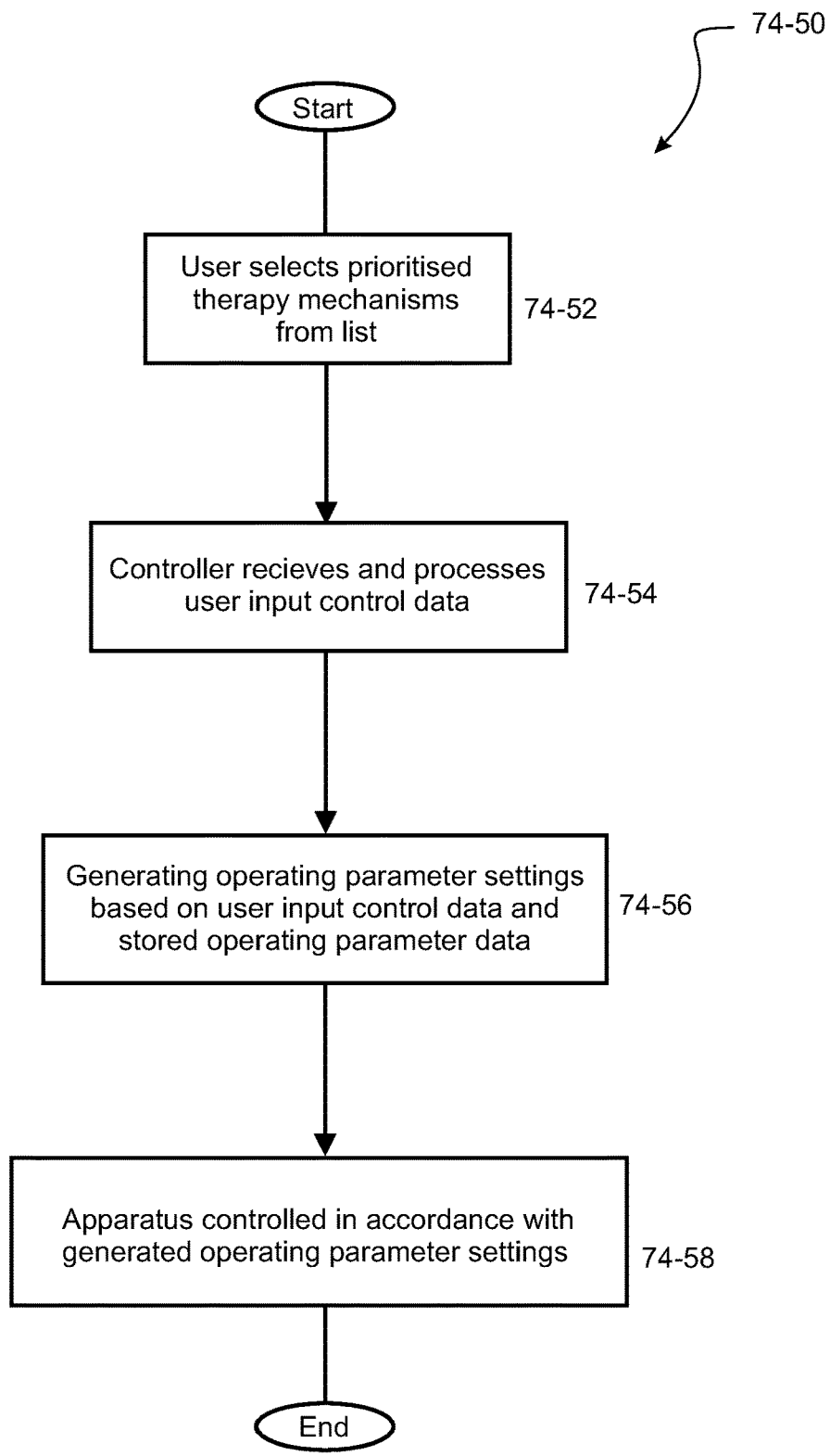
FIG. 74 is a flow diagram of a main control algorithm in accordance with an embodiment of the invention.

The main control algorithm implemented by the controller 13 in automatically configuring the operation of the apparatus will now be described generally. Referring to the flow diagram 50 of FIG. 74, the controller is configured to automatically configure or operate the flow therapy apparatus based on the user interaction with the user interface 14. In particular, when the user at step 74-52 selects the one or more therapy mechanisms to prioritise via the user interface 14 for the patient (as described previously with reference to FIGS. 71 and 72 for example), this generates user input control data that is indicative of the selected, prioritised therapy mechanisms, and any optional ranking order data. The user input control data is then received and processed by the controller 13 at step 74-54. The controller then generates operating parameter settings (e.g. flow rate(s), oxygen concentration, gasflow temperature) based on the user input data and stored operating parameter data associated with the therapy mechanisms, as shown at 74-56, so as to generate a gasflow having gas properties that are customised or configured to suit the prioritised therapy mechanisms selected. The apparatus is then automatically operated in accordance with those operating parameter settings, as shown at step 74-58, until such time as the apparatus is halted or reconfigured, such as if the user modifies the selected therapy mechanisms to prioritise, which loops the algorithm back to the start.

It will be appreciated that the control algorithm is typically implemented prior to the commencement of a new therapy session on the apparatus for a patient, before the apparatus commences delivery of any gasflow. However, the control algorithm may also be initiated during a current therapy session if, for example, the user wants to modify which therapy mechanisms have been prioritised, including any ranking order, if provided. Additionally or alternatively, in some configurations, the control system may be configured with one or more default operating settings at start-up, such as providing gasflow at maximum humidity and a constant flow rate to meet inspiratory demand. These default settings are maintained to deliver the patient a gasflow while the user or a clinician are configuring the desired settings, e.g. selecting which therapy mechanisms to prioritise, for the ongoing therapy. Once the desired settings have been configured, the apparatus switches from the default settings to the desired settings.

In the context of the five therapy mechanisms described in this example, each of the therapy mechanisms is associated with a particular gas property of the gasflow, and each gas property is controlled by a respective operating parameter setting. Some of the therapy mechanisms are associated with the same gas property. For example, the pressure support and $CO_2$ flushing therapy mechanisms when prioritised are concerned primarily with the flow rate of the gasflow delivered to the patient, and this is controlled by the operating parameter setting that controls the motor speed of the flow generator. The oxygen support therapy mechanism when prioritised is concerned primarily with the oxygen concentration of the gasflow, and this is controlled by the operating parameter setting that controls the oxygen controller to modify the oxygen flow rate of the oxygen supply received in the mixing chamber. The humidity support and mucous clearance therapy mechanisms when prioritised are concerned primarily with the temperature of the gasflow, and this is controlled by the operating parameter setting(s) that control the power delivered to the heater plate of the humidifier and/or heater wire of the patient conduit.

Various sub-control algorithms may be implemented or executed in steps 54 and 56 of the main control algorithm to generate the operating parameter settings based in the user control input data indicative of the prioritised therapy mechanisms selected, some examples of which will be described next.

5.6.2 First Example Sub-Control Algorithm for Generating Operating Parameter Settings In this first example, the controller stores operating parameter data for each therapy mechanism, which comprises a first operating parameter for controlling the gas property associated with the therapy mechanism when it is selected as a priority by the user, and a second operating parameter for controlling the gas property when the therapy mechanism is not selected as a priority. By way of example, Table 2 below summarises the stored operating parameter data for one possible configuration for each therapy mechanism, as previously explained above. Mucous clearance and humidity support have been combined into a single group for simplicity.

TABLE 2

| Stored operating parameter settings | | |
|---|---|---|
| Therapy Mechanism | Mechanism selected as priority ($1^{st}$ operating parameter setting) | Mechanism not selected as priority ($2^{nd}$ operating parameter setting) |
| Pressure Support | Flowrate = constant 60 lpm | Inspiratory flow rate = 35 lpm Expiratory flow rate = 2 lpm |
| $CO_2$ Flushing | Inspiratory flow rate = 35 lpm Expiratory flow rate = 2-60 lpm | Inspiratory flow rate = 35 lpm Expiratory flow rate = 2 lpm |
| Oxygenation | Oxygen concentration = 50% | Oxygen concentration = 21% |
| Humidity or Mucous Clearance | Temperature = 37° C., RH = 100% | Temperature = 30° C., RH = 100% |

The above table just shows possible examples and is not limiting. For example, in the third column inspiratory flow rate might be set to meet inspiratory demand, or in the second column might be set to or exceed patient's inspiratory demand. The amount of excess could be set as a default by the controller (eg: 25 lpm) or could be defined by the user eg: as an absolute value or percentage increase over the patient's insp demand.

Figure 75:
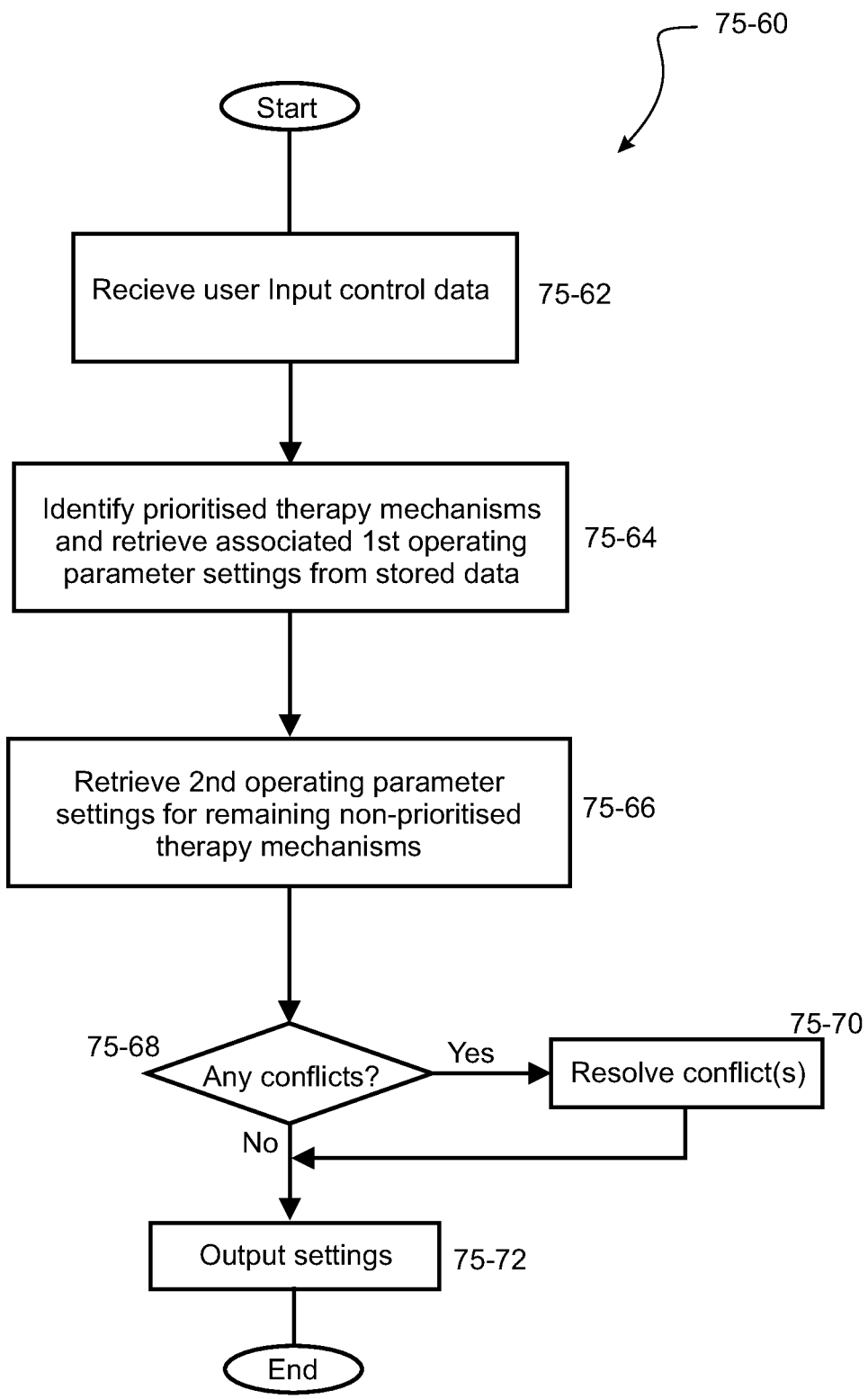
FIG. 75 is a flow diagram of a first example sub-control algorithm for configuring the operating settings of the flow therapy apparatus in accordance with an embodiment of the invention.

Referring to FIG. 75, the sub-control algorithm 75-60 for generating the operating parameter settings in this configuration works as follows. The user input control data indicative of the selected prioritised therapy mechanism(s) is received at step 75-62. The prioritised therapy mechanisms are then identified and the $1^{st}$ operating parameter settings associated with such mechanisms is retrieved from the stored operating parameter data (e.g. Table 2 above), as shown at step 75-64. The $2^{nd}$ operating parameter settings for the non-prioritised therapy mechanisms in the list are also retrieved from the stored data as shown at step 75-66.

The retrieved operating parameter settings are then analysed at step 75-68 for any conflicts. For example, pressure support and $CO_2$ flushing are both controlled by adjusting or controlling the flow rate of the gasflow, and the retrieved flow rate settings can conflict if at least one is prioritised. In this configuration oxygen and humidity are both controlled independently of flowrate, and of each other, so these two mechanisms may be selected in any combination without conflict.

If a conflict is identified, the algorithm moves to a conflict resolution algorithm at step 75-70, which is configured to resolve the conflict in accordance with stored rules. In this case for example where there is a potential for conflict between the pressure support and $CO_2$ flushing, if one therapy mechanism is prioritised, and the other isn't, the conflict is resolved in favour of the retrieved setting associated with the prioritised therapy. Alternatively, if both therapy mechanisms are prioritised, the conflict is resolved in favour of the higher ranked mechanism, if ranking order data was input by the user. If they are equally ranked, then the conflict is resolved based on a default rule setting. For example, in this case the default rule setting may dictate that the conflict is resolved in favour of the therapy mechanism having the higher retrieved flow rate setting. Once resolved, the final operating parameter setting associated with the conflict is output with the remaining retrieved operating parameter settings at step 75-72 to configure the apparatus. If no conflict is identified at step 75-68, then the retrieved operating parameter settings are output at step 75-72 and used to automatically configure and control the apparatus to deliver the gasflow with the desired gasflow properties based in the user selection input data, as discussed in the main control algorithm 75-50.

In an alternative modified approach to sub-control algorithm 75-60, each of the $2^{nd}$ operating parameter settings may be considered the default operating settings for the apparatus prior to any user input control data. Upon receiving user input control data indicative of one or more selected prioritised therapy mechanisms, the sub-control algorithm is configured to modify any required default operating parameter settings to match the $1^{st}$ operating parameter setting or settings associated with any prioritised therapy mechanisms. Again, if conflicts arise, these can be resolved as previously described. The apparatus is then automatically configured to operate in accordance with the modified operating parameter settings and any unmodified default parameter settings.

5.6.3 Second Example Sub-Control Algorithm for Generating Operating Parameter Settings In this second example, the controller accesses stored electronic data representing a list of therapy modes (therapy mode list). Each therapy mode corresponds one of the possible user input combinations of selected therapy mechanisms for priority. For example, the therapy mode list may comprise 'single-priority' therapy modes that corresponding to user input control data that defines a single therapy mechanism being selected as a priority, and 'multiple-priority' therapy modes corresponding to user input control data that defines a combination of two more therapy mechanisms being selected as a priority. Each therapy mode in the therapy mode list comprises respective set of stored operating parameter settings to generate a gasflow with a particular corresponding set of gas properties for that therapy mode.

Table 3 below shows an example of one possible therapy mode list electronically stored memory accessible or associated with the controller. As shown, therapy modes 1, 9, 13 and 15 are single-priority therapy modes, with the remaining being multiple-priority therapy modes. For each therapy mode, the flow rate, oxygen concentration, and temperature operating parameter settings are stored. These operating parameter settings are predefined for each therapy mode based on the same settings as Table 2, including resolution of any conflicts being predetermined.

Table 3 provides a look-up table of operating parameter settings for configuring the apparatus for each different therapy mode.

TABLE 3

Selection of a combination of mechanisms

| Therapy mode | Mechanisms selected as priority by user | Flow rate | Oxygen concentration | Temperature |
|---|---|---|---|---|
| 1 | Pressure Support | Constant 60 lpm | 21% | 30° C. |
| 2 | Pressure Support + $CO_2$ Flushing | Constant 60 lpm | 21% | 30° C. |
| 3 | Pressure Support + Oxygenation | Constant 60 lpm | 50% | 30° C. |
| 4 | Pressure Support + Humidity | Constant 60 lpm | 21% | 37° C. |
| 5 | Pressure Support + $CO_2$ Flushing + Oxygenation | Constant 60 lpm | 50% | 30° C. |
| 6 | Pressure Support + $CO_2$ Flushing + Humidity | Constant 60 lpm | 21% | 37° C. |
| 7 | Pressure Support + Oxygenation + Humidity | Constant 60 lpm | 50% | 37° C. |
| 8 | Pressure Support + $CO_2$ Flushing + Oxygenation + Humidity | Constant 60 lpm | 50% | 37° C. |
| 9 | $CO_2$ Flushing | Inspiratory flow rate = 35 lpm Expiratory flow rate = 2-60 lpm | 21% | 30° C. |
| 10 | $CO_2$ Flushing + Oxygenation | Inspiratory flow rate = 35 lpm Expiratory flow rate = 2-60 lpm | 50% | 30° C. |
| 11 | $CO_2$ Flushing + Humidity | Inspiratory flow rate = 35 lpm Expiratory flow rate = 2-60 lpm | 21% | 37° C. |

TABLE 3-continued

Selection of a combination of mechanisms

| Therapy mode | Mechanisms selected as priority by user | Flow rate | Oxygen concentration | Temperature |
| --- | --- | --- | --- | --- |
| 12 | $CO_2$ Flushing + Oxygenation + Humidity | Inspiratory flow rate = 35 lpm<br>Expiratory flow rate = 2-60 lpm | 50% | 37° C. |
| 13 | Oxygenation | Inspiratory flow rate = 35 lpm<br>Expiratory flow rate = 2 lpm | 50% | 30° C. |
| 14 | Oxygenation + Humidity | Inspiratory flow rate = 35 lpm<br>Expiratory flow rate = 2 lpm | 50% | 37° C. |
| 15 | Humidity | Inspiratory flow rate = 35 lpm<br>Expiratory flow rate = 2 lpm | 21% | 37° C. |

The therapy mode list of Table 3 comprises multiple-priority therapy modes of equal ranking only. However, it will be appreciated that the therapy model list may be expanded to include all the different combinations of differently ranked multiple-priority therapy modes to account for configurations in which the user interface allows the user to rank the order of prioritised therapy mechanisms.

Figure 76:
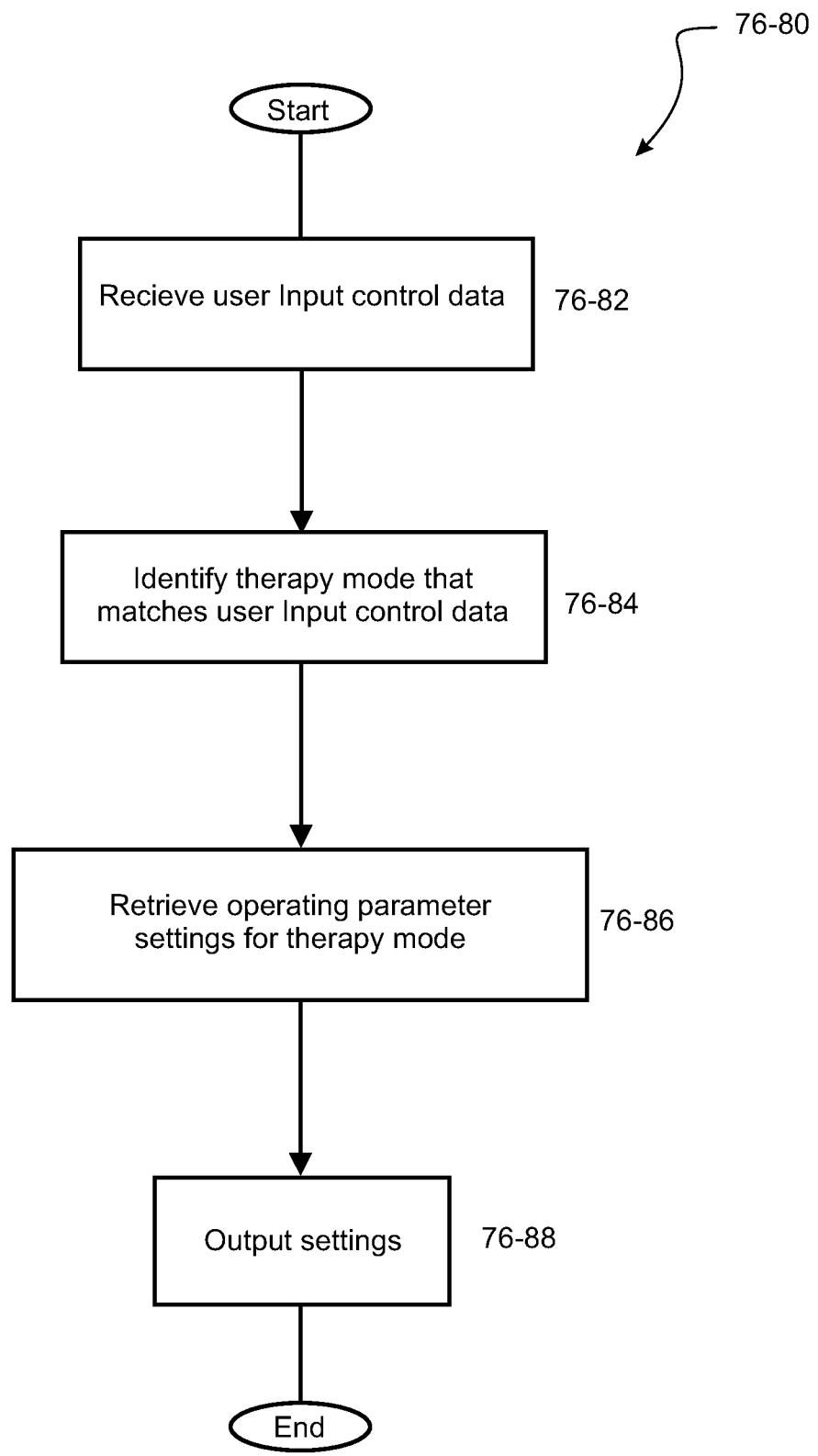
FIG. 76 is a flow diagram of a second example sub-control algorithm for configuring the operating settings of the flow therapy apparatus in accordance with an embodiment of the invention.

Referring to FIG. 76, the sub-control algorithm 76-80 for generating the operating parameter settings in this configuration works as follows. The user input control data indicative of the selected prioritised therapy mechanism(s) is received at step 76-82. The user input control data is then processed to identify which therapy mode in the stored therapy mode list (e.g. Table 3) matches the user's selections, as shown at step 76-84. The stored operating parameter settings for the identified matching therapy mode are then retrieved at step 76-86 and output at step 76-88 to automatically configure the apparatus to deliver the gasflow to the patient with the gas properties stored for the selected therapy mode.

5.7 User Customisation

In the configurations above, the apparatus is automatically configured based on stored operating parameter settings based on the user input control data indicative of the selected therapy mechanisms to prioritise. In some configurations, the stored operating parameter settings may be default settings, and the apparatus may enable the user to customise via the user interface those default stored operating parameter settings, either temporarily or permanently as desired. The stored operating parameter settings may be altered before the user selects which therapy mechanisms to prioritise such that the apparatus is automatically configured based on the modified customised stored settings when the user's selections are made, or after those selections have been made in which case the user may selectively modify one or more of the automatic configuration settings prior to or after initiating gasflow delivery. In other words, the stored operating parameter settings may be modified by a user prior to the main control algorithm 74-50 of FIG. 74 executing so that the output settings are generated based on customised stored parameter settings, or alternatively after the main control algorithm has executed such that the user may selectively modify the output settings generated as desired.

The apparatus is arranged such that the stored operating parameter settings may be modified by the user at any time during use, or may be set to alternative default values for each individual patient during set-up of the device, or may be set to default values specific to the unit/hospital, or may be adjustable within a range of default values, either set by the device, or specific to the unit/hospital. Any changed settings may be saved as customised 'modes' that may be recalled during future operations of the device. The user may wish to define a set of operating parameters according to various disease states, for example they may have an 'asthma' or a 'COPD' mode that can be recalled by themselves or other users in the future when appropriate patients present.

In the previous examples (e.g Tables 1-3), the operating parameter settings are indicative of flow rate settings for any adult. It will be appreciated that lower flow rates would likely be used for infants, and the stored operating parameter data may comprise both settings for adults and infants.

Additionally, the operating parameter settings, such as the flow rates, may be configured to be dependent on additional user-defined patient variables such as patient weight or age, which could be entered at the initiation of therapy. For example, the patient's age and/or weight could be used to approximate the patient's inspiratory demand flow rate, or could be found using the other methods described. Additionally, in some embodiments, the desired level of therapy received by the patient and set by the user (eg: delivered pressure, or amount of CO2 washout) may be approximated by similar user-defined patient variables. The operating parameters would then be controlled to achieve this level of therapy.

Various possible user customisation options that may be enabled by the controller in some configurations will now be described. In general, the apparatus has four main controllable gasflow parameters or gas properties: pressure, flow rate, temperature, and oxygen concentration. In some configurations, the user will be allowed to customise the stored operating parameter settings (e.g. the data in Tables 2 and 3) for each therapy mechanism and/or therapy mode. For each therapy mechanism and/or therapy mode, the user may set maximum or minimum limits for each parameter setting, thresholds or targets for particular operating parameter settings, they may select from or configure the setting to correspond to one of the modes described below that each have their own controls, or they may choose a combination of these options. In some embodiments, the apparatus and controller may be configured to allow the user to also change or customise the humidity level of the gasflow.

5.7.1 Pressure Support Modes

Pressure support may be implemented by various methods, including the previous flow rate approaches mentioned. Table 4 below describes some methods with examples of control levels.

TABLE 4

Examples of possible selectable pressure support modes

| Pressure Support Modes | Controls | Control Range |
|---|---|---|
| Flow | Flow rate | −250-250 l/min |
| Mean pressure | Mean pressure level | −30-30 cmH2O |
| PEEP | PEEP level | |
| PIP | PIP level | |
| PEEP/PIP | PEEP level PIP level | |
| Maximum pressure | Maximum pressure | |
| CPAP | CPAP level | |
| Bi-Level pressure/flow | Inspiratory pressure/ Inspiratory flow rate | −30-30 cmH2O |
| | Expiratory pressure/ Expiratory flow rate | −250-250 l/min |
| | Optional: Inspiratory/ expiratory time | 0-10 seconds |

In Table 4, PEEP=Peak End—Expiratory Pressure, PIP=Peak Inspiratory Pressure, and CPAP=Continuous Positive Airway Pressure. The user interface may be configured to allow the user to select which mode to use in a particular case or may choose to use the default—Flow, for example. Some pressure support modes are presented to the user as pressure controlled, however all modes may be implemented in practice by flow rate adjustments between about −250 and 250 lpm. Any pressure setting may be set to a target that the device will attempt to deliver. Actual pressure delivery will be limited by a number of factors, including but not limited to the patient's airway geometry, cannula size, device power and maximum flow rate setting. Measured pressure may be displayed to the user so that they can see what the actual reading is. The various examples of pressure support described below that use pressure control may be controlled by measuring the patient pressure using the method described in the previous section. The individual modes on Table 4 are further explained in the following:

Flow: Constant cannula flow rate. Increasing the flow rate increases the delivered pressure.

Mean Pressure: A constant flow rate is delivered and the flow rate adjusted to control the mean pressure. The mean pressure could be displayed, determined by measuring and taking the average over a number of the previous breaths.

PEEP: A positive level of end-expiratory pressure is often used to reduce or eliminate the likelihood of an atalectic patient's alveoli closing during the breath cycle. In this mode, a substantially constant or varying flow rate is delivered and continuously monitored by the device to increase, maximise, or target, the goal peak expiratory pressure set by the user. Table 5 below gives some examples of flow rates that would vary between inspiration and expiration to deliver PEEP with nasal high flow. Note that the flow rate may instead be substantially constant at a level that maintains the desired PEEP.

TABLE 5

Example relationships between flowrate and pressure to deliver PEEP on nasal high flow

| Inspiratory Pressure (cmH2O) | PEEP (cmH2O) | Inspiratory Flow rate (lpm) | Expiratory Flow rate (lpm) |
|---|---|---|---|
| 0.5 | 2 | 35 | 20 |
| 0.5 | 3 | 35 | 30 |

TABLE 5-continued

Example relationships between flowrate and pressure to deliver PEEP on nasal high flow

| Inspiratory Pressure (cmH2O) | PEEP (cmH2O) | Inspiratory Flow rate (lpm) | Expiratory Flow rate (lpm) |
|---|---|---|---|
| 0.5 | 4 | 35 | 40 |
| 0.5 | 5 | 35 | 50 |
| 0.5 | 10 | 35 | 100 |

PIP: A PIP level can be used to improve or optimise a patient's lung compliance and to reduce or eliminate the likelihood of exceeding the upper inflection point. In this mode, substantially constant, or varying flow rate is delivered and continuously monitored by the device to increase, decrease, maximise, minimise, or target, the goal PIP set by the user. Table 6 below gives some examples of flow rates that would vary between inspiration and expiration to deliver PIP with nasal high flow. Note that the flow rate may instead be substantially constant at a level that maintains the desired PIP.

TABLE 6

Example relationships between flowrate and pressure to deliver PIP on nasal high flow

| PIP (cmH2O) | Expiratory Pressure (cmH2O) | Inspiratory Flowrate (lpm) | Expiratory Flowrate (lpm) |
|---|---|---|---|
| −0.2 | 0.5 | 30 | 2 |
| 1 | 0.5 | 40 | 2 |
| 2 | 0.5 | 50 | 2 |
| 6.5 | 0.5 | 100 | 2 |

PEEP/PIP: The pressures and flow rates could be controlled to deliver both a set PEEP and PIP level.

Maximum pressure: The user is able to set a limit on the maximum pressure to be delivered to the patient. This can be helpful to treat patients that have a presence or risk of barotrauma or hyperinflation. The greatest patient pressure occurs during expiration will be relatively higher than the PEEP level and can be controlled by the delivered expiratory flow rate. The inspiratory flow rate could be set at a minimum (eg: 2 lpm), could be set to meet a high peak inspiratory demand (eg: 35 lpm) or the measured inspiratory demand or could be set at the same flow rate as the expiratory flow rate, or some other flow rate that may be defined by the user.

CPAP: During normal breathing, the pressure in the lungs drops during inspiration in order to draw air into the lungs, and rises on expiration in order to push air out. The amount the pressure has to drop on inspiration or rise on expiration (pressure amplitude) can affect the work of breathing: the higher the pressure amplitude, the higher the work of breathing. CPAP attempts to reduce the work of breathing by maintaining a constant pressure at the nose and/or mouth, which reduces the pressure amplitude in the lungs (there is still a pressure difference in the lung caused by the resistance to flow of the airways). With nasal high flow, the apparatus is configured to be able to deliver CPAP by delivering more flow on inspiration and less flow on expiration. CPAP pressures using conventional therapies can be set anywhere between 5 and 25 cmH2O. Table 7 gives some example flow rates to achieve CPAP with nasal high flow.

TABLE 7

Example relationships between flowrate and pressure to deliver CPAP on nasal high flow

| CPAP (cmH2O) | Inspiratory Flowrate (lpm) | Expiratory Flowrate (lpm) |
|---|---|---|
| 2 | 60 | 10 |
| 3 | 70 | 20 |
| 4 | 80 | 30 |
| 5 | 90 | 40 |
| 6 | 100 | 50 |

Basic CPAP may be achieved using only two flow rates (inspiratory and expiratory), or the patient pressure may be constantly monitored throughout the breath cycle and the delivered flow rate changed frequently (eg: every 0.1 seconds) in response to this to maintain a more constant pressure.

Bi-Level: A step further towards reducing or eliminating the work of breathing. Mechanically ventilated patients have zero work of breathing because a machine is forcing air into the lungs on inspiration (overcoming elastic and resistive work of breathing) and actively draws air out on expiration. Bi-Level is a step in this direction. The difference is that with Bi-Level the breaths are patient triggered and are supported by the apparatus rather than completely controlled by the apparatus. The user may select a separate inspiratory pressure and expiratory pressure. Setting the inspiratory and expiratory pressures to the same value is CPAP.

With nasal high flow therapy, the apparatus would adjust the delivered flow rate to achieve the set inspiratory and expiratory pressures or flow rates. Table 8 below gives some examples of the nasal high flow rates needed to achieve Bi-Level pressures. The flow rates could also be the main setting to control (to give 'Bi-level Flow').

TABLE 8

Example relationships between flow rate and pressure to deliver Bi-Level on nasal high flow

| Inspiratory Pressure (cmH2O) | Expiratory Pressure (cmH2O) | Inspiratory Flowrate (lpm) | Expiratory Flowrate (lpm) |
|---|---|---|---|
| 4 | 2 | 80 | 10 |
| 5 | 3 | 90 | 20 |
| 6 | 4 | 100 | 30 |

A set inspiratory/expiratory time may also be used to encourage a patient to alter their respiratory rate. For example, if a patient's respiratory rate was elevated, the user could set the inspiratory time to a longer interval. Thus the patient would receive the higher, inspiratory level of pressure for a longer period of time, despite their spontaneous breathing efforts. Because this would be harder to breathe out against, it would encourage the patient to lengthen their inspiratory time and slow their breathing. In other cases, the device may just fully synchronise with the patient's breaths.

If pressure support is not prioritised, the expiration flow rate can be reduced to decrease the expiratory pressure and, thus, the uncomfortable pressure amplitude, as previously described with reference to Table 1. As an alternative to this method, in this mode it could be selected that the pressure variation is instead reduced by increasing the inspiratory pressure to match the expiratory pressure more closely. For example, if the expiratory flow rate had been set by the user to about 30 lpm and the patient was experiencing a pressure amplitude of about 3 cmH2O, the inspiratory flow rate may be set to about 70 lpm which would maintain a more constant pressure throughout the breathing cycle (similar to CPAP). This would reduce the pressure amplitude in the lungs, improve comfort and reduce work of breathing. Compared with the method of Table 1, this strategy does mean that on average a higher level of positive airway pressure would be delivered, which would need to be communicated to the user.

If pressure support is not prioritised and the user wishes to manually set the flow rate to optimise comfort, it may be desirable to reduce pressure variation or reduce the mean airway pressure. It is useful to maintain a positive flow rate at all times to enhance cannula washout.

The example flow rates and corresponding pressures given in the tables above are examples only. In practice, the apparatus will need to determine the delivered flow rate that will achieve the desired pressure for each patient. To achieve this the apparatus may monitor the particular patient pressure of each individual breath (eg: PIP, PEEP, mean) and adjust the flow rate accordingly in response to each measurement. Alternatively, the apparatus may monitor the particular patient pressure over a period of time or number of breaths, and use the mean, median, minimum, maximum or some other metric of the measured pressure and compare this with the set pressure. The apparatus may then adjust the flow rate in response to this value. The flow rate may be adjusted in set increments (eg: +/−2 lpm), or may be adjusted proportionally to the difference between the measured pressure and the set pressure, or may use some other form of control such as PID. There may be apparatus set limits on the maximum rate of change of the flow rate.

5.7.2 $CO_2$ Flushing Mode

To control the $CO_2$ flushing algorithm described previously, the flow rates at inspiration, start of expiration and the end of expiration may be controlled between about −250 and 250 lpm. The user may configure or customise the delivered flow rates and the time over which the flow rate increases and the flushing time period. For example, it may be desirable that the inspiratory flow rate meets the patient's inspiratory demand, that the flow rate at the end of expiration is as high as is comfortable, and that the flushing period at this maximum flow rate is greater than zero. It may also be desirable to reduce the rate of flow rate increase to zero such that there is little or no ramp-up period and the patient is delivered the flushing flow rate as a 'spike', and the user may configure such settings. All flow rates may be constant during their independent phases (e.g. inspiratory phase, expiratory phase, end of expiratory phase such as the flushing spike), or may vary during their phase, for example in response to patient breathing throughout the breath cycle.

Another method of promoting CO2 flushing could be to superimpose oscillatory fluctuations on top of a delivered base pressure or flow rate. The method and possible implementations of this is described previously.

5.7.3 Oxygenation Mode

The oxygen concentration may be controlled by the user between about 21-100%.

In one embodiment oxygen may only be delivered during the inspiratory phase of the breath cycle to conserve oxygen resource. Delivering a flow rate that meets the instantaneous inspiratory demand of the patient, rather than a constant flow that may at time exceed the patient's inspiratory demand will further conserve oxygen.

Another method of promoting oxygenation could be to superimpose oscillatory fluctuations on top of a delivered base pressure or flow rate. The method and possible implementations of this is described previously.

5.7.4 Humidity and Mucous Clearance Mode

The gasflow temperature may be controlled by the user between 10 and about 37° C. It may also be possible to have the temperature output as a flow-dependent parameter. Dry gas becomes increasingly uncomfortable at higher flow rates, however excessive heat can also be unpleasant. Table 9 below gives some examples of temperatures that may be used with different flow rates to compromise between these considerations. In such a configuration, the user may be able to select the temperature setting to be dependent on the flow rate according to a function or set points or any other suitable dependent relationship. In Table 9 below, the relative humidity is set to be 100%.

TABLE 9

Flow-dependent temperature

| Flow rate (lpm) | Temperature |
|---|---|
| 30 | 25° C. |
| 40 | 26° C. |
| 50 | 28° C. |
| 60 | 30° C. |
| 70 | 37° C. |
| 100 | 37° C. |

It should be noted that any of the methods described for any of the mechanisms could be implemented in any combination, provided the appropriate conflict resolution is performed. It may also be possible for the user to choose which method is implemented for which mechanism, in case where there may be more than one similar method. For example CO2 flushing may be implemented by delivering an increased constant flow rate, a flow rate spike at the end of expiration or the start of inspiration, or oscillatory flow fluctuations. In this case the user may desire to choose their preferred method of CO2 flushing.

5.7.5 Other Dependent Settings

In some configurations, the user's choice to not prioritise a particular therapy mechanism may set up limits on certain apparatus parameters. For example, if it was desired by the user that the patient does not receive pressure support (i.e. it is not selected as a priority), the controller may then set limits on the delivered patient pressure and/or flow rate. For example, the delivered patient pressure may be limited to 3 cmH2O and/or the delivered flow rate limited to 30 lpm. Therefore, the range within which the user can change the pressure and/or flow rate is restricted. For example if the user then desired to increase the $CO_2$ flushing flow rate, they would not be permitted to adjust it to a value greater than 30 lpm.

5.8 Display

In any device mode, any, or all of the following sensor readings may be displayed: flow rate, oxygen concentration, temperature, PEEP, PIP, peak pressure, mean pressure, bi-level pressure, CPAP. Pressure display adds value to clinicians who are unsure of what levels of pressure nasal high flow is delivering and facilitates alarms for circuit disconnect (loss of pressure) or nostril blockages (excessive pressure). These sensor readings may be displayed as instantaneous values, rolling averages or maximum/minimums.

5.9 Pressure Measurements

An algorithm would be used which takes experimental and/or simulation data to estimate the patient pressure based on the measured circuit/chamber pressures and flow rate.

5.10 Breath Detection

Several support modes require breath detection to know when the patient is breathing in or out.

Breath detection can be achieved in several ways, including sensing changes in circuit/chamber pressure (a change in the phase of the breath could be indicated by variation in the order of 0.1-10 cmH2O), flowrate fluctuations at the chamber transmitted through the cannula and circuit (a change in the phase of the breath could be indicated by a variation of 0.5-15 lpm), use of respiratory inductance plethysmography (RIP) bands, electromyography (EMG), electrical diaphragmatic impulse (EDI), acoustic sensing, radar, or sensing the change in concentration of expired CO2.

5.11 General Comments on Embodiments

In the previous description, specific details are given to provide a thorough understanding of the embodiments. However, it will be understood by one of ordinary skill in the art that the embodiments may be practiced without these specific details. For example, software modules, functions, circuits, etc., may be shown in block diagrams in order not to obscure the embodiments in unnecessary detail. In other instances, well-known modules, structures and techniques may not be shown in detail in order not to obscure the embodiments.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc., in a computer program. When a process corresponds to a function, its termination corresponds to a return of the function to the calling function or a main function.

The embodiments above may be implemented by hardware, software, firmware, middleware, microcode, or any combination thereof. When implemented in software, firmware, middleware or microcode, the program code or code segments to perform the necessary tasks may be stored in a machine-readable medium such as a storage medium or other storage(s). A processor may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the foregoing, a storage medium may represent one or more devices for storing data, including read-only memory (ROM), random access memory (RAM), magnetic disk storage mediums, optical storage mediums, flash memory devices and/or other machine readable mediums for storing information. The terms "machine readable medium" and "computer readable medium" include, but are not limited to portable or fixed storage devices, optical storage devices, and/or various other mediums capable of storing, containing or carrying instruction(s) and/or data.

The various illustrative logical blocks, modules, circuits, elements, and/or components described in connection with the examples disclosed herein may be implemented or performed with a general purpose processor, a digital signal processor (DSP), an application specific integrated circuit (ASIC), a field programmable gate array (FPGA) or other programmable logic component, discrete gate or transistor logic, discrete hardware components, or any combination thereof designed to perform the functions described herein. A general purpose processor may be a microprocessor, but in the alternative, the processor may be any conventional processor, controller, microcontroller, circuit, and/or state machine. A processor may also be implemented as a combination of computing components, e.g., a combination of a DSP and a microprocessor, a number of microprocessors, one or more microprocessors in conjunction with a DSP core, or any other such configuration.

The methods or algorithms described in connection with the examples disclosed herein may be embodied directly in hardware, in a software module executable by a processor, or in a combination of both, in the form of processing unit, programming instructions, or other directions, and may be contained in a single device or distributed across multiple devices. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor.

One or more of the components and functions illustrated the figures may be rearranged and/or combined into a single component or embodied in several components without departing from the invention. Additional elements or components may also be added without departing from the invention. Additionally, the features described herein may be implemented in software, hardware, as a business method, and/or combination thereof.

In its various aspects, the invention can be embodied in a computer-implemented process, a machine (such as an electronic device, or a general purpose computer or other device that provides a platform on which computer programs can be executed), processes performed by these machines, or an article of manufacture. Such articles can include a computer program product or digital information product in which a computer readable storage medium containing computer program instructions or computer readable data stored thereon, and processes and machines that create and use these articles of manufacture.

6. Display of Parameters 6.1 Overview

A patient dealing with respiratory illness, for example chronic obstructive pulmonary disease (COPD), can have difficulty engaging in effective respiration. This difficulty may be the result of a variety of physiological faults, including a breakdown of lung tissue, dysfunctions of the small airways, excessive accumulation of sputum, infection, genetic disorders, or cardiac insufficiency. With such illnesses, it is useful to provide the patient with a therapy that can improve the ventilation and/or gas exchange of the patient. In some situations, the patient can be provided with a respiratory therapy system that includes a gas source, an interface that may be used to transmit gas to an airway of a patient, and a conduit extending between the gas source and the interface. Gas delivered to an airway of the patient from the gas source can help to promote adequate ventilation of the patient. The gas source may, for example, include a container of air and/or another gas suitable for inspiration, e.g. oxygen or nitric oxide, a mechanical blower capable of propelling a gas through the conduit to the interface, or some combination of both. The respiratory therapy system may include a means for heating and/or humidifying gases passing through the system to improve patient comfort and/or improve the prognosis of the patient's respiratory illness. The respiratory therapy system may be one configured to deliver high flow therapy, or gas therapy involving delivery of gases (e.g. heated and/or humidified gases, for example air and/or oxygen) at a relatively high flow rate to a patient through, for example, a nasal cannula.

Particularly for flow therapy applications involving delivery of gases, it is advantageous to study or control the course of the therapy for a given patient. It can be difficult for physicians or other users of devices adapted to deliver, for example, high flow therapy, to easily obtain relevant data regarding the nature or progress of the therapy delivered. Facilitating the proper operation and setting of parameters of such devices can also be difficult.

6.2 Possible Embodiments for Displaying Parameters

A flow therapy apparatus 10 is shown in FIG. 38. It provides gas flow to a patient through a non-sealing interface 17. It comprises a housing 4 that contains a flow source 11 (such as a flow generator/blower), humidifier 12, controller 13 and user I/O interface 14 (described in greater detail below). The controller 13 is programmed to control the components of the flow therapy apparatus 10, including: operating the flow generator 11 to create a flow of gas (gas flow) for delivery to a patient, operating the humidifier 12 to humidify and/or heat the generated gas flow, adjusting the flow rate of other introduced gases, e.g. oxygen, receiving user input from the user interface for reconfiguration and/or user-defined operation of the apparatus, and/or outputting information (for example on the display) to the user. The user could be a patient, healthcare professional or anyone else interested in using the apparatus. In an alternative, the flow source could be another source of flow such as compressed gas (e.g. $O_2$). Furthermore, the flow source need not actually be in the housing but instead could be outside the housing. The flow source could be controlled in the apparatus and/or at the source.

A patient breathing conduit 16 is coupled to a gas flow output in the housing 4 of the high flow therapy apparatus 10, and is coupled to a patient interface 17, such as a nasal cannula with a manifold 19 and nasal prongs 18. The humidified gas flow that is generated by the high flow therapy apparatus is delivered to the patient via the patient conduit 16 through the cannula 17. The patient conduit 16a can have a heater wire to heat gas flow passing through to the patient, under control of the controller 13. The patient conduit 16 and/or patient interface can be considered part of the high flow therapy apparatus 10, or alternatively peripheral to it. Use of the term "(high) flow therapy apparatus" can be utilized for either alternative.

General operation of a flow therapy breathing apparatus 10 will be known to those skilled in the art, and need not be described in detail here. However, in general terms the controller 13: controls the flow generator 11 to generate a gas flow of the desired flow rate (generated gas flow), and controls the humidifier 12 to humidify the gas flow and/or heat it. The gas flow is directed out through the patient conduit 16 and cannula 17 to the patient. The controller 13 can also control heating elements 16a in the humidifier 12 and/or patient conduit 16 to heat the gas to a desired temperature (also termed "target temperature" or "set point") that achieves the required level of therapy and/or comfort for the patient. The controller 13 can be programmed with or determine a suitable target temperature.

Additionally, the user I/O interface 14 may provide screen display that allows a user to adjust various settings of the flow therapy apparatus 10.

Operation sensors, such as flow, temperature, humidity, gas concentration and/or pressure sensors can be placed in various locations on the flow therapy apparatus and/or the breathing conduit and/or cannula. Output from the sensors can be received by the controller 13, to assist it to operate the flow therapy apparatus in a manner that provides optimal therapy, including delivering a set pressure.

Figure 77:
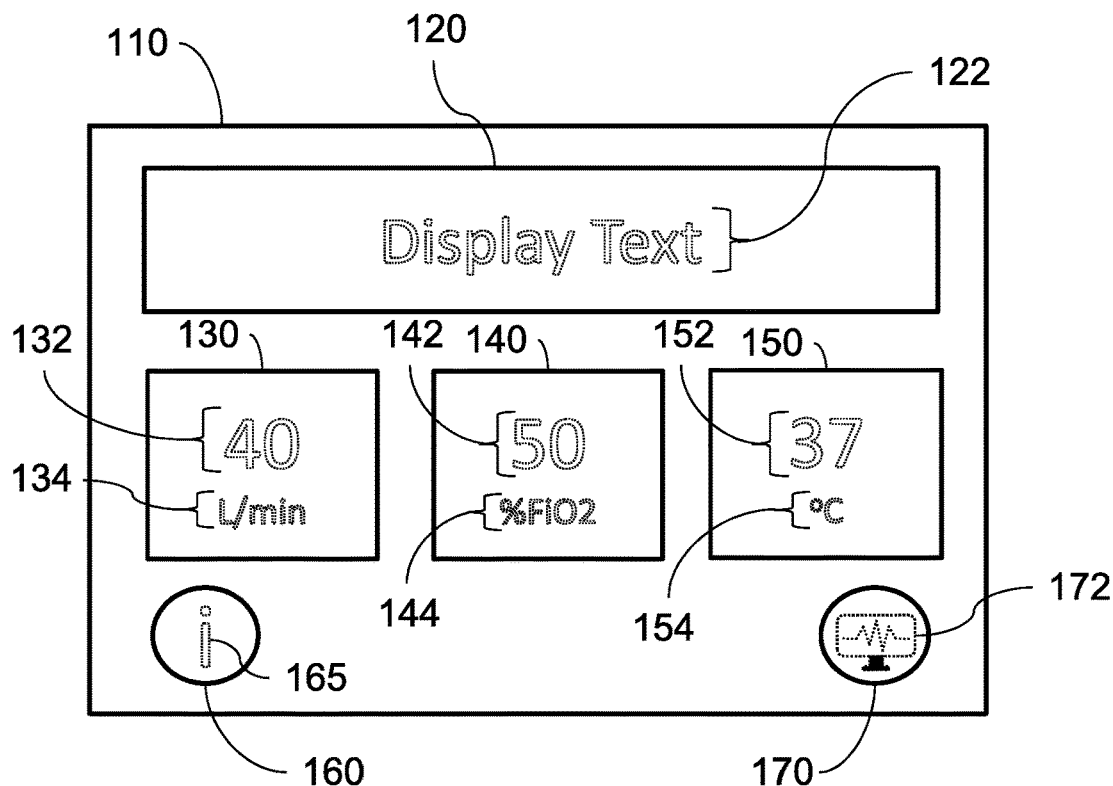
FIG. 77 shows a non-limiting exemplary embodiment of a flow therapy display.

Shown in FIG. 77 is a non-limiting exemplary embodiment of a flow therapy display 110 for use as the I/O interface 14 of the flow apparatus 10 (FIG. 38), or used separately as a display that receives information from sensors of a flow generator/apparatus. As shown, there may be a display portion 120 that optionally displays a predetermined "Display Text" or message, which may include, but is not limited to, therapy type (e.g., nasal high flow), equipment, brand, patient information, etc. The display portion 120 may further be a selection element that enables a user to select, by touch screen, for example, and navigate to different display screens, sub-screens, or sub-menus that provide additional information, such as settings or diagnostic information.

A first value display or selection portion 130 ("first portion") is shown. Displayed in the first portion 130, for example, may be a first value 132 and a first unit 134 or measurement parameter, for example litres per minute (L/min), that is associated with the first value 132.

A second value display or selection portion 140 ("second portion") is shown, and includes a second value 142 and an associated second unit 144 or measurement parameter, for example percentage or fraction of inspired oxygen (% FiO2).

A third value display or selection portion 150 ("third portion") is shown, and includes a third value 152 and an associated third unit 154 or measurement parameter, for example temperature (° C. or ° F.).

The first, second, and third values 132, 142, 152 and associated first, second, and third units 134, 144, 154 may represent various flow therapy settings, for example, temperature, flow rate, fraction of inspired oxygen, humidity, etc.

An information portion 160 with an information icon 165, which when selected, for example, via touch screen, brings up a sub-menu that displays additional information and/or available settings.

Also shown is a monitoring selection portion 170, with a monitoring icon 172 therein. This portion 170 allows a user to access, for example, a sub-menu or additional patient monitoring information.

Figure 79:
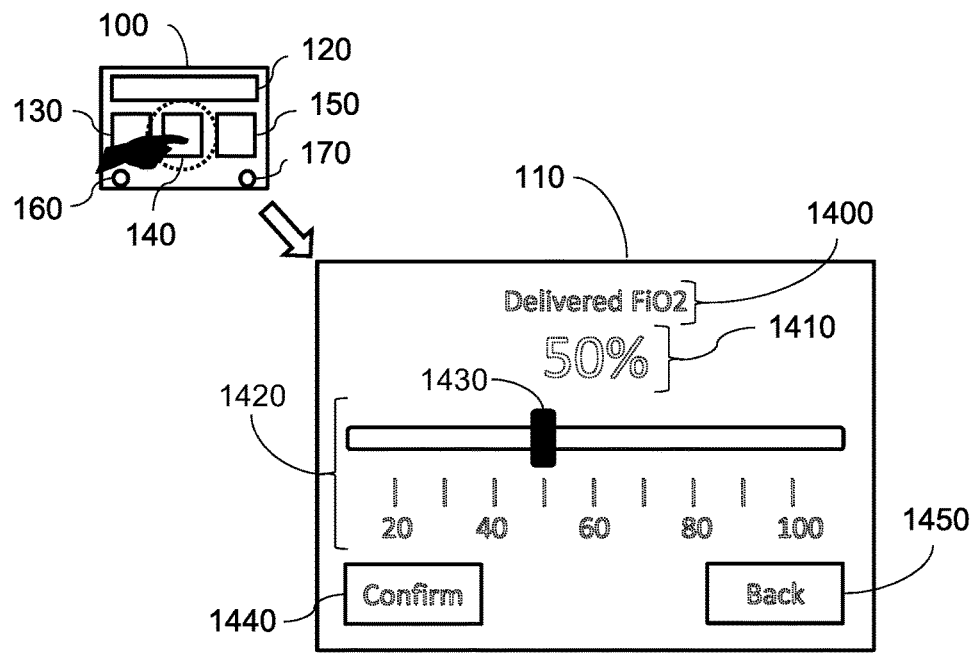
FIG. 79 shows a non-limiting exemplary embodiment of a flow therapy display for displaying delivered oxygen.
Figure 80:
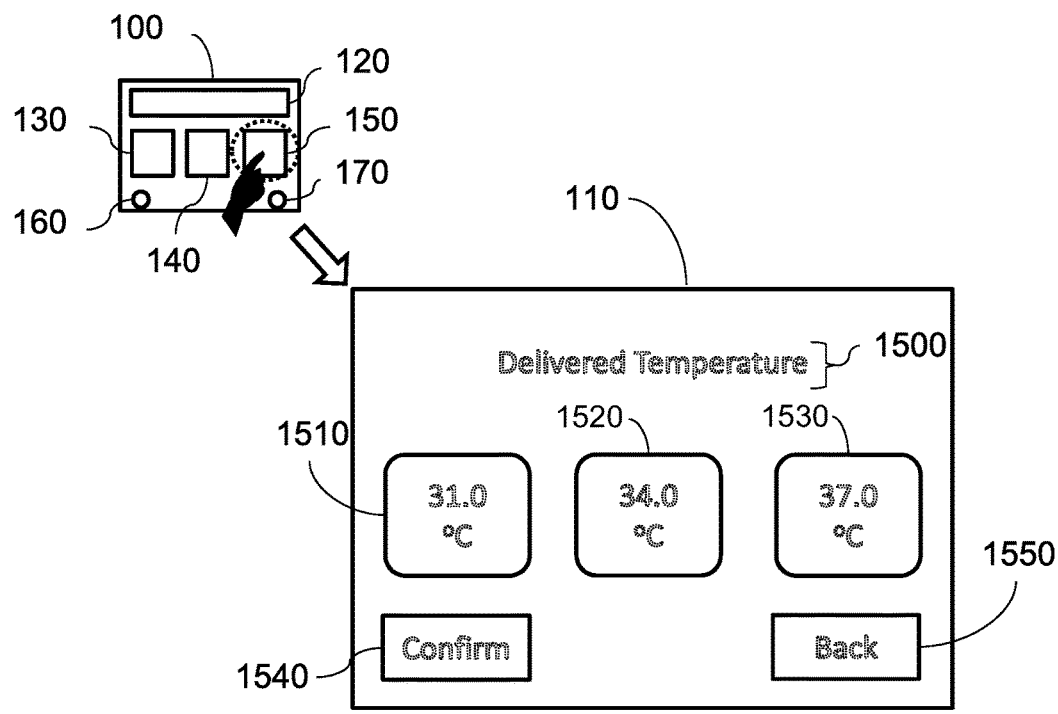
FIG. 80 shows a non-limiting exemplary embodiment of a flow therapy display for displaying delivered temperature of a gas flow.

The first, second, and third portions 130, 140, 150 may also comprise selection icons that, when selected via touch screen, bring up or display a sub-menu or additional information. Shown in FIGS. 78-80 are non-limiting exemplary embodiments of the display screen 110 that may be displayed upon selection of the first, second, and third portions 130, 140, 150.

Figure 78:
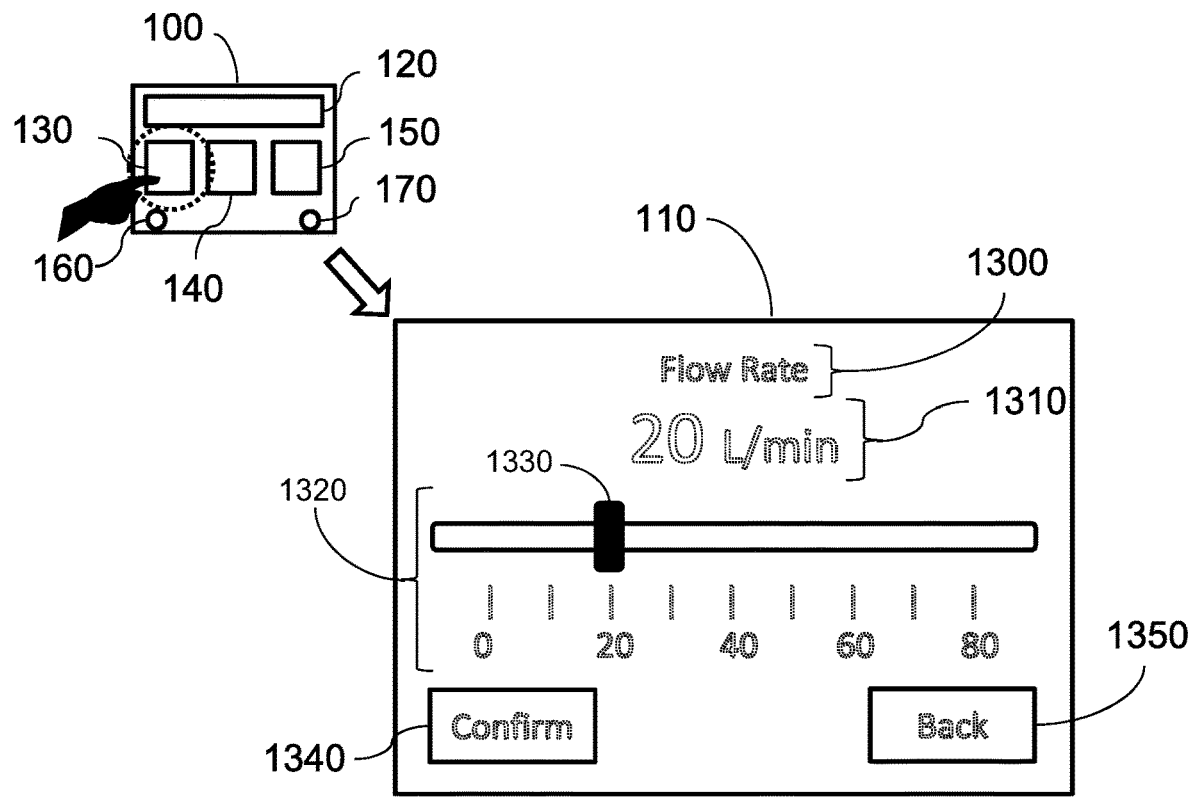
FIG. 78 shows a non-limiting exemplary embodiment of a flow therapy display for displaying flow rate.

In the non-limiting exemplary embodiment shown in FIG. 78, the display 110 displays a sub-menu for adjusting the flow rate of the flow therapy apparatus 10. A title portion 1300 displays "Flow Rate" as an exemplary title of this sub-menu. Below the title portion 1300 is a flow value and unit 1310, which, in this exemplary embodiment, indicates that the flow rate of the flow therapy apparatus 10 is set to 20 L/min (litres per minute). A slider and scale 1320 is provided with a movable or slidable setting icon 1330. The slider and scale 1320 includes a range 0 L/min to 80 L/min in 20 L/min increments, with 10 L/min increments therebetween. As shown, the setting icon 1330 is set to correspond to a flow rate of 20 L/min.

To set, change, or adjust the flow rate, a user may touch the display 110 in the area of the setting icon 1330 and slide or move it to the desired setting. Alternatively, a user may touch the slider and scale 1320 in an area on the slider near the desired setting (flow rate) and the setting icon 1330 will shift to that position corresponding flow rate on the scale. For example, if a user touched the display in an area near the "60" on the slider and scale 1320, the setting icon would move to "60", which would correspond to a flow rate of 60 litres per minute.

Also provided is a confirmation button 1340. When an adjustment is made, such as described above, selection or pressing of the confirmation button 1340 confirms the setting adjustment. Once the adjustment is confirmed, an exit or back icon 1350 may be selected in order to return to a previous menu or display, such as shown in FIG. 77. In some configurations, if an adjustment has been made, selection of the confirmation button 1340 can relay feedback to the user indicating that the new setting has been confirmed. For example, the display 110 or parts thereof, including the confirmation button 1340, may display a colour or image, or a component of the flow therapy apparatus 10 (FIG. 38) may be configured to generate an audible sound. Alternatively, selection of the exit or back button 1350 allows a user to return to a previous menu or display without any adjustment being made or confirmed. If the exit or back button 1350 is selected without selecting the confirmation button 1340, the setting (e.g., flow rate) of the flow therapy apparatus 10 may not be changed even if the slidable setting icon 1330 has been moved. In some embodiments, a query window may be displayed if the exit or back button 1350 is selected without confirming an adjustment. For example, the query window may display a message such as "Do you want to exit without changing the flow rate?" In the non-limiting exemplary embodiment shown in FIG. 79, the display 110 displays a sub-menu for adjusting the percentage of delivered (inspired) $O_2$ of the flow therapy apparatus 10. A title portion 1400 displays "Delivered FiO2" as an exemplary title of this sub-menu. Below the title portion 1400 is a value and unit 1410, which, in this exemplary embodiment, indicates that the percentage of delivered (inspired) O2 of the flow therapy apparatus 10 is set to 50%. A slider and scale 1420 is provided with a movable or slidable setting icon 1430. The slider and scale 1420 includes a range 20 to 100 in increments of 20, with increments of 10 therebetween. These values correspond to the percentage (%) of delivered (inspired) O2. As shown, the setting icon 1430 is set to correspond to a fraction of delivered (inspired) O2 is set to 50%. Although these embodiments describe scales with even increments it would also be possible to have non-linear scales. For example it may be desirable to have more increments at the lower end of a scale for fine adjustment and larger interval increments at the upper end where fine resolution may not be required.

Similar to FIG. 78, the display 110 also includes a confirmation button 1440 and an exit or back button 1450. The settings described with reference to FIG. 79 may be changed or adjusted in a manner similar to the description to FIG. 78.

In the non-limiting exemplary embodiment shown in FIG. 80, the display 110 displays a sub-menu for selecting the delivered temperature of gas delivered by the flow therapy apparatus 10. A title portion 1500 displays "Delivered Temperature" as an exemplary title of this sub-menu. In this particular embodiment, a first temperature icon 1510, a second temperature icon 1520, and a third temperature icon 1530 are provided. Each of the temperature icons 1510, 1520, 1530 include a value and a corresponding unit. The first temperature icon 1510 includes "31.0° C.", indicating that selecting the first temperature icon 1510 sets the delivered temperature to 31 degrees Celsius. Similarly, the second temperature icon 1520 and the third temperature icon 1530 include "34.0° C." and "37.0° C.", respectively, thus indicating the delivered temperatures associated with selecting those temperature icons. Additionally, any parameter could be adjusted via sliders, icon selection or any other selection method.

The display 110 shown in FIG. 80 also includes a confirmation button 1540 and an exit or back button 1550. These buttons function in a similar manner to those previously described.

Figure 81:
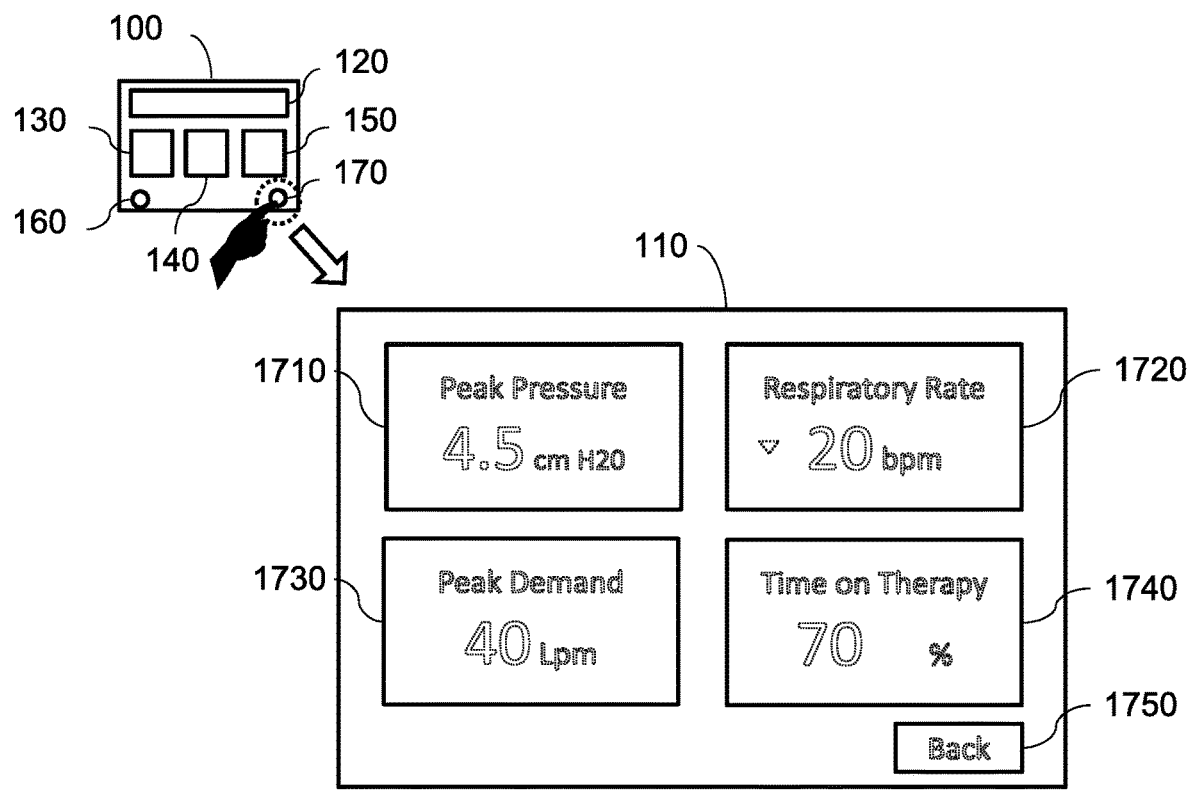
FIG. 81 shows a non-limiting exemplary embodiment of a flow therapy display for displaying various monitoring information.

Shown in FIG. 81 is a non-limiting exemplary embodiment of the display 110 that appears upon selection of the monitoring selection portion 170. A first information section 1710 displays "Peak Pressure", along with a value and a corresponding unit of measure, in this example, 4.5 centimeters of H2O. A second information section 1720 displays "Respiratory Rate", along with a value and a corresponding unit of measure, in this example, 20 breaths per minute (bpm). A third information section 1730 displays "Peak Demand", along with a value and corresponding unit of measure, in this example, 40 litres per minute (Lpm). A fourth information section 1740 displays "Time on Therapy", along with a value and a corresponding unit of measure, in this example, 70%, which is an indication of patient compliance.

In flow therapy, and in particular nasal high flow therapy, it may be desirable to provide gas flow at a flow rate that meets or exceeds a patient's peak inspiratory demand (PID). Meeting inspiratory demand means to supply a flow of gas through a patient interface at a rate that approximates, equals or exceeds the flowrate of gas desired by a patient's normal or augmented inspiratory breath pattern such that no ambient air outside of the supplied gas flow is required or entrained to supplement the supplied flowrate. In the case of providing a constant flow, providing gas flow that meets inspiratory demand will mean providing a gas flow that meets peak inspiratory demand, although this is not essential in other cases. Peak inspiratory demand is a special case of inspiratory demand (that is, at the peak of inspiration), and is covered by any reference to inspiratory demand.

Displaying peak inspiratory demand (peak demand), as shown in third information section 1730 of FIG. 81, allows a user to set the flow rate of gas to meet the peak inspiratory demand such that no room air is entrained and the desired FiO2 may be accurately delivered. In particular, when the delivered flow rate is less than PID, the delivered flow rate may be adjusted to a value that meets or exceeds PID.

In an additional embodiment, a flow comparison value could be displayed. The flow comparison value is a comparison or difference between the delivered flow rate and PID. In this embodiment, a flow comparison value of zero (0) would indicate that delivered flow rate meets PID. A flow comparison value that is a positive value would indicate that delivered flow rate exceeds PID. A flow comparison value that is a negative value would indicate that the delivered flow rate is not sufficient to meet PID. The flow comparison value may also comprise the reverse comparison (i.e., the comparison or difference between PID and the delivered flow rate), such that a negative value indicates that PID is exceeded and a positive value indicates that PID is not exceeded by the delivered flow rate.

Additionally, an absolute value of the difference between the delivered flow rate and PID may be displayed, and another mechanism, such as colour, may be used to indicate whether the value is positive (PID exceeded) or negative (PID not exceeded). For example, if the delivered flow rate is 20 Lpm and PID is 30 Lpm, a value of 10 Lpm may be displayed in red to indicate that the delivered flow rate does not exceed PID. If the delivered flow rate is 30 Lpm and PID is 20 Lpm, a value of 10 Lpm may be displayed in, for example, green to indicate that the delivered flow rate exceeds PID by 10 Lpm. If both the delivered flow rate and PID are 25 Lpm, a value of zero (0) may be displayed in, for example, a green/red icon to indicate that the delivered flow rate meets PID.

In alternative embodiments, it is possible to display an "entrained flow", "excess flow", or "flow support". Entrained flow could represent a value that is a comparison between the cannula flow rate and the PID of the user. For example, if the flow rate is 20 L/min and the PID is determined to be 30 L/min, the entrained flow is 10 L/min (i.e., the difference between the flow rate and the PID). Displaying entrained flow effectively eliminates the need of a clinician or user to evaluate whether the flow rate is set to a level that meets or exceeds the PID of the patient.

In alternative exemplary embodiments, the entrained flow value display could include a colour indication to provide an indication as to whether the therapy is at an appropriate level (i.e., entrained flow is zero or a negative value, thus the delivered flow is meeting or exceeding PID). For example, the entrained flow display may be coloured red until the cannula flow rate is increased to a level in which the entrained flow reaches zero or a negative value, upon which the display may include a green and/or a red/green coloured icon or symbol.

In another exemplary embodiment, once PID is met or exceeded the entrained flow may be re-labelled as "excess flow" or "flow support". These values represent a scenario where the delivered flow rate is higher than the PID. For example, where the PID is 25 L/min and the flow rate is 40 L/min, there is an excess flow or flow support of 15 L/min (i.e., the difference between the flow rate and the PID. Where there is excess flow or flow support, the display may be represented in green, for example, as to indicate that the delivered flow rate meets or exceed the PID. Additionally, changing or re-characterising the comparison of flow rate and PID avoids negative values, which may cause confusion.

Further display embodiments include displaying fraction of delivered oxygen (FdO2) and displaying the result of calculated (true) fraction of inspired oxygen (FiO2). This may be relevant in situations where PID is not met and room air is entrained. In such a situation, the FiO2 may be lower than FdO2. For example, 50% O2 may be delivered by the cannula (FdO2), however, if PID is not met or exceeded, entrained room air may dilute the FiO2 to a lower level, (e.g., 35%). For example if FdO2=50%, the delivered flow rate=20 L/min and PID is determined to equal 35 L/min, then at PID 15 L/min of room air is entrained at an oxygen concentration of 21%. Therefore at PID FiO2=38%.

An additional embodiment may display delivered oxygen in litres per minute (Lpm), for example. This particular embodiment may advantageously provide information regarding the delivered therapy in a format that may be easier to understand or correlate to other flow therapies, such as therapies that deliver 100% oxygen, measured in Lpm. In this embodiment the correct FiO2 is calculated, and a value of delivered oxygen, in Lpm, is displayed. For example if the FiO2 is 35% and the PID is 30 Lpm the delivered oxygen at PID, in Lpm, is 10.5 Lpm (equivalent to 10.5 Lpm of 100% oxygen)

Figure 82:
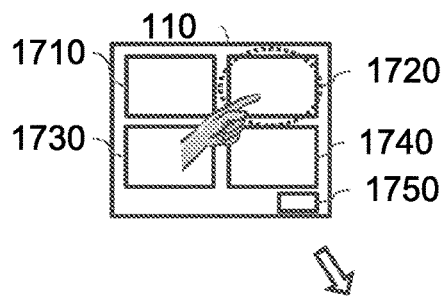
FIG. 82 shows a non-limiting exemplary embodiment of a flow therapy display for displaying respiratory rate over time.
Figure 82:
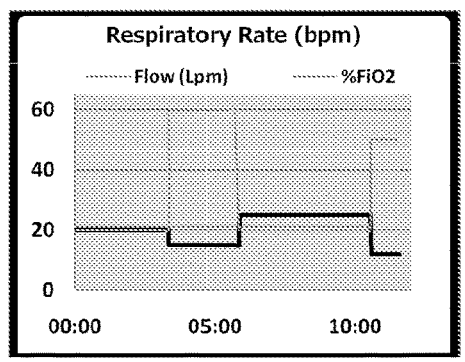
Figure 82:
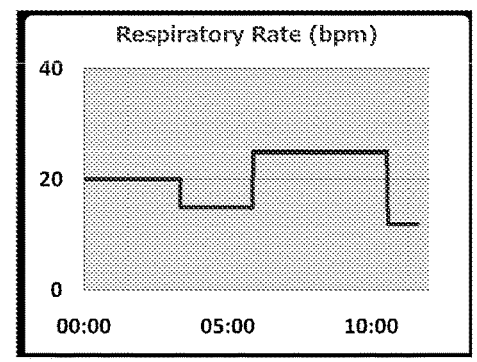
Figure 83:
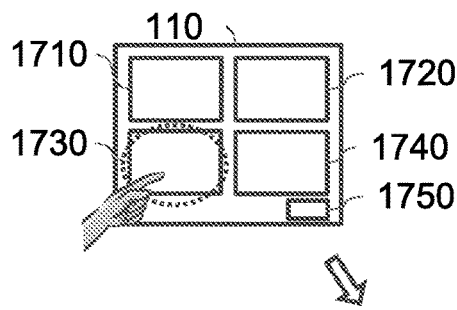
FIG. 83 shows a non-limiting exemplary embodiment of a flow therapy display for displaying peak inspiratory demand over time.
Figure 83:
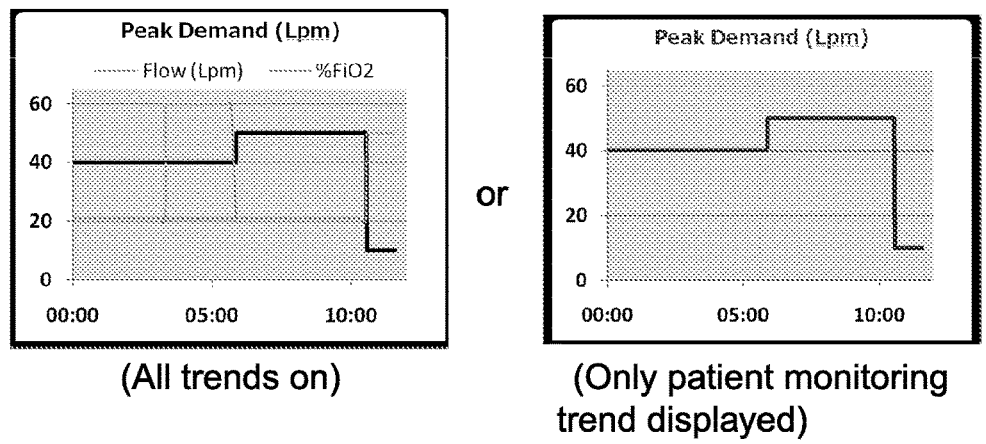
Figure 84:
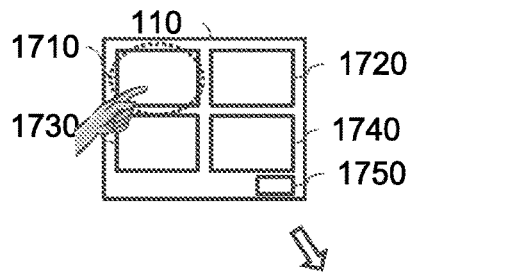
FIG. 84 shows a non-limiting exemplary embodiment of a flow therapy display for displaying short term patient pressure and long term patient pressure.
Figure 84:
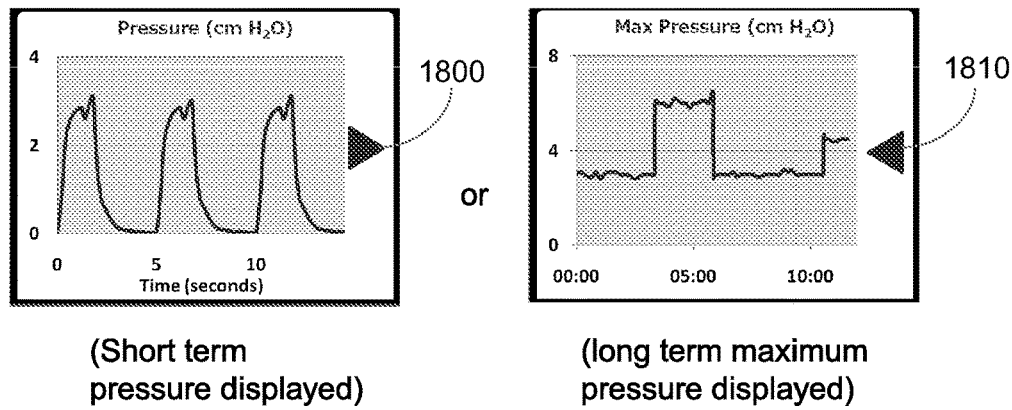

Shown in FIGS. 82-84 are non-limiting exemplary embodiments of sub-menu displays. In particular, FIG. 82 shows graphs of "Respiratory Rate" over time that may be displayed when the second information section 1720 is selected. This embodiment may further include a toggle option which allows a user to turn on and off trends of the delivered flow and FiO2 that are recorded simultaneously with each of the patient monitoring parameters. Additional embodiments may further include additional information or provide access to additional sub-menu displays that display various delivered therapy parameters in isolation. Similarly, in FIG. 83, a plot of peak demand (peak inspiratory demand (PID)) over time may be displayed. Similar to the display description of FIG. 7, all trends may be toggled on or off.

In FIG. 84, selecting the first information section 1710 brings up a display of pressure in cm H2O. In this example, short term pressure associated with each breath may be displayed and/or long term maximum pressure may be displayed. A selector or navigator 1800, 1810 may be provided to alternate between display information. By way of additional non-limiting example, the displayed value may also be the mean pressure, maximum pressure, minimum pressure, inspiratory pressure, expiratory pressure, pressure amplitude, pressure-time product, change or trend in one of these values over a time, or a ratio or other combination of these parameters. Additionally, it may be possible to display more than one of these values, or various combinations of these values, simultaneously.

Figure 85:
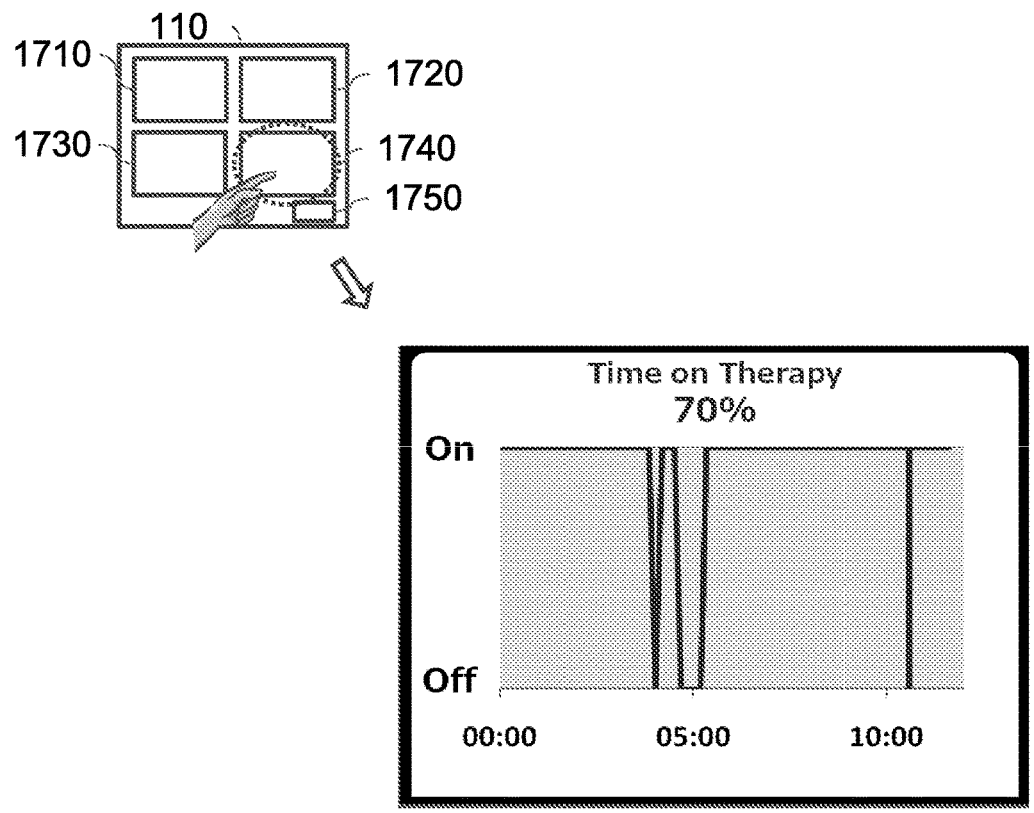
FIG. 85 shows a non-limiting exemplary embodiment of a flow therapy display for displaying patient time on therapy or patient compliance.
Figure 86:
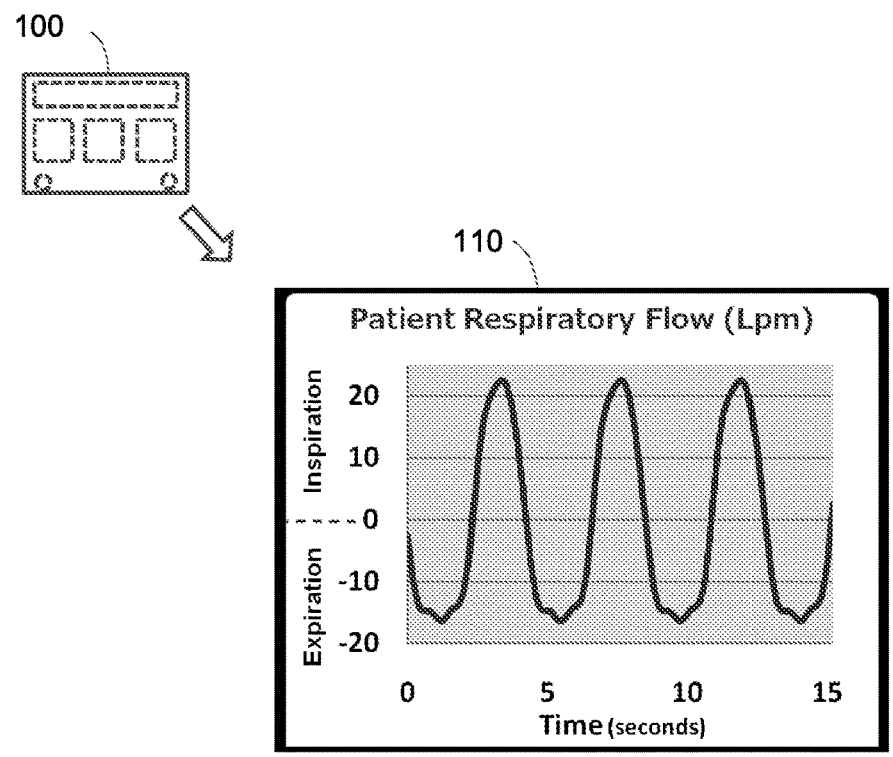
FIG. 86 shows a non-limiting exemplary embodiment of a flow therapy display for displaying patient respiratory flow.

In FIG. 85, selecting the fourth information section 1740 brings up a display of "Time on Therapy" which indicates a percentage of time in which a patient has been "On" or "Off" therapy. This percentage, as well as, the total time in which the patient is on/off flow therapy may also be characterised as patient compliance. In additional non-limiting embodiments, display 110 is configured to display and/or provide for selection of various nasal high flow settings and information thereof. Examples include, but are not limited to, selecting various mechanism prioritization settings, displaying respiratory flow (inspiration and expiration) and displaying the patient inspiratory: expiratory ratio. For example, in FIG. 86, "Patient Respiratory Flow (LPM)" is displayed.

7. Combinations of Embodiments Described

As described, many of aspects of the described embodiments may be combined or interrelated. Additionally, many of the aspects of the described embodiments may be used to support, facilitate, and/or enhance other described embodiments. In this respect, combinations of various described embodiments may provide for additional features, not necessarily available in existing methods and systems.

By way of non-limited example, methods and systems for mechanism prioritisation may be supported or enhanced by methods and systems described with respect to respiratory flow. For example, when prioritising the oxygenation mechanism described with respect to mechanism prioritisation, the systems and methods for determining respiratory flow may be used to determine the phase of the respiratory cycle (i.e., inspiration or expiration).

In such an embodiment, the oxygen supplied may be controlled such that oxygen is only delivered during inspiration. Oxygen supplied on expiration is largely wasted since oxygen delivered at this time will not reach the lungs. Conserving oxygen is advantageous, in particular where only a limited storage of oxygen is available, as an oxygen tank will last longer, sometimes twice as long. In a transport situation this may mean the difference between whether nasal high flow therapy is used or if more invasive therapies, such as ventilation, are required which may waste less oxygen, but have considerable side effects.

Additionally, conservation of oxygen can be made by delivering a flow rate that meets but not significantly exceed the instantaneous inspiratory demand of the patient. In this respect, the flow delivered during inspiration can match the air inhaled into the lungs, providing the minimum oxygen needed, and further enabling nasal high flow therapy to be used in situations where only a limited storage of oxygen is available.

By way of additional non-limiting example, in the method of promoting gas exchange by providing a varying gas flow oscillating about the base flow rate (opti-oscillate), the base flow rate may be the peak inspiratory demand, as determined by described methods of determining respiratory flow (inspiration and expiration). This would allow accurate levels of inhaled oxygen (FiO2) and humidity to be maintained without the entrainment of room air.

Additionally, the CO2 flushing mechanism described with respect to mechanism prioritisation could be implemented by flushing CO2 during the expiratory pause or using the method of promoting gas exchange by providing a varying gas flow oscillating about the base flow rate (opti-oscillate). The addition of flow oscillations can reduce the flow rate necessary to achieve a certain level of flushing or increases the total flushing capacity of the therapy. It may be desirable to minimise the cannula flow rate for the same level of flushing because high flow rates can be perceived as less comfortable. With this, the option could be available for the user to choose between the two methods for implementing the CO2 flushing mechanism. The methods for implementing flushing have different mechanisms of action, and as such could be more or less effective on different patients and/or patient groups.

The methods for estimating respiratory flow, in particular (peak) inspiratory demand, could be utilised in the mechanism prioritisation function. For example where a low inspiratory flow rate is desirable and/or a high inspiratory flow rate is not the priority of the mechanism selected the inspiratory flow rate could be set to meet the determined (peak) inspiratory demand. This would allow accurate levels of inhaled oxygen (FiO2) and humidity to be maintained without the entrainment of room air, or the delivery of excessive inspiratory flows.

The invention claimed is:

1. A method of promoting gas exchange in an airway of a patient comprising:
   providing a unidirectional oscillating gas flow to the patient's nares through a non-sealing nasal cannula by continuously modulating a gas flow rate resulting in a positive net flow of gas toward the patient at the non-sealing nasal cannula irrespective of a patient's breathing cycle; and
   controlling the unidirectional oscillating gas flow by providing a positive base flow rate modulated with at least one frequency targeting a positive and varying flow rate oscillating between a minimum flow rate and a maximum flow rate about the positive base flow rate, wherein the at least one frequency is in a range of 2-250 Hz.

2. The method of promoting gas exchange of claim 1, wherein the unidirectional oscillating gas flow has a gas flow rate that oscillates between 25 liters/minute and 26 liters/minute at a frequency of 15 Hz.

3. The method of promoting gas exchange of claim 1, wherein the unidirectional oscillating gas flow has a mean gas flow rate of 30 liters/minute and an oscillatory gas flow rate of +/−5 liters/minute at a frequency of 15 Hz.

4. The method of promoting gas exchange of claim 1, wherein the unidirectional oscillating gas flow has a gas flow pressure that oscillates between 6 cm-$H_2O$ and 6.5 cm-$H_2O$ at a frequency of 15 Hz.

5. The method of promoting gas exchange according to claim 1, further comprising modulating a flow pressure.

6. The method of promoting gas exchange according to claim 1, wherein the at least one frequency promotes $CO_2$ washout of the airway of the patient or increased $O_2$ in the airway of the patient.

7. The method of promoting gas exchange according to claim 6, wherein the at least one frequency is at least one resonant frequency of the airway of the patient.

8. The method of promoting gas exchange according to claim 7, wherein the at least one frequency comprises a plurality of resonant frequencies.

9. The method of promoting gas exchange according to claim 1, wherein a controller operates a fan of a blower of a flow therapy apparatus and a flow modulating device, the controller operating the fan at a base speed and the controller operating the flow modulating device to providing the unidirectional oscillating gas flow at the at least one frequency.

10. The method of promoting gas exchange according to claim 1, the method comprising providing the unidirectional oscillating gas flow by providing a first flow of gases and superimposing a second flow of gases onto the first flow of gases.

11. The method of promoting gas exchange according to claim 10, wherein the first flow of gases is provided at a constant rate.

12. The method of promoting gas exchange according to claim 10, wherein the first flow of gases is varied during a therapy session.

13. The method of promoting gas exchange according to claim 12, wherein the first flow of gases is varied in response to expiratory and inspiratory transitions.

14. The method of promoting gas exchange according to claim 1, wherein providing the unidirectional oscillating gas flow comprises providing a single varying flow of gases.

15. The method of promoting gas exchange according to claim 14, wherein the single varying flow of gases is provided by a flow therapy apparatus with a blower operated by a controller.

16. The method of promoting gas exchange according to claim 15, wherein the controller operates a fan of the blower at a first speed to provide the positive base flow rate and varies the first speed of the fan of the blower to provide the single varying flow at the at least one frequency.

17. The method of promoting gas exchange according to claim 1, wherein the unidirectional oscillating gas flow oscillates about at least one of the positive base flow rate and a base flow pressure.

18. The method of promoting gas exchange of claim 17, wherein at least one of the at least one frequency, an oscillation amplitude, the positive base flow rate, and the base flow pressure is imparted by input from a user or the patient.

19. The method of promoting gas exchange of claim 17, wherein at least one of the at least one frequency, an oscillation amplitude, the positive base flow rate, and the base flow pressure is selected by a controller implementing an automatic frequency sweep testing routine.

20. The method of promoting gas exchange of claim 19, wherein the at least one of the at least one frequency, the oscillation amplitude, the positive base flow rate, and the base flow pressure that is selected by the automatic frequency sweep testing routine is selected to promote at least one of carbon dioxide washout and oxygen in the airway of the patient.

21. The method of promoting gas exchange of claim 19, wherein the automatic frequency sweep testing routine is performed at least one of at a beginning of operations of the method, at a plurality of regular intervals during the method, when initiated by at least one of a user and the patient, and whenever a change in a condition of the patient is detected.

22. The method of promoting gas exchange of claim 17, wherein at least one of the at least one frequency, an oscillation amplitude, the positive base flow rate, and the base flow pressure is selected based on a patient-dependent variable that is input into a controller.

23. The method of promoting gas exchange of claim 22, wherein the patient-dependent variable comprises at least one of patient height and tidal volume.

24. The method of promoting gas exchange of claim 1, further comprising using a linear actuator to provide the unidirectional oscillating gas flow.

25. The method of promoting gas exchange according to claim 1, wherein the unidirectional oscillating gas flow oscillates at a modulation frequency that is higher than a breathing frequency of the patient.

26. The method of claim 1, wherein the positive base flow rate is at least 20 lpm.

\* \* \* \* \*